US011965197B2

(12) United States Patent
Koffas et al.

(10) Patent No.: US 11,965,197 B2
(45) Date of Patent: *Apr. 23, 2024

(54) MICROBIAL POLYCULTURES AND METHODS OF USE THEREOF

(71) Applicant: RENSSELAER POLYTECHNIC INSTITUTE, Troy, NY (US)

(72) Inventors: Mattheos Koffas, Niskayuna, NY (US); John Andrew Jones, Liberty Township, OH (US)

(73) Assignee: Rensselaer Polytechnic Institute, Troy, NY (US)

(*) Notice: Subject to any disclaimer, the term of this patent is extended or adjusted under 35 U.S.C. 154(b) by 175 days.

This patent is subject to a terminal disclaimer.

(21) Appl. No.: 17/197,468

(22) Filed: Mar. 10, 2021

(65) Prior Publication Data

US 2021/0198712 A1 Jul. 1, 2021

Related U.S. Application Data

(63) Continuation of application No. 15/341,911, filed on Nov. 2, 2016, now Pat. No. 10,954,543.

(60) Provisional application No. 62/249,476, filed on Nov. 2, 2015.

(51) Int. Cl.
| | |
|---|---|
| C12N 9/90 | (2006.01) |
| C12N 9/00 | (2006.01) |
| C12N 9/02 | (2006.01) |
| C12N 9/04 | (2006.01) |
| C12N 9/10 | (2006.01) |
| C12N 9/88 | (2006.01) |
| C12N 15/52 | (2006.01) |
| C12P 7/42 | (2006.01) |
| C12P 7/52 | (2006.01) |
| C12P 17/06 | (2006.01) |
| C12P 19/58 | (2006.01) |

(52) U.S. Cl.
CPC ............ *C12P 19/58* (2013.01); *C12N 9/0006* (2013.01); *C12N 9/0071* (2013.01); *C12N 9/0093* (2013.01); *C12N 9/1037* (2013.01); *C12N 9/88* (2013.01); *C12N 9/90* (2013.01); *C12N 9/93* (2013.01); *C12N 15/52* (2013.01); *C12P 7/42* (2013.01); *C12P 7/52* (2013.01); *C12P 17/06* (2013.01); *C12Y 101/01219* (2013.01); *C12Y 114/11009* (2013.01); *C12Y 117/01003* (2013.01); *C12Y 203/01074* (2013.01); *C12Y 403/01023* (2013.01); *C12Y 505/01006* (2013.01); *C12Y 602/01012* (2013.01); *C12Y 602/01014* (2013.01)

(58) Field of Classification Search
CPC .. C12P 19/58; C12P 17/06; C12Y 602/01014; C12Y 403/01023; C12Y 602/01012; C12Y 203/01074; C12Y 101/01219; C12N 9/88; C12N 9/93; C12N 9/90

USPC ..................... 435/253.2, 125, 410
See application file for complete search history.

(56) References Cited

U.S. PATENT DOCUMENTS

| 7,338,791 B2 | 3/2008 | Koffas et al. |
| 7,807,422 B2 | 10/2010 | Koffas et al. |
| 2015/0203880 A1 | 7/2015 | Stephanopoulus et al. |
| 2016/0017317 A1 | 1/2016 | Church et al. |

FOREIGN PATENT DOCUMENTS

| CN | 101948794 A | 1/2011 |
| CN | 105087534 A | 11/2015 |

OTHER PUBLICATIONS

Boock, J.T., et al., "Screening and modular design for metabolic pathway optimization," Current Opinion in Biotechnology, vol. 36, pp. 189-198, 2015.
Brenner, K., et al., "Engineering microbial consortia: a new frontier in synthetic biology," Trends in Biotechnology, vol. 26, No. 9, pp. 483-489, 2008.
Brown, E.J., et al., "Pentachlorophenol degradation: a Pure Bacterial Culture and an Epilithic Microbial Consortium," Applied and Environmental Microbiology, vol. 52, No. 1, pp. 92-97, 1986.
Chemler, J.A., et al., "Standardized biosynthesis of flavan-3-ols with effects on pancreatic beta-cell insulin secretion," Appl. Microbiol. Biotechnol., vol. 77, pp. 797-807, 2007.
Cress, B.F., et al., "Sensitive cells: enabling tools for static and dynamic control of microbial metabolic pathways," Current Opinion in Biotechnology, vol. 36, pp. 205-214, 2015.
Devos, D., et al., "Practical Limits of Function Prediction," Proteins: Structure, Function and Genetics, vol. 41, pp. 98-107, 2000.
Gaikwad, G.L., "Development of Microbial Consortia for the Effective Treatment of Complex Wastewater," Journal of Bioremediation & Biodegradation, vol. 5, No. 4, 100227, pp. 1-6, 2014.
Grosskopf, T., et al., "Synthetic microbial communities," Current Opinion in Microbiology, vol. 18, pp. 72-77, 2014.
Hatcher, B.G., "Coral reef ecosystems: how much greater is the whole than the sum of the parts?," Coral Reefs, vol. 16, Suppl., pp. S77-S91, 1997.
Hays, S.G., et al., "Better together: engineering and application of microbial symbioses," Current Opinion in Biotechnology, vol. 36, pp. 40-49, 2015.
Huang, Q., et al., "Caffeic Acid Production Enhancement by Engineering a Phenylalanine Over-Producing *Escherichia coli* strain," Biotechnology and Bioengineering, vol. 110, No. 12, pp. 3188-3196, 2013.

(Continued)

*Primary Examiner* — Robert B Mondesi
*Assistant Examiner* — Mohammad Y Meah
(74) *Attorney, Agent, or Firm* — Murtha Cullina LLP; Anthony P. Gangemi

(57) ABSTRACT

Disclosed herein are novel microbial polycultures of two or more cell strains, capable of producing flavanones, flavonoids, and anthocyanidin-3-O-glucosides, and methods of use thereof. Also disclosed is a microbial cell capable of producing phenylpropanoic acids, and methods of use thereof.

10 Claims, 7 Drawing Sheets

Specification includes a Sequence Listing.

(56) References Cited

OTHER PUBLICATIONS

Jones, J.A., et al., "Experimental and computational optimization of an *Escherichia coli* co-culture for the efficient production of flavonoids," Metabolic Engineering, vol. 35, pp. 55-63, 2016.

Jones, J.A., et al., "Metabolic pathway balancing and its role in the production of biofuels and chemicals," Current Opinion in Biotechnology, vol. 33, pp. 52-59, 2015.

Jones, J.A., et al., "ePathOptimize: A Combinatorial Approach for Transcriptional Balancing of Metabolic Pathways," Scientific Reports, vol. 5, 11301, pp. 1-10, 2015.

Jones, J.A., et al., "Optimization of Naringenin and p-Coumaric Acid Hydroxylation Using the Native *E. coli* Hydroxylase Complex, HpaBC," Biotechnol. Prog., vol. 00, No. 00, pp. 1-10, 2015.

Jones, J.A., et al., "Optimizing Metabolic Pathways for the Improved Production of Natural Products," Methods in Enzymology, pp. 1-15, 2016.

Kang, S.-Y., et al., "Artificial biosynthesis of phenylpropanoic acids in a tyrosine overproducing *Escherichia coli* strain," Microbial Cell Factories, vol. 11, No. 153, pp. 1-9, 2012.

Kisselev, L., "Polypeptide Release Factors in Prokaryotes and Eukaryotes: Same Function, Different Structure," Biochemistry, vol. 38, pp. 11643-11650, 1999.

Koenig, J.E., et al., "Succession of microbial consortia in the developing infant gut microbiom," Proceedings of the National Academy of Sciences of the United States of America, vol. 108, Suppl 1, pp. 4578-4585, 2011.

Lin, Y., et al., "Biosynthesis of caffeic acid in *Escherichia coli* using its endogenous hydroxylase complex," Microbial Cell Factories, vol. 11, No. 42, pp. 1-9, 2012.

Lin, Y., et al., "Biotechnological Production of Plant-Specific Hydroxylated Phenylpropanoids," Biotechnology and Bioengineering, vol. 111, No. 9, pp. 1895-1899, 2014.

Lindemann, S.R., et al., "Engineering microbial consortia for controllable outputs," ISME Journal, vol. 10, pp. 2077-2084, 2016.

Manz, W., et al., "In situ characterization of the microbial consortia active in two wastewater treatment plants," Water Res., vol. 28, No. 8, pp. 1715-1723, 1994.

Olson, J.B., et al., "N2-Fixing Microbial Consortia Associated with the Ice Cover of Lake Bonney, Antarctica," Microbial Ecology, vol. 36, pp. 231-238, 1998.

Paerl, H.W., et al., "A Mini-Review of Microbial Consortia: Their Roles in Aquatic Production and Biogeochemical Cycling," Microbial Ecology, vol. 31, No. 3, pp. 225-247, 1996.

Rabaey, K., et al., "Biofuel Cells Select for Microbial Consortia That Self-Mediate Electron Transfer," Applied and Environmental Microbiology, vol. 70, No. 9, pp. 5373-5382, 2004.

Roze, L.V., et al., "Compartmentalization and molecular traffic in secondary metabolism: A new understanding of established cellular processes," Fungal Genet. Biol., vol. 48, No. 1, pp. 35-48, 2011.

Saini, M., et al., "Potential production platform of n-butanol in *Escherichia coli*," Metabolic Engineering, vol. 27, pp. 76-82, 2015.

Santos, C.N.S., et al., "Optimization of a heterologous pathway for the production of flavonoids from glucose," Metabolic Engineering, vol. 13, pp. 392-400, 2011.

Santos, C.N.S., "Combinatorial Search Strategies for the Metabolic Engineering of Microorganisms," Massachusetts Institute of Technology, Doctor of Philosophy submission, pp. 1-253, 2010.

Shindo, K., et al., "Enzymatic synthesis of novel antioxidant flavonoids by *Escherichia coli* cells expressing modified metabolic genes involved in biphenyl catabolism," Journal of Molecular Catalysis B: Enzymatic, vol. 23, pp. 9-16, 2003.

Smid, E.J., et al., "Microbe-microbe interactions in mixed culture food fermentations," Current Opinion in Biotechnology, vol. 24, pp. 148-154, 2013.

Teague, B.P., et al., "Synthetic communities, the sum of parts," Science, vol. 349, Issue 6251, pp. 924-925, 2015.

Umar, K.M., et al., "Response surface optimization of process variables for catechin production in recombinant *Escherichia coli* BL (DE3) harbouring an artificial gene cluster," Journal of Food, Agriculture & Environment (JFAE), Online ISSN: 1459-0263, vol. 12, No. 2, pp. 74-77, 2014.

Whisstock, J.C., et al., "Prediction of protein function from protein sequence and structure," Quarterly Reviews of Biophysics, vol. 36, No. 3, pp. 307-340, 2003.

Willrodt, C., et al., "Coupling Limonene Formation and Oxyfunctionalization by Mixed-Culture Resting Cell Fermentation," Biotechnology and Bioengineering, vol. 112, No. 9, pp. 1738-1750, 2015.

Witkowski, A., et al., "Conversion of a B-Ketoacyl Synthase to a Malonyl Decarboxylase by Replacement of the Active-Site Cysteine with Glutamine," Biochemistry, vol. 38, pp. 11643-11650, 1999.

Xu, P., et al., "Genome-scale metabolic network modeling results in minimal interventions that cooperatively force carbon flux towards malonyl-CoA," Metabolic Engineering, vol. 13, pp. 578-587, 2011.

Yadav, V.G., et al., "The Future of Metabolic Engineering and Synthetic Biology: Towards a Systematic Practice," Metab. Eng., vol. 14, No. 3, pp. 233-241, 2012.

Young, V.A., et al., "Kimchi: Spicy Science for the Undergraduate Microbiology Laboratory," J. Microbiol. Biol. Educ., vol. 15, No. 2, pp. 297-298, 2014.

Zhang, H., et al., "Modular co-culture engineering, a new approach for metabolic engineering," Metabolic Engineering, vol. 37, pp. 114-121, 2016.

Zhang, H., et al., "Engineering *E. coli-E. coli* cocultures for production of muconic acid from glycerol," Microbial Cell Factories, vol. 14, No. 134, pp. 1-10, 2015.

Zhang, H., et al., "Engineering *Escherichia coli* coculture systems for the production of biochemical products," Proceedings of the National Academy of Sciences of the United States of America, vol. 112, No. 27, pp. 8266-8271, 2015.

Zhao, S., et al., "Improvement of catechin production in *Escherichia coli* through combinatorial metabolic enginering," Metabolic Engineering, vol. 28, pp. 43-53, 2015.

Zhou, K., et al., "Distributing a metabolic pathway among a microbial consortium enhances production of natural products," Nat. Biotechnol., vol. 33, No. 4, pp. 377-383, 2015.

SEQUENCE LISTING

<160> NUMBER OF SEQ ID NOS: 84

<210> SEQ ID NO 1
<211> LENGTH: 28
<212> TYPE: DNA
<213> ORGANISM: Artificial Sequence
<220> FEATURE:
<223> OTHER INFORMATION: At4CL_FWD with NdeI Primer

<400> SEQUENCE: 1
gcgccgcata tggcgccaca agaacaag                28

-continued

<210> SEQ ID NO 2
<211> LENGTH: 28
<212> TYPE: DNA
<213> ORGANISM: Artificial Sequence
<220> FEATURE:
<223> OTHER INFORMATION: At4CL_REV with XhoI Primer

<400> SEQUENCE: 2
gcgcggctcg agtcacaatc catttgct                                          28

<210> SEQ ID NO 3
<211> LENGTH: 20
<212> TYPE: DNA
<213> ORGANISM: Artificial Sequence
<220> FEATURE:
<223> OTHER INFORMATION: Seq_T7_FWD Primer

<400> SEQUENCE: 3
taatacgact cactataggg                                                    20

<210> SEQ ID NO 4
<211> LENGTH: 19
<212> TYPE: DNA
<213> ORGANISM: Artificial Sequence
<220> FEATURE:
<223> OTHER INFORMATION: Seq_T7Term_REV Primer

<400> SEQUENCE: 4
gctagttatt gctcagcgg                                                     19

<210> SEQ ID NO 5
<211> LENGTH: 50
<212> TYPE: DNA
<213> ORGANISM: Artificial Sequence
<220> FEATURE:
<223> OTHER INFORMATION: SDM_At4CL_NheI_FWD Primer

<400> SEQUENCE: 5
gaatgacgga agcaggtcca gtgctcgcaa tgtcgttagg ttttgcaaag                   50

<210> SEQ ID NO 6
<211> LENGTH: 50
<212> TYPE: DNA
<213> ORGANISM: Artificial Sequence
<220> FEATURE:
<223> OTHER INFORMATION: SDM_At4CL_NheI_REV Primer

<400> SEQUENCE: 6
ctttgcaaaa cctaacgaca ttgcgagcac tggacctgct tccgtcattc                   50

<210> SEQ ID NO 7
<211> LENGTH: 65
<212> TYPE: DNA
<213> ORGANISM: Artificial Sequence
<220> FEATURE:
<223> OTHER INFORMATION: ANS_XbaI_F Primer

<400> SEQUENCE: 7
ccctctagaa ataattttgt ttaactttaa gaaggagata tacatatggt gaatgcagta       60
gttac                                                                    65

<210> SEQ ID NO 8
<211> LENGTH: 34
<212> TYPE: DNA
<213> ORGANISM: Artificial Sequence

```
<220> FEATURE:
<223> OTHER INFORMATION: ANS_XhoI_R Primer

<400> SEQUENCE: 8
cgatctcgag ctatttagat tcttcagcag caac                          34

<210> SEQ ID NO 9
<211> LENGTH: 26
<212> TYPE: DNA
<213> ORGANISM: Artificial Sequence
<220> FEATURE:
<223> OTHER INFORMATION: 3GT_NdeI_F Primer

<400> SEQUENCE: 9
gcatcatatg accaaaccct ccgacc                                   26

<210> SEQ ID NO 10
<211> LENGTH: 35
<212> TYPE: DNA
<213> ORGANISM: Artificial Sequence
<220> FEATURE:
<223> OTHER INFORMATION: 3GT_XhoI_R Primer

<400> SEQUENCE: 10
cgatctcgag tcaaataatg tttacaactg catcc                         35

<210> SEQ ID NO 11
<211> LENGTH: 25
<212> TYPE: DNA
<213> ORGANISM: Artificial Sequence
<220> FEATURE:
<223> OTHER INFORMATION: pETM6_ALL_inserts_flank_F Primer

<400> SEQUENCE: 11
ccatcggtga tgtcggcgat atagg                                    25

<210> SEQ ID NO 12
<211> LENGTH: 27
<212> TYPE: DNA
<213> ORGANISM: Artificial Sequence
<220> FEATURE:
<223> OTHER INFORMATION: pETM6_ALL_inserts_flank_R Primer

<400> SEQUENCE: 12
gtcgaggtgc cgtaaagcac taaatcg                                  27

<210> SEQ ID NO 13
<211> LENGTH: 31
<212> TYPE: DNA
<213> ORGANISM: Artificial Sequence
<220> FEATURE:
<223> OTHER INFORMATION: ANS_mid_seq_F Primer

<400> SEQUENCE: 13
ccatctggcc taaaaatcct actgactaca c                             31

<210> SEQ ID NO 14
<211> LENGTH: 29
<212> TYPE: DNA
<213> ORGANISM: Artificial Sequence
<220> FEATURE:
<223> OTHER INFORMATION: ANS_mid_seq_R Primer

<400> SEQUENCE: 14
cctctttgaa gactttgtgt tcaacagcg                                29
```

<210> SEQ ID NO 15
<211> LENGTH: 26
<212> TYPE: DNA
<213> ORGANISM: Artificial Sequence
<220> FEATURE:
<223> OTHER INFORMATION: 3GT_mid_seq_F Primer

<400> SEQUENCE: 15
gcttcatcaa atgggtcttg ctttgc         26

<210> SEQ ID NO 16
<211> LENGTH: 27
<212> TYPE: DNA
<213> ORGANISM: Artificial Sequence
<220> FEATURE:
<223> OTHER INFORMATION: 3GT_mid_seq_R Primer

<400> SEQUENCE: 16
ggtgtcatga ccgtaccaaa gctaatg        27

<210> SEQ ID NO 17
<211> LENGTH: 29
<212> TYPE: DNA
<213> ORGANISM: Artificial Sequence
<220> FEATURE:
<223> OTHER INFORMATION: RgTALsyn_FWD w/NdeI Primer

<400> SEQUENCE: 17
gcggcgcata tggcgcctcg cccgacttc      29

<210> SEQ ID NO 18
<211> LENGTH: 40
<212> TYPE: DNA
<213> ORGANISM: Artificial Sequence
<220> FEATURE:
<223> OTHER INFORMATION: RgTALsyn_REV w/SpeI Primer

<400> SEQUENCE: 18
gcggcgacta gtttatgcca gcatcttcag cagaacattg    40

<210> SEQ ID NO 19
<211> LENGTH: 36
<212> TYPE: DNA
<213> ORGANISM: Artificial Sequence
<220> FEATURE:
<223> OTHER INFORMATION: SDM_RgTALsyn_FWD Primer

<400> SEQUENCE: 19
gcactgcacg acgcgcacat gttgagcctg ttgagc        36

<210> SEQ ID NO 20
<211> LENGTH: 36
<212> TYPE: DNA
<213> ORGANISM: Artificial Sequence
<220> FEATURE:
<223> OTHER INFORMATION: SDM_RgTALsyn_REV Primer

<400> SEQUENCE: 20
gctcaacagg ctcaacatgt gcgcgtcgtg cagtgc        36

<210> SEQ ID NO 21
<211> LENGTH: 18
<212> TYPE: DNA
<213> ORGANISM: Artificial Sequence
<220> FEATURE:
<223> OTHER INFORMATION: pXylA_FOR Primer

<400> SEQUENCE: 21
gcaagcatgc gaaatgca                                                    18

<210> SEQ ID NO 22
<211> LENGTH: 19
<212> TYPE: DNA
<213> ORGANISM: Artificial Sequence
<220> FEATURE:
<223> OTHER INFORMATION: pXylA_REV Primer

<400> SEQUENCE: 22
gagtttcgtt cgagatcgc                                                   19

<210> SEQ ID NO 23
<211> LENGTH: 312
<212> TYPE: DNA
<213> ORGANISM: Artificial Sequence
<220> FEATURE:
<223> OTHER INFORMATION: gBlock Sequence for cloning pXylA

<400> SEQUENCE: 23
gcaagcatgc gaaatgcacc taggaaaaaa aacattgaaa taaacattta ttttgtatat      60
gatgagataa agttagttta ttggataaac aaactaactc aattaagata gttgatggat     120
aaacttgttc acttaaatca aaggggggaa tgtacacata tggcagatct caattggata     180
tcggccggcc acgcgatcgc tgacgtcggt accctcgagt ctggtaaaga aaccgctgct     240
gcgaaatttg aacgccagca catggactcg tctactagtc gcagcttaat taagcgatct     300
cgaacgaaac tc                                                         312

<210> SEQ ID NO 24
<211> LENGTH: 1515
<212> TYPE: DNA
<213> ORGANISM: Rhizobium trifolii

<400> SEQUENCE: 24
gtgagcaacc atcttttcga cgccatgcgg ccgccgcgc ccggtaacgc accattcatc       60
cggatcgata acacgcgcac atggacctat gacgacgccg tcgctctttc cggccgcatt    120
gccggcgcga tggacacgct cggcattcgc cccggcgacc gcgttgcggt gcaggtcgag    180
aaaagtgccg aggcattgat cctctatctc gcctgtcttc gaagcggcgc cgtttacctg    240
ccgctcaaca ccgcctatac gctggctgag ctcgattatt ttatcggcga tgcggagccg    300
cgtttggtgg ttgttgcatc gtcggctcga gcgggcgtgg agacaatcgc caagcccgc    360
ggtgcgatcg tcgaaactct cgacgctgat ggcagcggct cgttgctgga tctcgcccgc    420
gatgagccgg ctgactttgt cgatgcctcg cgctccgccg atgatctggc tgcgatcctc    480
tacacctcgg gaacgacggg acgctccaag ggggcgatgc tcacgcatgg gaacctgctc    540
tcgaacgccc tgaccttgcg agattttttgg cgcgtcaccg ccggcgatcg actgatccat    600
gccttgccga tcttccacac gcatgggctg ttcgtcgcca cgaacgtcac tttactcgcc    660
ggcgcctcga tgttcctgct gtcgaagttc gacccggagg agatcctgtc gctgatgccg    720
caggcaacga tgctgatggg cgtgccgacc ttctacgtgc gcctcctgca aagcccgcgc    780
ctcgacaagc aagcagtcgc caacatccgc ctcttcattt ccggttcggc tccactgctt    840
gcagaaacac ataccgagtt ccaggcacgt accggtcacg ccattctcga gcgctacggc    900
atgacggaaa ccaatatgaa cacgtccaac ccttatgagg ggaaacggat tgccggaacg    960

```
gtcggcttcc cgctgcctga tgtgacggtg cgcgtcaccg atcccgccac cgggctcgcg      1020
ctgccgcctg aagaaacagg catgatcgag atcaaggggc cgaacgtttt caagggctat      1080
tggcgcatgc ccgaaaaaac cgcggccgaa ttcaccgccg acggtttctt catcagcggc      1140
gatctcggca agatcgaccg ggacggttat gtccacatcg tcggccgtgg caaggatctg      1200
gtgatttccg gtggatacaa catctatccg aaagaggtgg agggcgagat cgaccagatc      1260
gagggtgtgg ttgagagcgc tgtgatcggc gtgccgcatc ccgatttcgg agaaggcgtg      1320
accgccgtcg tcgtgcgcaa acccggcgct gtcctcgatg aaaaggccat cgtcagcgcc      1380
ctccaggacc ggctcgcgcg ctacaaacaa cccaagcgca tcatctttgc cgaagacttg      1440
ccgcgcaaca cgatgggcaa ggttcagaaa aacatcctgc ggcagcaata cgccgatctt      1500
tacaccagga cgtaa                                                       1515
```

<210> SEQ ID NO 25
<211> LENGTH: 504
<212> TYPE: PRT
<213> ORGANISM: Rhizobium trifolii

<400> SEQUENCE: 25

```
Met Ser Asn His Leu Phe Asp Ala Met Arg Ala Ala Pro Gly Asn
1               5                   10                  15

Ala Pro Phe Ile Arg Ile Asp Asn Thr Arg Thr Trp Thr Tyr Asp Asp
            20                  25                  30

Ala Val Ala Leu Ser Gly Arg Ile Ala Gly Ala Met Asp Thr Leu Gly
        35                  40                  45

Ile Arg Pro Gly Asp Arg Val Ala Val Gln Val Glu Lys Ser Ala Glu
    50                  55                  60

Ala Leu Ile Leu Tyr Leu Ala Cys Leu Arg Ser Gly Ala Val Tyr Leu
65                  70                  75                  80

Pro Leu Asn Thr Ala Tyr Thr Leu Ala Glu Leu Asp Tyr Phe Ile Gly
                85                  90                  95

Asp Ala Glu Pro Arg Leu Val Val Ala Ser Ser Ala Arg Ala Gly
            100                 105                 110

Val Glu Thr Ile Ala Lys Pro Arg Gly Ala Ile Val Glu Thr Leu Asp
        115                 120                 125

Ala Asp Gly Ser Gly Ser Leu Leu Asp Leu Ala Arg Asp Glu Pro Ala
    130                 135                 140

Asp Phe Val Asp Ala Ser Arg Ser Ala Asp Asp Leu Ala Ala Ile Leu
145                 150                 155                 160

Tyr Thr Ser Gly Thr Thr Gly Arg Ser Lys Gly Ala Met Leu Thr His
                165                 170                 175

Gly Asn Leu Leu Ser Asn Ala Leu Thr Leu Arg Asp Phe Trp Arg Val
            180                 185                 190

Thr Ala Gly Asp Arg Leu Ile His Ala Leu Pro Ile Phe His Thr His
        195                 200                 205

Gly Leu Phe Val Ala Thr Asn Val Thr Leu Leu Ala Gly Ala Ser Met
    210                 215                 220

Phe Leu Leu Ser Lys Phe Asp Pro Glu Glu Ile Leu Ser Leu Met Pro
225                 230                 235                 240

Gln Ala Thr Met Leu Met Gly Val Pro Thr Phe Tyr Val Arg Leu Leu
                245                 250                 255

Gln Ser Pro Arg Leu Asp Lys Gln Ala Val Ala Asn Ile Arg Leu Phe
            260                 265                 270
```

```
Ile Ser Gly Ser Ala Pro Leu Leu Ala Glu Thr His Thr Glu Phe Gln
            275                 280                 285

Ala Arg Thr Gly His Ala Ile Leu Glu Arg Tyr Gly Met Thr Glu Thr
        290                 295                 300

Asn Met Asn Thr Ser Asn Pro Tyr Glu Gly Lys Arg Ile Ala Gly Thr
305                 310                 315                 320

Val Gly Phe Pro Leu Pro Asp Val Thr Val Arg Val Thr Asp Pro Ala
                325                 330                 335

Thr Gly Leu Ala Leu Pro Pro Glu Glu Thr Gly Met Ile Glu Ile Lys
            340                 345                 350

Gly Pro Asn Val Phe Lys Gly Tyr Trp Arg Met Pro Glu Lys Thr Ala
        355                 360                 365

Ala Glu Phe Thr Ala Asp Gly Phe Phe Ile Ser Gly Asp Leu Gly Lys
    370                 375                 380

Ile Asp Arg Asp Gly Tyr Val His Ile Val Gly Arg Gly Lys Asp Leu
385                 390                 395                 400

Val Ile Ser Gly Gly Tyr Asn Ile Tyr Pro Lys Glu Val Glu Gly Glu
                405                 410                 415

Ile Asp Gln Ile Glu Gly Val Val Glu Ser Ala Val Ile Gly Val Pro
            420                 425                 430

His Pro Asp Phe Gly Glu Gly Val Thr Ala Val Val Arg Lys Pro
        435                 440                 445

Gly Ala Val Leu Asp Glu Lys Ala Ile Val Ser Ala Leu Gln Asp Arg
    450                 455                 460

Leu Ala Arg Tyr Lys Gln Pro Lys Arg Ile Ile Phe Ala Glu Asp Leu
465                 470                 475                 480

Pro Arg Asn Thr Met Gly Lys Val Gln Lys Asn Ile Leu Arg Gln Gln
                485                 490                 495

Tyr Ala Asp Leu Tyr Thr Arg Thr
            500

<210> SEQ ID NO 26
<211> LENGTH: 1347
<212> TYPE: DNA
<213> ORGANISM: Rhizobium trifolii

<400> SEQUENCE: 26
atgggcatcg aactgctgag tattggtctg ctgattgcta tgtttattat tgctacgatt      60
caaccgatta acatgggtgc tctggcattc gcaggcgctt ttgtgctggg tagcatgatt     120
atcggcatga aaaccaacga aattttcgca ggctttccgt ctgacctgtt tctgaccctg     180
gtggcggtta cgtacctgtt tgcgattgcc cagatcaatg caccatcga ctggctggtt      240 gaatgcgcgt gcgtctggt tcgtggccgc attggtctga tcccgtgggt gatgttcctg      300
gttgcggcca ttatcaccgg ttttggtgca ctgggtccgg cagctgttgc aattctggca     360
ccggtcgcac tgagcttcgc agtgcaatat cgcattcatc cggttatgat gggtctgatg     420
gtcatccacg gcgcacaggc tggcggtttt tcaccgattt cgatctacgg cggtattacc     480
aaccaaatcg tggcaaaagc aggtctgccg ttcgcaccga cgagtctgtt tctgagcagc     540 tttttctta atctggcaat tgctgtcctg tgttctttg tgtttggcgg tgcacgtgtt       600
atgaaacacg atccggcttc tctgggtccg ctgccggaac tgcatccgga aggcgtgagc     660
gcgtctattc gtggtcatgg cggcacccccg gcaaaaccga tccgcgaaca tgcgtatggc    720
accgcagcag acacggcaac cacgctgcgt ctgaacaatg aacgcattac cacgctgatc    780
```

-continued

```
ggtctgaccg cactgggtat tggtgcactg gttttcaaat ttaacgtcgg tctggtggct    840
atgaccgtgg cagtggttct ggcactgctg agcccgaaaa cgcagaaagc agctattgat    900
aaagtcagtt ggtccaccgt gctgctgatc gcgggtatta tcacgtatgt tggcgtcatg    960
gaaaaagcgg gcaccgttga ctacgtcgcc aatggtatta gttccctggg tatgccgctg    1020
ctggtcgcgc tgctgctgtg tttcaccggc gccatcgtgt ccgcgtttgc ctcatcgacg    1080
gcactgctgg gtgctattat cccgctggcc gttccgttcc tgctgcaggg ccatattagt    1140
gcaatcggtg tcgtggcggc cattgctatc tccaccacga ttgtggatac cagcccgttt    1200
tctacgaacg cgcgctggt tgtcgcaaat gctccggatg actcacgtga acaggttctg    1260
cgccaactgc tgatctattc ggccctgatt gctattattg tccgattgt cgcctggctg    1320
gttttcgttg tgccgggtct ggtctaa                                        1347
```

<210> SEQ ID NO 27
<211> LENGTH: 448
<212> TYPE: PRT
<213> ORGANISM: Rhizobium trifolii

<400> SEQUENCE: 27

```
Met Gly Ile Glu Leu Leu Ser Ile Gly Leu Leu Ile Ala Met Phe Ile
1               5                   10                  15

Ile Ala Thr Ile Gln Pro Ile Asn Met Gly Ala Leu Ala Phe Ala Gly
            20                  25                  30

Ala Phe Val Leu Gly Ser Met Ile Gly Met Lys Thr Asn Glu Ile
        35                  40                  45

Phe Ala Gly Phe Pro Ser Asp Leu Phe Leu Thr Leu Val Ala Val Thr
    50                  55                  60

Tyr Leu Phe Ala Ile Ala Gln Ile Asn Gly Thr Ile Asp Trp Leu Val
65                  70                  75                  80

Glu Cys Ala Val Arg Leu Val Arg Gly Arg Ile Gly Leu Ile Pro Trp
                85                  90                  95

Val Met Phe Leu Val Ala Ala Ile Ile Thr Gly Phe Gly Ala Leu Gly
            100                 105                 110

Pro Ala Ala Val Ala Ile Leu Ala Pro Val Ala Leu Ser Phe Ala Val
        115                 120                 125

Gln Tyr Arg Ile His Pro Val Met Met Gly Leu Met Val Ile His Gly
    130                 135                 140

Ala Gln Ala Gly Gly Phe Ser Pro Ile Ser Ile Tyr Gly Gly Ile Thr
145                 150                 155                 160

Asn Gln Ile Val Ala Lys Ala Gly Leu Pro Phe Ala Pro Thr Ser Leu
                165                 170                 175

Phe Leu Ser Ser Phe Phe Asn Leu Ala Ile Ala Val Leu Val Phe
            180                 185                 190

Phe Val Phe Gly Gly Ala Arg Val Met Lys His Asp Pro Ala Ser Leu
        195                 200                 205

Gly Pro Leu Pro Glu Leu His Pro Glu Gly Val Ser Ala Ser Ile Arg
    210                 215                 220

Gly His Gly Gly Thr Pro Ala Lys Pro Ile Arg Glu His Ala Tyr Gly
225                 230                 235                 240

Thr Ala Ala Asp Thr Ala Thr Thr Leu Arg Leu Asn Asn Glu Arg Ile
                245                 250                 255

Thr Thr Leu Ile Gly Leu Thr Ala Leu Gly Ile Gly Ala Leu Val Phe
            260                 265                 270
```

```
Lys Phe Asn Val Gly Leu Val Ala Met Thr Val Ala Val Leu Ala
            275                 280                 285

Leu Leu Ser Pro Lys Thr Gln Lys Ala Ala Ile Asp Lys Val Ser Trp
        290                 295                 300

Ser Thr Val Leu Leu Ile Ala Gly Ile Ile Thr Tyr Val Gly Val Met
305                 310                 315                 320

Glu Lys Ala Gly Thr Val Asp Tyr Val Ala Asn Gly Ile Ser Ser Leu
                325                 330                 335

Gly Met Pro Leu Leu Val Ala Leu Leu Leu Cys Phe Thr Gly Ala Ile
            340                 345                 350

Val Ser Ala Phe Ala Ser Ser Thr Ala Leu Leu Gly Ala Ile Ile Pro
        355                 360                 365

Leu Ala Val Pro Phe Leu Leu Gln Gly His Ile Ser Ala Ile Gly Val
    370                 375                 380

Val Ala Ala Ile Ala Ile Ser Thr Thr Ile Val Asp Thr Ser Pro Phe
385                 390                 395                 400

Ser Thr Asn Gly Ala Leu Val Val Ala Asn Ala Pro Asp Asp Ser Arg
                405                 410                 415

Glu Gln Val Leu Arg Gln Leu Leu Ile Tyr Ser Ala Leu Ile Ala Ile
            420                 425                 430

Ile Gly Pro Ile Val Ala Trp Leu Val Phe Val Val Pro Gly Leu Val
        435                 440                 445

<210> SEQ ID NO 28
<211> LENGTH: 2082
<212> TYPE: DNA
<213> ORGANISM: Rhodotorula glutinis

<400> SEQUENCE: 28
atggcgcctc gcccgacttc gcaaagccag gcccgcactt gcccgacgac gcaggttacc      60
caagttgata tcgttgagaa aatgttggcg gctcctactg atagcacgct ggagctggac     120
ggttatagcc tgaatctggg tgatgtcgtg agcgctgcgc gtaagggtcg tcctgtccgt     180
gtcaaagata gcgatgaaat ccgcagcaaa atcgacaaga gcgttgaatt cctgcgcagc     240
caactgagca tgtcggttta cggtgtgacg accggctttg gcggctccgc ggacacgcgc     300
acggaggacg caattagcct gcaaaaggcg ttgctggaac accagctgtg tggtgtgttg     360
ccgagcagct tcgacagctt tcgcttgggt cgtggtctgg agaatagcct gccgttggaa     420
gtcgttcgcg gtgcaatgac cattcgtgtg aattcgctga cccgtggcca tagcgctgtt     480
cgtctggttg ttctggaagc actgacgaac tttctgaacc acggtattac cccgattgtt     540
ccgctgcgcg gtacgatctc cgcgagcggc gatctgtctc cactgtcgta cattgcagcg     600
gcgattagcg gtcacccgga tagcaaagtt cacgtggtcc atgaaggcaa agagaagatc     660
ctgtacgcgc gcgaagcgat ggcgctgttt aacctggagc cggtggtttt gggtccgaag     720
gagggcctgg gtctggtgaa tggtacggca gtctccgcga gcatggcaac gctggcactg     780
cacgacgcgc atatgttgag cctgttgagc caatcgctga ccgcgatgac cgtggaggcg     840
atggtcggtc acgcgggcag cttccatcca ttcctgcacg atgttacgcg tccgcacccg     900
acgcaaatcg aggtcgcggg taacattcgc aaactgctgg agggctcgcg cttcgcggtc     960
caccacgagg aagaggttaa ggtcaaggat gatgaaggca ttttgcgtca ggatcgttat    1020
ccgttgcgca cgagcccgca atggtttggg ccgctggtgt ccgacctgat tcacgctcat    1080
gccgtcttga cgatcgaagc gggtcaaagc accaccgata ccccactgat cgatgttgag    1140
```

```
aataagacca gccatcacgg tggcaacttt caagcggcag cggttgccaa cacgatggaa   1200
aagacccgtc tgggcttggc ccaaatcggt aaactgaatt tcacccagct gacggagatg   1260
ctgaacgcgg gcatgaatcg tggcttgccg agctgcctgg cggctgaaga cccatccctg   1320
agctatcatt gcaaaggtct ggacattgcg gcggctgcat atacgagcga actgggccac   1380
ctggctaacc cggtcaccac ccacgtccaa ccggctgaaa tggcaaacca ggcggtgaat   1440
agcttggcgt tgattagcgc acgtcgtacc acggaatcta acgacgttct gtccctgctg   1500
ctggcaacgc acctgtactg cgtgctgcag gcgatcgacc tgcgtgcgat tgagttcgag   1560
ttcaagaaac agtttggtcc tgccattgtt agcctgatcg accaacactt tggtagcgcg   1620
atgacgggta gcaatctgcg tgatgagctg gttgaaaagg tcaataagac tctggccaag   1680
cgtttggagc aaaccaatag ctacgatctg gttccgcgct ggcacgacgc ttttagcttc   1740
gctgcaggca ctgttgtcga ggttctgtcc agcacgagcc tgagcttggc ggccgtgaac   1800
gcatggaagg ttgcggcagc cgagagcgcg atctccttga cgcgccaggt ccgtgaaacg   1860
ttttggtccg ctgcaagcac ctccagcccg gcgttgtctt acttgagccc gcgcacgcag   1920
atcctgtacg catttgtgcg tgaggaactg ggtgtcaaag cccgccgtgg tgacgtcttc   1980
ttgggtaaac aagaagttac catcggcagc aacgttagca agatttacga agccatcaag   2040
agcggccgta tcaacaatgt tctgctgaag atgctggcat aa                      2082
```

```
<210> SEQ ID NO 29
<211> LENGTH: 693
<212> TYPE: PRT
<213> ORGANISM: Rhodotorula glutinis

<400> SEQUENCE: 29
```

Met Ala Pro Arg Pro Thr Ser Gln Ser Gln Ala Arg Thr Cys Pro Thr
1               5                   10                  15

Thr Gln Val Thr Gln Val Asp Ile Val Glu Lys Met Leu Ala Ala Pro
                20                  25                  30

Thr Asp Ser Thr Leu Glu Leu Asp Gly Tyr Ser Leu Asn Leu Gly Asp
            35                  40                  45

Val Val Ser Ala Ala Arg Lys Gly Arg Pro Val Arg Val Lys Asp Ser
        50                  55                  60

Asp Glu Ile Arg Ser Lys Ile Asp Lys Ser Val Glu Phe Leu Arg Ser
65                  70                  75                  80

Gln Leu Ser Met Ser Val Tyr Gly Val Thr Thr Gly Phe Gly Gly Ser
                85                  90                  95

Ala Asp Thr Arg Thr Glu Asp Ala Ile Ser Leu Gln Lys Ala Leu Leu
            100                 105                 110

Glu His Gln Leu Cys Gly Val Leu Pro Ser Ser Phe Asp Ser Phe Arg
        115                 120                 125

Leu Gly Arg Gly Leu Glu Asn Ser Leu Pro Leu Glu Val Val Arg Gly
    130                 135                 140

Ala Met Thr Ile Arg Val Asn Ser Leu Thr Arg Gly His Ser Ala Val
145                 150                 155                 160

Arg Leu Val Val Leu Glu Ala Leu Thr Asn Phe Leu Asn His Gly Ile
                165                 170                 175

Thr Pro Ile Val Pro Leu Arg Gly Thr Ile Ser Ala Ser Gly Asp Leu
            180                 185                 190

Ser Pro Leu Ser Tyr Ile Ala Ala Ala Ile Ser Gly His Pro Asp Ser
        195                 200                 205

```
Lys Val His Val Val His Glu Gly Lys Glu Lys Ile Leu Tyr Ala Arg
    210             215                 220
Glu Ala Met Ala Leu Phe Asn Leu Glu Pro Val Val Leu Gly Pro Lys
225             230                 235                 240
Glu Gly Leu Gly Leu Val Asn Gly Thr Ala Val Ser Ala Ser Met Ala
                245                 250                 255
Thr Leu Ala Leu His Asp Ala His Met Leu Ser Leu Leu Ser Gln Ser
            260                 265                 270
Leu Thr Ala Met Thr Val Glu Ala Met Val Gly His Ala Gly Ser Phe
        275                 280                 285
His Pro Phe Leu His Asp Val Thr Arg Pro His Pro Thr Gln Ile Glu
    290                 295                 300
Val Ala Gly Asn Ile Arg Lys Leu Leu Glu Gly Ser Arg Phe Ala Val
305             310                 315                 320
His His Glu Glu Glu Val Lys Val Lys Asp Asp Gly Ile Leu Arg
                325                 330                 335
Gln Asp Arg Tyr Pro Leu Arg Thr Ser Pro Gln Trp Leu Gly Pro Leu
                340                 345                 350
Val Ser Asp Leu Ile His Ala His Ala Val Leu Thr Ile Glu Ala Gly
        355                 360                 365
Gln Ser Thr Thr Asp Asn Pro Leu Ile Asp Val Glu Asn Lys Thr Ser
    370                 375                 380
His His Gly Gly Asn Phe Gln Ala Ala Ala Val Ala Asn Thr Met Glu
385             390                 395                 400
Lys Thr Arg Leu Gly Leu Ala Gln Ile Gly Lys Leu Asn Phe Thr Gln
                405                 410                 415
Leu Thr Glu Met Leu Asn Ala Gly Met Asn Arg Gly Leu Pro Ser Cys
            420                 425                 430
Leu Ala Ala Glu Asp Pro Ser Leu Ser Tyr His Cys Lys Gly Leu Asp
        435                 440                 445
Ile Ala Ala Ala Ala Tyr Thr Ser Glu Leu Gly His Leu Ala Asn Pro
    450                 455                 460
Val Thr Thr His Val Gln Pro Ala Glu Met Ala Asn Gln Ala Val Asn
465             470                 475                 480
Ser Leu Ala Leu Ile Ser Ala Arg Arg Thr Thr Glu Ser Asn Asp Val
                485                 490                 495
Leu Ser Leu Leu Leu Ala Thr His Leu Tyr Cys Val Leu Gln Ala Ile
            500                 505                 510
Asp Leu Arg Ala Ile Glu Phe Glu Phe Lys Lys Gln Phe Gly Pro Ala
        515                 520                 525
Ile Val Ser Leu Ile Asp Gln His Phe Gly Ser Ala Met Thr Gly Ser
    530                 535                 540
Asn Leu Arg Asp Glu Leu Val Glu Lys Val Asn Lys Thr Leu Ala Lys
545             550                 555                 560
Arg Leu Glu Gln Thr Asn Ser Tyr Asp Leu Val Pro Arg Trp His Asp
                565                 570                 575
Ala Phe Ser Phe Ala Ala Gly Thr Val Val Glu Val Leu Ser Ser Thr
            580                 585                 590
Ser Leu Ser Leu Ala Ala Val Asn Ala Trp Lys Val Ala Ala Ala Glu
        595                 600                 605
Ser Ala Ile Ser Leu Thr Arg Gln Val Arg Glu Thr Phe Trp Ser Ala
    610                 615                 620
Ala Ser Thr Ser Ser Pro Ala Leu Ser Tyr Leu Ser Pro Arg Thr Gln
```

```
                  625                 630                 635                 640
Ile Leu Tyr Ala Phe Val Arg Glu Glu Leu Gly Val Lys Ala Arg Arg
                      645                 650                 655
Gly Asp Val Phe Leu Gly Lys Gln Glu Val Thr Ile Gly Ser Asn Val
              660                 665                 670
Ser Lys Ile Tyr Glu Ala Ile Lys Ser Gly Arg Ile Asn Asn Val Leu
          675                 680                 685
Leu Lys Met Leu Ala
      690

<210> SEQ ID NO 30
<211> LENGTH: 1686
<212> TYPE: DNA
<213> ORGANISM: Arabidopsis thaliana

<400> SEQUENCE: 30
atggcgccac aagaacaagc agtttctcag gtgatggaga acagagcaa caacaacaac      60 agtgacgtca ttttccgatc aaagttaccg gatatttaca tcccgaacca cctatctctc    120
cacgactaca tcttccaaaa catctccgaa ttcgccacta agccttgcct aatcaacgga    180
ccaaccggcc acgtgtacac ttactccgac gtccacgtca tctcccgcca aatcgccgcc    240
aattttcaca aactcggcgt taaccaaaac gacgtcgtca tgctcctcct cccaaactgt    300
cccgaattcg tcctctcttt cctcgccgcc tccttccgcg cgcaaccgc caccgccgca    360 aacccttttct tcactccggc ggagatagct aaacaagcca agcctccaa caccaaactc    420 ataatcaccg aagctcgtta cgtcgacaaa atcaaaccac ttcaaaacga cgacggagta    480
gtcatcgtct gcatcgacga caacgaatcc gtgccaatcc tgaaggctg cctccgcttc    540 accgagttga ctcagtcgac aaccgaggca tcagaagtca tcgactcggt ggagatttca    600
ccggacgacg tggtggcact accttactcc tctggcacga cgggattacc aaaaggagtg    660
atgctgactc acaagggact agtcacgagc gttgctcagc aagtcgacgg cgagaacccg    720
aatctttatt tccacagcga tgacgtcata ctctgtgttt tgcccatgtt tcatatctac    780
gctttgaact cgatcatgtt gtgtggtctt agagttggtg cggcgattct gataatgccg    840
aagtttgaga tcaatctgct attggagctg atccagaggt gtaaagtgac ggtggctccg    900
atggttccgc cgattgtgtt ggccattgcg aagtcttcgg agacggagaa gtatgatttg    960
agctcgataa gagtggtgaa atctggtgct gctcctcttg gtaaagaact tgaagatgcc   1020
gttaatgcca gtttcctaa tgccaaactc ggtcagggat acggaatgac ggaagcaggt   1080
ccagtgctcg caatgtcgtt aggttttgca aaggaacctt ttccggttaa gtcaggagct   1140
tgtggtactg ttgtaagaaa tgctgagatg aaaatagttg atccagacac cggagattct   1200
ctttcgagga atcaacccgg tgagatttgt attcgtggtc accagatcat gaaaggttac   1260
ctcaacaatc cggcagctac agcagagacc attgataaag acggttggct tcatactgga   1320
gatattggat tgatcgatga cgatgacgag cttttcatcg ttgatcgatt gaaagaactt   1380
atcaagtata aaggttttca ggtagctccg gctgagctag aggctttgct catcggtcat   1440
cctgacatta ctgatgttgc tgttgtcgca atgaaagaag aagcagctgg tgaagttcct   1500
gttgcatttg tggtgaaatc gaaggattcg gagttatcag aagatgatgt gaagcaattc   1560
gtgtcgaaac aggttgtgtt ttacaagaga atcaacaaag tgttcttcac tgaatccatt   1620
cctaaagctc catcagggaa gatattgagg aaagatctga gggcaaaact agcaaatgga   1680
ttgtga                                                             1686
```

<210> SEQ ID NO 31
<211> LENGTH: 561
<212> TYPE: PRT
<213> ORGANISM: Arabidopsis thaliana

<400> SEQUENCE: 31

```
Met Ala Pro Gln Glu Gln Ala Val Ser Gln Val Met Glu Lys Gln Ser
1               5                   10                  15
Asn Asn Asn Asn Ser Asp Val Ile Phe Arg Ser Lys Leu Pro Asp Ile
            20                  25                  30
Tyr Ile Pro Asn His Leu Ser Leu His Asp Tyr Ile Phe Gln Asn Ile
        35                  40                  45
Ser Glu Phe Ala Thr Lys Pro Cys Leu Ile Asn Gly Pro Thr Gly His
    50                  55                  60
Val Tyr Thr Tyr Ser Asp Val His Val Ile Ser Arg Gln Ile Ala Ala
65                  70                  75                  80
Asn Phe His Lys Leu Gly Val Asn Gln Asn Asp Val Val Met Leu Leu
                85                  90                  95
Leu Pro Asn Cys Pro Glu Phe Val Leu Ser Phe Leu Ala Ala Ser Phe
            100                 105                 110
Arg Gly Ala Thr Ala Thr Ala Ala Asn Pro Phe Phe Thr Pro Ala Glu
        115                 120                 125
Ile Ala Lys Gln Ala Lys Ala Ser Asn Thr Lys Leu Ile Ile Thr Glu
    130                 135                 140
Ala Arg Tyr Val Asp Lys Ile Lys Pro Leu Gln Asn Asp Asp Gly Val
145                 150                 155                 160
Val Ile Val Cys Ile Asp Asp Asn Glu Ser Val Pro Ile Pro Glu Gly
                165                 170                 175
Cys Leu Arg Phe Thr Glu Leu Thr Gln Ser Thr Thr Glu Ala Ser Glu
            180                 185                 190
Val Ile Asp Ser Val Glu Ile Ser Pro Asp Asp Val Val Ala Leu Pro
        195                 200                 205
Tyr Ser Ser Gly Thr Thr Gly Leu Pro Lys Gly Val Met Leu Thr His
    210                 215                 220
Lys Gly Leu Val Thr Ser Val Ala Gln Gln Val Asp Gly Glu Asn Pro
225                 230                 235                 240
Asn Leu Tyr Phe His Ser Asp Asp Val Ile Leu Cys Val Leu Pro Met
                245                 250                 255
Phe His Ile Tyr Ala Leu Asn Ser Ile Met Leu Cys Gly Leu Arg Val
            260                 265                 270
Gly Ala Ala Ile Leu Ile Met Pro Lys Phe Glu Ile Asn Leu Leu Leu
        275                 280                 285
Glu Leu Ile Gln Arg Cys Lys Val Thr Val Ala Pro Met Val Pro Pro
    290                 295                 300
Ile Val Leu Ala Ile Ala Lys Ser Ser Glu Thr Glu Lys Tyr Asp Leu
305                 310                 315                 320
Ser Ser Ile Arg Val Val Lys Ser Gly Ala Ala Pro Leu Gly Lys Glu
                325                 330                 335
Leu Glu Asp Ala Val Asn Ala Lys Phe Pro Asn Ala Lys Leu Gly Gln
            340                 345                 350
Gly Tyr Gly Met Thr Glu Ala Gly Pro Val Leu Ala Met Ser Leu Gly
        355                 360                 365
Phe Ala Lys Glu Pro Phe Pro Val Lys Ser Gly Ala Cys Gly Thr Val
```

```
                370               375                 380
Val Arg Asn Ala Glu Met Lys Ile Val Asp Pro Asp Thr Gly Asp Ser
385                 390                 395                 400

Leu Ser Arg Asn Gln Pro Gly Glu Ile Cys Ile Arg Gly His Gln Ile
            405                 410                 415

Met Lys Gly Tyr Leu Asn Asn Pro Ala Ala Thr Ala Glu Thr Ile Asp
        420                 425                 430

Lys Asp Gly Trp Leu His Thr Gly Asp Ile Gly Leu Ile Asp Asp Asp
        435                 440                 445

Asp Glu Leu Phe Ile Val Asp Arg Leu Lys Glu Leu Ile Lys Tyr Lys
        450                 455                 460

Gly Phe Gln Val Ala Pro Ala Glu Leu Glu Ala Leu Leu Ile Gly His
465                 470                 475                 480

Pro Asp Ile Thr Asp Val Ala Val Val Ala Met Lys Glu Glu Ala Ala
            485                 490                 495

Gly Glu Val Pro Val Ala Phe Val Val Lys Ser Lys Asp Ser Glu Leu
            500                 505                 510

Ser Glu Asp Asp Val Lys Gln Phe Val Ser Lys Gln Val Val Phe Tyr
        515                 520                 525

Lys Arg Ile Asn Lys Val Phe Phe Thr Glu Ser Ile Pro Lys Ala Pro
        530                 535                 540

Ser Gly Lys Ile Leu Arg Lys Asp Leu Arg Ala Lys Leu Ala Asn Gly
545                 550                 555                 560

Leu

<210> SEQ ID NO 32
<211> LENGTH: 1635
<212> TYPE: DNA
<213> ORGANISM: Petroselinum crispum

<400> SEQUENCE: 32
atgggagact gtgtagcacc caaagaagac cttattttcc gatcgaaact ccctgatatt      60
tacatcccga acaccttcc gttacatact tattgtttcg aaaacatctc gaaagttggc      120
gacaagtcct gtttaataaa tggcgctaca ggcgaaacgt tcacttattc ccaagttgag      180
ctcctttcca ggaaagttgc atcagggtta acaaactcg gcattcaaca gggcgatacc      240
atcatgcttt tgctccctaa ctcccctgag tattttttcg ctttcttagg cgcatcgtat      300
cgtggtgcaa tttctactat ggccaatccg ttttthcactt ctgctgaggt gatcaaacag      360
ctcaaagcat cccaagctaa gctcataatt acgcaagctt gttacgtaga caaagtgaaa      420
gactacgcag cagagaaaaa tatacagatc atttgcatcg atgatgctcc tcaggattgt      480
ttacatttct ccaaactat ggaagctgat gaatcagaaa tgcctgaggt tgtgatcaat      540
tcagacgatg tcgtcgcgtt accttactca tcgggtacta caggactacc gaaaggtgtt      600
atgttgacac acaaaggact tgttactagc gtggcacaac aagttgatgg agacaatccg      660
aatttatata tgcatagcga ggatgtgatg atctgcatat tgcctttgtt tcatatttat      720
tcgcttaacg cggtgttgtg ctgtggactc agagcagggg tgacgatctt gattatgcag      780
aaatttgata ttgtgccatt tttggaactg atacagaaat ataaagttac aattggaccg      840
tttgtgccac caattgtgtt ggcaattgcg aaaagtccag tggtggataa atatgacttg      900
tcgtcggtga ggacggttat gtctggagct gctccgttag gaaggagct tgaagatgct      960 gttagagcta agtttcctaa tgccaaactt ggtcagggat atggaatgac agaggcaggg     1020
```

```
ccagttttag caatgtgcct ggcgtttgca aaggaaccat acgagatcaa atcgggtgcc   1080
tgtggaactg ttgtgaggaa tgctgaaatg aaaattgtgg atcctgagac caacgcctct   1140
cttccacgaa accaacgcgg agagatttgc attcgaggtg accaaattat gaaaggctac   1200
ctcaatgatc ctgaatcaac aaggacaaca atagacgaag aaggctggtt gcacacagga   1260
gatataggct tcattgacga cgatgatgag ctatttattg ttgatagact taaggaaata   1320
atcaaataca aaggcttcca ggttgcccct gctgaacttg aagctctgct acttactcat   1380
cctaccattt ccgatgctgc agttgttccc atgatagatg agaaagcagg agaggtgcct   1440
gtggcttttg ttgtgagaac aaacggtttc accaccactg aggaagaaat caagcaattc   1500
gtctcgaaac aggtggtgtt ctacaagaga atatttcgtg tatttttttgt tgatgcaatt   1560 ccgaaatcac catctggaaa gattcttcga aaggacttga gagcaaaaat agcatccggt   1620
gatcttccca aataa                                                   1635

<210> SEQ ID NO 33
<211> LENGTH: 544
<212> TYPE: PRT
<213> ORGANISM: Petroselinum crispum

<400> SEQUENCE: 33

Met Gly Asp Cys Val Ala Pro Lys Glu Asp Leu Ile Phe Arg Ser Lys
1               5                   10                  15

Leu Pro Asp Ile Tyr Ile Pro Lys His Leu Pro Leu His Thr Tyr Cys
            20                  25                  30

Phe Glu Asn Ile Ser Lys Val Gly Asp Lys Ser Cys Leu Ile Asn Gly
        35                  40                  45

Ala Thr Gly Glu Thr Phe Thr Tyr Ser Gln Val Glu Leu Leu Ser Arg
    50                  55                  60

Lys Val Ala Ser Gly Leu Asn Lys Leu Gly Ile Gln Gln Gly Asp Thr
65                  70                  75                  80

Ile Met Leu Leu Leu Pro Asn Ser Pro Glu Tyr Phe Phe Ala Phe Leu
                85                  90                  95

Gly Ala Ser Tyr Arg Gly Ala Ile Ser Thr Met Ala Asn Pro Phe Phe
            100                 105                 110

Thr Ser Ala Glu Val Ile Lys Gln Leu Lys Ala Ser Gln Ala Lys Leu
        115                 120                 125

Ile Ile Thr Gln Ala Cys Tyr Val Asp Lys Val Lys Asp Tyr Ala Ala
    130                 135                 140

Glu Lys Asn Ile Gln Ile Ile Cys Ile Asp Asp Ala Pro Gln Asp Cys
145                 150                 155                 160

Leu His Phe Ser Lys Leu Met Glu Ala Asp Glu Ser Glu Met Pro Glu
                165                 170                 175

Val Val Ile Asn Ser Asp Asp Val Val Ala Leu Pro Tyr Ser Ser Gly
            180                 185                 190

Thr Thr Gly Leu Pro Lys Gly Val Met Leu Thr His Lys Gly Leu Val
        195                 200                 205

Thr Ser Val Ala Gln Gln Val Asp Gly Asp Asn Pro Asn Leu Tyr Met
    210                 215                 220

His Ser Glu Asp Val Met Ile Cys Ile Leu Pro Leu Phe His Ile Tyr
225                 230                 235                 240

Ser Leu Asn Ala Val Leu Cys Cys Gly Leu Arg Ala Gly Val Thr Ile
                245                 250                 255

Leu Ile Met Gln Lys Phe Asp Ile Val Pro Phe Leu Glu Leu Ile Gln
```

260                 265                 270
Lys Tyr Lys Val Thr Ile Gly Pro Phe Val Pro Ile Val Leu Ala
            275                 280                 285
Ile Ala Lys Ser Pro Val Val Asp Lys Tyr Asp Leu Ser Ser Val Arg
    290                 295                 300
Thr Val Met Ser Gly Ala Ala Pro Leu Gly Lys Glu Leu Glu Asp Ala
305                 310                 315                 320
Val Arg Ala Lys Phe Pro Asn Ala Lys Leu Gly Gln Gly Tyr Gly Met
                325                 330                 335
Thr Glu Ala Gly Pro Val Leu Ala Met Cys Leu Ala Phe Ala Lys Glu
            340                 345                 350
Pro Tyr Glu Ile Lys Ser Gly Ala Cys Gly Thr Val Val Arg Asn Ala
        355                 360                 365
Glu Met Lys Ile Val Asp Pro Glu Thr Asn Ala Ser Leu Pro Arg Asn
370                 375                 380
Gln Arg Gly Glu Ile Cys Ile Arg Gly Asp Gln Ile Met Lys Gly Tyr
385                 390                 395                 400
Leu Asn Asp Pro Glu Ser Thr Arg Thr Thr Ile Asp Glu Glu Gly Trp
                405                 410                 415
Leu His Thr Gly Asp Ile Gly Phe Ile Asp Asp Asp Glu Leu Phe
            420                 425                 430
Ile Val Asp Arg Leu Lys Glu Ile Ile Lys Tyr Lys Gly Phe Gln Val
        435                 440                 445
Ala Pro Ala Glu Leu Glu Ala Leu Leu Leu Thr His Pro Thr Ile Ser
    450                 455                 460
Asp Ala Ala Val Val Pro Met Ile Asp Glu Lys Ala Gly Glu Val Pro
465                 470                 475                 480
Val Ala Phe Val Val Arg Thr Asn Gly Phe Thr Thr Glu Glu Glu
                485                 490                 495
Ile Lys Gln Phe Val Ser Lys Gln Val Val Phe Tyr Lys Arg Ile Phe
            500                 505                 510
Arg Val Phe Phe Val Asp Ala Ile Pro Lys Ser Pro Ser Gly Lys Ile
        515                 520                 525
Leu Arg Lys Asp Leu Arg Ala Arg Ile Ala Ser Gly Asp Leu Pro Lys
    530                 535                 540

<210> SEQ ID NO 34
<211> LENGTH: 1710
<212> TYPE: DNA
<213> ORGANISM: Vitis vinifera

<400> SEQUENCE: 34
atgattagta ttgaaacgca aaacccggat gttagcaacc tggacacctc gcactctatt      60
ccgaaaatgg caaaccgtat tgatgaccat gtgtttcgtt ctaaactgcc ggaaattccg     120
atcagtaacc atctgccgct gcacacgtat tgcttcgaaa attactcgca gtttgcagac     180
cgtccgtgtc tgattgttgg ctcgacgaac aaaacctata gcttcgctga acccatctg     240 atctctcgca aagtgggcgc aggttttgct cacctgggtc tgaaacaggg cgatgtggtt     300
atgattctgc tgcaaaattg cgcggaattt gccttcagct ttctgggtgc gtctatggtt     360
ggcgccgtca ccacgaccgc aaacccgttc tacacgtccg cggaaatctt caaacagctg     420
aacgcatcaa aagctaaaat cgtcgtgacc caggcgcaat atgtggataa actgcgcgac     480
tacccggatg gtcaagttgc caaaattggc gaaggtttca cggtcattac catcgatgac     540

```
ccgccggaaa actgtatgca ttttagtgtt gtctccgaag cgaacgaaag cgaactgccg      600
gaagtctcaa ttaattcgga tgacccggtg gccctgccgt ttagctctgg tacgaccggc      660
ctgccgaaag gcgtggttct gacgcacaaa tcactgatca cctcggtcgc ccagcaagtg      720
gatggtgaaa acccgaatct gcatctgacc ccggatgacg tcgtgctgtg cgtgctgccg      780
ctgttccaca tttatagcct gaactctgtt ctgctgtgta gtctgcgtgc aggtgcagca      840
gtgctgctga tgcagaaatt tgaaattggt accctgctgg aactgatcca acgttaccgc      900
gtgagcgttg cagctgttgt cccgccgctg gttctggcac tggctaaaaa tccgatggtg      960
gaatcgtttg atctgagttc catccgtgtg gttctgagcg gtgcagcacc gctgggcaaa     1020
gaactggaag cagctctgcg ttcccgcgtt ccgcaggcag tcctgggcca aggttatggc     1080
atgacggaag caggcccggt gctgtcaatg tgcctgggtt tcgctaaaca gccgtttccg     1140
acgaaatcag gttcgtgtgg caccgtcgtg cgtaacgcgg aactgaaagt tgtggatccg     1200
gaaaccggtt gctccctggg ccgtaatcag ccgggtgaaa tttgtatccg cggccagcaa     1260
attatgaaag gttatctgaa tgatccggaa gcgacggcct ctaccattga cgttgatggc     1320
tggctgcata ccggtgacat cggctacgtg gatgacgatg aagaagtgtt cattgttgat     1380
cgcgtcaaag aactgatcaa attcaaaggt tttcaggttc cgccggcaga actggaagct     1440
ctgctggtgt ctcacccgtc cattgccgat gcggccgtgg ttccgcaaaa agacgatgtt     1500
gctggcgaag tcccggtggc gttcgtcgtg cgttctaacg gttttgaact gaccgaagaa     1560
gcagtgaaag aattcatcag taaacaggtt gtctttttata aacgcctgca taaagtgtac     1620
tttgttcacg cgattccgaa aagcccgtct ggcaaaatcc tgcgtaaaga tctgcgcgcg     1680
aaactggccg aaaaaacccc ggaaccgaac                                      1710
```

<210> SEQ ID NO 35
<211> LENGTH: 570
<212> TYPE: PRT
<213> ORGANISM: Vitis vinifera

<400> SEQUENCE: 35

```
Met Ile Ser Ile Glu Thr Gln Asn Pro Asp Val Ser Asn Leu Asp Thr
1               5                   10                  15

Ser His Ser Ile Pro Lys Met Ala Asn Arg Ile Asp Asp His Val Phe
            20                  25                  30

Arg Ser Lys Leu Pro Glu Ile Pro Ile Ser Asn His Leu Pro Leu His
        35                  40                  45

Thr Tyr Cys Phe Glu Asn Tyr Ser Gln Phe Ala Asp Arg Pro Cys Leu
    50                  55                  60

Ile Val Gly Ser Thr Asn Lys Thr Tyr Ser Phe Ala Glu Thr His Leu
65                  70                  75                  80

Ile Ser Arg Lys Val Gly Ala Gly Phe Ala His Leu Gly Leu Lys Gln
                85                  90                  95

Gly Asp Val Val Met Ile Leu Leu Gln Asn Cys Ala Glu Phe Ala Phe
            100                 105                 110

Ser Phe Leu Gly Ala Ser Met Val Gly Ala Val Thr Thr Thr Ala Asn
        115                 120                 125

Pro Phe Tyr Thr Ser Ala Glu Ile Phe Lys Gln Leu Asn Ala Ser Lys
    130                 135                 140

Ala Lys Ile Val Val Thr Gln Ala Gln Tyr Val Asp Lys Leu Arg Asp
145                 150                 155                 160

Tyr Pro Asp Gly Gln Val Ala Lys Ile Gly Glu Gly Phe Thr Val Ile
```

```
            165                 170                 175
Thr Ile Asp Asp Pro Glu Asn Cys Met His Phe Ser Val Val Ser
            180                 185                 190

Glu Ala Asn Glu Ser Glu Leu Pro Glu Val Ser Ile Asn Ser Asp Asp
            195                 200                 205

Pro Val Ala Leu Pro Phe Ser Ser Gly Thr Thr Gly Leu Pro Lys Gly
            210                 215                 220

Val Val Leu Thr His Lys Ser Leu Ile Thr Ser Val Ala Gln Gln Val
225                 230                 235                 240

Asp Gly Glu Asn Pro Asn Leu His Leu Thr Pro Asp Asp Val Val Leu
            245                 250                 255

Cys Val Leu Pro Leu Phe His Ile Tyr Ser Leu Asn Ser Val Leu Leu
            260                 265                 270

Cys Ser Leu Arg Ala Gly Ala Ala Val Leu Leu Met Gln Lys Phe Glu
            275                 280                 285

Ile Gly Thr Leu Leu Glu Leu Ile Gln Arg Tyr Arg Val Ser Val Ala
            290                 295                 300

Ala Val Val Pro Pro Leu Val Leu Ala Leu Ala Lys Asn Pro Met Val
305                 310                 315                 320

Glu Ser Phe Asp Leu Ser Ser Ile Arg Val Val Leu Ser Gly Ala Ala
            325                 330                 335

Pro Leu Gly Lys Glu Leu Glu Ala Ala Leu Arg Ser Arg Val Pro Gln
            340                 345                 350

Ala Val Leu Gly Gln Gly Tyr Gly Met Thr Glu Ala Gly Pro Val Leu
            355                 360                 365

Ser Met Cys Leu Gly Phe Ala Lys Gln Pro Phe Pro Thr Lys Ser Gly
            370                 375                 380

Ser Cys Gly Thr Val Val Arg Asn Ala Glu Leu Lys Val Val Asp Pro
385                 390                 395                 400

Glu Thr Gly Cys Ser Leu Gly Arg Asn Gln Pro Gly Glu Ile Cys Ile
            405                 410                 415

Arg Gly Gln Gln Ile Met Lys Gly Tyr Leu Asn Asp Pro Glu Ala Thr
            420                 425                 430

Ala Ser Thr Ile Asp Val Asp Gly Trp Leu His Thr Gly Asp Ile Gly
            435                 440                 445

Tyr Val Asp Asp Asp Glu Glu Val Phe Ile Val Asp Arg Val Lys Glu
            450                 455                 460

Leu Ile Lys Phe Lys Gly Phe Gln Val Pro Pro Ala Glu Leu Glu Ala
465                 470                 475                 480

Leu Leu Val Ser His Pro Ser Ile Ala Asp Ala Ala Val Val Pro Gln
            485                 490                 495

Lys Asp Asp Val Ala Gly Glu Val Pro Val Ala Phe Val Val Arg Ser
            500                 505                 510

Asn Gly Phe Glu Leu Thr Glu Glu Ala Val Lys Glu Phe Ile Ser Lys
            515                 520                 525

Gln Val Val Phe Tyr Lys Arg Leu His Lys Val Tyr Phe Val His Ala
            530                 535                 540

Ile Pro Lys Ser Pro Ser Gly Lys Ile Leu Arg Lys Asp Leu Arg Ala
545                 550                 555                 560

Lys Leu Ala Glu Lys Thr Pro Glu Pro Asn
            565                 570

<210> SEQ ID NO 36
```

```
<211> LENGTH: 1170
<212> TYPE: DNA
<213> ORGANISM: Petunia x hybrida

<400> SEQUENCE: 36
atggtgacag tcgaggagta tcgtaaggca caacgtgctg aaggtccagc cactgtcatg      60
gccattggaa cagccacacc ttcaaactgt gttgatcaaa gcacttaccc tgattttttat    120
tttcgtatca ctaacagtga gcacaagact gatcttaagg agaaatttaa gcgcatgtgt    180
gaaaaatcaa tgattaagaa aggtacatg cacttaacag aggaaatctt gaaagagaat     240
cctagtatgt gtgaatacat ggcaccttct cttgatgcta ggcaagacat agtggtggtt    300
gaagtgccca acttggcaa agaggcagct caaaaggcca tcaaggaatg gggccagccc     360
aagtccaaaa ttacccattt ggtcttttgc acaaccagtg gtgtggacat gcctgggtgt    420
gactatcaac tcactaagct acttgggctt cgtccatcgg tcaagaggct tatgatgtac    480
caacaaggtt gctttgctgg tggcacggtt cttcggttag ccaaggactt ggctgaaaac    540
aacaagggcg ctcgagtcct tgttgttgt tcagaaatca ccgcggtcac tttccgtggg     600
ccaaatgata ctcatttgga tagtttagtt ggccaagcac ttttggtga tggggcaggc     660
gcgatcatta taggttctga tccaattcca ggggtcgaaa ggccttttgtt cgagctcgtt   720
tcagcagccc aaactcttct cccagatagc catggtgcta tgatggcca tctccgtgaa    780
gttgggctta cattccactt actcaaagat gttcctgggc tgatctcaaa aaatattgag   840
aagagccttg aggaagcatt caaacctttg gcatttctg attggaactc tctattctgg    900
attgctcatc caggtgggcc tgcaattttg gaccaagttg aaataaagtt gggcctaaag  960
cccgagaaac ttaaggctac aaggaatgtg ttaagtaact atggtaacat gtcaagtgct   1020
tgtgtactgt ttattttgga tgaaatgaga aaggcctcag ccaagaagg tttaggaact   1080
actggtgaag gcttgagtg gggtgttctt tttggatttg ggctgggct aacagttgag    1140
actgttgtcc tccacagtgt tgctacttaa                                      1170

<210> SEQ ID NO 37
<211> LENGTH: 389
<212> TYPE: PRT
<213> ORGANISM: Petunia x hybrida

<400> SEQUENCE: 37

Met Val Thr Val Glu Glu Tyr Arg Lys Ala Gln Arg Ala Glu Gly Pro
1               5                   10                  15

Ala Thr Val Met Ala Ile Gly Thr Ala Thr Pro Ser Asn Cys Val Asp
            20                  25                  30

Gln Ser Thr Tyr Pro Asp Phe Tyr Phe Arg Ile Thr Asn Ser Glu His
        35                  40                  45

Lys Thr Asp Leu Lys Glu Lys Phe Lys Arg Met Cys Glu Lys Ser Met
    50                  55                  60

Ile Lys Lys Arg Tyr Met His Leu Thr Glu Glu Ile Leu Lys Glu Asn
65                  70                  75                  80

Pro Ser Met Cys Glu Tyr Met Ala Pro Ser Leu Asp Ala Arg Gln Asp
                85                  90                  95

Ile Val Val Glu Val Pro Lys Leu Gly Lys Glu Ala Ala Gln Lys
            100                 105                 110

Ala Ile Lys Glu Trp Gly Gln Pro Lys Ser Lys Ile Thr His Leu Val
        115                 120                 125

Phe Cys Thr Thr Ser Gly Val Asp Met Pro Gly Cys Asp Tyr Gln Leu
```

```
                130                 135                 140
Thr Lys Leu Leu Gly Leu Arg Pro Ser Val Lys Arg Leu Met Met Tyr
145                 150                 155                 160

Gln Gln Gly Cys Phe Ala Gly Thr Val Leu Arg Leu Ala Lys Asp
                165                 170                 175

Leu Ala Glu Asn Asn Lys Gly Ala Arg Val Leu Val Val Cys Ser Glu
                180                 185                 190

Ile Thr Ala Val Thr Phe Arg Gly Pro Asn Asp Thr His Leu Asp Ser
                195                 200                 205

Leu Val Gly Gln Ala Leu Phe Gly Asp Gly Ala Gly Ala Ile Ile Ile
                210                 215                 220

Gly Ser Asp Pro Ile Pro Gly Val Glu Arg Pro Leu Phe Glu Leu Val
225                 230                 235                 240

Ser Ala Ala Gln Thr Leu Leu Pro Asp Ser His Gly Ala Ile Asp Gly
                245                 250                 255

His Leu Arg Glu Val Gly Leu Thr Phe His Leu Leu Lys Asp Val Pro
                260                 265                 270

Gly Leu Ile Ser Lys Asn Ile Glu Lys Ser Leu Glu Glu Ala Phe Lys
                275                 280                 285

Pro Leu Gly Ile Ser Asp Trp Asn Ser Leu Phe Trp Ile Ala His Pro
                290                 295                 300

Gly Gly Pro Ala Ile Leu Asp Gln Val Glu Ile Lys Leu Gly Leu Lys
305                 310                 315                 320

Pro Glu Lys Leu Lys Ala Thr Arg Asn Val Leu Ser Asn Tyr Gly Asn
                325                 330                 335

Met Ser Ser Ala Cys Val Leu Phe Ile Leu Asp Glu Met Arg Lys Ala
                340                 345                 350

Ser Ala Lys Glu Gly Leu Gly Thr Thr Gly Glu Gly Leu Glu Trp Gly
                355                 360                 365

Val Leu Phe Gly Phe Gly Pro Gly Leu Thr Val Glu Thr Val Val Leu
                370                 375                 380

His Ser Val Ala Thr
385

<210> SEQ ID NO 38
<211> LENGTH: 1254
<212> TYPE: DNA
<213> ORGANISM: Citrus maxima

<400> SEQUENCE: 38
atggctacgg tccaagaaat ccgcaacgct caacgcgcag atggtccggc gacggtcctg      60
gcaatcggca cggcaacccc ggctcatagc gtgaaccagg cagattatcc ggactattac     120
tttcgtatta ccaaatctga acacatgacg gaactgaaag aaaaattcaa acgtatgtgc     180
gataaaagta tgattaaaaa acgctacatg tacctgaccg aagaaatcct gaaagaaaac     240
ccgaatatgt gtgcctacat ggcaccgagc ctggatcgcg ccaggacat tgtggttgtc     300 gaagttccga aactgggtaa agaagcggcc accaaagcca tcaaagaatg gggccaaccg     360
aaatcaaaaa ttacgcacct gatcttttgc accacgtcgg tgtggatat gccgggtgca     420 gactatcagc tgaccaaaact gctgggtctg cgtccgagcg ttaaacgctt tatgatgtac     480
cagcaaggct gcttcgcagg cggtacggtc ctgcgtctgg ctaaagatct ggcggaaaac     540
aataaaggtg ctcgcgttct ggtggttttgt agtgaaatta ccgctgtcac gtttcgtggt     600
ccggcggata cccatctgga ctccctggtt ggccaggccc tgttcggcga tggtgcagct     660
```

```
gcggttatcg tcggcgcaga tccggacacg agtgtggaac gtccgctgta tcagctggtt    720
tcaacctcgc aaacgattct gccggattcc gacggtgcga tcgatggcca tctgcgcgaa    780
gtgggtctga cctttcacct gctgaaagac gttccgggcc tgatttcaaa aaacatcgaa    840
aaaagcctgt ctgaagcctt tgcaccggtt ggtatttcgg attggagctc tattttctgg    900
atcgcacatc cgggcggtcc ggcaatcctg gaccaggtgg aaagcaaact gggtctgaaa    960
gaagaaaaac tgaaagctac ccgtcaagtc ctgtctgaat acggcaatat gagttccgcg   1020
tgtgtgctgt tcattctgga tgaaatgcgc aaaaaatctg ccgaagaagc taaagcgacc   1080
acgggcgaag tctggattg ggcgtgctg tttggtttcg gtccgggtct gaccgtcgaa     1140
acggtcgtgc tgcacagtgt gccgatcaaa gcgggcggtg gcggttccgg cggtggtggt   1200
agtggtggtg gtggctctcc gccgccggcc ctgccgccga aacgtcgtcg ctaa         1254
```

<210> SEQ ID NO 39
<211> LENGTH: 417
<212> TYPE: PRT
<213> ORGANISM: Citrus maxima

<400> SEQUENCE: 39

```
Met Ala Thr Val Gln Glu Ile Arg Asn Ala Gln Arg Ala Asp Gly Pro
1               5                   10                  15

Ala Thr Val Leu Ala Ile Gly Thr Ala Thr Pro Ala His Ser Val Asn
            20                  25                  30

Gln Ala Asp Tyr Pro Asp Tyr Tyr Phe Arg Ile Thr Lys Ser Glu His
        35                  40                  45

Met Thr Glu Leu Lys Glu Lys Phe Lys Arg Met Cys Asp Lys Ser Met
    50                  55                  60

Ile Lys Lys Arg Tyr Met Tyr Leu Thr Glu Glu Ile Leu Lys Glu Asn
65                  70                  75                  80

Pro Asn Met Cys Ala Tyr Met Ala Pro Ser Leu Asp Ala Arg Gln Asp
                85                  90                  95

Ile Val Val Val Glu Val Pro Lys Leu Gly Lys Glu Ala Ala Thr Lys
            100                 105                 110

Ala Ile Lys Glu Trp Gly Gln Pro Lys Ser Lys Ile Thr His Leu Ile
        115                 120                 125

Phe Cys Thr Thr Ser Gly Val Asp Met Pro Gly Ala Asp Tyr Gln Leu
    130                 135                 140

Thr Lys Leu Leu Gly Leu Arg Pro Ser Val Lys Arg Phe Met Met Tyr
145                 150                 155                 160

Gln Gln Gly Cys Phe Ala Gly Gly Thr Val Leu Arg Leu Ala Lys Asp
                165                 170                 175

Leu Ala Glu Asn Asn Lys Gly Ala Arg Val Leu Val Val Cys Ser Glu
            180                 185                 190

Ile Thr Ala Val Thr Phe Arg Gly Pro Ala Asp Thr His Leu Asp Ser
        195                 200                 205

Leu Val Gly Gln Ala Leu Phe Gly Asp Gly Ala Ala Ala Val Ile Val
    210                 215                 220

Gly Ala Asp Pro Asp Thr Ser Val Glu Arg Pro Leu Tyr Gln Leu Val
225                 230                 235                 240

Ser Thr Ser Gln Thr Ile Leu Pro Asp Ser Asp Gly Ala Ile Asp Gly
                245                 250                 255

His Leu Arg Glu Val Gly Leu Thr Phe His Leu Leu Lys Asp Val Pro
            260                 265                 270
```

Gly Leu Ile Ser Lys Asn Ile Glu Lys Ser Leu Ser Glu Ala Phe Ala
            275                 280                 285

Pro Val Gly Ile Ser Asp Trp Ser Ser Ile Phe Trp Ile Ala His Pro
        290                 295                 300

Gly Gly Pro Ala Ile Leu Asp Gln Val Glu Ser Lys Leu Gly Leu Lys
305                 310                 315                 320

Glu Glu Lys Leu Lys Ala Thr Arg Gln Val Leu Ser Glu Tyr Gly Asn
                325                 330                 335

Met Ser Ser Ala Cys Val Leu Phe Ile Leu Asp Glu Met Arg Lys Lys
            340                 345                 350

Ser Ala Glu Glu Ala Lys Ala Thr Thr Gly Gly Leu Asp Trp Gly
        355                 360                 365

Val Leu Phe Gly Phe Gly Pro Gly Leu Thr Val Glu Thr Val Val Leu
    370                 375                 380

His Ser Val Pro Ile Lys Ala Gly Gly Gly Ser Gly Gly Gly Gly
385                 390                 395                 400

Ser Gly Gly Gly Gly Ser Pro Pro Pro Ala Leu Pro Pro Lys Arg Arg
                405                 410                 415

Arg

<210> SEQ ID NO 40
<211> LENGTH: 735
<212> TYPE: DNA
<213> ORGANISM: Citrus maxima

<400> SEQUENCE: 40
atgaatccgt cgccgtctgt taccgaactg caagtggaaa atgtcacctt tacgccgagt     60
ctgcaaccgc cgggctctac caaatcgcat tttctgggcg gtgcaggtga acgtggcctg    120
gaaatcgaag gcaaatttgt taaattcacc gctattggtg tctatctgga gaaaacgcc    180 gtgccgctgc tggcaggcaa atggaaaggc aaaaccgccg gtgaactgac ggaatctgtc    240 gaattttcc gcgatgtggt taccggcccg tttgaaaaat tcatgaaagt gaccatgatc    300
ctgccgctga cgggtgcgca gtattcagaa aaagttgctg aaaattgcat ggcgatttgg    360 aaattttcg gcatctacac cgatgcagaa gctaaagcga ttgaaaaatt tacggaagtg    420
ttcaaagacg aaatttttcc gccgggcagc tctatcctgt tcacccaaag ttccggttcg    480
ctgacgattt cattttcgaa agatggcagc atcccgaaag acggtgtcgc ggtgattgaa    540
aacaatctgc tgagcgaagc cgttctggaa tctatgatcg gtaaaaacgg cgtcagtccg    600
gcggccaaaa atccctggcc gaacgtctg tcagcactgc tgaatgttgc ttccgacaaa    660
atgaaaggcg gtggcggctc aggtggcggt ggctctggtg gcggtggttc aggcgtcaaa    720
gaaagtctgg tgtga                                                    735

<210> SEQ ID NO 41
<211> LENGTH: 244
<212> TYPE: PRT
<213> ORGANISM: Citrus maxima

<400> SEQUENCE: 41

Met Asn Pro Ser Pro Ser Val Thr Glu Leu Gln Val Glu Asn Val Thr
1                 5                  10                  15

Phe Thr Pro Ser Leu Gln Pro Pro Gly Ser Thr Lys Ser His Phe Leu
            20                  25                  30

Gly Gly Ala Gly Glu Arg Gly Leu Glu Ile Glu Gly Lys Phe Val Lys

```
                 35                  40                  45
Phe Thr Ala Ile Gly Val Tyr Leu Glu Glu Asn Ala Val Pro Leu Leu
 50                  55                  60

Ala Gly Lys Trp Lys Gly Lys Thr Ala Gly Glu Leu Thr Glu Ser Val
 65                  70                  75                  80

Glu Phe Phe Arg Asp Val Val Thr Gly Pro Phe Glu Lys Phe Met Lys
                 85                  90                  95

Val Thr Met Ile Leu Pro Leu Thr Gly Ala Gln Tyr Ser Glu Lys Val
                100                 105                 110

Ala Glu Asn Cys Met Ala Ile Trp Lys Phe Phe Gly Ile Tyr Thr Asp
            115                 120                 125

Ala Glu Ala Lys Ala Ile Glu Lys Phe Thr Glu Val Phe Lys Asp Glu
        130                 135                 140

Ile Phe Pro Pro Gly Ser Ser Ile Leu Phe Thr Gln Ser Ser Gly Ser
145                 150                 155                 160

Leu Thr Ile Ser Phe Ser Lys Asp Gly Ser Ile Pro Lys Asp Gly Val
                165                 170                 175

Ala Val Ile Glu Asn Asn Leu Leu Ser Glu Ala Val Leu Glu Ser Met
            180                 185                 190

Ile Gly Lys Asn Gly Val Ser Pro Ala Ala Lys Lys Ser Leu Ala Glu
        195                 200                 205

Arg Leu Ser Ala Leu Leu Asn Val Ala Ser Asp Lys Met Lys Gly Gly
    210                 215                 220

Gly Gly Ser Gly Gly Gly Gly Ser Gly Gly Gly Gly Ser Gly Val Lys
225                 230                 235                 240

Glu Ser Leu Val

<210> SEQ ID NO 42
<211> LENGTH: 669
<212> TYPE: DNA
<213> ORGANISM: Medicago sativa

<400> SEQUENCE: 42
atggctgcat caatcaccgc aatcactgtg gagaaccttg aatacccagc ggtggttacc      60
tctccggtca ccggcaaatc atatttcctc ggtggcgctg gggagagagg attgaccatt     120
gaaggaaact tcatcaagtt cactgccata ggtgtttatt tggaagatat agcagtggct     180
tcactagctg ccaaatggaa gggtaaatca tctgaagagt tacttgagac ccttgacttt     240
tacagagaca tcatctcagg tcccttgaa aagttaatta gagggtcaaa gattagggaa      300
ttgagtggtc ctgagtactc aaggaaggtt atggagaact gtgtggcaca cttgaaatca     360
gttggaactt atggagatgc agaagctgaa gctatgcaaa aatttgctga agctttcaag     420
cctgttaatt ttccacctgg tgcctctgtt ttctacaggc aatcacctaa tggaatatta     480
gggcttagtt tctctccgga tacaagtata ccagaaaagg aggctgcact catagagaac     540
aaggcagttt catcagcagt gttggagact atgatcggcg agcacgctgt tcccctgat      600 cttaagcgct gtttagctgc aagattacct gcgttgttga acgagggtgc tttcaagatt     660
ggaaactga                                                             669

<210> SEQ ID NO 43
<211> LENGTH: 222
<212> TYPE: PRT
<213> ORGANISM: Medicago sativa

<400> SEQUENCE: 43
```

```
Met Ala Ala Ser Ile Thr Ala Ile Thr Val Glu Asn Leu Glu Tyr Pro
1               5                   10                  15

Ala Val Val Thr Ser Pro Val Thr Gly Lys Ser Tyr Phe Leu Gly Gly
            20                  25                  30

Ala Gly Glu Arg Gly Leu Thr Ile Glu Gly Asn Phe Ile Lys Phe Thr
        35                  40                  45

Ala Ile Gly Val Tyr Leu Glu Asp Ile Ala Val Ala Ser Leu Ala Ala
    50                  55                  60

Lys Trp Lys Gly Lys Ser Ser Glu Glu Leu Leu Glu Thr Leu Asp Phe
65                  70                  75                  80

Tyr Arg Asp Ile Ile Ser Gly Pro Phe Glu Lys Leu Ile Arg Gly Ser
                85                  90                  95

Lys Ile Arg Glu Leu Ser Gly Pro Glu Tyr Ser Arg Lys Val Met Glu
            100                 105                 110

Asn Cys Val Ala His Leu Lys Ser Val Gly Thr Tyr Gly Asp Ala Glu
        115                 120                 125

Ala Glu Ala Met Gln Lys Phe Ala Glu Ala Phe Lys Pro Val Asn Phe
    130                 135                 140

Pro Pro Gly Ala Ser Val Phe Tyr Arg Gln Ser Pro Asn Gly Ile Leu
145                 150                 155                 160

Gly Leu Ser Phe Ser Pro Asp Thr Ser Ile Pro Glu Lys Glu Ala Ala
                165                 170                 175

Leu Ile Glu Asn Lys Ala Val Ser Ser Ala Val Leu Glu Thr Met Ile
            180                 185                 190

Gly Glu His Ala Val Ser Pro Asp Leu Lys Arg Cys Leu Ala Ala Arg
        195                 200                 205

Leu Pro Ala Leu Leu Asn Glu Gly Ala Phe Lys Ile Gly Asn
    210                 215                 220

<210> SEQ ID NO 44
<211> LENGTH: 1200
<212> TYPE: DNA
<213> ORGANISM: Camellia sinensis

<400> SEQUENCE: 44
atggcaccga ccaccaccct gaccgcactg gcagaagaaa aaagcctgca gcagaaattt       60
gttcgtgatg aagatgaacg tccgaaagtt gcctataatg tgtttagcaa tgaaatcccg      120
gttattagcc tggcaggtat tgatgaaatt gaaggtcgtc gtagcgaaat ttgccgtaaa      180
attgttgaag catgtgaagg ttggggtgtt tttcaggttg ttgatcatgg tgttgatgca      240
aatctgattg cagaaatgac ccgtctggca cgtgaatttt ttgcactgcc tccggaagaa      300
aaactgcgtt ttgatatgag cggtggtaaa aaaggtggtt ttattgttag cagccatctg      360
cagggtgaag cagttcagga ttggcgtgaa attgttacct atttcagcta tccgattcgt      420
gcacgtgatt atagccgttg gcctgataaa ccggaaggtt ggcgtgcagt taccgaaacc      480
tatagcgaaa aactgatgga tctggcatgt aaactgctgg aagttctgag cgaagcaatg      540
ggtctggaaa aagaggcact gaccaaagca tgtgttgata tggatcagaa agtggtgatc      600
aacttctatc gaaatgtcc gcagccggat ctgaccctgg tctgaaacg tcataccgat      660 ccgggtacaa ttaccctgct gctgcaagat caggtgggtg tctgcaggc aacccgtgat      720 ggtggcaaaa cctggattac cgttcagccg gttgaaggtg catttgttgt taatctgggt      780
gatcatggcc attatctgag caatggtcgc tttaaaaacg cagatcatca ggcagttgtt      840
```

-continued

```
aatagcaatt gtagccgtct gagcattgca acctttcaga atccggcacc ggaagcaacc    900
gtttatccgc tgaaaattcg tgaaggtgaa aaaccgattc tggaagaacc gattaccttt    960
gccgatatgt ataaacgcaa aatgagcaaa gatatcgagc tggccaaact gaaaaaactg   1020
gcgaaagaaa aaaaactgct gcaagaccag caggatatcg aaaaagcaaa actggaaatc   1080
aaaagcaccg atgaaatctt cgccctggtt ggtgcactga tgcatgttat gcagaaacgt   1140
agccgtgcaa ttcatagcag tgatgaaggt gaagatcaag ccggtgatga agatgaggat   1200
```

<210> SEQ ID NO 45
<211> LENGTH: 400
<212> TYPE: PRT
<213> ORGANISM: Camellia sinensis

<400> SEQUENCE: 45

```
Met Ala Pro Thr Thr Leu Thr Ala Leu Ala Glu Glu Lys Ser Leu
1               5                   10                  15

Gln Gln Lys Phe Val Arg Asp Glu Asp Glu Arg Pro Lys Val Ala Tyr
            20                  25                  30

Asn Val Phe Ser Asn Glu Ile Pro Val Ile Ser Leu Ala Gly Ile Asp
        35                  40                  45

Glu Ile Glu Gly Arg Arg Ser Glu Ile Cys Arg Lys Ile Val Glu Ala
    50                  55                  60

Cys Glu Gly Trp Gly Val Phe Gln Val Val Asp His Gly Val Asp Ala
65                  70                  75                  80

Asn Leu Ile Ala Glu Met Thr Arg Leu Ala Arg Glu Phe Phe Ala Leu
                85                  90                  95

Pro Pro Glu Glu Lys Leu Arg Phe Asp Met Ser Gly Gly Lys Lys Gly
            100                 105                 110

Gly Phe Ile Val Ser Ser His Leu Gln Gly Glu Ala Val Gln Asp Trp
        115                 120                 125

Arg Glu Ile Val Thr Tyr Phe Ser Tyr Pro Ile Arg Ala Arg Asp Tyr
    130                 135                 140

Ser Arg Trp Pro Asp Lys Pro Glu Gly Trp Arg Ala Val Thr Glu Thr
145                 150                 155                 160

Tyr Ser Glu Lys Leu Met Asp Leu Ala Cys Lys Leu Leu Glu Val Leu
                165                 170                 175

Ser Glu Ala Met Gly Leu Glu Lys Glu Ala Leu Thr Lys Ala Cys Val
            180                 185                 190

Asp Met Asp Gln Lys Val Val Ile Asn Phe Tyr Pro Lys Cys Pro Gln
        195                 200                 205

Pro Asp Leu Thr Leu Gly Leu Lys Arg His Thr Asp Pro Gly Thr Ile
    210                 215                 220

Thr Leu Leu Leu Gln Asp Gln Val Gly Gly Leu Gln Ala Thr Arg Asp
225                 230                 235                 240

Gly Gly Lys Thr Trp Ile Thr Val Gln Pro Val Glu Gly Ala Phe Val
                245                 250                 255

Val Asn Leu Gly Asp His Gly His Tyr Leu Ser Asn Gly Arg Phe Lys
            260                 265                 270

Asn Ala Asp His Gln Ala Val Val Asn Ser Asn Cys Ser Arg Leu Ser
        275                 280                 285

Ile Ala Thr Phe Gln Asn Pro Ala Pro Glu Ala Thr Val Tyr Pro Leu
    290                 295                 300

Lys Ile Arg Glu Gly Glu Lys Pro Ile Leu Glu Glu Pro Ile Thr Phe
305                 310                 315                 320
```

```
Ala Asp Met Tyr Lys Arg Lys Met Ser Lys Asp Ile Glu Leu Ala Lys
            325                 330                 335

Leu Lys Lys Leu Ala Lys Glu Lys Lys Leu Leu Gln Asp Gln Gln Asp
            340                 345                 350

Ile Glu Lys Ala Lys Leu Glu Ile Lys Ser Thr Asp Glu Ile Phe Ala
            355                 360                 365

Leu Val Gly Ala Leu Met His Val Met Gln Lys Arg Ser Arg Ala Ile
    370                 375                 380

His Ser Ser Asp Glu Gly Asp Gln Ala Gly Asp Glu Asp Glu Asp
385                 390                 395                 400

<210> SEQ ID NO 46
<211> LENGTH: 1191
<212> TYPE: DNA
<213> ORGANISM: Malus domestica

<400> SEQUENCE: 46
atggcaccgc ctgcaaccac cctgaccagc attgcacatg aaaaaaccct gcagcagaaa      60
tttgttcgtg atgaagatga acgtccgaaa gtggcctata tgaatttag caacgaaatc     120 ccgattatta gcctggcagg tattgatgaa gttgaaggtc gtcgtgccga aatctgcaaa     180
aaaatcgttg aagcatgtga agattggggc attttttcaga ttgttgatca tggtgttgat     240
gccgaactga ttagcgaaat gaccggtctg caaaagaat tttttgatct gccgagcgaa     300
gaaaaactgc gttttgatat gagcggtggt aaaaaaggtg ttttattgt tagcagccat     360 ctgcagggta agcagttca ggattggcgt gaaattgtta cctatttct gtatccgatt     420 cgccaccgtg attatagccg ttggcctgat aaaccggaag catggcgtga agttaccaaa     480
aaatacagtg atgaactgat gggtctggca tgtaaactgc tggtgttct gagcgaagca     540 atgggcctgg ataccgaagc actgaccaaa gcatgtgttg atatggatca gaaagtggtg     600
gttaacttct atccgaaatg tccgcagccg atctgaccc tgggtctgaa cgtcataccc     660
gatccgggta caattaccct gctgctgcaa gatcaggttg gcggtctgca ggcaacccgt     720
gatgatggta aacctggat taccgttcag ccggttgaag tgcatttgt tgttaatctg     780 ggtgatcatg gccattttct gagcaatggt cgctttaaaa acgcagatca tcaggcagtt     840
gttaatagca atagcagccg tctgagcatt gcaaccttc agaatccggc acaggatgca     900
attgtttatc cgctgagcgt tcgtgaaggt gaaaaccga ttctggaagc accgattacc     960
tataccgaga tgtataaaaa aaaatgagc aaagatctgg aactggcacg cctgaaaaaa    1020
ctggccaaag aacagcagct gcaggatctg gaaaagcaa agttgaaac caaaccggca    1080 gatgatatct tgccctggt tggtgcactg atgcatgtta tgcagaaacg tagccgtgca    1140 attcatgca gtgatgaagg tgaagatcaa gccggtgatg aagatgagga t            1191

<210> SEQ ID NO 47
<211> LENGTH: 397
<212> TYPE: PRT
<213> ORGANISM: Malus domestica

<400> SEQUENCE: 47

Met Ala Pro Pro Ala Thr Thr Leu Thr Ser Ile Ala His Glu Lys Thr
1               5                   10                  15

Leu Gln Gln Lys Phe Val Arg Asp Glu Asp Glu Arg Pro Lys Val Ala
            20                  25                  30

Tyr Asn Glu Phe Ser Asn Glu Ile Pro Ile Ile Ser Leu Ala Gly Ile
```

```
             35                  40                  45
Asp Glu Val Glu Gly Arg Arg Ala Glu Ile Cys Lys Lys Ile Val Glu
 50                  55                  60

Ala Cys Glu Asp Trp Gly Ile Phe Gln Ile Val Asp His Gly Val Asp
 65                  70                  75                  80

Ala Glu Leu Ile Ser Glu Met Thr Gly Leu Ala Lys Glu Phe Phe Asp
                 85                  90                  95

Leu Pro Ser Glu Glu Lys Leu Arg Phe Asp Met Ser Gly Gly Lys Lys
                100                 105                 110

Gly Gly Phe Ile Val Ser Ser His Leu Gln Gly Glu Ala Val Gln Asp
                115                 120                 125

Trp Arg Glu Ile Val Thr Tyr Phe Leu Tyr Pro Ile Arg His Arg Asp
            130                 135                 140

Tyr Ser Arg Trp Pro Asp Lys Pro Glu Ala Trp Arg Glu Val Thr Lys
145                 150                 155                 160

Lys Tyr Ser Asp Glu Leu Met Gly Leu Ala Cys Lys Leu Leu Gly Val
                165                 170                 175

Leu Ser Glu Ala Met Gly Leu Asp Thr Glu Ala Leu Thr Lys Ala Cys
                180                 185                 190

Val Asp Met Asp Gln Lys Val Val Asn Phe Tyr Pro Lys Cys Pro
            195                 200                 205

Gln Pro Asp Leu Thr Leu Gly Leu Lys Arg His Thr Asp Pro Gly Thr
210                 215                 220

Ile Thr Leu Leu Leu Gln Asp Gln Val Gly Gly Leu Gln Ala Thr Arg
225                 230                 235                 240

Asp Asp Gly Lys Thr Trp Ile Thr Val Gln Pro Val Glu Gly Ala Phe
                245                 250                 255

Val Val Asn Leu Gly Asp His Gly His Phe Leu Ser Asn Gly Arg Phe
                260                 265                 270

Lys Asn Ala Asp His Gln Ala Val Val Asn Ser Asn Ser Ser Arg Leu
                275                 280                 285

Ser Ile Ala Thr Phe Gln Asn Pro Ala Gln Asp Ala Ile Val Tyr Pro
                290                 295                 300

Leu Ser Val Arg Glu Gly Glu Lys Pro Ile Leu Glu Ala Pro Ile Thr
305                 310                 315                 320

Tyr Thr Glu Met Tyr Lys Lys Met Ser Lys Asp Leu Glu Leu Ala
                325                 330                 335

Arg Leu Lys Lys Leu Ala Lys Glu Gln Gln Leu Gln Asp Leu Glu Lys
                340                 345                 350

Ala Lys Val Glu Thr Lys Pro Ala Asp Asp Ile Phe Ala Leu Val Gly
                355                 360                 365

Ala Leu Met His Val Met Gln Lys Arg Ser Arg Ala Ile His Ser Ser
            370                 375                 380

Asp Glu Gly Glu Asp Gln Ala Gly Asp Glu Asp Glu Asp
385                 390                 395

<210> SEQ ID NO 48
<211> LENGTH: 1200
<212> TYPE: DNA
<213> ORGANISM: Petroselinum crispum

<400> SEQUENCE: 48
atggcaccga gcaccctgac cgcactggca caagaaaaaa ccctgaatag caaatttgtg     60
cgcgacgaag atgaacgtcc gaaaattgca tataacaaat tcagcgacga aatcccggtt    120
```

```
attagcctgg caggtattga tgatgatagc gttgataaac gtagccagat ttgccgtaaa    180
attgttgaag catgtgaaga ttggggcatt tttcaggttg ttgatcatgg cattgatatc    240
gatctgatta gcgaaatgac ccgtctggca cgtcagtttt ttgcactgcc tgcagaagaa    300
aaactgcgtt ttgatatgac cggtggtaaa aaaggtggtt ttattgttag cagccatctg    360
cagggtgaag cagttcagga ttggcgtgaa attgttacct atttcagcta tccgattcag    420
gcacgtgatt atagccgttg gcctgataaa ccggaaggtt ggcgtagcat taccgaaatg    480
tatagtgatg aactgatggc actggcatgt aaactgctgg aagttctgag cgaagcaatg    540
ggtctggaaa aagagggtct gaccaaagca tgtgttgata tggatcagaa agtgatcgtg    600
aactactatc cgaaatgtcc gcagccgaat ctgaccctgg gtctgaaacg tcataccgat    660
ccgggtacaa ttaccctgct gctgcaggat caggttggtg gtctgcaggc gacccgtgat    720
ggtggcaaaa cctggattac cgttcagccg gttgaaggtg catttgttgt taatctgggt    780
gatcatggtc actatctgag caatggtcgc tttaaaaacg cagatcatca ggcagttgtt    840
aatagcaata gcagccgtat gagcattgca acctttcaga atccggcacc gaatgcaacc    900
gtttatccgc tgaaaattcg tgaaggtgaa aaagccgtta tggaagaacc gattacccttt    960 gccgagatgt ataaacgtaa aatgagccgt gatattgaaa tggccaccct gaaaaaactg   1020
gccaaagaaa aagttctgca ggaccaagaa gtggaaaaag caaaactgca gatgacccccg   1080 aaaagcgcag atgaaatttt tgccctggtt ggtgcactga tgcatgttat gcagaaacgt   1140
agccgtgcaa ttcatagcag tgatgaaggt gaagatcaag ccggtgatga agatgaggat   1200
```

<210> SEQ ID NO 49
<211> LENGTH: 400
<212> TYPE: PRT
<213> ORGANISM: Petroselinum crispum

<400> SEQUENCE: 49

Met Ala Pro Ser Thr Leu Thr Ala Leu Ala Gln Glu Lys Thr Leu Asn
1               5                   10                  15

Ser Lys Phe Val Arg Asp Glu Asp Arg Pro Lys Ile Ala Tyr Asn
        20                  25                  30

Lys Phe Ser Asp Glu Ile Pro Val Ile Ser Leu Ala Gly Ile Asp Asp
        35                  40                  45

Asp Ser Val Asp Lys Arg Ser Gln Ile Cys Arg Lys Ile Val Glu Ala
    50                  55                  60

Cys Glu Asp Trp Gly Ile Phe Gln Val Val Asp His Gly Ile Asp Ile
65                  70                  75                  80

Asp Leu Ile Ser Glu Met Thr Arg Leu Ala Arg Gln Phe Phe Ala Leu
                85                  90                  95

Pro Ala Glu Glu Lys Leu Arg Phe Asp Met Thr Gly Gly Lys Lys Gly
            100                 105                 110

Gly Phe Ile Val Ser Ser His Leu Gln Gly Glu Ala Val Gln Asp Trp
        115                 120                 125

Arg Glu Ile Val Thr Tyr Phe Ser Tyr Pro Ile Gln Ala Arg Asp Tyr
    130                 135                 140

Ser Arg Trp Pro Asp Lys Pro Glu Gly Trp Arg Ser Ile Thr Glu Met
145                 150                 155                 160

Tyr Ser Asp Glu Leu Met Ala Leu Ala Cys Lys Leu Leu Glu Val Leu
                165                 170                 175

Ser Glu Ala Met Gly Leu Glu Lys Glu Gly Leu Thr Lys Ala Cys Val

|  |  | 180 |  |  | 185 |  |  | 190 |  |  |  |
|---|---|---|---|---|---|---|---|---|---|---|---|

Asp Met Asp Gln Lys Val Ile Val Asn Tyr Tyr Pro Lys Cys Pro Gln
            195                    200                  205

Pro Asn Leu Thr Leu Gly Leu Lys Arg His Thr Asp Pro Gly Thr Ile
        210                    215                  220

Thr Leu Leu Leu Gln Asp Gln Val Gly Gly Leu Gln Ala Thr Arg Asp
225                  230                    235                  240

Gly Gly Lys Thr Trp Ile Thr Val Gln Pro Val Glu Gly Ala Phe Val
            245                    250                  255

Val Asn Leu Gly Asp His Gly His Tyr Leu Ser Asn Gly Arg Phe Lys
        260                    265                  270

Asn Ala Asp His Gln Ala Val Val Asn Ser Asn Ser Ser Arg Met Ser
            275                  280                  285

Ile Ala Thr Phe Gln Asn Pro Ala Pro Asn Ala Thr Val Tyr Pro Leu
        290                    295                  300

Lys Ile Arg Glu Gly Glu Lys Ala Val Met Glu Glu Pro Ile Thr Phe
305                  310                    315                  320

Ala Glu Met Tyr Lys Arg Lys Met Ser Arg Asp Ile Glu Met Ala Thr
            325                    330                  335

Leu Lys Lys Leu Ala Lys Glu Lys Val Leu Gln Asp Gln Glu Val Glu
                340                    345                  350

Lys Ala Lys Leu Gln Met Thr Pro Lys Ser Ala Asp Glu Ile Phe Ala
            355                    360                  365

Leu Val Gly Ala Leu Met His Val Met Gln Lys Arg Ser Arg Ala Ile
370                  375                    380

His Ser Ser Asp Glu Gly Glu Asp Gln Ala Gly Asp Glu Asp Glu Asp
385                  390                    395                  400

<210> SEQ ID NO 50
<211> LENGTH: 1074
<212> TYPE: DNA
<213> ORGANISM: Anthurium andraeanum

<400> SEQUENCE: 50

| | | |
|---|---|---|
| atgatgcata aaggcaccgt tgtgttacc ggtgcagcag gttttgttgg tagctggctg | 60 |
| attatgcgtc tgctggaaca gggttatagc gttaaagcaa ccgttcgtga tccgagcaat | 120 |
| atgaaaaaag ttaaacatct gctggatctg cctggtgcag caaatcgtct gaccctgtgg | 180 |
| aaagcagatc tggttgatga aggtagcttt gatgaaccga ttcagggttg taccggtgtt | 240 |
| tttcatgttg caaccccgat ggattttgaa agcaaagatc cggaaagcga atgattaaa | 300 |
| ccgaccattg aaggtatgct gaatgttctg cgtagctgtg cccgtgcaag cagcaccgtt | 360 |
| cgtcgtgttg tttttaccag cagcgcaggt acagttagca ttcatgaagg tcgtcgtcat | 420 |
| ctgtatgatg aaaccagttg gagtgatgtt gattttttgcc gtgccaaaaa aatgaccggc | 480 |
| tggatgtatt tgttagcaa aaccctggca gaaaaagcag catgggattt tgcagagaaa | 540 |
| aataacatcg acttcatcag cattattccg accctggtta atggtccgtt tgttatgccg | 600 |
| accatgcctc cgagcatgct gagcgcactg gcactgatta cccgtaatga accgcattat | 660 |
| agcattctga atccggtgca gtttgttcat ctggatgatc tgtgtaacgc ccacatttt | 720 |
| ctgtttgaat gtccggatgc aaaaggtcgt tatatttgta gcagccatga tgttaccatt | 780 |
| gcaggtctgg cacagattct gcgtcagcgt atccggaat ttgatgttcc gaccgaattt | 840 |
| ggtgaaatgg aagtgtttga tatcatcagc tatagcagca aaaaactgac ggatctgggt | 900 |

```
ttcgaattca aatatagcct ggaagatatg ttcgatggtg caattcagag ctgtcgtgaa       960
aaaggtctgc tgcctccggc aaccaaagaa ccgagctatg caaccgaaca gctgattgca      1020
accggtcagg ataatggtca tcctcctcct gcactgcctc cgaaacgtcg tcgt            1074
```

<210> SEQ ID NO 51
<211> LENGTH: 358
<212> TYPE: PRT
<213> ORGANISM: Anthurium andraeanum

<400> SEQUENCE: 51

```
Met Met His Lys Gly Thr Val Cys Val Thr Gly Ala Ala Gly Phe Val
1               5                   10                  15

Gly Ser Trp Leu Ile Met Arg Leu Leu Glu Gln Gly Tyr Ser Val Lys
            20                  25                  30

Ala Thr Val Arg Asp Pro Ser Asn Met Lys Lys Val Lys His Leu Leu
        35                  40                  45

Asp Leu Pro Gly Ala Ala Asn Arg Leu Thr Leu Trp Lys Ala Asp Leu
    50                  55                  60

Val Asp Glu Gly Ser Phe Asp Glu Pro Ile Gln Gly Cys Thr Gly Val
65                  70                  75                  80

Phe His Val Ala Thr Pro Met Asp Phe Glu Ser Lys Asp Pro Glu Ser
                85                  90                  95

Glu Met Ile Lys Pro Thr Ile Glu Gly Met Leu Asn Val Leu Arg Ser
            100                 105                 110

Cys Ala Arg Ala Ser Ser Thr Val Arg Arg Val Val Phe Thr Ser Ser
        115                 120                 125

Ala Gly Thr Val Ser Ile His Glu Gly Arg Arg His Leu Tyr Asp Glu
    130                 135                 140

Thr Ser Trp Ser Asp Val Asp Phe Cys Arg Ala Lys Lys Met Thr Gly
145                 150                 155                 160

Trp Met Tyr Phe Val Ser Lys Thr Leu Ala Glu Lys Ala Ala Trp Asp
                165                 170                 175

Phe Ala Glu Lys Asn Asn Ile Asp Phe Ile Ser Ile Ile Pro Thr Leu
            180                 185                 190

Val Asn Gly Pro Phe Val Met Pro Thr Met Pro Ser Met Leu Ser
        195                 200                 205

Ala Leu Ala Leu Ile Thr Arg Asn Glu Pro His Tyr Ser Ile Leu Asn
    210                 215                 220

Pro Val Gln Phe Val His Leu Asp Asp Leu Cys Asn Ala His Ile Phe
225                 230                 235                 240

Leu Phe Glu Cys Pro Asp Ala Lys Gly Arg Tyr Ile Cys Ser Ser His
                245                 250                 255

Asp Val Thr Ile Ala Gly Leu Ala Gln Ile Leu Arg Gln Arg Tyr Pro
            260                 265                 270

Glu Phe Asp Val Pro Thr Glu Phe Gly Glu Met Glu Val Phe Asp Ile
        275                 280                 285

Ile Ser Tyr Ser Ser Lys Lys Leu Thr Asp Leu Gly Phe Glu Phe Lys
    290                 295                 300

Tyr Ser Leu Glu Asp Met Phe Asp Gly Ala Ile Gln Ser Cys Arg Glu
305                 310                 315                 320

Lys Gly Leu Leu Pro Pro Ala Thr Lys Glu Pro Ser Tyr Ala Thr Glu
                325                 330                 335

Gln Leu Ile Ala Thr Gly Gln Asp Asn Gly His Pro Pro Pro Ala Leu
            340                 345                 350
```

<210> SEQ ID NO 52
<211> LENGTH: 1074
<212> TYPE: DNA
<213> ORGANISM: Camellia sinensis

<400> SEQUENCE: 52

```
atgaaagata gcgttgcaag cgcaaccgca agcgcaccgg gtacagtttg tgttaccggt      60
gcagcaggtt ttattggtag ctggctggtt atgcgtctgc tggaacgtgg ttatattgtt     120
cgtgcaaccg ttcgtgatcc ggcaaatctg aaaaaagtta acatctgct ggatctgccg      180
aaagcagata ccaatctgac cctgtggaaa gccgatctga atgaagaggg tagctttgat     240
gaagcaattg aaggttgtag cggtgttttt catgttgcaa ccccgatgga ttttgaaagc     300
aaagatccgg aaaacgaagt gattaaaccg accattaacg gtgtgctgag cattattcgt     360
agctgtacca agcaaaaac cgttaaacgt ctggtttta ccagcagcgc aggtacagtt       420
aatgttcaag aacatcagca gccggtgttt gatgaaaaca attggagcga tctgcacttc     480
atcaacaaaa aaaaatgac cggctggatg tattttgtga gcaaaacct ggcagaaaaa       540
gcagcatggg aagcagcaaa agaaaacaac attgatttca tcagcattat cccgaccctg    600
gttggtggtc cgtttattat gccgaccttt ccgcctagcc tgattaccgc actgagcccg    660
attaccgta tgaaggtca ttattccatt atcaacagg gccagtttgt gcatctggat       720
gatctgtgtg aaagccacat ttttctgtat gaacgtccgc aggcagaagg tcgttatatt    780
tgtagcagcc atgatgcaac cattcatgat ctggccaaac tgatgcgtga aaaatggcct    840
gaatataatg ttccgaccga attcaaaggc atcgataaag atctgccggt tgttagcttt    900
tccagcaaaa aactgattgg catgggcttc gagttcaaat atagcctgga agatatgttt    960
cgtggtgcca ttgatacctg tcgtgaaaaa ggtctgctgc cgcatagctt tgcagaaaat    1020
ccggttaatg caacaaagt gcctcctcct gcactgcctc cgaaacgtcg tcgt           1074
```

<210> SEQ ID NO 53
<211> LENGTH: 358
<212> TYPE: PRT
<213> ORGANISM: Camellia sinensis

<400> SEQUENCE: 53

Met Lys Asp Ser Val Ala Ser Ala Thr Ala Ser Ala Pro Gly Thr Val
1               5                   10                  15

Cys Val Thr Gly Ala Ala Gly Phe Ile Gly Ser Trp Leu Val Met Arg
            20                  25                  30

Leu Leu Glu Arg Gly Tyr Ile Val Arg Ala Thr Val Arg Asp Pro Ala
        35                  40                  45

Asn Leu Lys Lys Val Lys His Leu Leu Asp Leu Pro Lys Ala Asp Thr
    50                  55                  60

Asn Leu Thr Leu Trp Lys Ala Asp Leu Asn Glu Glu Gly Ser Phe Asp
65                  70                  75                  80

Glu Ala Ile Glu Gly Cys Ser Gly Val Phe His Val Ala Thr Pro Met
                85                  90                  95

Asp Phe Glu Ser Lys Asp Pro Glu Asn Glu Val Ile Lys Pro Thr Ile
            100                 105                 110

Asn Gly Val Leu Ser Ile Ile Arg Ser Cys Thr Lys Ala Lys Thr Val
        115                 120                 125

Lys Arg Leu Val Phe Thr Ser Ser Ala Gly Thr Val Asn Val Gln Glu
130                 135                 140

His Gln Gln Pro Val Phe Asp Glu Asn Asn Trp Ser Asp Leu His Phe
145                 150                 155                 160

Ile Asn Lys Lys Lys Met Thr Gly Trp Met Tyr Phe Val Ser Lys Thr
                165                 170                 175

Leu Ala Glu Lys Ala Ala Trp Glu Ala Ala Lys Glu Asn Asn Ile Asp
            180                 185                 190

Phe Ile Ser Ile Ile Pro Thr Leu Val Gly Gly Pro Phe Ile Met Pro
        195                 200                 205

Thr Phe Pro Pro Ser Leu Ile Thr Ala Leu Ser Pro Ile Thr Arg Asn
    210                 215                 220

Glu Gly His Tyr Ser Ile Ile Lys Gln Gly Gln Phe Val His Leu Asp
225                 230                 235                 240

Asp Leu Cys Glu Ser His Ile Phe Leu Tyr Glu Arg Pro Gln Ala Glu
                245                 250                 255

Gly Arg Tyr Ile Cys Ser Ser His Asp Ala Thr Ile His Asp Leu Ala
            260                 265                 270

Lys Leu Met Arg Glu Lys Trp Pro Glu Tyr Asn Val Pro Thr Glu Phe
        275                 280                 285

Lys Gly Ile Asp Lys Asp Leu Pro Val Val Ser Phe Ser Ser Lys Lys
    290                 295                 300

Leu Ile Gly Met Gly Phe Glu Phe Lys Tyr Ser Leu Glu Asp Met Phe
305                 310                 315                 320

Arg Gly Ala Ile Asp Thr Cys Arg Glu Lys Gly Leu Leu Pro His Ser
                325                 330                 335

Phe Ala Glu Asn Pro Val Asn Gly Asn Lys Val Pro Pro Ala Leu
            340                 345                 350

Pro Pro Lys Arg Arg Arg
        355

<210> SEQ ID NO 54
<211> LENGTH: 1056
<212> TYPE: DNA
<213> ORGANISM: Fragaria x ananassa

<400> SEQUENCE: 54
atgggtctgg gtgcagaaag cggtagcgtt tgtgttaccg gtgcaagcgg ttttgttggt     60
agctggctgg ttatgcgtct gctggaacat ggttataccg ttcgtgcaac cgtgcgtgat    120
ccggcaaatc tgaaaaaagt tcgtcatctg ctggaactgc cgcaggcagc aacccgtctg    180
accctgtgga agcagatctg gatgttgaa ggtagctttg atgaagccat taaaggttgt    240
accggtgttt ttcatgttgc aaccccgatg gattttgaaa gcgaagatcc ggaaaacgaa    300
gttattaaac cgaccattaa cggcatgctg gatattatga agcatgcct gaaagcaaaa    360 accgttcgtc gtctggtttt taccagcagt gccggtgcag ttgcaattga agaacatccg    420
aaagaagtgt acagcgaaaa taactggtca gatgttgtgt tttgccgcaa agttaaaatg    480
accggctgga tgtattttgt gagcaaaacc ctggcagaac aggcagcatg gaaatttgca    540
aaagaaaaca acatcgactt catcaccatt attccgaccc tggttattgg tccgtttctg    600
gcaccgagca tgcctccgag cctgattagc ggtctgagtc cgctgaccgg taatgaagca    660
cattatggta ttatcaaaca gtgccagtat gtgcatctgg atgatctgtg tcagagccat    720
atttttctgt atgaacatgc aaaagccgag ggtcgttata tttgtagcag ccatgatgca    780

```
accattcacg atattgcaaa actgctgaac gagaaatacc cgaaatacaa cgttccgaaa    840
aaattcaaag gcatcgaaga aaacctgacc aacattcact ttagcagcaa aaaactgaaa    900
gagatgggct tcgaatttaa acacagcctg gaagatatgt ttacaggtgc cgttgatgca    960
tgtcgtgaaa aaggtctgct gccgctgccg caagaagaag aaaccgaaaa acgtcgtgca   1020
ggtcctcctc ctgcactgcc tccgaaacgt cgtcgt                              1056
```

<210> SEQ ID NO 55
<211> LENGTH: 352
<212> TYPE: PRT
<213> ORGANISM: Fragaria x ananassa

<400> SEQUENCE: 55

```
Met Gly Leu Gly Ala Glu Ser Gly Ser Val Cys Val Thr Gly Ala Ser
1               5                   10                  15

Gly Phe Val Gly Ser Trp Leu Val Met Arg Leu Leu Glu His Gly Tyr
            20                  25                  30

Thr Val Arg Ala Thr Val Arg Asp Pro Ala Asn Leu Lys Lys Val Arg
        35                  40                  45

His Leu Leu Glu Leu Pro Gln Ala Ala Thr Arg Leu Thr Leu Trp Lys
    50                  55                  60

Ala Asp Leu Asp Val Glu Gly Ser Phe Asp Glu Ala Ile Lys Gly Cys
65                  70                  75                  80

Thr Gly Val Phe His Val Ala Thr Pro Met Asp Phe Glu Ser Glu Asp
                85                  90                  95

Pro Glu Asn Glu Val Ile Lys Pro Thr Ile Asn Gly Met Leu Asp Ile
            100                 105                 110

Met Lys Ala Cys Leu Lys Ala Lys Thr Val Arg Arg Leu Val Phe Thr
        115                 120                 125

Ser Ser Ala Gly Ala Val Ala Ile Glu Glu His Pro Lys Glu Val Tyr
    130                 135                 140

Ser Glu Asn Asn Trp Ser Asp Val Val Phe Cys Arg Lys Val Lys Met
145                 150                 155                 160

Thr Gly Trp Met Tyr Phe Val Ser Lys Thr Leu Ala Glu Gln Ala Ala
                165                 170                 175

Trp Lys Phe Ala Lys Glu Asn Asn Ile Asp Phe Ile Thr Ile Ile Pro
            180                 185                 190

Thr Leu Val Ile Gly Pro Phe Leu Ala Pro Ser Met Pro Pro Ser Leu
        195                 200                 205

Ile Ser Gly Leu Ser Pro Leu Thr Gly Asn Glu Ala His Tyr Gly Ile
    210                 215                 220

Ile Lys Gln Cys Gln Tyr Val His Leu Asp Asp Leu Cys Gln Ser His
225                 230                 235                 240

Ile Phe Leu Tyr Glu His Ala Lys Ala Glu Gly Arg Tyr Ile Cys Ser
                245                 250                 255

Ser His Asp Ala Thr Ile His Asp Ile Ala Lys Leu Leu Asn Glu Lys
            260                 265                 270

Tyr Pro Lys Tyr Asn Val Pro Lys Lys Phe Lys Gly Ile Glu Glu Asn
        275                 280                 285

Leu Thr Asn Ile His Phe Ser Ser Lys Lys Leu Lys Glu Met Gly Phe
    290                 295                 300

Glu Phe Lys His Ser Leu Glu Asp Met Phe Thr Gly Ala Val Asp Ala
305                 310                 315                 320
```

Cys Arg Glu Lys Gly Leu Leu Pro Leu Pro Gln Glu Glu Thr Glu
            325                 330                 335

Lys Arg Arg Ala Gly Pro Pro Pro Ala Leu Pro Pro Lys Arg Arg
        340                 345                 350

<210> SEQ ID NO 56
<211> LENGTH: 1062
<212> TYPE: DNA
<213> ORGANISM: Camellia sinensis

<400> SEQUENCE: 56

| | | | | | |
|---|---|---|---|---|---|
| atggcaatgg | ccatggcaac | caccaccaca | accaccaaac | cgatgattgg | tgcaaaagca | 60 |
| gcatgtgttg | ttggtggcac | cggttttgtt | gcagcaaccc | tggttaaaat | gctgctggaa | 120 |
| cgtggttata | gcgttaatac | caccgttcgt | gatccggaca | caaaaaaaaa | cattagccat | 180 |
| ctggttgcac | tggaaggtat | gggtaatctg | aaaatctttc | gtgcagatct | gaccgatgaa | 240 |
| cagagctttg | atgcaccgat | tgcaggttgt | gatctggttt | ttgatgttgc | cacaccggtt | 300 |
| aattttgcaa | gcgaagatcc | ggaaaacgac | atgattaaaa | tggcaattca | gggtgttctg | 360 |
| aatgtgctga | agcatgtgc | caaagcaggc | accgttaaac | gtgttattct | gaccagcagc | 420 |
| gcagcaagcg | ttaccattaa | tcagctggat | ggtacaggtc | tggttatgga | tgaaagccat | 480 |
| tggagtgatg | ttgaatttct | gacctcagtt | aaaccgccta | cctggggtca | tccggttagc | 540 |
| aaaaccctgg | cagaaaaagc | agcctggaaa | tttgcagaag | aaaataacct | gaatctgatt | 600 |
| accgttgttc | cgaccctgac | cgcaggtccg | agcctgacca | gcgaagttcc | gaatagcatt | 660 |
| gaactggcca | tgagcctgat | tacgggtaat | gaattcctga | ttgatggtct | gaaaggtatg | 720 |
| cgtattctgt | caggtagcat | tagcattacc | catgttgaag | atgtttgtgg | tgcccatatt | 780 |
| tttgtggccg | aaaaagaaag | cgcaagcggt | cgttatattt | ttgtggtgt | taatagcagc | 840 |
| gtgccggaac | tggcacgttt | tctgaataaa | cgttatccgc | agtataatgt | gccgaccgat | 900 |
| tttggtgatc | tgccgagcaa | agcaaaactg | attattagca | gcgagaaact | gatcaaagaa | 960 |
| ggcttcagct | tcaaatatgg | catcgaagaa | attttttgcac | acagcgttgc | atatctgaaa | 1020 |
| accaaaggtc | tgctgcagaa | cggtgttaaa | gaaagcctgg | tt | | 1062 |

<210> SEQ ID NO 57
<211> LENGTH: 354
<212> TYPE: PRT
<213> ORGANISM: Camellia sinensis

<400> SEQUENCE: 57

Met Ala Met Ala Met Ala Thr Thr Thr Thr Thr Thr Lys Pro Met Ile
1               5                   10                  15

Gly Ala Lys Ala Ala Cys Val Val Gly Gly Thr Gly Phe Val Ala Ala
            20                  25                  30

Thr Leu Val Lys Met Leu Leu Glu Arg Gly Tyr Ser Val Asn Thr Thr
        35                  40                  45

Val Arg Asp Pro Asp Asn Lys Lys Asn Ile Ser His Leu Val Ala Leu
    50                  55                  60

Glu Gly Met Gly Asn Leu Lys Ile Phe Arg Ala Asp Leu Thr Asp Glu
65                  70                  75                  80

Gln Ser Phe Asp Ala Pro Ile Ala Gly Cys Asp Leu Val Phe Asp Val
                85                  90                  95

Ala Thr Pro Val Asn Phe Ala Ser Glu Asp Pro Glu Asn Asp Met Ile
            100                 105                 110

```
Lys Leu Ala Ile Gln Gly Val Leu Asn Val Leu Lys Ala Cys Ala Lys
            115                 120                 125
Ala Gly Thr Val Lys Arg Val Ile Leu Thr Ser Ala Ala Ser Val
    130                 135                 140
Thr Ile Asn Gln Leu Asp Gly Thr Gly Leu Val Met Asp Glu Ser His
145                 150                 155                 160
Trp Ser Asp Val Glu Phe Leu Thr Ser Val Lys Pro Pro Thr Trp Gly
                165                 170                 175
His Pro Val Ser Lys Thr Leu Ala Glu Lys Ala Ala Trp Lys Phe Ala
            180                 185                 190
Glu Glu Asn Asn Leu Asn Leu Ile Thr Val Val Pro Thr Leu Thr Ala
        195                 200                 205
Gly Pro Ser Leu Thr Ser Glu Val Pro Asn Ser Ile Glu Leu Ala Met
    210                 215                 220
Ser Leu Ile Thr Gly Asn Glu Phe Leu Ile Asp Gly Leu Lys Gly Met
225                 230                 235                 240
Arg Ile Leu Ser Gly Ser Ile Ser Ile Thr His Val Glu Asp Val Cys
                245                 250                 255
Gly Ala His Ile Phe Val Ala Glu Lys Glu Ser Ala Ser Gly Arg Tyr
            260                 265                 270
Ile Cys Cys Gly Val Asn Ser Ser Val Pro Glu Leu Ala Arg Phe Leu
        275                 280                 285
Asn Lys Arg Tyr Pro Gln Tyr Asn Val Pro Thr Asp Phe Gly Asp Leu
    290                 295                 300
Pro Ser Lys Ala Lys Leu Ile Ile Ser Ser Glu Lys Leu Ile Lys Glu
305                 310                 315                 320
Gly Phe Ser Phe Lys Tyr Gly Ile Glu Glu Ile Phe Ala His Ser Val
                325                 330                 335
Ala Tyr Leu Lys Thr Lys Gly Leu Leu Gln Asn Gly Val Lys Glu Ser
            340                 345                 350
Leu Val

<210> SEQ ID NO 58
<211> LENGTH: 1167
<212> TYPE: DNA
<213> ORGANISM: Desmodium uncinatum

<400> SEQUENCE: 58
atgaccgtta gcggtgcaat tccgagcatg accaaaaatc gtaccctggt tgttggtggc      60
accggtttta ttggtcagtt tattaccaaa gcaagcctgg ttttggtta tccgaccttt      120
ctgctggttc gtccgggtcc ggttagcccg agcaaagcag ttattatcaa aacctttcag      180
gataaaggtg ccaaagtgat ttatggcgtg atcaacgata agaatgcat ggaaaaaatt       240
ctgaaagagt acgagatcga cgttgttatt agcctggtgg gtggtgcacg tctgctggat      300
cagctgaccc tgctggaagc aattaaaagc gttaaaacca tcaaacgttt tctgccgagc      360
gaatttggcc atgatgttga tcgtaccgat ccggttgaac cgggtctgac catgtataaa      420
gaaaaacgtc tggtgcgtcg tgccgttgaa gaatatggta ttccgtttac caatatctgc      480
tgcaatagca ttgcaagctg gccgtattat gataattgtc atccgagcca ggttccgcct      540
ccgatggatc agtttcagat ttatggtgat ggtaacacca agcctatttt cattgatggc      600
aacgatatcg gcaaatttac catgaaaacc atcgatgata ttcgcacccct gaacaaaaat      660
gttcattttc gtccgagcag caactgctac agcattaatg aactggcaag cctgtgggag      720
```

-continued

```
aaaaaaatcg tcgtacact gcctcgtttt accgttaccg cagataaact gctggcacat    780
gcagcagaaa acattattcc ggaaagcatt gttagcagct ttacccacga tatctttatt    840
aacggttgcc aggtgaactt tagcatcgat gaacatagtg atgtggaaat cgatacactg    900
tatccggata aaaaatttcg tagcctggat gattgctatg aagattttgt tccgatggtg    960
cacgataaaa ttcatgcagg taaaagcggt gaaatcaaaa tcaaagatgg taaaccgctg   1020
gttcagaccg gcaccattga agaaattaac aaagacatta aaaccctggt ggaaacccag   1080
ccgaatgaag agatcaaaaa agatatgaaa gcactggttg aagccgttcc gattagcgca   1140
atgggtggtg ttaaagaaag cctggtt                                       1167
```

<210> SEQ ID NO 59
<211> LENGTH: 389
<212> TYPE: PRT
<213> ORGANISM: Desmodium uncinatum

<400> SEQUENCE: 59

```
Met Thr Val Ser Gly Ala Ile Pro Ser Met Thr Lys Asn Arg Thr Leu
1               5                   10                  15

Val Val Gly Gly Thr Gly Phe Ile Gly Gln Phe Ile Thr Lys Ala Ser
            20                  25                  30

Leu Gly Phe Gly Tyr Pro Thr Phe Leu Leu Val Arg Pro Gly Pro Val
        35                  40                  45

Ser Pro Ser Lys Ala Val Ile Ile Lys Thr Phe Gln Asp Lys Gly Ala
    50                  55                  60

Lys Val Ile Tyr Gly Val Ile Asn Asp Lys Glu Cys Met Glu Lys Ile
65                  70                  75                  80

Leu Lys Glu Tyr Glu Ile Asp Val Val Ile Ser Leu Val Gly Gly Ala
                85                  90                  95

Arg Leu Leu Asp Gln Leu Thr Leu Leu Glu Ala Ile Lys Ser Val Lys
            100                 105                 110

Thr Ile Lys Arg Phe Leu Pro Ser Glu Phe Gly His Asp Val Asp Arg
        115                 120                 125

Thr Asp Pro Val Glu Pro Gly Leu Thr Met Tyr Lys Glu Lys Arg Leu
    130                 135                 140

Val Arg Arg Ala Val Glu Glu Tyr Gly Ile Pro Phe Thr Asn Ile Cys
145                 150                 155                 160

Cys Asn Ser Ile Ala Ser Trp Pro Tyr Tyr Asp Asn Cys His Pro Ser
                165                 170                 175

Gln Val Pro Pro Met Asp Gln Phe Gln Ile Tyr Gly Asp Gly Asn
            180                 185                 190

Thr Lys Ala Tyr Phe Ile Asp Gly Asn Asp Ile Gly Lys Phe Thr Met
        195                 200                 205

Lys Thr Ile Asp Asp Ile Arg Thr Leu Asn Lys Asn Val His Phe Arg
    210                 215                 220

Pro Ser Ser Asn Cys Tyr Ser Ile Asn Glu Leu Ala Ser Leu Trp Glu
225                 230                 235                 240

Lys Lys Ile Gly Arg Thr Leu Pro Arg Phe Thr Val Thr Ala Asp Lys
                245                 250                 255

Leu Leu Ala His Ala Ala Glu Asn Ile Ile Pro Glu Ser Ile Val Ser
            260                 265                 270

Ser Phe Thr His Asp Ile Phe Ile Asn Gly Cys Gln Val Asn Phe Ser
        275                 280                 285

Ile Asp Glu His Ser Asp Val Glu Ile Asp Thr Leu Tyr Pro Asp Glu
```

```
            290             295             300
Lys Phe Arg Ser Leu Asp Asp Cys Tyr Glu Asp Phe Val Pro Met Val
305             310             315             320

His Asp Lys Ile His Ala Gly Lys Ser Gly Glu Ile Lys Ile Lys Asp
                325             330             335

Gly Lys Pro Leu Val Gln Thr Gly Thr Ile Glu Ile Asn Lys Asp
                340             345             350

Ile Lys Thr Leu Val Glu Thr Gln Pro Asn Glu Ile Lys Lys Asp
            355             360             365

Met Lys Ala Leu Val Glu Ala Val Pro Ile Ser Ala Met Gly Gly Val
            370             375             380

Lys Glu Ser Leu Val
385

<210> SEQ ID NO 60
<211> LENGTH: 1296
<212> TYPE: DNA
<213> ORGANISM: Petunia x hybrida

<400> SEQUENCE: 60
atggtgaatg cagtagttac aactccttca agagttgaaa gcttggctaa aagtggaatc       60
caggccatcc ctaaggagta tgtgaggcca caagaagagt tgaatggaat cggaaacatc      120
ttcgaggaag agaagaaaga tgaagggcct caagtaccaa caattgattt gaagaaaatt      180
gactccgagg acaaggagat cgcgagaaaa tgccaccagg agttgaagaa agcagccatg      240
gaatggggtg tcatgcacct tgtgaatcat ggcatatccg atgagctaat caatcgtgtc      300
aaggttgctg gagagacctt cttttgatcaa cctgttgaag aaaaggagaa gtatgctaat      360
gaccaagcca atggcaatgt ccaaggctac ggcagcaagc tagcaaatag tgcttgtggt      420
cagcttgagt gggaggatta tttcttccat tgtgctttcc ctgaagacaa gcgcgacttg      480
tccatctggc ctaaaaatcc tactgactac actccagcaa caagtgaata tgccaagcag      540
atcagggccc tagcaacaaa gattttgaca gtgctttcta ttgggctggg gctggaagaa      600
ggaagactag agaaggaagt tggaggcatg gaggatctgc tgcttcaaat gaagattaac      660
tactatccca agtgccccca accagaacta gcacttggcg tcgaagctca tacagatgtc      720
agcgcactga cttttcatcct ccacaatatg gtgcccggct tgcaactctt ctatgaaggc      780
cagtgggtaa ctgctaagtg tgtgcctaat tctatcatca tgcacatagg ggacaccatt      840
gaaatcctaa gcaatggaaa gtacaagagc atccttcata gaggggttgt gaataaagag      900
aaagtaagga tctcatgggc catttttctgc gagccaccta aggagaagat catccttaag      960
cccctacctg agactgtcac tgaggctgag ccacctcgat tcccacctcg cacctttgca     1020
cagcatatgg cacacaagct cttcaggaag gatgacaagg atgccgctgt tgaacacaaa     1080
gtcttcaaag aggatgaact ggatactgct gctgaacata aggtcctcaa gaaggataat     1140
caggatgctg ttgctgagaa taagacatc aaggaggatg aacagtgtgg ccctgctgag     1200
cacaaagata tcaaggagga tggacagggt gccgctgctg agaacaaagt cttcaaggag     1260
aataatcagg atgttgctgc tgaagaatct aaatag                              1296

<210> SEQ ID NO 61
<211> LENGTH: 431
<212> TYPE: PRT
<213> ORGANISM: Petunia x hybrida

<400> SEQUENCE: 61
```

-continued

```
Met Val Asn Ala Val Val Thr Thr Pro Ser Arg Val Glu Ser Leu Ala
1               5                   10                  15

Lys Ser Gly Ile Gln Ala Ile Pro Lys Glu Tyr Val Arg Pro Gln Glu
                20                  25                  30

Glu Leu Asn Gly Ile Gly Asn Ile Phe Glu Glu Lys Lys Asp Glu
            35                  40                  45

Gly Pro Gln Val Pro Thr Ile Asp Leu Lys Glu Ile Asp Ser Glu Asp
    50                  55                  60

Lys Glu Ile Arg Glu Lys Cys His Gln Glu Leu Lys Lys Ala Ala Met
65                  70                  75                  80

Glu Trp Gly Val Met His Leu Val Asn His Gly Ile Ser Asp Glu Leu
                85                  90                  95

Ile Asn Arg Val Lys Val Ala Gly Glu Thr Phe Phe Asp Gln Pro Val
            100                 105                 110

Glu Glu Lys Glu Lys Tyr Ala Asn Asp Gln Ala Asn Gly Asn Val Gln
        115                 120                 125

Gly Tyr Gly Ser Lys Leu Ala Asn Ser Ala Cys Gly Gln Leu Glu Trp
    130                 135                 140

Glu Asp Tyr Phe Phe His Cys Ala Phe Pro Glu Asp Lys Arg Asp Leu
145                 150                 155                 160

Ser Ile Trp Pro Lys Asn Pro Thr Asp Tyr Thr Pro Ala Thr Ser Glu
                165                 170                 175

Tyr Ala Lys Gln Ile Arg Ala Leu Ala Thr Lys Ile Leu Thr Val Leu
            180                 185                 190

Ser Ile Gly Leu Gly Leu Glu Gly Arg Leu Glu Lys Glu Val Gly
        195                 200                 205

Gly Met Glu Asp Leu Leu Leu Gln Met Lys Ile Asn Tyr Tyr Pro Lys
    210                 215                 220

Cys Pro Gln Pro Glu Leu Ala Leu Gly Val Glu Ala His Thr Asp Val
225                 230                 235                 240

Ser Ala Leu Thr Phe Ile Leu His Asn Met Val Pro Gly Leu Gln Leu
                245                 250                 255

Phe Tyr Glu Gly Gln Trp Val Thr Ala Lys Cys Val Pro Asn Ser Ile
            260                 265                 270

Ile Met His Ile Gly Asp Thr Ile Glu Ile Leu Ser Asn Gly Lys Tyr
        275                 280                 285

Lys Ser Ile Leu His Arg Gly Val Val Asn Lys Glu Lys Val Arg Ile
    290                 295                 300

Ser Trp Ala Ile Phe Cys Glu Pro Pro Lys Glu Lys Ile Ile Leu Lys
305                 310                 315                 320

Pro Leu Pro Glu Thr Val Thr Glu Ala Glu Pro Pro Arg Phe Pro Pro
                325                 330                 335

Arg Thr Phe Ala Gln His Met Ala His Lys Leu Phe Arg Lys Asp Asp
            340                 345                 350

Lys Asp Ala Ala Val Glu His Lys Val Phe Lys Glu Asp Leu Asp
        355                 360                 365

Thr Ala Ala Glu His Lys Val Leu Lys Lys Asp Asn Gln Asp Ala Val
    370                 375                 380

Ala Glu Asn Lys Asp Ile Lys Glu Asp Glu Gln Cys Gly Pro Ala Glu
385                 390                 395                 400

His Lys Asp Ile Lys Glu Asp Gly Gln Gly Ala Ala Glu Asn Lys
                405                 410                 415
```

```
Val Phe Lys Glu Asn Asn Gln Asp Val Ala Ala Glu Glu Ser Lys
            420                 425                 430
```

```
<210> SEQ ID NO 62
<211> LENGTH: 1383
<212> TYPE: DNA
<213> ORGANISM: Arabidopsis thaliana

<400> SEQUENCE: 62
```

| | | | | | |
|---|---|---|---|---|---|
| atgaccaaac | cctccgaccc | aaccagagac | tcccacgtgg | cagttctcgc | ttttcctttc      60 |
| ggcactcatg | cagctcctct | cctcaccgtc | acgcgccgcc | tcgcctccgc | tctccttcc     120 |
| accgtcttct | ctttcttcaa | caccgcacaa | tccaactctt | cgttattttc | ctccggtgac    180 |
| gaagcagatc | gtccggcgaa | catcagagta | tacgatattg | ccgacggtgt | tccggaggga    240 |
| tacgtgttta | gcgggagacc | acaggaggcg | atcgagctgt | tcttcaagc  | tgcgccggag    300 |
| aatttccgga | gagaaatcgc | gaaggcggag | acggaggttg | gtacggaagt | gaaatgtttg    360 |
| atgactgatg | cgttcttctg | gttcgcggct | gatatggcga | cggagataaa | tgcgtcgtgg    420 |
| attgcgtttt | ggaccgccgg | agcaaactca | ctctctgctc | atctctacac | agatctcatc    480 |
| agagaaacca | tcggtgtcaa | agaagtaggt | gagcgtatgg | aggagacaat | aggggttatc    540 |
| tcaggaatgg | agaagatcag | agtcaaagat | acaccagaag | gagttgtgtt | tgggaattta    600 |
| gactctgttt | tctcaaagat | gcttcatcaa | atgggtcttg | ctttgcctcg | tgccactgct    660 |
| gttttcatca | attcttttga | agatttggat | cctacattga | cgaataaccct | cagatcgaga    720 |
| tttaaacgat | atctgaacat | cggtcctctc | gggttattat | cttctacatt | gcaacaacta    780 |
| gtgcaagatc | ctcacggttg | tttggcttgg | atggagaaga | gatcttctgg | ttctgtggcg    840 |
| tacattagct | ttggtacggt | catgacaccg | cctcctggag | agcttgcggc | gatagcagaa    900 |
| gggttggaat | cgagtaaagt | gccgtttgtt | tggtcgctta | aggagaagag | cttggttcag    960 |
| ttaccaaaag | gttttttgga | taggacaaga | gagcaaggga | tagtggttcc | atgggcaccg   1020 |
| caagtggaac | tgctgaaaca | cgaagcaacg | ggtgtgtttg | tgacgcattg | tggatggaac   1080 |
| tcggtgttgg | agagtgtatc | gggtggtgta | ccgatgattt | gcaggccatt | ttttggggat   1140 |
| cagagattga | acgaagagc  | ggtggaggtt | gtgtgggaga | ttggaatgac | gattatcaat   1200 |
| ggagtcttca | cgaaagatgg | gtttgagaag | tgttttggata | aagttttagt | tcaagatgat   1260 |
| ggtaagaaga | tgaaatgtaa | tgctaagaaa | cttaaagaac | tagcttacga | agctgtctct   1320 |
| tctaaaggaa | ggtcctctga | gaatttcaga | ggattgttgg | atgcagttgt | aaacattatt   1380 |
| tga        |            |            |            |            |           1383 |

```
<210> SEQ ID NO 63
<211> LENGTH: 460
<212> TYPE: PRT
<213> ORGANISM: Arabidopsis thaliana

<400> SEQUENCE: 63
```

```
Met Thr Lys Pro Ser Asp Pro Thr Arg Asp Ser His Val Ala Val Leu
1               5                   10                  15

Ala Phe Pro Phe Gly Thr His Ala Ala Pro Leu Leu Thr Val Thr Arg
            20                  25                  30

Arg Leu Ala Ser Ala Ser Pro Ser Thr Val Phe Ser Phe Phe Asn Thr
        35                  40                  45

Ala Gln Ser Asn Ser Ser Leu Phe Ser Ser Gly Asp Glu Ala Asp Arg
    50                  55                  60
```

```
Pro Ala Asn Ile Arg Val Tyr Asp Ile Ala Asp Gly Val Pro Glu Gly
 65                  70                  75                  80

Tyr Val Phe Ser Gly Arg Pro Gln Glu Ala Ile Glu Leu Phe Leu Gln
                 85                  90                  95

Ala Ala Pro Glu Asn Phe Arg Arg Glu Ile Ala Lys Ala Glu Thr Glu
            100                 105                 110

Val Gly Thr Glu Val Lys Cys Leu Met Thr Asp Ala Phe Phe Trp Phe
        115                 120                 125

Ala Ala Asp Met Ala Thr Glu Ile Asn Ala Ser Trp Ile Ala Phe Trp
    130                 135                 140

Thr Ala Gly Ala Asn Ser Leu Ser Ala His Leu Tyr Thr Asp Leu Ile
145                 150                 155                 160

Arg Glu Thr Ile Gly Val Lys Glu Val Gly Glu Arg Met Glu Glu Thr
                165                 170                 175

Ile Gly Val Ile Ser Gly Met Glu Lys Ile Arg Val Lys Asp Thr Pro
            180                 185                 190

Glu Gly Val Val Phe Gly Asn Leu Asp Ser Val Phe Ser Lys Met Leu
        195                 200                 205

His Gln Met Gly Leu Ala Leu Pro Arg Ala Thr Ala Val Phe Ile Asn
    210                 215                 220

Ser Phe Glu Asp Leu Asp Pro Thr Leu Thr Asn Asn Leu Arg Ser Arg
225                 230                 235                 240

Phe Lys Arg Tyr Leu Asn Ile Gly Pro Leu Gly Leu Leu Ser Ser Thr
                245                 250                 255

Leu Gln Gln Leu Val Gln Asp Pro His Gly Cys Leu Ala Trp Met Glu
            260                 265                 270

Lys Arg Ser Ser Gly Ser Val Ala Tyr Ile Ser Phe Gly Thr Val Met
        275                 280                 285

Thr Pro Pro Pro Gly Glu Leu Ala Ala Ile Ala Glu Gly Leu Glu Ser
    290                 295                 300

Ser Lys Val Pro Phe Val Trp Ser Leu Lys Glu Lys Ser Leu Val Gln
305                 310                 315                 320

Leu Pro Lys Gly Phe Leu Asp Arg Thr Arg Glu Gln Gly Ile Val Val
                325                 330                 335

Pro Trp Ala Pro Gln Val Glu Leu Leu Lys His Glu Ala Thr Gly Val
            340                 345                 350

Phe Val Thr His Cys Gly Trp Asn Ser Val Leu Glu Ser Val Ser Gly
        355                 360                 365

Gly Val Pro Met Ile Cys Arg Pro Phe Phe Gly Asp Gln Arg Leu Asn
    370                 375                 380

Gly Arg Ala Val Glu Val Trp Glu Ile Gly Met Thr Ile Ile Asn
385                 390                 395                 400

Gly Val Phe Thr Lys Asp Gly Phe Glu Lys Cys Leu Asp Lys Val Leu
                405                 410                 415

Val Gln Asp Asp Gly Lys Lys Met Lys Cys Asn Ala Lys Lys Leu Lys
            420                 425                 430

Glu Leu Ala Tyr Glu Ala Val Ser Ser Lys Gly Arg Ser Ser Glu Asn
        435                 440                 445

Phe Arg Gly Leu Leu Asp Ala Val Val Asn Ile Ile
    450                 455                 460

<210> SEQ ID NO 64
<211> LENGTH: 515
<212> TYPE: PRT
```

<213> ORGANISM: Fragaria x ananassa

<400> SEQUENCE: 64

```
Met Gly Ser Ala Val Ala Val Glu Leu Val Phe Ile Pro Ala Pro Gly
1               5                   10                  15

Val Gly His Ile Met Ser Thr Met Glu Met Ala Lys Leu Leu Ile Asn
            20                  25                  30

Arg His Gln Ser Ile Ala Thr Thr Val Leu Leu Ile His Pro Pro Tyr
        35                  40                  45

Ser Ser Ser Val Leu Thr Asn Tyr Ile Gln Ser Leu Leu Thr Asn Pro
    50                  55                  60

Ile Gln Arg Ile Arg Phe Ile Gln Leu Pro Gln Asp Gln Glu Thr Ala
65                  70                  75                  80

Ser Lys Leu Asp Leu Lys Ala Pro Phe Thr Ser Phe Tyr Glu Phe Ile
                85                  90                  95

Asn Ser His Arg Asn Tyr Val Arg Asn Val Val Ser Asp Met Leu Ser
            100                 105                 110

Arg Pro Gly Ser Val Arg Ile Thr Gly Leu Val Val Asp Ile Leu Cys
        115                 120                 125

Thr Gly Met Ile Asp Val Ala Asn Glu Phe Ser Ile Pro Ser Tyr Ala
130                 135                 140

Phe Phe Thr Ser Asn Ala Ala Phe Leu Gly Phe Lys Leu Tyr Met Asp
145                 150                 155                 160

Thr Leu Cys Arg Asn Gln Lys Gln Glu Gly Ile Ile Ala Leu Ser Lys
                165                 170                 175

Ser Asp Gly Glu Leu Arg Ile Pro Ser Phe Val Lys Pro Val Pro Met
            180                 185                 190

Thr Val Tyr Pro Ala Val Tyr Gln Thr Arg Asp Gly Leu Asp Phe Leu
        195                 200                 205

Thr Val Ser Ile Gln Lys Phe Arg Glu Ala Lys Ala Ile Met Val Asn
    210                 215                 220

Thr Phe Leu Glu Leu Glu Thr His Ala Ile Glu Ser Phe Ser Ser Tyr
225                 230                 235                 240

Thr Asn Phe Pro Ser Val Tyr Ala Val Gly Pro Val Leu Asn Leu Asn
                245                 250                 255

Gly Val Ala Gly Lys Asp Glu Asp Lys Asp Val Ile Arg Trp Leu Asp
            260                 265                 270

Gly Gln Pro Pro Ser Ser Val Val Phe Leu Cys Phe Gly Ser Met Gly
        275                 280                 285

Ser Phe Glu Glu Val Gln Leu Lys Gly Ile Ala Tyr Ala Leu Glu Arg
    290                 295                 300

Ser Gly His Arg Phe Val Trp Ser Val Arg Arg Pro Pro Ser Pro Glu
305                 310                 315                 320

Gln Ser Phe Lys Val Leu Pro Asp Asp Tyr Asp Asp Pro Arg Ser Ile
                325                 330                 335

Leu Pro Asp Gly Phe Leu Glu Arg Thr Asn Gly Phe Gly Lys Val Ile
            340                 345                 350

Gly Trp Ala Pro Gln Val Ser Ile Leu Ala His Glu Ala Val Gly Gly
        355                 360                 365

Phe Val Ser His Cys Gly Trp Asn Ser Val Leu Glu Ser Ile Cys Cys
    370                 375                 380

Lys Val Pro Ile Leu Ala Trp Pro Met Met Ala Glu Gln His Leu Asn
385                 390                 395                 400
```

```
Ala Arg Met Val Val Glu Glu Ile Lys Ile Gly Leu Arg Val Glu Thr
                405                 410                 415

Cys Asp Gly Ser Val Arg Gly Phe Val Gln Ala Asp Gly Leu Lys Lys
            420                 425                 430

Met Val Lys Glu Leu Met Glu Gly Glu Asn Gly Glu Ile Val Arg Lys
        435                 440                 445

Arg Val Glu Gly Ile Gly Gly Ala Lys Lys Ala Met Ala Glu Gly
    450                 455                 460

Gly Ser Ser Trp Arg Thr Leu Asn Glu Leu Ile Asp Glu Leu Gln Cys
465                 470                 475                 480

Val Arg Asn Ser Asn Gly Gly Arg Phe Pro Ser Ser Glu Gly Asp Ser
                485                 490                 495

Asp Lys Ser Lys Gly Glu Ser Tyr Val Pro Met Asp Asn Leu Ser Leu
                500                 505                 510

Val Ser Ile
        515

<210> SEQ ID NO 65
<211> LENGTH: 456
<212> TYPE: PRT
<213> ORGANISM: Vitis vinifera

<400> SEQUENCE: 65

Met Ser Gln Thr Thr Thr Asn Pro His Val Ala Val Leu Ala Phe Pro
1               5                   10                  15

Phe Ser Thr His Ala Ala Pro Leu Leu Ala Val Val Arg Arg Leu Ala
                20                  25                  30

Ala Ala Ala Pro His Ala Val Phe Ser Phe Phe Ser Thr Ser Gln Ser
            35                  40                  45

Asn Ala Ser Val Phe His Asp Ser Met His Thr Met Gln Cys Asn Ile
    50                  55                  60

Lys Ser Tyr Asp Val Ser Asp Gly Val Pro Glu Gly Tyr Val Phe Ala
65                  70                  75                  80

Gly Arg Pro Gln Glu Asp Ile Glu Leu Phe Met Arg Ala Ala Pro Glu
                85                  90                  95

Gly Phe Arg Gln Gly Met Val Met Ala Val Ala Glu Thr Gly Arg Pro
            100                 105                 110

Val Ser Cys Leu Val Ala Asp Ala Phe Ile Trp Phe Ala Ala Asp Met
        115                 120                 125

Ala Ala Glu Met Gly Val Ala Trp Leu Pro Phe Trp Thr Ala Gly Pro
    130                 135                 140

Asn Ser Leu Ser Thr His Val Tyr Thr Asp Glu Ile Arg Glu Lys Ile
145                 150                 155                 160

Gly Val Ser Gly Ile Gln Gly Arg Glu Asp Glu Leu Leu Asn Phe Ile
                165                 170                 175

Pro Gly Met Tyr Glu Val Arg Phe Arg Asp Leu Gln Glu Gly Ile Val
            180                 185                 190

Phe Gly Asn Leu Asn Ser Leu Phe Ser Arg Met Leu His Arg Met Gly
        195                 200                 205

Gln Val Leu Pro Lys Ala Thr Ala Val Phe Ile Asn Ser Phe Glu Glu
    210                 215                 220

Leu Asp Asp Ser Leu Thr Asn Asp Leu Lys Ser Lys Leu Lys Thr Tyr
225                 230                 235                 240

Leu Asn Ile Gly Pro Phe Asn Leu Ile Thr Pro Pro Pro Val Val Pro
                245                 250                 255
```

Asn Thr Thr Gly Cys Leu Gln Trp Leu Lys Glu Arg Lys Pro Thr Ser
                260                 265                 270

Val Val Tyr Ile Ser Phe Gly Thr Val Thr Pro Pro Ala Glu
        275                 280                 285

Leu Val Ala Leu Ala Glu Ala Leu Glu Ala Ser Arg Val Pro Phe Ile
    290                 295                 300

Trp Ser Leu Arg Asp Lys Ala Arg Val His Leu Pro Glu Gly Phe Leu
305                 310                 315                 320

Glu Lys Thr Arg Gly Tyr Gly Met Val Val Pro Trp Ala Pro Gln Ala
                325                 330                 335

Glu Val Leu Ala His Glu Ala Val Gly Ala Phe Val Thr His Cys Gly
                340                 345                 350

Trp Asn Ser Leu Trp Glu Ser Val Ala Gly Gly Val Pro Leu Ile Cys
                355                 360                 365

Arg Pro Phe Phe Gly Asp Gln Arg Leu Asn Gly Arg Met Val Glu Asp
    370                 375                 380

Val Leu Glu Ile Gly Val Arg Ile Glu Gly Gly Val Phe Thr Lys Ser
385                 390                 395                 400

Gly Leu Met Ser Cys Phe Asp Gln Ile Leu Ser Gln Glu Lys Gly Lys
                405                 410                 415

Lys Leu Arg Glu Asn Leu Arg Ala Leu Arg Glu Thr Ala Asp Arg Ala
                420                 425                 430

Val Gly Pro Lys Gly Ser Ser Thr Glu Asn Phe Lys Thr Leu Val Asp
                435                 440                 445

Leu Val Ser Lys Pro Lys Asp Val
    450                 455

<210> SEQ ID NO 66
<211> LENGTH: 454
<212> TYPE: PRT
<213> ORGANISM: Forsynthia

<400> SEQUENCE: 66

Met Ala Ile His Ser His Ile Gly Val Leu Ala Phe Pro Phe Gly Thr
1               5                   10                  15

His Ala Ala Pro Leu Leu Thr Leu Val Arg Arg Leu Val Leu Asp Ser
                20                  25                  30

Ser Ser Gln Gly Ile Thr Phe Ser Phe Phe Asn Thr Ala Lys Ser Asn
            35                  40                  45

Cys Ala Ile Phe Ser Gly Gln Glu Phe Asp Asn Ile Lys Ala Tyr Asp
    50                  55                  60

Val Trp Asp Gly Thr His Glu Gly Glu Ala Phe Thr Gly Ser Asn Ile
65                  70                  75                  80

Leu Glu Ala Met Gln Leu Phe Leu Ala Ala Thr Pro Gly Asn Phe Glu
                85                  90                  95

Lys Val Met Lys Glu Ala Glu Val Lys Asn Gly Met Lys Ile Ser Cys
                100                 105                 110

Leu Leu Ser Asp Ala Phe Leu Trp Phe Thr Cys Asp Leu Ala Glu Glu
            115                 120                 125

Arg Gly Ile Pro Trp Val Ser Phe Trp Thr Ala Ala Ser Cys Ser Leu
    130                 135                 140

Ser Ala His Met Tyr Thr Asp Gln Ile Trp Ser Leu Met Arg Ser Thr
145                 150                 155                 160

Gly Thr Ala Lys Thr Glu Glu Lys Thr Leu Ser Phe Val Pro Gly Met

```
                165                 170                 175
Thr Ser Val Arg Phe Ser Asp Leu Pro Glu Glu Ile Leu Ser Asp Asn
            180                 185                 190

Leu Glu Ser Pro Leu Thr Leu Met Ile Tyr Lys Met Val Gln Lys Leu
            195                 200                 205

Ser Lys Ser Thr Ala Ile Val Val Asn Ser Phe Glu Ile Asp Pro
    210                 215                 220

Val Ile Thr Asn Asp Leu Lys Ser Lys Phe Gln Asn Phe Leu Asn Ile
225                 230                 235                 240

Gly Pro Ser Ile Leu Ser Ser Pro Thr Leu Ser Asn Gly Asp Ser Gly
                245                 250                 255

Gln Glu Cys Leu Leu Trp Leu Glu Lys Gln Arg His Ala Ser Val Ile
                260                 265                 270

Tyr Ile Ser Phe Gly Thr Val Ile Thr Pro Gln Pro Arg Glu Met Ala
                275                 280                 285

Gly Leu Ala Glu Ala Leu Glu Thr Gly Glu Phe Pro Phe Leu Trp Ser
            290                 295                 300

Leu Arg Asp Asn Ala Met Lys Leu Leu Pro Asp Gly Phe Leu Asp Arg
305                 310                 315                 320

Thr Ser Lys Phe Gly Met Ile Val Ser Trp Ala Pro Gln Leu Lys Val
                325                 330                 335

Leu Glu Asn Pro Ser Val Gly Ala Phe Ile Thr His Cys Gly Trp Asn
                340                 345                 350

Ser Ile Leu Glu Ser Ile Ser Phe Gly Val Pro Met Ile Cys Arg Pro
                355                 360                 365

Phe Phe Gly Asp Gln Asn Leu Asn Ser Lys Met Val Glu Asp Val Trp
            370                 375                 380

Lys Ile Gly Val Arg Leu Glu Gly Gly Val Phe Thr Lys Asn Gly Thr
385                 390                 395                 400

Ile Glu Ala Leu His Ser Val Met Leu Asn Glu Thr Gly Lys Ala Ile
                405                 410                 415

Arg Glu Asn Ile Asn Lys Leu Lys Arg Lys Ala Gln Asn Ala Val Lys
                420                 425                 430

Phe Asp Gly Thr Ser Thr Lys Asn Phe Arg Ala Leu Leu Glu Leu Ile
            435                 440                 445

Lys Ser Pro Arg Gly Ile
    450

<210> SEQ ID NO 67
<211> LENGTH: 433
<212> TYPE: PRT
<213> ORGANISM: Eggplant

<400> SEQUENCE: 67

Met Thr Thr Ser Gln Leu His Ile Ala Phe Leu Ala Phe Pro Phe Gly
1               5                   10                  15

Thr His Ala Thr Pro Leu Leu Thr Leu Val Gln Lys Ile Ser Pro Phe
                20                  25                  30

Leu Pro Ser Ser Thr Ile Phe Ser Phe Phe Asn Thr Ser Ser Ser Asn
            35                  40                  45

Ser Ser Ile Phe Ser Lys Val Pro Asn Gln Glu Asn Ile Lys Ile Tyr
        50                  55                  60

Asn Val Trp Asp Gly Val Lys Glu Gly Asn Asp Thr Pro Phe Gly Leu
65                  70                  75                  80
```

Glu Ala Ile Lys Leu Phe Ile Gln Ser Thr Leu Leu Ile Ser Lys Ile
            85                  90                  95

Thr Glu Glu Ala Glu Glu Thr Gly Val Lys Phe Ser Cys Ile Phe
        100                 105                 110

Ser Asp Ala Phe Leu Trp Cys Phe Leu Val Lys Leu Pro Lys Lys Met
        115                 120                 125

Asn Ala Pro Gly Val Ala Tyr Trp Thr Gly Gly Ser Cys Ser Leu Ala
        130                 135                 140

Val His Leu Tyr Thr Asp Leu Ile Arg Ser Asn Lys Glu Thr Ser Leu
145                 150                 155                 160

Lys Ile Pro Gly Phe Ser Ser Thr Leu Ser Ile Asn Asp Ile Pro Pro
                165                 170                 175

Glu Val Thr Ala Glu Asp Leu Glu Gly Pro Met Ser Ser Met Leu Tyr
            180                 185                 190

Asn Met Ala Leu Asn Leu His Lys Ala Asp Ala Val Val Leu Asn Ser
        195                 200                 205

Phe Gln Glu Leu Asp Arg Asp Pro Leu Ile Asn Lys Asp Leu Gln Lys
        210                 215                 220

Asn Leu Gln Lys Val Phe Asn Ile Gly Pro Leu Val Leu Gln Ser Ser
225                 230                 235                 240

Arg Lys Leu Asp Glu Ser Gly Cys Ile Gln Trp Leu Asp Lys Gln Lys
                245                 250                 255

Glu Lys Ser Val Val Tyr Leu Ser Phe Gly Thr Val Thr Thr Leu Pro
            260                 265                 270

Pro Asn Glu Ile Gly Ser Ile Ala Glu Ala Leu Glu Thr Lys Lys Thr
        275                 280                 285

Pro Phe Ile Trp Ser Leu Arg Asn Asn Gly Val Lys Asn Leu Pro Lys
        290                 295                 300

Gly Phe Leu Glu Arg Thr Lys Glu Phe Gly Lys Ile Val Ser Trp Ala
305                 310                 315                 320

Pro Gln Leu Glu Ile Leu Ala His Lys Ser Val Gly Val Phe Val Thr
                325                 330                 335

His Cys Gly Trp Asn Ser Ile Leu Glu Gly Ile Ser Phe Gly Val Pro
            340                 345                 350

Met Ile Cys Arg Pro Phe Phe Gly Asp Gln Lys Leu Asn Ser Arg Met
        355                 360                 365

Val Glu Ser Val Trp Glu Ile Gly Leu Gln Ile Glu Gly Gly Ile Phe
        370                 375                 380

Thr Lys Ser Gly Ile Ile Ser Ala Leu Asp Thr Phe Phe Asn Glu Glu
385                 390                 395                 400

Lys Gly Lys Ile Leu Arg Glu Asn Val Glu Gly Leu Lys Glu Lys Ala
                405                 410                 415

Leu Glu Ala Val Asn Gln Met Met Glu Val Gln Gln Lys Ile Ser Arg
            420                 425                 430

Phe

<210> SEQ ID NO 68
<211> LENGTH: 482
<212> TYPE: PRT
<213> ORGANISM: Gentian

<400> SEQUENCE: 68

Met Asp Gln Leu His Val Phe Phe Phe Pro Phe Leu Ala Asn Gly His
1               5                   10                  15

```
Ile Leu Pro Thr Ile Asp Met Ala Lys Leu Phe Ser Ser Arg Gly Val
             20                  25                  30
Lys Ala Thr Leu Ile Thr Thr His Asn Asn Ser Ala Ile Phe Leu Lys
         35                  40                  45
Ala Ile Asn Arg Ser Lys Ile Leu Gly Phe Asp Ile Ser Val Leu Thr
     50                  55                  60
Ile Lys Phe Pro Ser Ala Glu Phe Gly Leu Pro Glu Gly Tyr Glu Thr
 65                  70                  75                  80
Ala Asp Gln Ala Arg Ser Ile Asp Met Met Asp Glu Phe Phe Arg Ala
                 85                  90                  95
Cys Ile Leu Leu Gln Glu Pro Leu Glu Glu Leu Leu Lys Glu His Arg
             100                 105                 110
Pro Gln Ala Leu Val Ala Asp Leu Phe Phe Tyr Trp Ala Asn Asp Ala
         115                 120                 125
Ala Ala Lys Phe Gly Ile Pro Arg Leu Leu Phe His Gly Ser Ser Ser
    130                 135                 140
Phe Ala Met Ile Ala Ala Glu Ser Val Arg Arg Asn Lys Pro Tyr Lys
145                 150                 155                 160
Asn Leu Ser Ser Asp Ser Asp Pro Phe Val Val Pro Asp Ile Pro Asp
                165                 170                 175
Lys Ile Ile Leu Thr Lys Ser Gln Val Pro Thr Pro Asp Glu Thr Glu
            180                 185                 190
Glu Asn Asn Thr His Ile Thr Glu Met Trp Lys Asn Ile Ser Glu Ser
        195                 200                 205
Glu Asn Asp Cys Tyr Gly Val Ile Val Asn Ser Phe Tyr Glu Leu Glu
    210                 215                 220
Pro Asp Tyr Val Asp Tyr Cys Lys Asn Val Leu Gly Arg Arg Ala Trp
225                 230                 235                 240
His Ile Gly Pro Leu Ser Leu Cys Asn Asn Glu Gly Glu Asp Val Ala
                245                 250                 255
Glu Arg Gly Lys Lys Ser Asp Ile Asp Ala His Glu Cys Leu Asn Trp
            260                 265                 270
Leu Asp Ser Lys Asn Pro Asp Ser Val Val Tyr Val Cys Phe Gly Ser
        275                 280                 285
Met Ala Asn Phe Asn Ala Ala Gln Leu His Glu Leu Ala Met Gly Leu
    290                 295                 300
Glu Glu Ser Gly Gln Glu Phe Ile Trp Val Val Arg Thr Cys Val Asp
305                 310                 315                 320
Glu Glu Asp Glu Ser Lys Trp Phe Pro Asp Gly Phe Glu Lys Arg Val
                325                 330                 335
Gln Glu Asn Asn Lys Gly Leu Ile Ile Lys Gly Trp Ala Pro Gln Val
            340                 345                 350
Leu Ile Leu Glu His Glu Ala Val Gly Ala Phe Val Ser His Cys Gly
        355                 360                 365
Trp Asn Ser Thr Leu Glu Gly Ile Cys Gly Gly Val Ala Met Val Thr
    370                 375                 380
Trp Pro Leu Phe Ala Glu Gln Phe Tyr Asn Glu Lys Leu Met Thr Asp
385                 390                 395                 400
Ile Leu Arg Thr Gly Val Ser Val Gly Ser Leu Gln Trp Ser Arg Val
                405                 410                 415
Thr Thr Ser Ala Val Val Lys Arg Glu Ser Ile Ser Lys Ala Val
            420                 425                 430
Arg Arg Leu Met Ala Glu Glu Glu Gly Val Asp Ile Arg Asn Arg Ala
```

```
                435                 440                 445
Lys Ala Leu Lys Glu Lys Ala Lys Lys Ala Val Glu Gly Gly Gly Ser
450                 455                 460

Ser Tyr Ser Asp Leu Ser Ala Leu Leu Val Glu Leu Ser Ser Tyr Pro
465                 470                 475                 480

His Asn

<210> SEQ ID NO 69
<211> LENGTH: 448
<212> TYPE: PRT
<213> ORGANISM: Petunia x hybrida

<400> SEQUENCE: 69

Met Thr Thr Ser Gln Leu His Ile Ala Leu Leu Ala Phe Pro Phe Gly
1               5                  10                  15

Ser His Ala Ala Pro Leu Leu Thr Leu Val Gln Lys Leu Ser Pro Phe
            20                  25                  30

Leu Pro Ser Asp Thr Ile Phe Ser Phe Asn Thr Ser Gln Ser Asn
        35                  40                  45

Thr Ser Ile Phe Ser Glu Gly Ser Lys Pro Asp Asn Ile Lys Val Tyr
50                  55                  60

Asn Val Trp Asp Gly Val Thr Glu Thr Asn Gly Asn Lys Pro Val Gly
65                  70                  75                  80

Leu Glu Ala Ile Lys Leu Phe Ile Gln Ala Thr Pro Thr Asn Phe Glu
                85                  90                  95

Lys Val Met Lys Glu Ala Glu Glu Thr Gly Val Lys Phe Ser Cys
            100                 105                 110

Ile Phe Ser Asp Ala Phe Leu Trp Phe Ser Tyr Lys Leu Ala Glu Lys
        115                 120                 125

Ile Asn Val Pro Trp Ile Ala Phe Trp Thr Ala Ser Gly Ser Leu
130                 135                 140

Ser Val His Leu Tyr Thr Asp Phe Ile Arg Ser Asn Asp Glu Thr Ser
145                 150                 155                 160

Leu Asn Ile Pro Gly Phe Ser Ser Thr Leu Lys Ile Ser Asp Met Pro
                165                 170                 175

Pro Glu Val Met Ala Glu Asn Leu Asp Leu Pro Met Pro Ser Met Leu
            180                 185                 190

Tyr Asn Met Ala Leu Asn Leu His Lys Ala Ala Val Val Leu Asn
        195                 200                 205

Ser Phe Glu Glu Leu Asp Pro Thr Ile Asn Lys Asp Leu Lys Val Lys
210                 215                 220

Leu Gln Lys Val Leu Asn Ile Gly Pro Leu Val Leu Gln Pro Thr Ser
225                 230                 235                 240

Pro Lys Lys Val Leu Asp Ala Cys Asp Glu Arg Gly Cys Ile Ile Trp
                245                 250                 255

Leu Glu Lys Gln Lys Glu Glu Ser Val Val Tyr Leu Ser Phe Gly Thr
            260                 265                 270

Val Thr Thr Leu Pro Pro Asn Glu Ile Val Ala Val Ala Glu Ala Leu
        275                 280                 285

Glu Ala Lys Lys Phe Pro Phe Ile Trp Ser Leu Lys Asp Asn Gly Ile
290                 295                 300

Lys Asn Leu Pro Thr Gly Phe Leu Glu Arg Thr Gly Gln Phe Gly Lys
305                 310                 315                 320

Ile Val Ser Trp Ala Pro Gln Leu Glu Ile Leu Asn His Ser Ala Val
```

```
                    325                 330                 335
Gly Val Phe Val Thr His Cys Gly Trp Asn Ser Ile Leu Glu Gly Ile
                340                 345                 350

Ser Cys Gly Val Pro Met Ile Cys Arg Pro Phe Phe Gly Asp Gln Lys
                355                 360                 365

Leu Asn Ser Arg Met Val Glu Ser Val Trp Gln Ile Gly Leu Gln Ile
                370                 375                 380

Glu Gly Gly Ser Phe Thr Lys Ile Gly Thr Ile Ser Ala Leu Asp Thr
385                 390                 395                 400

Phe Phe Ser Glu Glu Lys Gly Lys Val Leu Arg Glu Asn Val Lys Gly
                405                 410                 415

Leu Lys Glu Arg Ala Leu Glu Ala Val Lys Pro Asp Gly Ser Ser Ser
                420                 425                 430

Lys Asn Phe Lys Asp Leu Val Glu Leu Val Lys Cys His Lys Leu Thr
                435                 440                 445

<210> SEQ ID NO 70
<211> LENGTH: 357
<212> TYPE: PRT
<213> ORGANISM: Malus domestica

<400> SEQUENCE: 70

Met Val Ser Ser Asp Ser Val Asn Ser Arg Val Glu Thr Leu Ala Gly
1               5                   10                  15

Ser Gly Ile Ser Thr Ile Pro Lys Glu Tyr Ile Arg Pro Lys Asp Glu
                20                  25                  30

Leu Val Asn Ile Gly Asp Ile Phe Glu Gln Glu Lys Asn Asn Glu Gly
                35                  40                  45

Pro Gln Val Pro Thr Ile Asp Leu Lys Glu Ile Glu Ser Asp Asn Glu
                50                  55                  60

Lys Val Arg Ala Lys Cys Arg Glu Lys Leu Lys Ala Thr Val Asp
65                  70                  75                  80

Trp Gly Val Met His Leu Val Asn His Gly Ile Ser Asp Glu Leu Met
                85                  90                  95

Asp Lys Val Arg Lys Ala Gly Lys Ala Phe Phe Asp Leu Pro Ile Glu
                100                 105                 110

Gln Lys Glu Lys Tyr Ala Asn Asp Gln Ala Ser Gly Lys Ile Gln Gly
                115                 120                 125

Tyr Gly Ser Lys Leu Ala Asn Asn Ala Ser Gly Gln Leu Glu Trp Glu
130                 135                 140

Asp Tyr Phe Phe His Cys Val Tyr Pro Glu Asp Lys Arg Asp Leu Ser
145                 150                 155                 160

Ile Trp Pro Gln Thr Pro Ala Asp Tyr Ile Glu Ala Thr Ala Glu Tyr
                165                 170                 175

Ala Lys Gln Leu Arg Glu Leu Ala Thr Lys Val Leu Lys Val Leu Ser
                180                 185                 190

Leu Gly Leu Gly Leu Asp Glu Gly Arg Leu Glu Lys Glu Val Gly Gly
                195                 200                 205

Leu Glu Glu Leu Leu Leu Gln Met Lys Ile Asn Tyr Tyr Pro Lys Cys
                210                 215                 220

Pro Gln Pro Glu Leu Ala Leu Gly Val Glu Ala His Thr Asp Val Ser
225                 230                 235                 240

Ala Leu Thr Phe Ile Leu His Asn Met Val Pro Gly Leu Gln Leu Phe
                245                 250                 255
```

Tyr Glu Gly Lys Trp Val Thr Ala Lys Cys Val Pro Asn Ser Ile Val
            260                 265                 270

Met His Ile Gly Asp Thr Leu Glu Ile Leu Ser Asn Gly Lys Tyr Lys
        275                 280                 285

Ser Ile Leu His Arg Gly Met Val Asn Lys Glu Lys Val Arg Ile Ser
    290                 295                 300

Trp Ala Val Phe Cys Glu Pro Pro Lys Glu Lys Ile Ile Leu Lys Pro
305                 310                 315                 320

Leu Pro Glu Thr Val Ser Glu Asp Glu Pro Ala Met Phe Pro Pro Arg
                325                 330                 335

Thr Phe Ala Glu His Ile Gln His Lys Leu Phe Arg Lys Ser Gln Glu
            340                 345                 350

Ala Leu Leu Pro Lys
        355

<210> SEQ ID NO 71
<211> LENGTH: 357
<212> TYPE: PRT
<213> ORGANISM: Pyrus communis

<400> SEQUENCE: 71

Met Val Ser Ser Asp Ser Val Asn Ser Arg Val Glu Thr Leu Ala Gly
1               5                   10                  15

Ser Gly Ile Ser Thr Ile Pro Lys Glu Tyr Ile Arg Pro Lys Asp Glu
            20                  25                  30

Leu Val Asn Ile Gly Asp Ile Phe Glu Gln Glu Lys Asn Asn Glu Gly
        35                  40                  45

Pro Gln Val Pro Thr Ile Asp Leu Lys Glu Ile Glu Ser Asp Asn Glu
    50                  55                  60

Lys Val Arg Ala Lys Cys Arg Glu Glu Leu Lys Lys Ala Ala Val Asp
65                  70                  75                  80

Trp Gly Val Met His Leu Val Asn His Gly Ile Ser Asp Glu Leu Met
                85                  90                  95

Asp Lys Val Arg Lys Ala Gly Lys Ala Phe Phe Asp Leu Pro Ile Glu
            100                 105                 110

Gln Lys Glu Lys Tyr Ala Asn Asp Gln Ala Ser Gly Lys Ile Gln Gly
        115                 120                 125

Tyr Gly Ser Lys Leu Ala Asn Asn Ala Ser Gly Gln Leu Glu Trp Glu
    130                 135                 140

Asp Tyr Phe Phe His Cys Val Tyr Pro Glu Asp Lys Arg Asp Leu Ser
145                 150                 155                 160

Ile Trp Pro Gln Thr Pro Ala Asp Tyr Ile Glu Ala Thr Ala Glu Tyr
                165                 170                 175

Ala Lys Gln Leu Arg Glu Leu Ala Thr Lys Val Leu Lys Val Leu Ser
            180                 185                 190

Leu Gly Leu Gly Leu Asp Glu Gly Arg Leu Glu Lys Val Gly Gly
        195                 200                 205

Leu Glu Glu Leu Leu Leu Gln Met Lys Ile Asn Tyr Tyr Pro Lys Cys
    210                 215                 220

Pro Gln Pro Glu Leu Ala Leu Gly Val Glu Ala His Thr Asp Val Ser
225                 230                 235                 240

Ala Leu Thr Phe Ile Leu His Asn Met Val Pro Gly Leu Gln Leu Phe
                245                 250                 255

Tyr Glu Gly Lys Trp Val Thr Ala Lys Cys Val Pro Asn Ser Ile Val
            260                 265                 270

```
Met His Ile Gly Asp Thr Leu Glu Ile Leu Ser Asn Gly Lys Tyr Lys
            275                 280                 285

Ser Ile Leu His Arg Gly Met Val Asn Lys Glu Lys Val Arg Ile Ser
        290                 295                 300

Trp Ala Val Phe Cys Glu Pro Lys Glu Lys Ile Ile Leu Lys Pro
305                 310                 315                 320

Leu Pro Glu Thr Val Ser Glu Asp Pro Ala Met Phe Pro Pro Arg
                325                 330                 335

Thr Phe Ala Glu His Ile Gln His Lys Leu Phe Arg Lys Ser Gln Glu
                340                 345                 350

Ala Leu Leu Pro Lys
            355

<210> SEQ ID NO 72
<211> LENGTH: 357
<212> TYPE: PRT
<213> ORGANISM: Prunus avium

<400> SEQUENCE: 72

Met Val Ser Ser Asp Ser Val Asn Ser Arg Val Glu Thr Leu Ala Ser
1               5                   10                  15

Ser Gly Ile Ala Thr Ile Pro Lys Glu Tyr Ile Arg Pro Lys Glu Glu
                20                  25                  30

Leu Ile Asn Ile Gly Asp Ile Phe Glu Gln Glu Lys Ser Thr Asp Gly
            35                  40                  45

Pro Gln Val Pro Thr Ile Asp Leu Lys Glu Ile Asp Ser Glu Asn Glu
50                  55                  60

Lys Val Arg Glu Arg Cys Arg Glu Glu Leu Asn Lys Ala Ala Val Asp
65                  70                  75                  80

Trp Gly Val Met His Leu Val Asn His Gly Ile Ser Asp Glu Leu Met
                85                  90                  95

Asp Arg Val Arg Lys Ala Gly Lys Ala Phe Phe Asp Leu Pro Ile Glu
                100                 105                 110

Gln Lys Glu Lys Tyr Ala Asn Asp Gln Ala Ser Gly Lys Ile Gln Gly
            115                 120                 125

Tyr Gly Ser Lys Leu Ala Asn Asn Ala Ser Gly Gln Leu Glu Trp Glu
130                 135                 140

Asp Tyr Phe Phe His Leu Ile Phe Pro Glu Asp Lys Arg Asp Leu Ser
145                 150                 155                 160

Ile Trp Pro Gln Thr Pro Ala Asp Tyr Ile Glu Ala Thr Ala Glu Tyr
                165                 170                 175

Ala Lys Glu Leu Arg Ala Leu Ala Thr Lys Val Leu Arg Val Leu Ser
            180                 185                 190

Leu Gly Leu Gly Leu Glu Glu Gly Arg Leu Glu Lys Glu Val Gly Gly
        195                 200                 205

Leu Glu Glu Leu Leu Leu Gln Met Lys Ile Asn Tyr Tyr Pro Val Cys
    210                 215                 220

Pro Gln Pro Glu Leu Ala Leu Gly Val Glu Ala His Thr Asp Val Ser
225                 230                 235                 240

Ala Leu Thr Phe Ile Leu His Asn Met Val Pro Gly Leu Gln Leu Phe
                245                 250                 255

Tyr Glu Gly Lys Trp Val Thr Ala Lys Cys Val Pro Asn Ser Ile Val
            260                 265                 270

Met His Ile Gly Asp Thr Ile Glu Ile Leu Ser Asn Gly Lys Tyr Lys
```

```
                275                 280                 285

Ser Ile Leu His Arg Gly Met Val Asn Lys Glu Lys Val Arg Ile Ser
    290                 295                 300

Trp Ala Val Phe Cys Glu Pro Pro Lys Glu Lys Ile Ile Leu Lys Pro
305                 310                 315                 320

Leu Pro Glu Thr Val Ser Glu Thr Glu Pro Ile Phe Pro Arg
                    325                 330                 335

Thr Phe Ala Glu His Ile Gln His Lys Leu Phe Arg Lys Ser Gln Glu
                340                 345                 350

Ala Leu Leu Asn Lys
            355

<210> SEQ ID NO 73
<211> LENGTH: 383
<212> TYPE: PRT
<213> ORGANISM: Fragaria x ananassa

<400> SEQUENCE: 73

Met Val Thr Ala Ala Ser Ile Gly Ser Arg Val Glu Ser Leu Ala Ser
1               5                   10                  15

Ser Gly Ile Ser Thr Ile Pro Lys Glu Tyr Val Arg Pro Glu Glu Glu
            20                  25                  30

Leu Val Asn Ile Gly Asp Ile Phe Glu Asp Lys Ser Thr Glu Gly
        35                  40                  45

Pro Gln Val Pro Thr Ile Asp Leu Lys Glu Ile Asp Ser Glu Asp Ile
    50                  55                  60

Lys Val Arg Glu Lys Cys Arg Glu Glu Leu Lys Lys Ala Ala Ile Asp
65                  70                  75                  80

Trp Gly Val Met His Leu Val Asn His Gly Ile Ser Asp Glu Leu Met
                85                  90                  95

Glu Arg Val Lys Lys Ala Gly Lys Ala Phe Phe Asp Leu Pro Val Glu
            100                 105                 110

Gln Lys Glu Lys Tyr Ala Asn Asp Gln Ala Ser Gly Lys Ile Gln Gly
        115                 120                 125

Tyr Gly Ser Lys Leu Ala Asn Asn Ala Ser Gly Gln Leu Glu Trp Glu
    130                 135                 140

Asp Tyr Phe Phe His Cys Val Tyr Pro Glu Asp Lys Arg Asp Leu Ser
145                 150                 155                 160

Ile Trp Pro Gln Thr Pro Ser Asp Tyr Ile Val Ala Thr Ser Glu Tyr
                165                 170                 175

Ala Lys Glu Leu Arg Gly Leu Thr Thr Lys Ile Leu Ser Ile Leu Ser
            180                 185                 190

Leu Gly Leu Gly Leu Glu Glu Gly Arg Leu Glu Lys Glu Val Gly Gly
        195                 200                 205

Leu Glu Glu Leu Leu Leu Gln Met Lys Ile Asn Tyr Tyr Pro Lys Cys
    210                 215                 220

Pro Gln Pro Glu Leu Ala Leu Gly Val Glu Ala His Thr Asp Ile Ser
225                 230                 235                 240

Ala Leu Thr Phe Ile Leu His Asn Met Val Pro Gly Leu Gln Leu Phe
                245                 250                 255

Tyr Gly Gly Lys Trp Val Thr Ala Lys Cys Val Pro Asn Ser Val Val
            260                 265                 270

Met His Ile Gly Asp Thr Leu Glu Ile Leu Ser Asn Gly Lys Tyr Lys
        275                 280                 285
```

-continued

```
Ser Ile Leu His Arg Gly Leu Val Asn Lys Glu Lys Val Arg Ile Ser
    290                 295                 300

Trp Ala Val Phe Cys Glu Pro Lys Glu Lys Ile Ile Leu Lys Pro
305                 310                 315                 320

Leu Pro Glu Thr Val Ser Glu Glu Pro Ala Ile Phe Pro Pro Arg
                325                 330                 335

Thr Phe Phe Glu His Ile Gln His Lys Leu Phe Arg Gln Ser Gln Glu
                340                 345                 350

Ala Leu Val Ser Thr Lys Glu Ser Ala Ala Leu Lys Ser Thr Lys Glu
                355                 360                 365

Ser Ala Leu Lys Ser Thr Lys Glu Ala Ala Leu Ile Ser Thr Asn
    370                 375                 380

<210> SEQ ID NO 74
<211> LENGTH: 355
<212> TYPE: PRT
<213> ORGANISM: Vitis vinifera

<400> SEQUENCE: 74

Met Val Thr Ser Val Ala Pro Arg Val Glu Ser Leu Ser Ser Ser Gly
1               5                   10                  15

Ile Gln Ser Ile Pro Lys Glu Tyr Ile Arg Pro Gln Glu Glu Leu Thr
                20                  25                  30

Ser Ile Gly Asn Val Phe Glu Glu Lys Lys Asp Glu Gly Pro Gln
            35                  40                  45

Val Pro Thr Ile Asp Leu Lys Asp Ile Glu Ser Glu Asp Val Val
50                  55                  60

Arg Glu Arg Cys Arg Glu Glu Leu Lys Lys Ala Ala Met Glu Trp Gly
65                  70                  75                  80

Val Met His Leu Val Asn His Gly Ile Ser Asp Asp Leu Ile Asn Arg
                85                  90                  95

Val Lys Val Ala Gly Glu Thr Phe Phe Asn Leu Pro Met Glu Glu Lys
                100                 105                 110

Glu Lys Tyr Ala Asn Asp Gln Ala Ser Gly Lys Ile Ala Gly Tyr Gly
            115                 120                 125

Ser Lys Leu Ala Asn Asn Ala Ser Gly Gln Leu Glu Trp Glu Asp Tyr
    130                 135                 140

Phe Phe His Leu Ile Phe Pro Glu Asp Lys Arg Asp Met Thr Ile Trp
145                 150                 155                 160

Pro Lys Thr Pro Ser Asp Tyr Val Pro Ala Thr Cys Glu Tyr Ser Val
                165                 170                 175

Lys Leu Arg Ser Leu Ala Thr Lys Ile Leu Ser Val Leu Ser Leu Gly
                180                 185                 190

Leu Gly Leu Glu Glu Gly Arg Leu Glu Lys Glu Val Gly Gly Met Glu
            195                 200                 205

Glu Leu Leu Leu Gln Lys Lys Ile Asn Tyr Tyr Pro Lys Cys Pro Gln
    210                 215                 220

Pro Glu Leu Ala Leu Gly Val Glu Ala His Thr Asp Val Ser Ala Leu
225                 230                 235                 240

Thr Phe Ile Leu His Asn Met Val Pro Gly Leu Gln Leu Phe Tyr Glu
                245                 250                 255

Gly Lys Trp Val Thr Ala Lys Cys Val Pro Asn Ser Ile Ile Met His
                260                 265                 270

Ile Gly Asp Thr Ile Glu Ile Leu Ser Asn Gly Lys Tyr Lys Ser Ile
            275                 280                 285
```

Leu His Arg Gly Leu Val Asn Lys Glu Lys Val Arg Ile Ser Trp Ala
        290                 295                 300

Val Phe Cys Glu Pro Pro Lys Glu Lys Ile Ile Leu Lys Pro Leu Pro
305                 310                 315                 320

Glu Thr Val Ser Glu Thr Glu Pro Pro Leu Phe Pro Pro Arg Thr Phe
                325                 330                 335

Ser Gln His Ile Gln His Lys Leu Phe Arg Lys Thr Gln Glu Ala Leu
                340                 345                 350

Leu Ser Lys
        355

<210> SEQ ID NO 75
<211> LENGTH: 371
<212> TYPE: PRT
<213> ORGANISM: Ipomoea purpurea

<400> SEQUENCE: 75

Met Leu Ser Thr Ile Thr Ala Thr Val Pro Ser Arg Val Glu Arg Leu
1               5                   10                  15

Ala Gly Ser Gly Ile Glu Arg Ile Pro Lys Glu Tyr Ile Arg Pro Glu
                20                  25                  30

Glu Glu Arg Arg Ser Ile Gly Asp Ile Phe Glu Glu Glu Lys Ile Ala
            35                  40                  45

Gly Gly Pro Gln Val Pro Thr Val Asp Leu Lys Gly Ile Asn Ser Glu
        50                  55                  60

Asp Leu Glu Val Arg Glu Lys Cys Arg Glu Glu Leu Arg Lys Ala Ala
65                  70                  75                  80

Val Asp Trp Gly Val Met His Leu Val Asn His Gly Ile Pro Glu Glu
                85                  90                  95

Leu Thr Gly Arg Val Lys Ala Ala Gly Glu Gly Phe Phe Gly Gln Pro
                100                 105                 110

Ile Glu Glu Lys Glu Lys Tyr Ala Asn Asp Gln Ala Ala Gly Asn Val
            115                 120                 125

Gln Gly Tyr Gly Ser Lys Leu Ala Asn Asn Ala Ser Gly Gln Leu Glu
        130                 135                 140

Trp Glu Asp Tyr Phe Phe His Cys Ile Phe Pro Glu Asp Lys Thr Asp
145                 150                 155                 160

Leu Ser Ile Trp Pro Lys Thr Pro Ser Asp Tyr Ile Asp Ala Thr Arg
                165                 170                 175

Glu Tyr Ala Lys Gln Leu Arg Ala Leu Ala Thr Lys Val Leu Ala Val
            180                 185                 190

Leu Ser Leu Gly Leu Gly Leu Glu Glu Gly Arg Leu Glu Lys Glu Val
        195                 200                 205

Gly Gly Met Glu Glu Leu Leu Leu Gln Met Lys Ile Asn Tyr Tyr Pro
    210                 215                 220

Lys Cys Pro Gln Pro Glu Leu Ala Leu Gly Val Glu Ala His Thr Asp
225                 230                 235                 240

Val Ser Ala Leu Thr Phe Ile Leu His Asn Met Val Pro Gly Leu Gln
                245                 250                 255

Leu Phe Tyr Gly Gly Lys Trp Val Thr Ala Lys Cys Val Pro Asn Ser
            260                 265                 270

Ile Ile Met His Val Gly Asp Thr Val Glu Ile Leu Ser Asn Gly Lys
        275                 280                 285

Tyr Lys Ser Ile Leu His Arg Gly Val Val Asn Arg Glu Lys Val Arg

```
                290                 295                 300
Val Ser Trp Ala Val Phe Cys Glu Pro Pro Lys Asp Lys Ile Leu Leu
305                 310                 315                 320

Gln Pro Leu Pro Glu Thr Val Ser Glu Ala Glu Pro Pro Arg Phe Pro
                325                 330                 335

Pro Arg Thr Phe Ala Gln His Ile Lys His Lys Leu Phe Arg Gln Ser
                340                 345                 350

Asp Gln Glu Ala Ala His Thr Pro Lys Pro Asp Asn Asp Asp Asp His
            355                 360                 365

Gln Ser Asn
    370

<210> SEQ ID NO 76
<211> LENGTH: 354
<212> TYPE: PRT
<213> ORGANISM: Camellia sinensis

<400> SEQUENCE: 76

Met Thr Thr Val Ala Ala Pro Arg Val Gln Ser Leu Ala Thr Ser Gly
1               5                   10                  15

Ile Glu Ser Ile Pro Lys Glu Tyr Val Arg Pro Lys Glu Glu Leu Thr
            20                  25                  30

Gly Ile Gly Asn Ile Phe Glu Glu Lys Asn Glu Glu Gly Pro Gln
        35                  40                  45

Val Pro Thr Ile Asp Leu Lys Asp Ile Asp Ser Glu Val Glu Glu Val
    50                  55                  60

Arg Glu Arg Cys Arg Glu Ala Leu Lys Lys Ala Val Asp Trp Gly
65                  70                  75                  80

Val Met His Leu Val Asn His Gly Ile Ala Asp Asp Val Arg Glu Arg
                85                  90                  95

Val Lys Val Ala Gly Glu Gly Phe Phe Glu Gln Pro Val Glu Glu Lys
            100                 105                 110

Glu Lys Tyr Ala Asn Asp Pro Asp Asn Gly Asn Leu Gln Gly Tyr Gly
        115                 120                 125

Ser Lys Leu Ala Asn Asn Ala Cys Gly Gln Phe Glu Trp Glu Asp Tyr
    130                 135                 140

Phe Phe His Leu Ala Tyr Pro Glu Asp Lys Cys Asp Met Ser Ile Trp
145                 150                 155                 160

Pro Lys Thr Pro Thr Asp Tyr Ile Pro Ala Thr Val Glu Tyr Ala Lys
                165                 170                 175

Gln Leu Arg Ala Leu Ala Thr Lys Thr Leu Ser Ile Leu Ser Leu Gly
            180                 185                 190

Leu Gly Leu Glu Glu Asn Lys Leu Glu Lys Glu Val Gly Gly Lys Glu
        195                 200                 205

Glu Leu Leu Leu Gln Met Lys Ile Asn Tyr Tyr Pro Lys Cys Pro Gln
    210                 215                 220

Pro Glu Leu Ala Leu Gly Val Glu Ala His Thr Asp Leu Ser Ala Val
225                 230                 235                 240

Ser Phe Ile Leu Pro Ser Met Val Pro Gly Leu Gln Leu Phe Tyr Glu
                245                 250                 255

Gly Lys Trp Ile Thr Ala Lys Cys Val Pro Asn Ser Ile Ile Met Leu
            260                 265                 270

Ile Gly Asp Thr Val Glu Ile Leu Ser Asn Gly Lys Tyr Lys Ser Ile
        275                 280                 285
```

```
Leu His Arg Gly Leu Val Asn Lys Glu Lys Val Arg Ile Ser Trp Ala
    290                 295                 300

Val Phe Cys Glu Pro Pro Lys Glu Lys Ile Ile Leu Lys Pro Leu Pro
305                 310                 315                 320

Glu Thr Val Ser Glu Ala Glu Pro Pro Leu Phe Pro Pro Arg Thr Phe
                325                 330                 335

Ala Gln His Ile Gln His Lys Leu Phe Arg Lys Ser Gln Glu Leu Gly
                340                 345                 350

Ser Lys

<210> SEQ ID NO 77
<211> LENGTH: 357
<212> TYPE: PRT
<213> ORGANISM: Citrus sinensis

<400> SEQUENCE: 77

Met Val Thr Pro Thr Ala Arg Arg Val Glu Ser Leu Ala Arg Ser Gly
1               5                   10                  15

Ile Gln Ala Ile Pro Lys Glu Tyr Val Arg Pro Lys Glu Glu Leu Met
                20                  25                  30

Gly Ile Gly Asn Ile Phe Glu Glu Glu Lys Asp Glu Gly Pro Gln
            35                  40                  45

Val Pro Thr Ile Asp Leu Lys Glu Ile Asp Ser Glu Asp Arg Val Glu
50                  55                  60

Arg Glu Lys Cys Arg Glu Glu Leu Lys Lys Ala Ala Met Asp Trp Gly
65                  70                  75                  80

Val Met His Leu Val Asn His Gly Ile Ser Asp Asp Leu Thr Glu Arg
                85                  90                  95

Val Lys Arg Ala Gly Gln Ala Phe Phe Asp Gln Pro Val Glu Glu Lys
                100                 105                 110

Glu Lys Tyr Ala Asn Glu Gln Ala Ser Gly Lys Ile Gln Gly Tyr Gly
            115                 120                 125

Ser Lys Leu Ala Asn Asn Ala Ser Gly Gln Leu Glu Trp Glu Asp Tyr
130                 135                 140

Phe Phe His Leu Ile Tyr Pro Glu Asp Lys Arg Asp Met Ser Ile Trp
145                 150                 155                 160

Pro Lys Thr Pro Ser Asp Tyr Thr Glu Ala Thr Ser Glu Tyr Ala Arg
                165                 170                 175

Gln Leu Arg Ser Leu Ala Thr Lys Ile Leu Ala Val Leu Ser Leu Gly
            180                 185                 190

Leu Gly Leu Glu Glu Gly Arg Leu Glu Lys Glu Val Gly Gly Leu Glu
        195                 200                 205

Glu Leu Leu Leu Gln Met Lys Ile Asn Tyr Tyr Pro Lys Cys Pro Gln
210                 215                 220

Pro Glu Leu Ala Leu Gly Val Glu Ala His Thr Asp Val Ser Ala Leu
225                 230                 235                 240

Thr Phe Ile Leu His Asn Met Val Pro Gly Leu Gln Leu Phe Tyr Lys
                245                 250                 255

Asp Lys Trp Val Thr Ala Lys Cys Val Pro Asn Ser Ile Ile Leu His
            260                 265                 270

Ile Gly Asp Thr Ile Glu Ile Leu Ser Asn Gly Glu Tyr Lys Ser Ile
        275                 280                 285

Leu His Arg Gly Leu Val Asn Lys Glu Lys Val Arg Ile Ser Trp Ala
    290                 295                 300
```

```
Val Phe Cys Glu Pro Pro Lys Asp Lys Ile Ile Leu Lys Pro Leu Pro
305                 310                 315                 320

Glu Thr Val Ser Glu Gln Lys Pro Ala Met Phe Pro Pro Arg Thr Phe
                325                 330                 335

Gln Gln His Ile Glu His Lys Leu Phe Arg Arg Thr Gln Asp Ala Leu
            340                 345                 350

Leu Ser Asp Glu Glu
        355

<210> SEQ ID NO 78
<211> LENGTH: 360
<212> TYPE: PRT
<213> ORGANISM: Vaccinium ashei

<400> SEQUENCE: 78

Met Val Ser Thr Met Val Ala Ala Pro Ser Arg Val Glu Ser Leu Ala
1               5                   10                  15

Ser Ser Gly Ile Gln Ser Ile Pro Lys Glu Tyr Val Arg Pro Lys Glu
            20                  25                  30

Glu Leu Thr Ser Ile Gly Asn Ile Phe Glu Glu Lys Lys His Glu
        35                  40                  45

Gly Pro Gln Val Pro Thr Ile Asp Leu Glu Asp Leu Val Ser Glu Asp
    50                  55                  60

Lys Glu Ala Arg Glu Arg Cys His Glu Ala Leu Lys Lys Ala Ala Thr
65                  70                  75                  80

Glu Trp Gly Val Met His Leu Val Asn His Gly Val Pro Glu Glu Leu
                85                  90                  95

Met Asp Arg Val Arg Val Ala Gly Glu Gly Phe Phe Asn Gln Pro Val
            100                 105                 110

Glu Glu Lys Glu Lys Tyr Ala Asn Asp His Asp Thr Gly Asn Ser Gly
        115                 120                 125

Lys Ile Gln Gly Tyr Gly Ser Lys Leu Ala Asn Asn Ala Ser Gly Gln
130                 135                 140

Leu Glu Trp Glu Asp Tyr Phe Phe His Thr Val Tyr Pro Glu Asp Lys
145                 150                 155                 160

Arg Asp Met Lys Ile Trp Pro Lys Asn Pro Ser Asp Tyr Ile Pro Ala
                165                 170                 175

Thr Ser Glu Tyr Ala Asn His Leu Arg Ala Leu Thr Thr Lys Val Leu
            180                 185                 190

Ser Ala Leu Ser Val Cys Leu Gly Leu Glu Glu Asp Arg Leu Glu Lys
        195                 200                 205

Glu Val Gly Gly Lys Asp Glu Leu Val Ile Gln Met Lys Ile Asn Tyr
210                 215                 220

Tyr Pro Lys Cys Pro Gln Pro Glu Leu Ala Leu Gly Val Glu Ala His
225                 230                 235                 240

Thr Asp Val Ser Ala Leu Thr Phe Ile Leu His Asn Met Val Pro Gly
                245                 250                 255

Leu Gln Leu Phe Tyr Glu Gly Lys Trp Ile Thr Ala Lys Cys Val Pro
            260                 265                 270

Asn Ser Ile Ile Met His Ile Gly Asp Thr Val Glu Ile Leu Ser Asn
        275                 280                 285

Gly Lys Tyr Lys Ser Ile Leu His Arg Gly Leu Val Asn Lys Glu Lys
290                 295                 300

Val Arg Ile Ser Trp Ala Ala Phe Cys Glu Pro Pro Lys Glu Lys Ile
305                 310                 315                 320
```

```
Ile Leu Lys Pro Leu Pro Glu Thr Val Ser Glu Thr Glu Pro Ala Arg
                325                 330                 335

Tyr Pro Pro Arg Thr Phe Ser Gln His Ile Glu His Lys Leu Phe Arg
                340                 345                 350

Lys Thr Gln Ala Leu Asn Gly Ala
            355                 360

<210> SEQ ID NO 79
<211> LENGTH: 361
<212> TYPE: PRT
<213> ORGANISM: Populus trichocarpa

<400> SEQUENCE: 79

Met Met Val Thr Ser Ser Phe Val Val Pro Arg Val Glu Ser Leu Ala
1               5                   10                  15

Ser Ser Gly Ile Gln Ser Ile Pro Lys Glu Tyr Ile Arg Pro Gln Glu
            20                  25                  30

Glu Leu Ser Ser Ile Arg Asp Val Phe Glu Glu Lys Lys Val Glu
        35                  40                  45

Gly Pro Gln Val Pro Thr Ile Asp Leu Lys Glu Met Glu Ser Glu Asp
    50                  55                  60

Lys Val Val Arg Glu Lys Cys Arg Glu Glu Leu Val Lys Ala Ala Thr
65                  70                  75                  80

Glu Trp Gly Val Met His Leu Val Asn His Gly Ile Pro Asp Asp Leu
                85                  90                  95

Ile Asp Arg Val Lys Lys Ala Gly Gln Ala Phe Phe Asp Leu Pro Ile
            100                 105                 110

Glu Glu Lys Glu Lys His Ala Asn Asp Gln Ala Ser Gly Asn Val Gln
        115                 120                 125

Gly Tyr Gly Ser Lys Leu Ala Asn Asn Ala Ser Gly Gln Leu Glu Trp
    130                 135                 140

Glu Asp Tyr Phe Phe His Leu Ile Phe Pro Glu Asp Lys Arg Asp Phe
145                 150                 155                 160

Ser Ile Trp Pro Lys Thr Pro Ser Asp Tyr Thr Glu Val Thr Ser Glu
                165                 170                 175

Tyr Ala Arg Gln Leu Arg Ser Leu Ala Thr Lys Ile Leu Ser Val Leu
            180                 185                 190

Ser Leu Gly Leu Gly Leu Glu Glu Gly Arg Leu Glu Lys Glu Val Gly
        195                 200                 205

Gly Leu Glu Glu Leu Leu Leu Gln Met Lys Ile Asn Tyr Tyr Pro Lys
    210                 215                 220

Cys Pro Gln Pro Asp Leu Ala Leu Gly Val Glu Ala His Ser Asp Val
225                 230                 235                 240

Ser Ala Leu Thr Phe Ile Leu His Asn Met Val Pro Gly Leu Gln Leu
                245                 250                 255

Leu Tyr Glu Gly Lys Trp Ile Thr Ala Lys Cys Val Pro Asn Ser Ile
            260                 265                 270

Ile Met His Ile Gly Asp Thr Val Glu Ile Leu Ser Asn Gly Lys Tyr
        275                 280                 285

Lys Ser Ile Ile His Arg Gly Leu Val Asn Lys Glu Lys Val Arg Ile
    290                 295                 300

Ser Trp Ala Val Phe Cys Glu Pro Pro Lys Ala Lys Ile Ile Leu Lys
305                 310                 315                 320

Pro Leu Ala Glu Ile Val Thr Glu Ala Glu Pro Pro Leu Phe Pro Pro
```

```
                    325                 330                 335
Arg Thr Phe Ser Gln His Ile Glu His Lys Leu Phe Arg Lys Thr Gln
                340                 345                 350
Asp Ser Leu Leu Pro Arg Lys Ala Asn
            355                 360

<210> SEQ ID NO 80
<211> LENGTH: 541
<212> TYPE: PRT
<213> ORGANISM: Rhodobacter capsulatus

<400> SEQUENCE: 80

Met Leu Asp Ala Thr Ile Gly Arg Lys Arg Met Thr Leu Gln Ser Gln
1               5                   10                  15

Thr Ala Lys Asp Cys Leu Ala Leu Asp Gly Ala Leu Thr Leu Val Gln
                20                  25                  30

Cys Glu Ala Ile Ala Thr His Arg Ser Arg Ile Ser Val Thr Pro Ala
            35                  40                  45

Leu Arg Glu Arg Cys Ala Arg Ala His Ala Arg Leu Glu His Ala Ile
        50                  55                  60

Ala Glu Gln Arg His Ile Tyr Gly Ile Thr Thr Gly Phe Gly Pro Leu
65                  70                  75                  80

Ala Asn Arg Leu Ile Gly Ala Asp Gln Gly Ala Glu Leu Gln Gln Asn
                85                  90                  95

Leu Ile Tyr His Leu Ala Thr Gly Val Gly Pro Lys Leu Ser Trp Ala
            100                 105                 110

Glu Ala Arg Ala Leu Met Leu Ala Arg Leu Asn Ser Ile Leu Gln Gly
        115                 120                 125

Ala Ser Gly Ala Ser Pro Glu Thr Ile Asp Arg Ile Val Ala Val Leu
130                 135                 140

Asn Ala Gly Phe Ala Pro Glu Val Pro Ala Gln Gly Thr Val Gly Ala
145                 150                 155                 160

Ser Gly Asp Leu Thr Pro Leu Ala His Met Val Leu Ala Leu Gln Gly
                165                 170                 175

Arg Gly Arg Met Ile Asp Pro Ser Gly Arg Val Gln Glu Ala Gly Ala
            180                 185                 190

Val Met Asp Arg Leu Cys Gly Gly Pro Leu Thr Leu Ala Ala Arg Asp
        195                 200                 205

Gly Leu Ala Leu Val Asn Gly Thr Ser Ala Met Thr Ala Ile Ala Ala
210                 215                 220

Leu Thr Gly Val Glu Ala Ala Arg Ala Ile Asp Ala Ala Leu Arg His
225                 230                 235                 240

Ser Ala Val Leu Met Glu Val Leu Ser Gly His Ala Glu Ala Trp His
                245                 250                 255

Pro Ala Phe Ala Glu Leu Arg Pro His Pro Gly Gln Leu Arg Ala Thr
            260                 265                 270

Glu Arg Leu Ala Gln Ala Leu Asp Gly Ala Gly Arg Val Cys Arg Thr
        275                 280                 285

Leu Thr Ala Ala Arg Arg Leu Thr Ala Ala Asp Leu Arg Pro Glu Asp
        290                 295                 300

His Pro Ala Gln Asp Ala Tyr Ser Leu Arg Val Pro Gln Leu Val
305                 310                 315                 320

Gly Ala Val Trp Asp Thr Leu Asp Trp His Asp Arg Val Thr Cys
                325                 330                 335
```

```
Glu Leu Asn Ser Val Thr Asp Asn Pro Ile Phe Pro Glu Gly Cys Ala
                340                 345                 350

Val Pro Ala Leu His Gly Gly Asn Phe Met Gly Val His Val Ala Leu
                355                 360                 365

Ala Ser Asp Ala Leu Asn Ala Ala Leu Val Thr Leu Ala Gly Leu Val
            370                 375                 380

Glu Arg Gln Ile Ala Arg Leu Thr Asp Glu Lys Leu Asn Lys Gly Leu
385                 390                 395                 400

Pro Ala Phe Leu His Gly Gly Gln Ala Gly Leu Gln Ser Gly Phe Met
                405                 410                 415

Gly Ala Gln Val Thr Ala Thr Ala Leu Leu Ala Glu Met Arg Ala Asn
                420                 425                 430

Ala Thr Pro Val Ser Val Gln Ser Leu Ser Thr Asn Gly Ala Asn Gln
            435                 440                 445

Asp Val Val Ser Met Gly Thr Ile Ala Ala Arg Arg Ala Arg Ala Gln
            450                 455                 460

Leu Leu Pro Leu Ser Gln Ile Gln Ala Ile Leu Ala Leu Ala Leu Ala
465                 470                 475                 480

Gln Ala Met Asp Leu Leu Asp Asp Pro Glu Gly Gln Ala Gly Trp Ser
                485                 490                 495

Leu Thr Ala Arg Asp Leu Arg Asp Arg Ile Arg Ala Val Ser Pro Gly
                500                 505                 510

Leu Arg Ala Asp Arg Pro Leu Ala Gly His Ile Glu Ala Val Ala Gln
            515                 520                 525

Gly Leu Arg His Pro Ser Ala Ala Asp Pro Pro Ala
            530                 535                 540

<210> SEQ ID NO 81
<211> LENGTH: 701
<212> TYPE: PRT
<213> ORGANISM: Rice

<400> SEQUENCE: 81

Met Ala Gly Asn Gly Pro Ile Asn Lys Glu Asp Pro Leu Asn Trp Gly
1               5                   10                  15

Ala Ala Ala Ala Glu Met Ala Gly Ser His Leu Asp Glu Val Lys Arg
                20                  25                  30

Met Val Ala Gln Phe Arg Glu Pro Leu Val Lys Ile Gln Gly Ala Thr
            35                  40                  45

Leu Arg Val Gly Gln Val Ala Val Ala Gln Ala Lys Asp Ala Ala
    50                  55                  60

Arg Val Ala Val Glu Leu Asp Glu Glu Ala Arg Pro Arg Val Lys Ala
65                  70                  75                  80

Ser Ser Glu Trp Ile Leu Thr Cys Ile Ala His Gly Gly Asp Ile Tyr
                85                  90                  95

Gly Val Thr Thr Gly Phe Gly Thr Ser His Arg Arg Thr Lys Asp
            100                 105                 110

Gly Pro Ala Leu Gln Val Glu Leu Leu Arg Tyr Leu Asn Ala Gly Ile
        115                 120                 125

Phe Gly Thr Gly Ser Asp Gly His Thr Leu Pro Ser Glu Thr Val Arg
    130                 135                 140

Ala Ala Met Leu Val Arg Ile Asn Thr Leu Leu Gln Gly Tyr Ser Gly
145                 150                 155                 160

Ile Arg Phe Glu Ile Leu Glu Ala Ile Thr Lys Leu Leu Asn Thr Gly
                165                 170                 175
```

-continued

Val Thr Pro Cys Leu Pro Leu Arg Gly Thr Ile Thr Ala Ser Gly Asp
            180                 185                 190

Leu Val Pro Leu Ser Tyr Ile Ala Gly Leu Ile Thr Gly Arg Pro Asn
        195                 200                 205

Ala Gln Ala Ile Ser Pro Asp Gly Arg Lys Val Asp Ala Ala Glu Ala
    210                 215                 220

Phe Lys Leu Ala Gly Ile Glu Gly Phe Phe Thr Leu Asn Pro Lys
225                 230                 235                 240

Glu Gly Leu Ala Ile Val Asn Gly Thr Ser Val Gly Ser Ala Leu Ala
                245                 250                 255

Ala Thr Val Met Phe Asp Ala Asn Ile Leu Ala Val Leu Ser Glu Val
            260                 265                 270

Leu Ser Ala Val Phe Cys Glu Val Met Asn Gly Lys Pro Glu Tyr Thr
        275                 280                 285

Asp His Leu Thr His Lys Leu Lys His His Pro Gly Ser Ile Asp Ala
    290                 295                 300

Ala Ala Ile Met Glu His Ile Leu Ala Gly Ser Ser Phe Met Ser His
305                 310                 315                 320

Ala Lys Lys Val Asn Glu Met Asp Pro Leu Leu Lys Pro Lys Gln Asp
                325                 330                 335

Arg Tyr Ala Leu Arg Thr Ser Pro Gln Trp Leu Gly Pro Gln Ile Gln
            340                 345                 350

Val Ile Arg Ala Ala Thr Lys Ser Ile Glu Arg Glu Val Asn Ser Val
        355                 360                 365

Asn Asp Asn Pro Val Ile Asp Val His Arg Gly Lys Ala Leu His Gly
    370                 375                 380

Gly Asn Phe Gln Gly Thr Pro Ile Gly Val Ser Met Asp Asn Ala Arg
385                 390                 395                 400

Leu Ala Ile Ala Asn Ile Gly Lys Leu Met Phe Ala Gln Phe Ser Glu
                405                 410                 415

Leu Val Asn Glu Phe Tyr Asn Asn Gly Leu Thr Ser Asn Leu Ala Gly
            420                 425                 430

Ser Arg Asn Pro Ser Leu Asp Tyr Gly Phe Lys Gly Thr Glu Ile Ala
        435                 440                 445

Met Ala Ser Tyr Ser Ser Glu Leu Gln Tyr Leu Ala Asn Pro Ile Thr
    450                 455                 460

Asn His Val Gln Ser Ala Glu Gln His Asn Gln Asp Val Asn Ser Leu
465                 470                 475                 480

Gly Leu Val Ser Ala Arg Lys Thr Leu Glu Ala Val Asp Ile Leu Lys
                485                 490                 495

Leu Met Thr Ser Thr Tyr Ile Val Ala Leu Cys Gln Ala Val Asp Leu
            500                 505                 510

Arg His Leu Glu Glu Asn Ile Lys Ser Ser Val Lys Asn Cys Val Thr
        515                 520                 525

Gln Val Ala Lys Lys Val Leu Thr Met Asn Pro Thr Gly Asp Leu Ser
    530                 535                 540

Ser Ala Arg Phe Ser Glu Lys Asn Leu Leu Thr Ala Ile Asp Arg Glu
545                 550                 555                 560

Ala Val Phe Ser Tyr Ala Asp Asp Pro Cys Ser Ala Asn Tyr Pro Leu
                565                 570                 575

Met Gln Lys Leu Arg Ala Val Leu Val Glu His Ala Leu Thr Ser Gly
            580                 585                 590

```
Asp Arg Arg Ala Arg Gly Leu Arg Val Leu Gln Asp His Gln Val Arg
            595                 600                 605

Gly Gly Ala Pro Leu Cys Ala Ala Pro Gly Asp Arg Gly Arg Pro Arg
610                 615                 620

Arg Arg Arg Gln Arg Thr Ala Pro Val Ala Asn Arg Ile Val Glu Ser
625                 630                 635                 640

Arg Ser Phe Pro Leu Tyr Arg Phe Val Arg Glu Leu Gly Cys Val
            645                 650                 655

Phe Leu Thr Gly Glu Lys Leu Lys Ser Pro Gly Glu Glu Cys Asn Lys
                660                 665                 670

Val Phe Leu Gly Ile Ser Gln Gly Lys Leu Ile Asp Pro Met Leu Asp
            675                 680                 685

Cys Leu Lys Glu Trp Asn Gly Glu Pro Leu Pro Ile Asn
690                 695                 700

<210> SEQ ID NO 82
<211> LENGTH: 580
<212> TYPE: PRT
<213> ORGANISM: Parsley

<400> SEQUENCE: 82

Phe Leu Asn Ala Gly Ile Phe Gly Asn Gly Ser Asp Asn Thr Leu Pro
1               5                   10                  15

His Ser Ala Thr Arg Ala Ala Met Leu Val Arg Ile Asn Thr Leu Leu
            20                  25                  30

Gln Gly Tyr Ser Gly Ile Arg Phe Glu Ile Leu Glu Ala Ile Thr Lys
        35                  40                  45

Phe Leu Asn Gln Asn Ile Thr Pro Cys Leu Pro Leu Arg Gly Thr Ile
50                  55                  60

Thr Ala Ser Gly Asp Leu Val Pro Leu Ser Tyr Ile Ala Gly Leu Leu
65                  70                  75                  80

Thr Gly Arg Pro Asn Ser Lys Ala Val Gly Pro Thr Gly Val Ile Leu
                85                  90                  95

Ser Pro Glu Glu Ala Phe Lys Leu Ala Gly Val Glu Gly Gly Phe Phe
            100                 105                 110

Glu Leu Gln Pro Lys Glu Gly Leu Ala Leu Val Asn Gly Thr Ala Val
        115                 120                 125

Gly Ser Gly Met Ala Ser Met Val Leu Phe Glu Ala Asn Ile Leu Ala
130                 135                 140

Val Leu Ala Glu Val Met Ser Ala Ile Phe Ala Glu Val Met Gln Gly
145                 150                 155                 160

Lys Pro Glu Phe Thr Asp His Leu Thr His Lys Leu Lys His His Pro
                165                 170                 175

Gly Gln Ile Glu Ala Ala Ile Met Glu His Ile Leu Asp Gly Ser
            180                 185                 190

Ala Tyr Val Lys Ala Ala Gln Lys Leu His Glu Met Asp Pro Leu Gln
        195                 200                 205

Lys Pro Lys Gln Asp Arg Tyr Ala Leu Arg Thr Ser Pro Gln Trp Leu
210                 215                 220

Gly Pro Gln Ile Glu Val Ile Arg Ser Ser Thr Lys Met Ile Glu Arg
225                 230                 235                 240

Glu Ile Asn Ser Val Asn Asp Asn Pro Leu Ile Asp Val Ser Arg Asn
                245                 250                 255

Lys Ala Ile His Gly Gly Asn Phe Gln Gly Thr Pro Ile Gly Val Ser
            260                 265                 270
```

Met Asp Asn Thr Arg Leu Ala Ile Ala Ala Ile Gly Lys Leu Met Phe
            275                 280                 285

Ala Gln Phe Ser Glu Leu Val Asn Asp Phe Tyr Asn Asn Gly Leu Pro
    290                 295                 300

Ser Asn Leu Ser Gly Gly Arg Asn Pro Ser Leu Asp Tyr Gly Phe Lys
305                 310                 315                 320

Gly Ala Glu Ile Ala Met Ala Ser Tyr Cys Ser Glu Leu Gln Phe Leu
                325                 330                 335

Ala Asn Pro Val Thr Asn His Val Gln Ser Ala Glu Gln His Asn Gln
            340                 345                 350

Asp Val Asn Ser Leu Gly Leu Ile Ser Ser Arg Lys Thr Ser Glu Ala
            355                 360                 365

Val Glu Ile Leu Lys Leu Met Ser Thr Thr Phe Leu Val Gly Leu Cys
    370                 375                 380

Gln Ala Ile Asp Leu Arg His Leu Glu Glu Asn Leu Lys Ser Thr Val
385                 390                 395                 400

Lys Asn Thr Val Ser Ser Val Ala Lys Arg Val Leu Thr Met Gly Val
                405                 410                 415

Asn Gly Glu Leu His Pro Ser Arg Phe Cys Glu Lys Asp Leu Leu Arg
            420                 425                 430

Val Val Asp Arg Glu Tyr Ile Phe Ala Tyr Ile Asp Asp Pro Cys Ser
    435                 440                 445

Ala Thr Tyr Pro Leu Met Gln Lys Leu Arg Gln Thr Leu Val Glu His
    450                 455                 460

Ala Leu Lys Asn Gly Asp Asn Glu Arg Asn Leu Ser Thr Ser Ile Phe
465                 470                 475                 480

Gln Lys Ile Ala Thr Phe Glu Asp Glu Leu Lys Ala Leu Leu Pro Lys
                485                 490                 495

Glu Val Glu Ser Ala Arg Ala Ala Leu Glu Ser Gly Asn Pro Ala Ile
            500                 505                 510

Pro Asn Arg Ile Glu Glu Cys Arg Ser Tyr Pro Leu Tyr Lys Phe Val
    515                 520                 525

Arg Lys Glu Leu Gly Thr Glu Tyr Leu Thr Gly Glu Lys Val Thr Ser
    530                 535                 540

Pro Gly Glu Glu Phe Glu Lys Val Phe Ile Ala Met Ser Lys Gly Glu
545                 550                 555                 560

Ile Ile Asp Pro Leu Leu Glu Cys Leu Glu Ser Trp Asn Gly Ala Pro
                565                 570                 575

Leu Pro Ile Cys
            580

<210> SEQ ID NO 83
<211> LENGTH: 704
<212> TYPE: PRT
<213> ORGANISM: Tomato

<400> SEQUENCE: 83

Met Asp Leu Cys Lys Lys Ser Ile Asn Asp Pro Leu Asn Trp Glu Met
1               5                   10                  15

Ala Ala Asp Ser Leu Arg Gly Ser His Leu Asp Glu Val Lys Lys Met
                20                  25                  30

Val Asp Glu Phe Arg Lys Pro Ile Val Lys Leu Gly Gly Glu Thr Leu
            35                  40                  45

Ser Val Ala Gln Val Ala Ser Ile Ala Asn Val Asp Asp Lys Ser Asn

-continued

```
                50                  55                  60
Gly Val Lys Val Glu Leu Ser Glu Ser Ala Arg Ala Gly Val Lys Ala
65                  70                  75                  80

Ser Ser Asp Trp Val Met Asp Ser Met Ser Lys Gly Thr Asp Ser Tyr
                85                  90                  95

Gly Val Thr Ala Gly Phe Gly Ala Thr Ser His Arg Arg Thr Lys Asn
                100                 105                 110

Gly Gly Ala Leu Gln Lys Glu Leu Ile Arg Phe Leu Asn Ala Gly Val
                115                 120                 125

Phe Gly Asn Gly Ile Glu Ser Phe His Thr Leu Pro His Ser Ala Thr
130                 135                 140

Arg Ala Ala Met Leu Val Arg Ile Asn Thr Leu Leu Gln Gly Tyr Ser
145                 150                 155                 160

Gly Ile Arg Phe Glu Ile Leu Glu Ala Ile Thr Lys Leu Ile Asn Ser
                165                 170                 175

Asn Ile Thr Pro Cys Leu Pro Leu Arg Gly Thr Ile Thr Ala Ser Gly
                180                 185                 190

Asp Leu Val Pro Leu Ser Tyr Ile Ala Gly Leu Leu Thr Gly Arg Pro
                195                 200                 205

Asn Ser Lys Ala Val Gly Pro Asn Gly Glu Lys Leu Asn Ala Glu Glu
                210                 215                 220

Ala Phe Cys Val Ala Gly Ile Ser Gly Gly Phe Phe Glu Leu Gln Pro
225                 230                 235                 240

Lys Glu Gly Leu Ala Leu Val Asn Gly Thr Ala Val Gly Ser Ala Met
                245                 250                 255

Ala Ser Ile Val Leu Phe Glu Ser Asn Ile Phe Ala Val Met Ser Glu
                260                 265                 270

Val Leu Ser Ala Ile Phe Thr Glu Val Met Asn Gly Lys Pro Glu Phe
                275                 280                 285

Thr Asp Tyr Leu Thr His Lys Leu Lys His His Pro Gly Gln Ile Glu
                290                 295                 300

Ala Ala Ala Ile Met Glu His Ile Leu Asp Gly Ser Ser Tyr Val Lys
305                 310                 315                 320

Val Ala Gln Lys Leu His Glu Met Asp Pro Leu Gln Lys Pro Lys Gln
                325                 330                 335

Asp Arg Tyr Ala Leu Arg Thr Ser Pro Gln Trp Leu Gly Pro Gln Ile
                340                 345                 350

Glu Val Ile Arg Ala Ala Thr Lys Met Ile Glu Arg Glu Ile Asn Ser
                355                 360                 365

Val Asn Asp Asn Pro Leu Ile Asp Val Ser Arg Asn Lys Ala Leu His
                370                 375                 380

Gly Gly Asn Phe Gln Gly Thr Pro Ile Gly Val Ser Met Asp Asn Thr
385                 390                 395                 400

Arg Leu Ala Leu Ala Ser Ile Gly Lys Leu Met Phe Ala Gln Phe Ser
                405                 410                 415

Glu Leu Val Asn Asp Tyr Tyr Asn Asn Gly Leu Pro Ser Asn Leu Thr
                420                 425                 430

Ala Gly Arg Asn Pro Ser Leu Asp Tyr Gly Phe Lys Gly Ala Glu Ile
                435                 440                 445

Ala Met Ala Ser Tyr Cys Ser Glu Leu Gln Phe Leu Ala Asn Pro Val
                450                 455                 460

Thr Asn His Val Gln Ser Ala Glu Gln His Asn Gln Asp Val Asn Ser
465                 470                 475                 480
```

```
Leu Gly Leu Ile Ser Ala Arg Lys Thr Ala Lys Ala Val Asp Ile Leu
                485                 490                 495

Lys Ile Met Ser Ser Thr Tyr Leu Val Ala Leu Cys Gln Ala Ile Asp
            500                 505                 510

Leu Arg His Leu Glu Glu Asn Leu Lys Ser Val Val Lys Asn Thr Val
        515                 520                 525

Ser Gln Val Ala Lys Arg Thr Leu Thr Met Gly Ala Asn Gly Glu Leu
    530                 535                 540

His Pro Ala Arg Phe Ser Glu Lys Glu Leu Leu Arg Val Val Asp Arg
545                 550                 555                 560

Glu Tyr Leu Phe Ala Tyr Ala Asp Asp Pro Cys Ser Ser Asn Tyr Pro
                565                 570                 575

Leu Met Gln Lys Leu Arg Gln Val Leu Val Asp Gln Ala Met Lys Asn
            580                 585                 590

Gly Glu Ser Glu Lys Asn Val Asn Ser Ser Ile Phe Gln Lys Ile Gly
        595                 600                 605

Ala Phe Glu Asp Glu Leu Ile Ala Val Leu Pro Lys Glu Val Glu Ser
    610                 615                 620

Val Arg Ala Val Phe Glu Ser Gly Asn Pro Leu Ile Arg Asn Arg Ile
625                 630                 635                 640

Thr Glu Cys Arg Ser Tyr Pro Leu Tyr Arg Leu Val Arg Glu Glu Leu
                645                 650                 655

Gly Thr Glu Leu Leu Thr Gly Glu Lys Val Arg Ser Pro Gly Glu Glu
            660                 665                 670

Ile Asp Lys Val Phe Thr Ala Ile Cys Asn Gly Gln Ile Ile Asp Pro
        675                 680                 685

Leu Leu Glu Cys Leu Lys Ser Trp Asn Gly Ala Pro Leu Pro Ile Cys
    690                 695                 700

<210> SEQ ID NO 84
<211> LENGTH: 725
<212> TYPE: PRT
<213> ORGANISM: Arabidopsis

<400> SEQUENCE: 84

Met Glu Ile Asn Gly Ala His Lys Ser Asn Gly Gly Gly Val Asp Ala
1               5                   10                  15

Met Leu Cys Gly Gly Asp Ile Lys Thr Lys Asn Met Val Ile Asn Ala
            20                  25                  30

Glu Asp Pro Leu Asn Trp Gly Ala Ala Ala Glu Gln Met Lys Gly Ser
        35                  40                  45

His Leu Asp Glu Val Lys Arg Met Val Ala Glu Phe Arg Lys Pro Val
    50                  55                  60

Val Asn Leu Gly Gly Glu Thr Leu Thr Ile Gly Gln Val Ala Ala Ile
65                  70                  75                  80

Ser Thr Ile Gly Asn Ser Val Lys Val Glu Leu Ser Glu Thr Ala Arg
                85                  90                  95

Ala Gly Val Asn Ala Ser Ser Asp Trp Val Met Glu Ser Met Asn Lys
            100                 105                 110

Gly Thr Asp Ser Tyr Gly Val Thr Thr Gly Phe Gly Ala Thr Ser His
        115                 120                 125

Arg Arg Thr Lys Asn Gly Val Ala Leu Gln Lys Glu Leu Ile Arg Phe
    130                 135                 140

Leu Asn Ala Gly Ile Phe Gly Ser Thr Lys Glu Thr Ser His Thr Leu
```

```
145                 150                 155                 160
Pro His Ser Ala Thr Arg Ala Ala Met Leu Val Arg Ile Asn Thr Leu
                165                 170                 175
Leu Gln Gly Phe Ser Gly Ile Arg Phe Glu Ile Leu Glu Ala Ile Thr
                180                 185                 190
Ser Phe Leu Asn Asn Ile Thr Pro Ser Leu Pro Leu Arg Gly Thr
                195                 200                 205
Ile Thr Ala Ser Gly Asp Leu Val Pro Leu Ser Tyr Ile Ala Gly Leu
    210                 215                 220
Leu Thr Gly Arg Pro Asn Ser Lys Ala Thr Gly Pro Asn Gly Glu Ala
225                 230                 235                 240
Leu Thr Ala Glu Glu Ala Phe Lys Leu Ala Gly Ile Ser Ser Gly Phe
                245                 250                 255
Phe Asp Leu Gln Pro Lys Glu Gly Leu Ala Leu Val Asn Gly Thr Ala
                260                 265                 270
Val Gly Ser Gly Met Ala Ser Met Val Leu Phe Glu Thr Asn Val Leu
                275                 280                 285
Ser Val Leu Ala Glu Ile Leu Ser Ala Val Phe Ala Glu Val Met Ser
    290                 295                 300
Gly Lys Pro Glu Phe Thr Asp His Leu Thr His Arg Leu Lys His His
305                 310                 315                 320
Pro Gly Gln Ile Glu Ala Ala Val Met Glu His Ile Leu Asp Gly
                325                 330                 335
Ser Ser Tyr Met Lys Leu Ala Gln Lys Leu His Glu Met Asp Pro Leu
                340                 345                 350
Gln Lys Pro Lys Gln Asp Arg Tyr Ala Leu Arg Thr Ser Pro Gln Trp
                355                 360                 365
Leu Gly Pro Gln Ile Glu Val Ile Arg Tyr Ala Thr Lys Ser Ile Glu
                370                 375                 380
Arg Glu Ile Asn Ser Val Asn Asp Asn Pro Leu Ile Asp Val Ser Arg
385                 390                 395                 400
Asn Lys Ala Ile His Gly Gly Asn Phe Gln Gly Thr Pro Ile Gly Val
                405                 410                 415
Ser Met Asp Asn Thr Arg Leu Ala Ile Arg Ala Ile Gly Lys Leu Met
                420                 425                 430
Phe Ala Gln Phe Ser Glu Leu Val Asn Asp Phe Tyr Asn Asn Gly Leu
                435                 440                 445
Pro Ser Asn Leu Thr Ala Ser Arg Asn Pro Ser Leu Asp Tyr Gly Phe
                450                 455                 460
Lys Gly Ala Glu Ile Ala Met Ala Ser Tyr Cys Ser Glu Leu Gln Tyr
465                 470                 475                 480
Leu Ala Asn Pro Val Thr Ser His Val Gln Ser Ala Glu Gln His Asn
                485                 490                 495
Gln Asp Val Asn Ser Leu Gly Leu Ile Ser Ser Arg Lys Thr Ser Glu
                500                 505                 510
Ala Val Asp Ile Leu Lys Leu Met Ser Thr Thr Phe Leu Val Ala Ile
                515                 520                 525
Cys Gln Ala Val Asp Leu Arg His Leu Glu Glu Asn Leu Arg Gln Thr
                530                 535                 540
Val Lys Asn Thr Val Ser Gln Val Ala Lys Lys Val Leu Thr Thr Gly
545                 550                 555                 560
Val Asn Gly Glu Leu His Pro Ser Arg Phe Cys Glu Lys Asp Leu Leu
                565                 570                 575
```

```
Lys Val Val Asp Arg Glu Gln Val Tyr Thr Tyr Ala Asp Asp Pro Cys
            580                 585                 590

Ser Ala Thr Tyr Pro Leu Ile Gln Lys Leu Arg Gln Val Ile Val Asp
        595                 600                 605

His Ala Leu Val Asn Gly Glu Ser Glu Lys Asn Ala Val Thr Ser Ile
    610                 615                 620

Phe His Lys Ile Gly Ala Phe Glu Glu Glu Leu Lys Ala Val Leu Pro
625                 630                 635                 640

Lys Glu Val Glu Ala Ala Arg Ala Ala Tyr Asp Asn Gly Thr Ser Ala
            645                 650                 655

Ile Pro Asn Arg Ile Lys Glu Cys Arg Ser Tyr Pro Leu Tyr Arg Phe
            660                 665                 670

Val Arg Glu Glu Leu Gly Thr Glu Leu Leu Thr Gly Glu Lys Val Thr
        675                 680                 685

Ser Pro Gly Glu Glu Phe Asp Lys Val Phe Thr Ala Ile Cys Glu Gly
        690                 695                 700

Lys Ile Ile Asp Pro Met Met Glu Cys Leu Asn Glu Trp Asn Gly Ala
705                 710                 715                 720

Pro Ile Pro Ile Cys
                725
```

MICROBIAL POLYCULTURES AND METHODS OF USE THEREOF

CROSS-REFERENCE TO RELATED APPLICATIONS

This application is a continuation of U.S. Utility patent application Ser. No. 15/341,911, filed Nov. 2, 2016, now U.S. patent Ser. No. 10/954,543, which claims the benefit of priority under 35 U.S.C. § 119(e) to U.S. Provisional Patent Application Ser. No. 62/249,476, filed on Nov. 2, 2015, the disclosure of which is incorporated by reference herein in its entirety.

STATEMENT REGARDING FEDERALLY SPONSORED RESEARCH AND DEVELOPMENT

This invention was made with U.S. Government support under Grant Number DE-AR0000432 awarded by the Department of Energy. The United States Government has certain rights in the invention.

FIELD OF THE INVENTION

This invention relates to microbial polycultures useful for production of flavanones, flavonoids, and anthocyanidin-3-O-glucosides, and methods of use thereof. This invention also relates to microbial cell useful for production of phenylpropanoic acids, and methods of use thereof.

DESCRIPTION OF THE TEXT FILE SUBMITTED ELECTRONICALLY

The contents of the text file submitted electronically herewith are incorporated herein by reference in their entirety: A computer readable format copy of the Sequence Listing (filename: 0094204 Sequence Listing_ST25.txt, file size: 194 kilobytes).

BACKGROUND OF THE INVENTION

The microbial production of biofuels, commodity chemicals, and natural products is continually being improved through the use of various pathway optimization tools and techniques. Until recently, these efforts have focused primarily on optimization of single strain monocultures to facilitate conversion of substrate to product. See for example, U.S. Pat. Nos. 7,338,791 and 7,807,422. Although successful, these efforts are continually plagued with the trade-offs associated with choosing a single host strain to simultaneously perform multiple bioconversions, often having different precursor and co-factor requirements.

Nature has overcome these trade-offs through organelle compartmentalization of pathways in higher organisms and through microbial consortia in lower organisms. The presence of microbial communities is ubiquitous in nature. In much the same way that multicellular eukaryotic organisms have evolved to contain specialized organelles that work together to seamlessly perform their specialized tasks; communities of unicellular organisms have developed similar divisions within their populations, such that the consortia of microbes is more than simply a sum of its individual parts. These complex consortia allow for a cellular specialization enabling the community to withstand larger environmental perturbations and perform more complex tasks than any of its individual constituents. Employing this division of labor approach allows for burden to be distributed across the population permitting for increased efficiency and more complex behavior than is possible in monoculture.

Humans have taken advantage of co-culture approaches for wastewater treatment and fermented food products for decades. However, only recently have scientists begun to investigate the true potential of co-culture techniques in metabolic engineering and synthetic biology applications. Several groups have reported elegant applications utilizing co-cultures for the production of pharmaceutical precursors, commodity chemicals, and potential biofuels. In one such example, a S. cerevisiae-E. coli co-culture was engineered to take advantage of rapid taxadiene production from E. coli and the ability of S. cerevisiae to actively express cytochrome P450s to catalyze taxadiene functionalization into oxygenated taxanes. These steps have proven to be inefficient or impossible to accomplish in either a S. cerevisiae or E. coli monoculture. Albeit impressive, previous studies have lacked the rigorous optimization necessary to fully realize the complete production potential of these co-culture systems.

Although the study and application of natural microbial consortia have been a topic of interest in the scientific literature for decades, the development of synthetic consortium, and specifically consortia for metabolic engineering applications, has gained significant traction in the past three years. Several excellent examples of employing microbial communities for metabolic engineering have resulted in significant improvements over monoculture efforts. These gains were realized through utilizing the key advantages of microbial consortia, including: (1) selection of the most efficient organism for the bioconversion (i.e. mixing bacterial and fungal hosts in a single consortium); (2) using traditional metabolic engineering principles (Push, Pull, Block) to optimize each module for its specific co-factor and precursor needs; and (3) taking advantage of consortia modularity such that individual strains can be genetically optimized in monoculture then applied in mixed culture without the need to re-perform the genetic optimization.

However, there is still a need for efficient production of various useful compounds, such as flavanones, flavonoids, and anthocyanidin-3-O-glucosides. Accordingly, there is a need for development of polycultures, two or more strains in co-culture, for production of such useful compounds. Additionally, there is a need for cultures that can produce phenylpropanoic acids, which are also useful for various applications.

SUMMARY OF THE INVENTION

The present invention relates to microbial polycultures useful production of various useful compounds. Accordingly, in one embodiment, the present invention relates to a method of producing a product compound in a microbial polyculture;

wherein, optionally, the microbial polyculture includes a TAL module cell including an exogenous gene encoding for a tyrosine ammonia lyase (TAL); wherein, optionally, the microbial polyculture includes a C5 module cell including an exogenous gene encoding for a 4-coumaroyl-CoA ligase (4CL), an exogenous gene encoding for a chalcone synthase (CHS), an exogenous gene encoding for a chalcone isomerase (CHI), and wherein, optionally, the C5 module cell further includes an exogenous gene encoding for malonyl-CoA synthetase (MatB) and an exogenous gene encoding for putative dicarboxylate carrier protein (MatC); wherein, optionally, the microbial polyculture further includes a p168 module cell including an exogenous gene encoding for a flavanone 3β-hydroxylase (F3H), an exogenous gene encoding for a dihydroflavonol 4-reductase (DFR), and an exogenous gene encoding for a leucoanthocyanidin reductase (LAR); and wherein, optionally, the microbial polyculture further includes an Antho module cell including an exogenous gene encoding for an anthocyanidin synthase (ANS) and an exogenous gene encoding for a 3-glucosyl transferase (3GT); the method including:

providing a substrate to the microbial polyculture;
culturing the microbial polyculture under conditions permitting synthesis of the product compound by the microbial polyculture; and
isolating the product compound synthesized by the microbial polyculture; with a proviso (i.e., a condition) that:
the microbial polyculture includes the TAL module cell and the C5 module cell, the substrate is glucose, glycerol, or a combination thereof, and the product compound is a flavanone; or
the microbial polyculture includes the C5 module cell and the p168 module cell, the substrate is phenylpropanoic acid, and the product compound is a flavonoid; wherein, when the C5 module cell includes an exogenous gene encoding for malonyl-CoA synthetase (MatB) and an exogenous gene encoding for putative dicarboxylate carrier protein (MatC), the substrate is a phenylpropanoic acid, malonate, or a combination thereof and the product is a flavonoid; or
the microbial polyculture includes the p168 module cell and the Antho module cell, the substrate is a flavanone, and the product compound is an anthocyanidin-3-O-glucoside; or
the microbial polyculture includes the TAL module cell, the C5 module cell, and the p168 module cell, the substrate is glucose, glycerol, or a combination thereof, and the product compound is a flavonoid; or
the microbial polyculture includes the C5 module cell, the p168 module cell, and the Antho module cell, the substrate is a phenylpropanoic acid, and the product compound is an anthocyanidin-3-O-glucoside; wherein, when the C5 module cell includes an exogenous gene encoding for malonyl-CoA synthetase (MatB) and an exogenous gene encoding for putative dicarboxylate carrier protein (MatC), the substrate is phenylpropanoic acid, malonate, or a combination thereof and the product is an anthocyanidin-3-O-glucoside; or
the microbial polyculture includes the TAL module cell, the C5 module cell, the p168 module cell, and the Antho module cell, the substrate is glucose, glycerol, or a combination thereof, and the product compound is an anthocyanidin-3-O-glucoside.

The present invention is also directed to microbial polycultures of the above described methods.

Furthermore, the present invention is also directed to a method of producing a phenylpropanoic acid in a TAL module cell, wherein the TAL module cell is a microbial cell including an exogenous gene encoding for a tyrosine ammonia lyase (TAL); the method including: providing a substrate to the TAL module cell, wherein the substrate includes glucose, glycerol, or a combination thereof; culturing the TAL module cell under conditions permitting synthesis of the phenylpropanoic acid by the TAL module cell; and isolating the phenylpropanoic acid synthesized by the TAL module cell. In one embodiment, the method further includes creating the TAL module cell by introducing an exogenous gene encoding for a tyrosine ammonia lyase (TAL) into a host cell for the TAL module cell.

The present invention is also directed to a TAL module cell, wherein the TAL module cell is a microbial cell including an exogenous gene encoding for a tyrosine ammonia lyase (TAL).

BRIEF DESCRIPTION OF THE DRAWINGS

These and other features, aspects, and advantages of the present invention will become better understood when the following detailed description is read with reference to the accompanying drawings in which like characters represent like parts throughout the drawings, wherein.

DETAILED DESCRIPTION OF THE INVENTION

We developed and optimized polycultures for the efficient production of various compound types, including flavonoids. Flavonoids are high-value molecules with promising potential for pharmaceutical applications resulting from interesting bioactivity. In the case of flavan-3-ols, a subclass of flavonoid molecules, high-titer production has been achieved from both the malonyl-CoA requiring upstream module (phenylpropanoic acids to flavanones) and the NADPH requiring downstream module (flavanones to flavan-3-ols). However, when the complete pathway is expressed in monoculture, reported titers for flavan-3-ols from phenylpropanoic acids are greater than three orders of magnitude lower than the independent modules. This observation motivated the choice to attempt co-culture production of flavan-3-ols in *E. coli*.

To accomplish this task, careful experimental optimization of carbon source, induction temperature, induction point, inoculation ratio, and strain choice was used to map the production landscape. The experimental optimization was coupled with extensive empirical modeling techniques that were applied to predict conditions for optimal production. Searching the solution space surrounding the predicted optimum resulted in a 65% improvement in flavan-3-ol titer to 40.7±0.1 mg/L from p-coumaric acid, representing a 970-fold improvement over previous literature reports.

Figure 5:
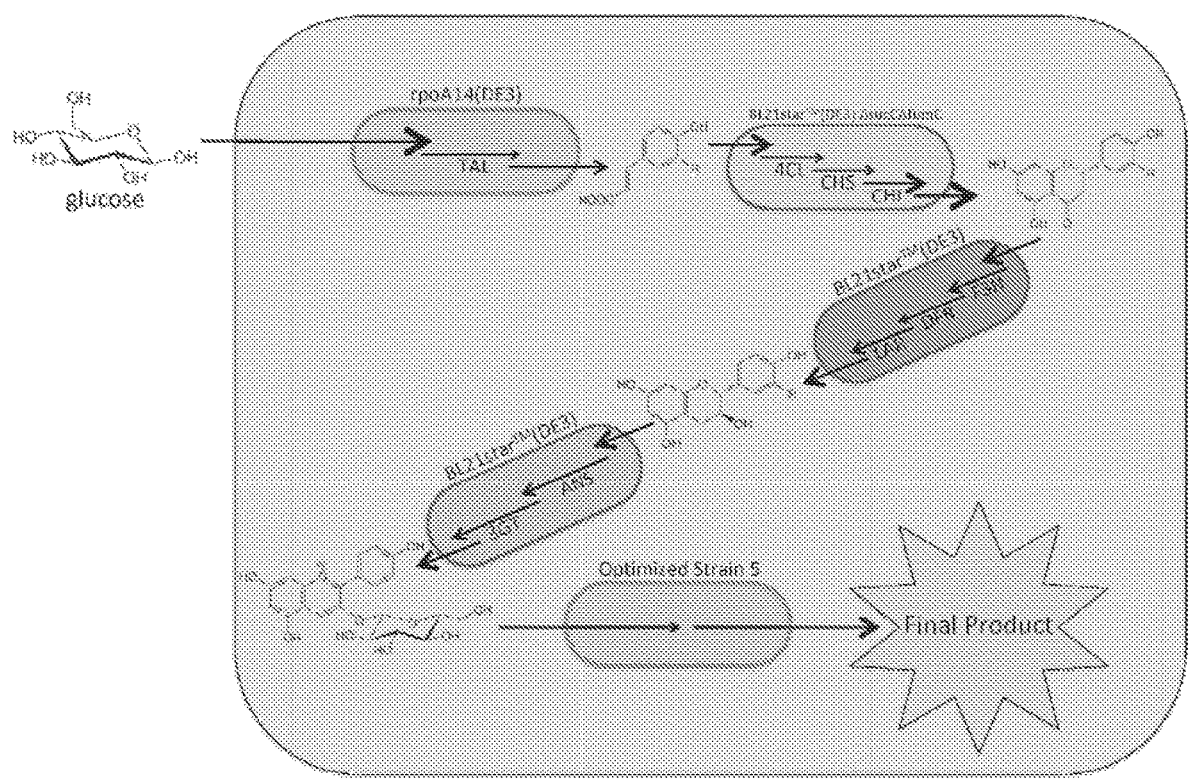
FIG. 5 shows a polyculture schematic representing the realized 4-strain polyculture. Inclusion of fifth strain shows potential for extension through addition of sequential modules.

Some of our novel polycultures are also capable of the de novo production of flavan-3-ols and anthocyanidin-3-O-glucosides in microbial hosts, FIG. 5. To accomplish this task, we built off of our previous co-culture demonstration by developing a phenylpropanoic acid production module capable of the highest titer production of p-coumaric and caffeic acid to date. Applying this module, together with the previously developed C5 and p168 modules, enabled production of 26.1 mg/L (+)-afzelechin from glucose. Finally, we further demonstrated the modularity of our system by realizing the production of anthocyanidin-3-glucosides from glucose by introduction of a fourth module for anthocyanin production to the system, resulting in a titer of 12.6±0.4 mg/L pelargonidin-3-O-glucoside de novo. This production was obtained with only minimal fermentation optimization at the polyculture level.

In one embodiment, the invention relates to a method of producing a product compound in a microbial polyculture; wherein, optionally, the microbial polyculture includes a TAL module cell including an exogenous gene encoding for a tyrosine ammonia lyase (TAL); wherein, optionally, the microbial polyculture includes a C5 module cell including an exogenous gene encoding for a 4-coumaroyl-CoA ligase (4CL), an exogenous gene encoding for a chalcone synthase (CHS), an exogenous gene encoding for a chalcone isomerase (CHI), and wherein, optionally, the C5 module cell further includes an exogenous gene encoding for malonyl-CoA synthetase (MatB) and an exogenous gene encoding for putative dicarboxylate carrier protein (MatC); wherein, optionally, the microbial polyculture further includes a p168 module cell including an exogenous gene encoding for a flavanone 3β-hydroxylase (F3H), an exogenous gene encoding for a dihydroflavonol 4-reductase (DFR), and an exogenous gene encoding for a leucoanthocyanidin reductase (LAR); and wherein, optionally, the microbial polyculture further includes an Antho module cell including an exogenous gene encoding for an anthocyanidin synthase (ANS) and an exogenous gene encoding for a 3-glucosyl transferase (3GT); the method including:

providing a substrate to the microbial polyculture;
culturing the microbial polyculture under conditions permitting synthesis of the product compound by the microbial polyculture; and
isolating the product compound synthesized by the microbial polyculture; with a proviso that:
the microbial polyculture includes the TAL module cell and the C5 module cell, the substrate is glucose, glycerol, or a combination thereof, and the product compound is a flavanone; or
the microbial polyculture includes the C5 module cell and the p168 module cell, the substrate is phenylpropanoic acid, and the product compound is a flavonoid; wherein, when the C5 module cell includes an exogenous gene encoding for malonyl-CoA synthetase (MatB) and an exogenous gene encoding for putative dicarboxylate carrier protein (MatC), the substrate is a phenylpropanoic acid, malonate, or a combination thereof and the product is a flavonoid; or
the microbial polyculture includes the p168 module cell and the Antho module cell, the substrate is a flavanone, and the product compound is an anthocyanidin-3-O-glucoside; or
the microbial polyculture includes the TAL module cell, the C5 module cell, and the p168 module cell, the substrate is glucose, glycerol, or a combination thereof, and the product compound is a flavonoid; or
the microbial polyculture includes the C5 module cell, the p168 module cell, and the Antho module cell, the substrate is a phenylpropanoic acid, and the product compound is an anthocyanidin-3-O-glucoside; wherein, when the C5 module cell includes an exogenous gene encoding for malonyl-CoA synthetase (MatB) and an exogenous gene encoding for putative dicarboxylate carrier protein (MatC), the substrate is phenylpropanoic acid, malonate, or a combination thereof and the product is an anthocyanidin-3-O-glucoside; or
the microbial polyculture includes the TAL module cell, the C5 module cell, the p168 module cell, and the Antho module cell, the substrate is glucose, glycerol, or a combination thereof, and the product compound is an anthocyanidin-3-O-glucoside.

Thus, the microbial polycultures of the invention may be any one of the following polycultures: (1) the TAL module cell and the C5 module cell; (2) the C5 module cell and the p168 module cell; (3) the p168 module cell and the Antho module cell; (4) the TAL module cell, the C5 module cell, and the p168 module cell; (5) the C5 module cell, the p168 module cell, and the Antho module cell; or (6) the TAL module cell, the C5 module cell, the p168 module cell, and the Antho module cell. Use of the singular term "cell" when referring to each module (i.e., TAL module, C5 module, p168 module, and Antho module) is meant to encompass both a single cell of the specified module and a plurality of cells of the specified module.

The TAL module cell includes an exogenous gene encoding for a tyrosine ammonia lyase (TAL). In some embodiments, the exogenous gene encoding for the tyrosine ammonia lyase (TAL) is a gene encoding for *Rhodotorula glutinis* tyrosine ammonia lyase (RgTAL). In some embodiments, the exogenous gene encoding for the tyrosine ammonia lyase (TAL) is a gene encoding for *Rhodotorula glutinis* tyrosine ammonia lyase (RgTAL), *Rhodobacter capsulatus* TAL, Rice TAL, Parsley TAL, Tomato TAL, *Arabidopsis* TAL, or a combination thereof.

The C5 module cell includes an exogenous gene encoding for a 4-coumaroyl-CoA ligase (4CL), an exogenous gene encoding for a chalcone synthase (CHS), an exogenous gene encoding for a chalcone isomerase (CHI). In addition to these three genes, the C5 module cell may optionally include an exogenous gene encoding for malonyl-CoA synthetase (MatB) and an exogenous gene encoding for putative dicarboxylate carrier protein (MatC).

In some embodiments, the exogenous gene encoding for the 4-coumaroyl-CoA ligase (4CL) is a gene encoding for *Arabidopsis thaliana* 4-coumaroyl-CoA ligase (At4CL), *Petrosehnum crispum* 4-coumaroyl-CoA ligase (Pc4CL), *Vitis vinifera* 4-coumaroyl-CoA ligase (Vv4CL), or a combination thereof. In some embodiments, the exogenous gene encoding for the chalcone synthase (CHS) is a gene encoding for *Petunia*.times.*hybrida* chalcone synthase (PhCHS), *Citrus maxima* chalcone synthase (CmCHS), or a combination thereof. In some embodiments, the exogenous gene encoding for the chalcone isomerase (CHI) is a gene encoding for *Medicago sativa* chalcone isomerase (MsCHI), *Citrus maxima* chalcone isomerase (CmCHI), or a combination thereof. In some embodiments, the exogenous gene encoding for the malonyl-CoA synthetase (MatB) is a gene encoding for *Rhizobium trifolii* malonyl-CoA synthetase (RtMatB). In some embodiments, the exogenous gene encoding for the dicarboxylate carrier protein (MatC) is a gene encoding for *Rhizobium trifolii* putative dicarboxylate carrier protein (RtMatC).

The p168 module cell includes an exogenous gene encoding for a flavanone 3β-hydroxylase (F3H), an exogenous gene encoding for a dihydroflavonol 4-reductase (DFR), and an exogenous gene encoding for a leucoanthocyanidin reductase (LAR).

In some embodiments, the exogenous gene encoding for the flavanone 3β-hydroxylase (F3H) is a gene encoding for *Camellia sinensis* flavanone 3β-hydroxylase (CsF3H), *Malus domestica* flavanone 3β-hydroxylase (MdF3H), *Petroselinum crispum* flavanone 3β-hydroxylase (PcF3H), or a combination thereof. In some embodiments, the exogenous gene encoding for the dihydroflavonol 4-reductase (DFR) is a gene encoding for *Anthrium andraeanum* dihydroflavonol 4-reductase (AaDFR), *Camellia sinensis* dihydroflavonol 4-reductase (CsDFR), *Fragaria*.times.*ananassa* dihydroflavonol 4-reductase (FaDFR), or a combination thereof. In some embodiments, the exogenous gene encoding for the leucoanthocyanidin reductase (LAR) is a gene encoding for *Camellia sinensis* leucoanthocyanidin reductase (CsLAR), *Desmodium uncinatum* leucoanthocyanidin reductase (DuLAR), or a combination thereof.

The Antho module cell includes an exogenous gene encoding for an anthocyanidin synthase (ANS) and an exogenous gene encoding for a 3-glucosyl transferase (3GT). In some embodiments, the exogenous gene encoding for the anthocyanidin synthase (ANS) is a gene encoding for *Petunia*.times.*hybrida* anthocyanidin synthase (PhANS). In some embodiments, the exogenous gene encoding for the anthocyanidin synthase (ANS) is a gene encoding for *Petunia*.times.*hybrida* anthocyanidin synthase (PhANS), *Malus domestica* ANS, *Pyrus communis* ANS, *Prunus avium* ANS, *Fragaria*.times.*ananassa* ANS, *Vitis vinifera* ANS, *Ipomoea purpurea* anthocyanidin synthase (ANS), *Camellia sinensis* ANS, *Citrus sinensis* anthocyanidin synthase (ANS), *Vaccinium ashei* ANS, *Populus trichocarpa* ANS, or a combination thereof. In some embodiments, the exogenous gene encoding for the 3-glucosyl transferase (3GT) is a gene encoding for *Arabidopsis thaliana* 3-glucosyl transferase (At3GT). In some embodiments, the exogenous gene encoding for the 3-glucosyl transferase (3GT) is a gene encoding for *Arabidopsis thaliana* 3-glucosyl transferase (At3GT), *Fragaria*.times.*ananassa* 3GT, *Vitis vinifera* 3GT, Forsynthia 3GT, Eggplant 3GT, Gentian 3GT, *Petunia*.times.*hybrida* 3GT, or a combination thereof.

In some embodiments, the exogenous gene encoding for the 4-coumaroyl-CoA ligase (4CL) is a gene encoding for *Arabidopsis thaliana* 4-coumaroyl-CoA ligase (At4CL); the exogenous gene encoding for the chalcone synthase (CHS) is a gene encoding for *Petunia*.times.*hybrida* chalcone synthase (PhCHS); the exogenous gene encoding for the chalcone isomerase (CHI) is a gene encoding for *Citrus maxima* chalcone isomerase (CmCHI); the exogenous gene encoding for the malonyl-CoA synthetase (MatB) is a gene encoding for *Rhizobium trifolii* malonyl-CoA synthetase (RtMatB); and the exogenous gene encoding for the dicarboxylate carrier protein (MatC) is a gene encoding for *Rhizobium trifolii* putative dicarboxylate carrier protein (RtMatC).

In some embodiments, the exogenous gene encoding for the flavanone 3β-hydroxylase (F3H) is a gene encoding for *Camellia sinensis* flavanone 3β-hydroxylase (CsF3H); the exogenous gene encoding for the dihydroflavonol 4-reductase (DFR) is a gene encoding for *Fragaria*.times.*ananassa* dihydroflavonol 4-reductase (FaDFR); and the exogenous gene encoding for the leucoanthocyanidin reductase (LAR) is a gene encoding for *Desmodium uncinatum* leucoanthocyanidin reductase (DuLAR).

The polypeptides encoded by the exogenous genes in the cells of the polyculture have various known functions. TAL converts tyrosine and phenylalanine to the corresponding phenylpropanoic acids, coumaric acid, and cinnamic acid. 4CL converts phenylpropanoic acids such as coumaric acid, cinnamic acid, ferulic acid, and caffeic acid to their CoA derivatives. CHS performs condensation of phenylpropanoic-CoA derivatives such as coumaroyl-CoA, cinnamoyl-CoA, caffeoyl-CoA, feruloyl-CoA with 3 moles of malonyl CoA and performs Claisen condensation to form chalcones. CHI performs isomerisation of chalcones to flavanones. Math converts the intracellular malonate to malonyl-CoA. MatC transports malonate across the cell membrane. F3H is a dioxygenase that hydroxylates flavanones such as naringenin and eriodictyol to the corresponding dihydroxyflavanones. DFR is a reductase reducing dixydroxyflavanones to the corresponding leucoanthocyanidins. LAR is a reductase that converts leucoanthocyanidins to flavan-3-ols. ANS is a dioxygenase that converts flavan-3-ols and leucoanthocyanidins to anthocyanidins. 3GT is a glycosyltransferase that adds a glucose group to the 3 OH group of anthocyanidins converting them to the corresponding anthocyanin 3-O-glucoside.

In some embodiments, the exogenous gene encoding for the tyrosine ammonia lyase (TAL) is a gene that encodes a polypeptide with at least 85%, 90%, or 95% amino acid sequence identity to any one of the TAL amino acid sequences identified herein.

In some embodiments, the exogenous gene encoding for the 4-coumaroyl-CoA ligase (4CL) is a gene that encodes a polypeptide with at least 85%, 90%, or 95% amino acid sequence identity to any one of the 4CL amino acid sequences identified herein.

In some embodiments, the exogenous gene encoding for the chalcone synthase (CHS) is a gene that encodes a polypeptide with at least 85%, 90%, or 95% amino acid sequence identity to any one of the CHS amino acid sequences identified herein.

In some embodiments, the exogenous gene encoding for the chalcone isomerase (CHI) is a gene that encodes a polypeptide with at least 85%, 90%, or 95% amino acid sequence identity to any one of the CHI amino acid sequences identified herein.

In some embodiments, the exogenous gene encoding for the malonyl-CoA synthetase (MatB) is a gene that encodes a polypeptide with at least 85%, 90%, or 95% amino acid sequence identity to any one of the MatB amino acid sequences identified herein.

In some embodiments, the exogenous gene encoding for the dicarboxylate carrier protein (MatC) is a gene that encodes a polypeptide with at least 85%, 90%, or 95% amino acid sequence identity to any one of the MatC amino acid sequences identified herein.

In some embodiments, the exogenous gene encoding for the flavanone 3β-hydroxylase (F3H) is a gene that encodes a polypeptide with at least 85%, 90%, or 95% amino acid sequence identity to any one of the F3H amino acid sequences identified herein.

In some embodiments, the exogenous gene encoding for the dihydroflavonol 4-reductase (DFR) is a gene that encodes a polypeptide with at least 85%, 90%, or 95% amino acid sequence identity to any one of the DFR amino acid sequences identified herein.

In some embodiments, the exogenous gene encoding for the leucoanthocyanidin reductase (LAR) is a gene that encodes a polypeptide with at least 85%, 90%, or 95% amino acid sequence identity to any one of the LAR amino acid sequences identified herein.

In some embodiments, the exogenous gene encoding for the anthocyanidin synthase (ANS) is a gene that encodes a polypeptide with at least 85%, 90%, or 95% amino acid sequence identity to any one of the ANS amino acid sequences identified herein.

In some embodiments, the exogenous gene encoding for the 3-glucosyl transferase (3GT) is a gene that encodes a polypeptide with at least 85%, 90%, or 95% amino acid sequence identity to any one of the 3GT amino acid sequences identified herein.

In all of the above instances of encoded polypeptides with at least 85%, 90%, or 95% amino acid sequence identity to a specified polypeptide, the function of the encoded polypeptide is the same as the function of the specified polypeptide. Those of skill in the art could readily determine amino acid sequences of such encoded polypeptides. Preservation of the function of the encoded polypeptide would be routine to a person of skill in the art with the benefit of the available information about functional domains of the specified polypeptides. Such information regarding domains includes disclosures in the references listed below, which are incorporated by reference in their entirety herein.

TAL: Crystal structure of phenylalanine ammonia lyase: multiple helix dipoles implicated in catalysis. Calabrese J C, Jordan D B, Boodhoo A, Sariaslani S, Vannelli T., Biochemistry. 2004 Sep. 14, 43(36):11403-16.

4CL: Identification of the substrate specificity-conferring amino acid residues of 4-coumarate:coenzyme A ligase allows the rational design of mutant enzymes with new catalytic properties, Stuible H P, Kombrink E., J Biol Chem. 2001 Jul. 20, 276(29):26893-7.

4CL: The substrate specificity-determining amino acid code of 4-coumarate:CoA ligase, Schneider K, Hovel K, Witzel K, Hamberger B, Schomburg D, Kombrink E, Stuible H P, Proc Natl Acad Sci USA. 2003 Jul. 8, 100(14):8601-6.

CHS: Structure of chalcone synthase and the molecular basis of plant polyketide biosynthesis, Ferrer J L, Jez J M, Bowman M E, Dixon R A, Noel J P., Nat Struct Biol. 1999 August, 6(8):775-84.

CHS: Dissection of malonyl-coenzyme A decarboxylation from polyketide formation in the reaction mechanism of a plant polyketide synthase, Jez J M, Ferrer J L, Bowman M E, Dixon R A, Noel J P., Biochemistry. 2000 Feb. 8, 39(5):890-902.

CHI: Structure and mechanism of the evolutionarily unique plant enzyme chalcone isomerase, Jez J M, Bowman M E, Dixon R A, Noel J P, Nat Struct Biol. 2000 September, 7(9):786-91.

DFR: Crystal structure of grape dihydroflavonol 4-reductase, a key enzyme in flavonoid biosynthesis, Petit P, Granier T, d'Estaintot B L, Manigand C, Bathany K, Schmitter J M, Lauvergeat V, Hamdi S, Gallois B., J Mol Biol. 2007 May 18, 368(5):1345-57.

LAR: Crystal structure and catalytic mechanism of leucoanthocyanidin reductase from *Vitis vinifera*., Mauge C, Granier T, d'Estaintot B L, Gargouri M, Manigand C, Schmitter J M, Chaudiere J, Gallois B., J Mol Biol., 2010 Apr. 9, 397(4):1079-91.

ANS: Structure and mechanism of anthocyanidin synthase from *Arabidopsis thaliana*, Wilmouth R C, Turnbull J J, Welford R W, Clifton U, Prescott A G, Schofield C J, Structure. 2002 January, 10(1):93-103.

3GT: Structural basis for acceptor-substrate recognition of UDP-glucose: anthocyanidin 3-O-glucosyltransferase from Clitoria ternatea, Hiromoto T, Honjo E, Noda N, Tamada T, Kazuma K, Suzuki M, Blaber M, Kuroki R., Protein Sci. 2015 March, 24(3):395-407. doi: 10.1002/pro.2630, PMID: 25556637.

3GT: Crystal structure of UDP-glucose:anthocyanidin 3-O-glucosyltransferase from Clitoria ternatea, Hiromoto T, Honjo E, Tamada T, Noda N, Kazuma K, Suzuki M, Kuroki R, J Synchrotron Radiat., 2013 November, 20(Pt 6):894-8.

In some embodiments, the method further includes: (a) when the microbial polyculture includes the TAL module cell, creating the TAL module cell by introducing an exogenous gene encoding for a tyrosine ammonia lyase (TAL) into a host cell for the TAL module cell; (b) when the microbial polyculture includes the C5 module cell, creating the C5 module cell by introducing an exogenous gene encoding for a 4-coumaroyl-CoA ligase (4CL), an exogenous gene encoding for a chalcone synthase (CHS), an exogenous gene encoding for a chalcone isomerase (CHI), and, optionally, introducing an exogenous gene encoding for malonyl-CoA synthetase (MatB) and an exogenous gene encoding for putative dicarboxylate carrier protein (MatC), into a host cell for the C5 module cell; (c) when the microbial polyculture includes the p168 module cell, creating the p168 module cell by introducing an exogenous gene encoding for a flavanone 3β-hydroxylase (F3H), an exogenous gene encoding for a dihydroflavonol 4-reductase (DFR), and an exogenous gene encoding for a leucoanthocyanidin reductase (LAR) into a host cell for the p168 module cell; and (d) when the microbial polyculture includes the TAL module cell, creating the Antho module cell by introducing an exogenous gene encoding for an anthocyanidin synthase (ANS), and an exogenous gene encoding for a 3-glucosyl transferase (3GT) into a host cell for the Antho module cell.

In some embodiments, the host cells are *E. coli* cells. In one embodiment, the host cell for the TAL module cell is *E. coli* rpoA14(DE3). In one embodiment, the host cell for the C5 module cell is *E. coli* BL21star™(DE3)ΔsucCΔfumC. In one embodiment, the host cell for the p168 module cell is *E. coli* BL21star™(DE3). In one embodiment, the host cell for the Antho module cell is *E. coli* BL21star™(DE3).

The substrate of the TAL module cell is glucose, glycerol, or a combination thereof. The TAL module cell's product compound is a phenylpropanoic acid.

The substrate of the C5 module cell is a phenylpropanoic acid. When the C5 module cell includes two additional genes, a gene for malonyl-CoA synthetase (MatB) and a gene for putative dicarboxylate carrier protein (MatC), the substrate of the C5 module cell is a phenylpropanoic acid, malonate, or a combination thereof. The C5 module cell's product compound is a flavanone.

The substrate of the p168 module cell is a flavanone. The p168 module cell's product compound is a flavonoid.

The substrate of the Antho module cell is a flavonoid. The Antho module cell's product compound is an anthocyanidin-3-O-glucoside.

The product compound is synthesized within a specified cell of the polyculture and is isolated from that cell, from the media, or from both the cell and the media.

In some embodiments, the phenylpropanoic acid is p-coumaric acid, caffeic acid, cinnamic acid, ferulic acid, or a combination thereof.

In some embodiments, the flavanone is naringenin, eriodictyol, pinocembrin, or a combination thereof.

In some embodiments, the flavonoid is a flavone, a flavan-3-ol, a flavan-4-ol, a flavonol, an anthocyanin, or a combination thereof.

In some embodiments, the flavone is luteolin, apigenin, chrysin, or a combination thereof.

In some embodiments, the flavan-3-ol is afzelechin, catechin (e.g., (+)-catechin), or a combination thereof.

In some embodiments, the flavan-4-ol is 4,5,7-trihydroxyflavan, 4,5,7,4'-tetrahydroxyflavan, 4,5,7,4',5'-pentahydroxyflavan, 4,5,7,4',5',6'-hexahydroxyflavan, 4,5,7,4'-tetrahydroxy-5'methoxyflavan, or a combination thereof.

In some embodiments, the flavonol is kaempferol, quercetin, or a combination thereof.

In some embodiments, the anthocyanin is pelargonidin, cyanidin, delphinidin, malvidin, peonidin, or a combination thereof.

In some embodiments, the anthocyanidin-3-O-glucoside is pelargonidin-3-O-glucoside, cyanidin-3-O-glucoside, delphinidin-3-O-glucoside, malvidin-3-O-glucoside, peonidin-3-O-glucoside, or a combination thereof.

In some embodiments, the phenylpropanoic acid is p-coumaric acid and the flavonoid is (+)-afzelechin. In some embodiments, the phenylpropanoic acid is caffeic acid and the flavonoid is (+)-catechin. In some embodiments, the phenylpropanoic acid is cinnamic acid and the flavonoid is 3,5,7-trihydroxyflavan. In some embodiments, the substrate is glucose and the flavonoid is pelargonidin-3-O-glucoside.

In some embodiments, the substrate is glucose and the flavonoid is cyanidin-3-O-glucoside. In some embodiments, the substrate is glucose and the flavonoid is delphinidin-3-O-glucoside. In some embodiments, the substrate is glucose and the flavonoid is peonidin-3-O-glucoside. In some embodiments, the substrate is glucose and the flavonoid is malvidin-3-O-glucoside. In some embodiments, the substrate is glycerol and the flavonoid is cyanidin-3-O-glucoside. In some embodiments, the substrate is glycerol and the flavonoid is pelargonidin-3-O-glucoside. In some embodiments, the substrate is glycerol and the flavonoid is delphinidin-3-O-glucoside. In some embodiments, the substrate is glycerol and the flavonoid is peonidin-3-O-glucoside. In some embodiments, the substrate is glycerol and the flavonoid is malvidin-3-O-glucoside.

In some embodiments, the conditions permitting synthesis of the product compound comprise providing a carbon source to the microbial polyculture, wherein the carbon source is glucose, glycerol, xylose, arabinose, galactose, yeast extract, or a combination thereof. In some embodiments, the carbon source is any suitable pentose or hexose sugar.

The conditions permitting synthesis of the flavonoid compound may include an induction point, an induction temperature, and an inoculation ratio.

Thus, in one embodiment, the induction temperature is from about 10° C. to about 42° C. In one embodiment, the induction temperature of about 30° C. In one embodiment, the induction point is from about 0 hours to about 24 hours. In one embodiment, the induction point is at about 5.5 hours. In another embodiment, the induction point is at about 5 hours.

When each module cell is used as a plurality of cells, the inoculation ratio of the C5 module cell to the p168 module cell (C5:p168) is a ratio of from about 1:99 to about 99:1. In one embodiment, the inoculation ratio of the C5 module cell to the p168 module cell (C5:p168) is a ratio of about 8:2.

In one embodiment, the inoculation ratio of the TAL module cell to the C5 module cell to the p168 module cell to the Antho module cell (TAL:C5:p168:Antho) is a ratio of about 1-97:1-97:1-97:1-97. In one embodiment, the inoculation ratio of the TAL module cell to the C5 module cell to the p168 module cell to the Antho module cell (TAL:C5:p168:Antho) is a ratio of about 8:8:2:7.

In one embodiment, the inoculation ratio of the TAL module cell to the C5 module cell (TAL:C5) is a ratio of about 1-99:1-99. In one embodiment, the inoculation ratio of the TAL module cell to the C5 module cell (TAL:C5) is a ratio of about 8:8.

In one embodiment, the inoculation ratio of the p168 module cell to the Antho module cell (p168:Antho) is a ratio of about 1-99:1-99. In one embodiment, the inoculation ratio of the p168 module cell to the Antho module cell (p168:Antho) is a ratio of about 2:7.

In one embodiment, the inoculation ratio of the TAL module cell to the C5 module cell to the p168 module cell (TAL:C5:p168) is a ratio of about 1-98:1-98:1-98. In one embodiment, the inoculation ratio of the TAL module cell to the C5 module cell to the p168 module cell (TAL:C5:p168) is a ratio of about 8:8:2.

In one embodiment, the inoculation ratio of the C5 module cell to the p168 module cell to the Antho module cell (C5:p168:Antho) is a ratio of about 1-98:1-98:1-98. In one embodiment, the inoculation ratio of the C5 module cell to the p168 module cell to the Antho module cell (C5:p168:Antho) is a ratio of about 8:2:7.

The inoculation ratios are either volumentric ratios or ratios of the numbers of cells. When using volumetric ratios, cell concentrations are initially starting around 10 7 total cells/mL and increase to around 10 9 total cells/mL. These total cell counts can be split between the two or more strains in the polyculture.

The present invention is also directed to microbial polycultures of the above described methods. Thus, the invention includes a microbial polyculture that includes:
optionally, a TAL module cell including an exogenous gene encoding for a tyrosine ammonia lyase (TAL); optionally, a C5 module cell including an exogenous gene encoding for a 4-coumaroyl-CoA ligase (4CL), an exogenous gene encoding for a chalcone synthase (CHS), an exogenous gene encoding for a chalcone isomerase (CHI), and wherein, optionally, the C5 module cell further includes an exogenous gene encoding for malonyl-CoA synthetase (MatB) and an exogenous gene encoding for putative dicarboxylate carrier protein (MatC); optionally, a p168 module cell including an exogenous gene encoding for a flavanone 3β-hydroxylase (F3H), an exogenous gene encoding for a dihydroflavonol 4-reductase (DFR), and an exogenous gene encoding for a leucoanthocyanidin reductase (LAR); and optionally, an Antho module cell including an exogenous gene encoding for an anthocyanidin synthase (ANS), and an exogenous gene encoding for a 3-glucosyl transferase (3GT); with a proviso that:
the microbial polyculture includes the TAL module cell and the C5 module cell; or
the microbial polyculture includes the C5 module cell and the p168 module cell; or
the microbial polyculture includes the p168 module cell and the Antho module cell; or
the microbial polyculture includes the TAL module cell, the C5 module cell, and the p168 module cell; or
the microbial polyculture includes the C5 module cell, the p168 module cell, and the Antho module cell; or
the microbial polyculture includes the TAL module cell, the C5 module cell, the p168 module cell, and the Antho module cell.

The invention is also directed to a method of producing a phenylpropanoic acid in a TAL module cell, wherein the TAL module cell is a microbial cell including an exogenous gene encoding for a tyrosine ammonia lyase (TAL); the method including: providing a substrate to the TAL module cell, wherein the substrate includes glucose, glycerol, or a combination thereof; culturing the TAL module cell under conditions permitting synthesis of the phenylpropanoic acid by the TAL module cell; and isolating the phenylpropanoic acid synthesized by the TAL module cell. In one embodiment, the method further includes creating the TAL module cell by introducing an exogenous gene encoding for a tyrosine ammonia lyase (TAL) into a host cell for the TAL module cell.

In one embodiment, the exogenous gene encoding for the tyrosine ammonia lyase (TAL) is a gene encoding for Rhodotorula glutinis tyrosine ammonia lyase (RgTAL). In some embodiments, the exogenous gene encoding for the tyrosine ammonia lyase (TAL) is a gene encoding for Rhodotorula glutinis tyrosine ammonia lyase (RgTAL), Rhodobacter capsulatus TAL, Rice TAL, Parsley TAL, Tomato TAL, Arabidopsis TAL, or a combination thereof.

In some embodiments, the phenylpropanoic acid is p-coumaric acid, caffeic acid, cinnamic acid, ferulic acid, or a combination thereof, all of which could derive from glucose substrate.

In some embodiments, the host cell for the TAL module cell is E. coli rpoA14(DE3).

The invention is also directed to a TAL module cell, wherein the TAL module cell is a microbial cell including an exogenous gene encoding for a tyrosine ammonia lyase (TAL). In one embodiment, the exogenous gene encoding for the tyrosine ammonia lyase (TAL) is a gene encoding for Rhodotorula glutinis tyrosine ammonia lyase (RgTAL). In one embodiment, a host cell for the TAL module cell is E. coli, for example, E. coli rpoA14(DE3).

In general, the terms and phrases used herein have their art-recognized meaning, which can be found by reference to standard texts, journal references and contexts known to those skilled in the art. The following definitions are provided to clarify their specific use in the context of the invention.

The following nucleic acid name abbreviations are used herein: C or c for cytosine, G or g for guanine, A or a for adenine, T or t for Thymine, and U or u for uracil.

The following amino acid name abbreviations are used herein: A or Ala for Alanine; M or Met for Methionine; C or Cys for Cysteine; D or Asp for Aspartic Acid; E or Glu for Glutamic Acid; F or Phe for Phenylalanine; G or Gly for Glycine; H or His for Histidine; I or Ile for Isoleucine; K or Lys for Lysine; L or Leu for Leucine; N or Asn for Asparagine; P or Pro for Proline; Q or Glu for Glutamine; R or Arg for Arginine; S or Ser for Serine; T or Thr for Threonine; V or Val for Valine; W or Trp for Tryptophan; and Y or Tyr for Tyrosine.

The terms "microbe" and "microbial" refer to a microscopic living organism, which may be single-celled or multicellular. Microbe, as used herein, includes bacteria, unicellular eukaryotes, archaea, and protozoa. An example of a microbe used in the inventions described herein is E. coli.

The term "isolating the product compound", as used herein, encompases any method that increases purity of the product compound.

When a reference is made to a gene that encodes for a specified polypeptide, such gene has the meaning of any nucleic acid sequence that encodes for the amino acid sequence of the specified polypeptide. Those of skill in the art could readily determine all possible nucleic acid sequences encoding for the specified polypeptide.

The term "induction point", as used herein, refers to the time point, after the culture has been initiated, at which the inducer is added to the medium.

The term "induction temperature", as used herein, refers to the temperature at which the culture is left to grow after the inducer has been added into the medium.

The following specific non-limiting examples are illustrative of the invention. Examples 1-14 describe studies that are also described in more detail in Jones, J. A. et al. Experimental and computational optimization of an *Escherichia coli* co-culture for the efficient production of flavonoids. Metab. Eng. 35, 55-63 (2016), entire disclosure of which, together with accompanying supplementary data available online at http://dx.doi.org/10.1016/j.ymben.2016.01.006, is incorporated by reference in its entirety.

Example 1

C5 Module and p168 Module Polyculture—Bacterial Strains, Vectors, and Media

*E. coli* DH5α was used to propagate all plasmids, while the BL21star™(DE3), BL21star™(DE3)ΔsucCΔfumC, or BL21star™(DE3)ΔpgiΔppc was used as the hosts for flavonoid production. The ePathBrick vector, pETM6, was used as the basis for all plasmid construction and pathway expression. Luria Broth (LB) Lennox modification (Sigma) and Andrew's Magic Medium (AMM) were used where noted. Sequences of all plasmid constructs are available through Addgene.org and are incorporated by reference herein.

Example 2

C5 Module and p168 Module Polyculture—Flavonoid Pathways and ePathOptimize Library Construction Genes involved in the 12 candidate upstream flavanone production pathways were obtained from previously published literature from the Koffas lab. Vv4CL, Pc4CL, CmCHS, PhCHS, CmCHI, and MsCHI were obtained in ePathBrick vector pETM6, while At4CL was acquired through PCR amplification (ACCUZYME 2.times. mix, Bioline) of plasmid #3 DNA using primers 1 and 2 (Table 2). The ePathBrick destination vector, pETM6, and At4CL PCR amplicon were digested with restriction enzymes NdeI/XhoI (FastDigest, Thermo Scientific) and gel purified (E.Z.N.A. MicroElute Gel Extraction Kit, Omega Bio-tek). Digested At4CL PCR product was ligated with digested pETM6 backbone to create plasmid 2, Table 1. Constructs were then transformed into chemically competent DH5α for verification and plasmid propagation. Colonies were screened via restriction digest and further verified with Sanger sequencing (GENEWIZ, Inc.) using the sequencing primers 3 and 4 in Table 2. Site directed mutagenesis was then preformed using standard protocols to silently remove the NheI restriction site from At4CL using primers 5 and 6 (Table 2). Complete candidate pathways were constructed in monocistronic form using standard ePathBrick methods resulting in plasmids 10-27, Table 1. Occasionally the restriction site ApaI was used to replace SalI when the pathway genes either contained internal SalI restriction sites or to optimize the insert:backbone ratio for improved ligation efficiency. Plasmids p148 and p168 containing complete downstream modules were not modified from previous reports.

TABLE 1

List of Strains and Plasmids

| Number | Strain or vector | Relevant properties | Reference |
|---|---|---|---|
| S1 | Escherichia coli DH5α | F−, φ80d lacZΔM15, Δ(lacZYA-argF)U169, recA1, endA1, hsdR17(rk−, mk+), phoA, supE44λ−, thi−1, gyrA96, relA1 | Novagen |
| S2 | E. coli BL21 Star™ (DE3) | F−ompT gal dcm rne131 lon hsdS$_B$ (r$_B$−m$_B$−) λ(DE3) | Invitrogen |
| S3 | BLΔpgiΔppc | BL21Star™ (DE3)Δpgi::FRTΔppc::FRT-KanR-FRT | (a) |
| S4 | BLΔsumCΔfumC | BL21Star™ (DE3)ΔfumC::FRTΔsucC::FRT | (b) |
| 1 | pETM6 | ePathBrick expression vector, ColE1 ori, AmpR | (c) |
| 2 | pETM6-At4CL | #1 with 4CL-1 from A. thaliana | This Study |
| 3 | pC-At4cl-Vvsts | pCDFDuet with 4CL-1 from A. thaliana, STS from V. vinifera | (d) |
| 4 | pETM6-Pc4CL | #1 with 4CL-2 from P. crispum | (c) |
| 5 | pETM6-Vv4CL | #1 with 4CL from V. vinifera | (e) |
| 6 | pETM6-PhCHS | #1 with CHS from P. hybrida | (c) |
| 7 | pETM6-CmCHS | #1 with CHS from C. maxima | (e) |
| 8 | pETM6-MsCHI | #1 with CHI from M. sativa | (c) |
| 9 | pETM6-CmCHI | #1 with CHI from C. maxima | (e) |
| 10 | pETM6-At4CL-PhCHS | #1 with At4CL and PhCHS, monocistronic form | This Study |
| 11 | pETM6-At4CL-CmCHS | #1 with At4CL and CmCHS, monocistronic form | This Study |
| 12 | pETM6-Pc4CL-PhCHS | #1 with Pc4CL and PhCHS, monocistronic form | This Study |
| 13 | pETM6-Pc4CL-CmCHS | #1 with Pc4CL and CmCHS, monocistronic form | This Study |
| 14 | pETM6-Vv4CL-PhCHS | #1 with Vv4CL and PhCHS, monocistronic form | This Study |
| 15 | pETM6-Vv4CL-CmCHS | #1 with Vv4CL and CmCHS, monocistronic form | This Study |
| 16 | pETM6-At4CL-PhCHS-MsCHI | #1 with At4CL, PhCHS, and MsCHI, monocistronic form | This Study |
| 17 | pETM6-At4CL-PhCHS-CmCHI | #1 with At4CL, PhCHS, and CmCHI, monocistronic form | This Study |
| 18 | pETM6-At4CL-CmCHS-MsCHI | #1 with At4CL, CmCHS, and MsCHI, monocistronic form | This Study |
| 19 | pETM6-At4CL-CmCHS-CmCHI | #1 with At4CL, CmCHS, and CmCHI, monocistronic form | This Study |
| 20 | pETM6-Pc4CL-PhCHS-MsCHI | #1 with Pc4CL, PhCHS, and MsCHI, monocistronic form | This Study |
| 21 | pETM6-Pc4CL-PhCHS-CmCHI | #1 with Pc4CL, PhCHS, and CmCHI, monocistronic form | This Study |
| 22 | pETM6-Pc4CL-CmCHS-MsCHI | #1 with Pc4CL, CmCHS, and MsCHI, monocistronic form | This Study |
| 23 | pETM6-Pc4CL-CmCHS-CmCHI | #1 with Pc4CL, CmCHS, and CmCHI, monocistronic form | This Study |
| 24 | pETM6-Vv4CL-PhCHS-MsCHI | #1 with Vv4CL, PhCHS, and MsCHI, monocistronic form | This Study |

TABLE 1-continued

List of Strains and Plasmids

| Number | Strain or vector | Relevant properties | Reference |
|---|---|---|---|
| 25 | pETM6-Vv4CL-PhCHS-CmCHI | #1 with Vv4CL, PhCHS, and CmCHI, monocistronic form | This Study |
| 26 | pETM6-Vv4CL-CmCHS-MsCHI | #1 with Vv4CL, CmCHS, and MsCHI, monocistronic form | This Study |
| 27 | pETM6-Vv4CL-CmCHS-CmCHI | #1 with Vv4CL, CmCHS, and CmCHI, monocistronic form | This Study |
| 28 | p148 | #1 with CsF3H$^{syn}$-AaDFR$^{syn}$-DuLAR$^{syn}$, monocistronic form | (f) |
| 29 | p168 | #1 with CsF3H$^{syn}$-FaDFR$^{syn}$-DuLAR$^{syn}$, monocistronic form | (f) |
| 30 | pETM6-mCherry | #1 with mCherry fluorescent reporter | (c) |
| 31 | pETM6-C4-mCherry | #30 Modified with mutated 'C4' T7 promoter sequence | (g) |
| 32 | pETM6-G6-mCherry | #30 Modified with mutated 'G6' T7 promoter sequence | (g) |
| 33 | pETM6-H9-mCherry | #30 Modified with mutated 'H9' T7 promoter sequence | (g) |
| 34 | pETM6-H10-mCherry | #30 Modified with mutated 'H10' T7 promoter sequence | (g) |
| 35 | pFlavo$^{opt}$ or C5 mutant | #17 with C4 mutant T7 promoter controlling CmCHI | This Study |

TABLE 2

List of Plasmids

| Number | Primer ID | Primer Sequence (5'→3') |
|---|---|---|
| 1 (SEQ ID NO: 1) | At4CL_FWD with NdeI | GCGCCGCATATGGCGCCACAAGAACAAG |
| 2 (SEQ ID NO: 2) | At4CL_REV with XhoI | GCGCGGCTCGAGTCACAATCCATTTGCT |
| 3 (SEQ ID NO: 3) | Seq_T7_FWD | TAATACGACTCACTATAGGG |
| 4 (SEQ ID NO: 4) | Seq_T7Term_REV | GCTAGTTATTGCTCAGCGG |
| 5 (SEQ ID NO: 5) | SDM_At4CL_NheI_FWD | GAATGACGGAAGCAGGTCCAGTGCTCGCAATGTCGTTAGGTTTTGCAAAG |
| 6 (SEQ ID NO: 6) | SDM_At4CL_NheI_REV | CTTTGCAAAACCTAACGACATTGCGAGCACTGGACCTGCTTCCGTCATTC |

The upstream pathway genes were cloned in monocistronic form with randomized promoter strengths using previously published methods. Multiple transformations were oftentimes completed to ensure sufficient library sampling and retention. The final plasmid library, pETM6-xxAt4CL-xxPhCHS-xxCmCHI, was transformed into BL21star™ (DE3)ΔsucCΔfumC for screening. The 'xx' feature represents the inclusion of a single random mutant T7 promoter from the five-member ePathOptimize library.

Example 3

C5 Module and p168 Module Polyculture—Small-Scale Cultivation Protocol

Single colonies of each strain were inoculated separately into 25 mL of AMM in a 125 mL non-baffled shake flask with ampicillin (80 μg/mL) and grown overnight at 37° C. After 14 hours, the overnight cultures were mixed volumetrically to the indicated inoculation ratios and were inoculated at 2% (40 μL) into 2 mL of AMM and allowed to grow at 37° C. before induction with 1 mM IPTG. Upon induction, the cultures were transferred to the appropriate induction temperature and grown for 48 hours. All small-scale screening was completed in polypropylene 48-well plates (5 mL, VWR). Except where noted, the cultures were grown in AMM with 20 g/L Glycerol, 100 mg/L of substrate was added at induction, and 30° C. was used as the induction temperature.

Example 4

C5 Module and p168 Module Polyculture—Bioreactor Fermentation Protocol

Fed-batch style fermentation was performed using a DASGIP parallel bioreactor at an initial working volume of 500 mL of AMM with 20 g/L glycerol as a carbon source. Overnight cultures were prepared identically to the small-scale protocol presented above. The bioreactor was inoculated at an initial ratio of 7:3 (C5:p168) at 2% of final volume. The pH and DO of the fermentation broth was maintained at 7.2 and 50 percent saturation through addition of 6M sodium hydroxide and application of stirring cascade control, respectively. The feed solution [250 g/L glycerol, 4 g/L casamino acids, 7 g/L $(NH_4)_2HPO_4$, and 80 µg/mL ampicillin] and 2.times.MOPS mix was fed at 2 mL per hour from 5-15 hours and 4 mL per hour from 15-26 hours. The fermentation was induced with IPTG to a final concentration of 1 mM after 7 hours of growth ($OD_{600}$=7.1) and the system was cooled to 30° C. The substrate, p-coumaric acid, was added in 50 mg/L aliquots at 1, 4, and 7 hours post induction. Samples were taken periodically for measurement of $OD_{600}$ and metabolite analysis.

Example 5

C5 Module and p168 Module Polyculture—Metabolite Analysis

Fermentation broth was mixed with an equal volume of absolute ethanol and vortexed for 10 seconds prior to centrifugation (10 min, 20,000.times.g). The supernatant (25 µL) was used for HPLC analysis carried out using Agilent 1200 series HPLC equipped with a ZORBAX SB-18 column (5 µm, 4.6.times.150 mm) and a diode array detector. The mobile phase was acetonitrile (solvent A) and water (solvent B) (both contain 0.1% formic acid) at a flow rate of 1 mL/min. HPLC program was as follows: 10 to 40% A (0-10 min) and 40 to 60% A (10-15 min). Absorbance at 280 nm was monitored in all cases. Titer of products was determined using authentic standards while (+)-afzelechin was quantified using the (+)-catechin calibration curve. All experiments were performed in duplicate. Error bars represent ±1 standard deviation of biological duplicate. Significance of data was determined using a two-tailed unpaired t-test with a 95 percent confidence interval.

Example 6

C5 Module and p168 Module Polyculture—Empirical Modeling Methods

Experimental conditions were modeled using empirical modeling methods, which are described in detail in Jones, J. A. et al. Experimental and computational optimization of an *Escherichia coli* co-culture for the efficient production of flavonoids. Metab. Eng. 35, 55-63 (2016).

Example 7

C5 Module and p168 Module Polyculture

Figure 1:
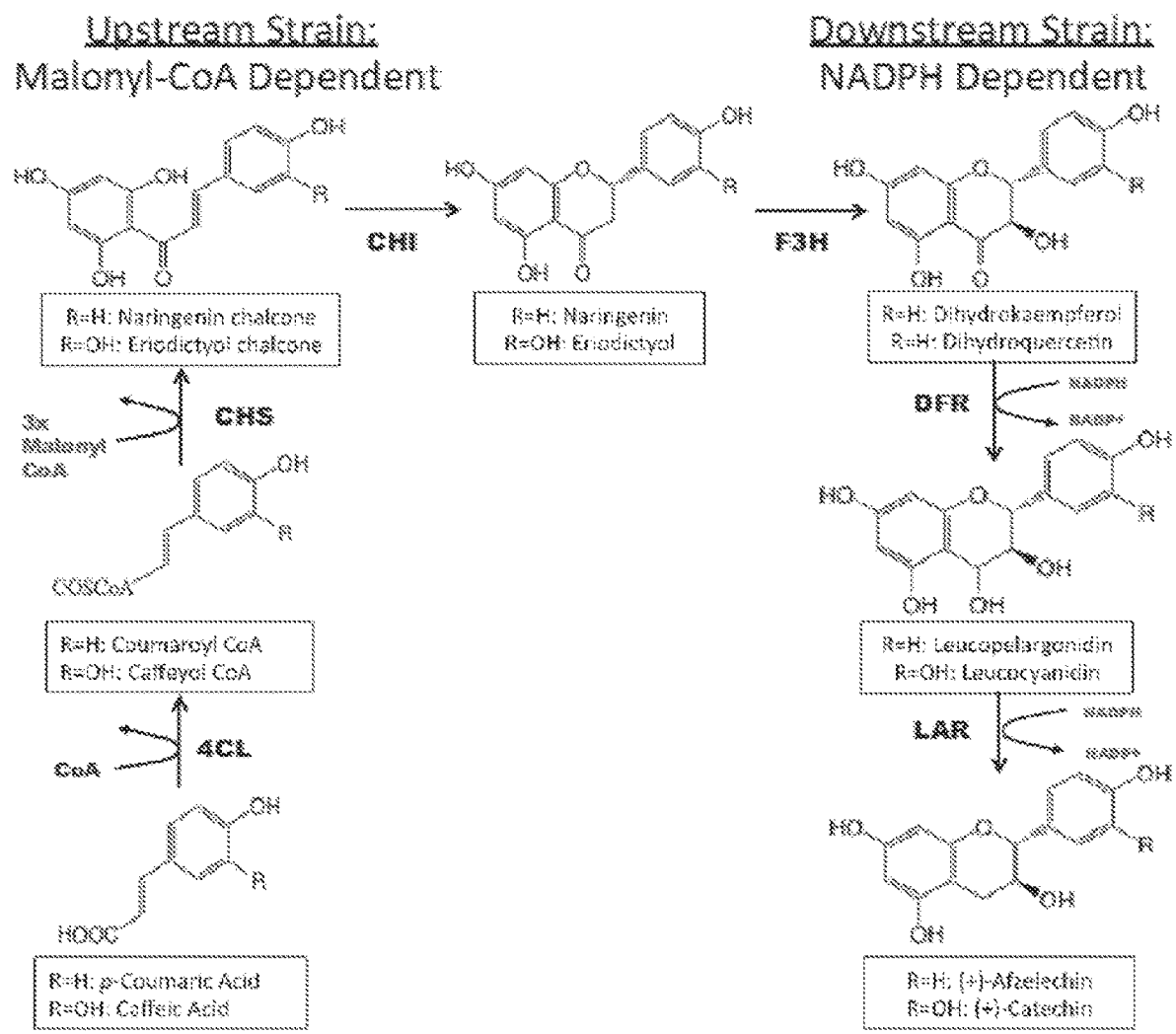
FIG. 1 illustrates flavonoid pathway highlighting upstream (left) malonyl-CoA dependent and downstream (right) NADPH dependent co-culture modules.

The production of flavan-3-ols from phenylpropanoic acid precursors proceeded through six enzymatic steps: 4-coumaroyl-CoA ligase, 4CL; chalcone synthase, CHS; chalcone isomerase, CHI; flavanone 3β-hydroxylase, F3H; dihydroflavonol 4-reductase, DFR; leucoanthocyanidin reductase, LAR; (FIG. 1). The complete pathway was partitioned such that both the upstream and downstream modules contained three genes. This modularization reduced the metabolic burden of enzyme overexpression and divided the pathway according to necessary co-factor requirements: malonyl-CoA (upstream) and NADPH (downstream).

Example 8

Figure 2A:
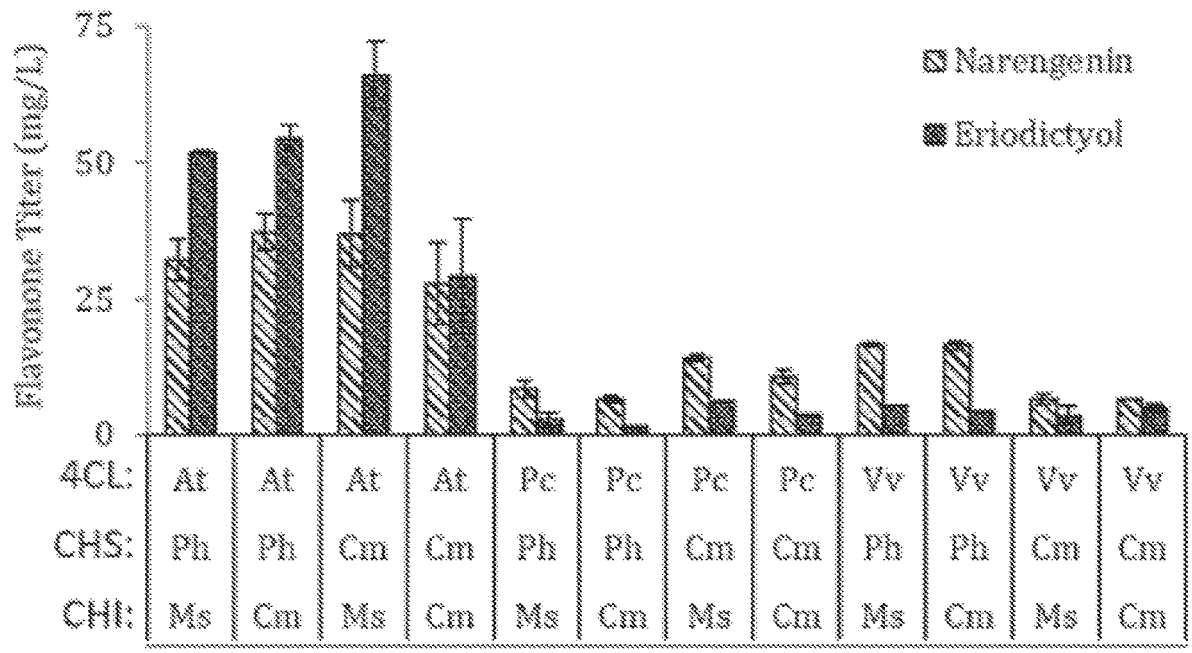
FIGS. 2A-2C show upstream strain optimization and co-culture compatibility determination. (A) Screening of twelve potential upstream homolog combinations resulted in several high-titer pathways. (B) Application of ePathOptimize technique for transcriptional optimization resulted in high sensitivity to changes in the transcriptional landscape. (C) Lead strains from the individual strain optimization studies were grown in co-culture to determine strain compatibility prior to additional fermentation optimization. All data was obtained in AMM −2% glucose, 30° C. induction temperature. Error bars represent ±1 standard deviation from duplicate experiments.

C5 Module and p168 Module Polyculture—Independent Optimization of Upstream and Downstream Modules The ability to tailor the genetic optimization of each strain in a co-culture system for improved flux towards necessary co-factors and substrates through the pathway of interest and away from unwanted side products is a major advantage over monoculture methods. We began our modular optimization by focusing on the upstream strain containing 4CL, CHS, and CHI. Building on previous efforts to optimize malonyl-CoA availability, BL21star™(DE3)ΔsucCΔfumC was chosen as the host strain for this upstream module. We then chose homologs for each of the three enzymes from different plant sources, resulting in 12 combinations of potential upstream pathways. Upon screening for functional conversion of two phenylpropanoic acid precursors to their corresponding flavanones, several high-titer homolog combinations were discovered (FIG. 2A). Constructs containing the 4CL from *Arabidopsis thaliana* (At4CL) showed significantly ($p<0.001$) higher conversion leading towards the choice of construct containing At4CL, PhCHS, and CmCHI for further optimization.

Figure 2B:
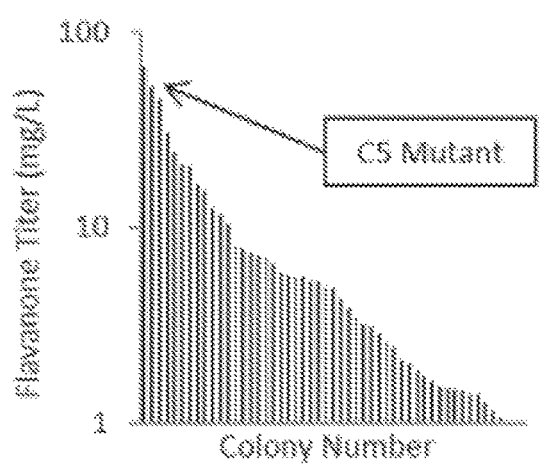

Using the recently published ePathOptimize technique for modulating the transcriptional landscape, the promoter strengths of each gene in the upstream module were randomized to one of five mutant T7 promoters of various strength. The library members were then screened for conversion of p-coumaric acid to naringenin in vivo (FIG. 2B). The results indicated high sensitivity to promoter strength and resulted in one mutant (C5 or $pFlavo^{opt}$) that outperformed the consensus T7 control strain by 24 percent. This $pFlavo^{opt}$ mutant was sequenced and was found to have the consensus T7 sequence controlling expression of At4CL and PhCHS, while the strong mutant promoter C4 was found to control expression of CmCHI. The nomenclature C5 or $pFlavo^{opt}$ refers to the transcriptionally optimized plasmid expressed in the flavanone expression strain BL21star™ (DE3) (Table 1) and contains the incorporation of ePathOptimize mutant T7 promoter C4 controlling the expression of CmCHI. This transcriptionally optimized plasmid was then utilized in future co-cultures.

Optimization of the downstream pathway has been previously explored through screening of 18 homolog gene combinations resulting in two combinations that exhibit efficient conversion of both naringenin and eriodictyol substrates across a wide range of substrate concentrations (67 Zhao et al., 2015). To confirm the findings of this previous study, both the p148 and p168 constructs were tested using a cultivation protocol and substrate concentration realistic to the levels expected in the current study. Similar titers and trends were obtained with p168 slightly out-performing p148, leading towards the choice of p168 for the downstream module in the co-culture optimization. Further optimization of plasmid p168 was not performed due to limiting fluxes through the upstream module. With independent genetic optimization of the upstream and downstream modules completed, the lead candidates for each module were then screened for strain compatibility in co-culture.

Example 9

C5 Module and p168 Module Polyculture—Determination of Co-Culture Compatibility

Strain compatibility is a significant factor in any co-culture system. The strains must be able to efficiently grow in the same media, have the same antibiotic selection, and must not produce toxic compounds that significantly harm the other members of the microbial community. Many of these criteria can be easily addressed by using strains of similar background, but module specific mutations towards improving intercellular conditions for the pathway of interest can impact cellular compatibility in co-culture. Furthermore, pathway metabolites that connect the individual members of the co-culture must be readily transferred across the cell membrane from the producer to the consumer.

Figure 2C:
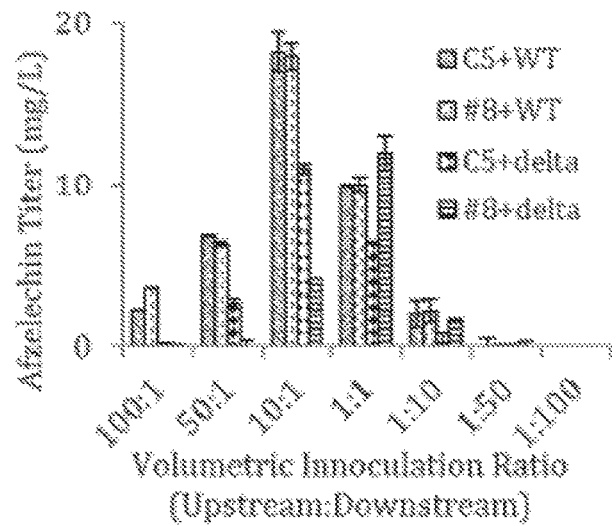

Two strains from each the upstream and downstream module were tested for their cross compatibility in co-culture. For the upstream strain, the transcriptionally optimized pFlavo$^{opt}$ mutant and the consensus control plasmid (#17, Table 1) were used in strain BL21star™(DE3) ΔsucCΔfumC, while for the downstream module a single plasmid, p168, was tested in two host strains: wild type BL21star™(DE3) and BL21star™(DE3)ΔpgiΔppc. We have noticed a significant decrease in cell growth for the ΔpgiΔppc strain background and hypothesized that this would affect strain performance in co-culture. Four co-culture combinations were tested across various initial inoculation cell ratios (FIG. 2C) and a significant reduction in flavan-3-ol titer was seen for the two co-cultures containing BL21*(DE3)ΔpgiΔppc (p<0.001). Nearly identical performance was achieved by strains containing either the consensus control or the pFlavo$^{opt}$ mutant upstream module. From these results, we chose BL21*(DE3)ΔsucCΔfumC with the pFlavo$^{opt}$ mutant upstream module and the wild type BL21*(DE3) with the p168 plasmid for further optimization.

Example 10

C5 Module and p168 Module Polyculture—Determination of Important Optimization Parameters To begin fermentation optimization of the co-culture system, we identified two key parameters predicted to result in high sensitivity: induction point and inoculation ratio. Both the upstream and downstream modules contain pET expression cassettes controlled by the T7-lac system, and therefore protein production is inducible with the addition of Isopropyl β-D-1-thiogalactopyranoside ("IPTG"). A wide variety of optimum induction points have been presented in the primary literature for pET-based systems indicating that the optimum induction point is linked to division of cellular resources and is more complex than purely affecting protein production levels. Due to this complexity, the optimum induction point is specific to the particular system and set of cultivation conditions and must be determined experimentally.

Figure 3A:
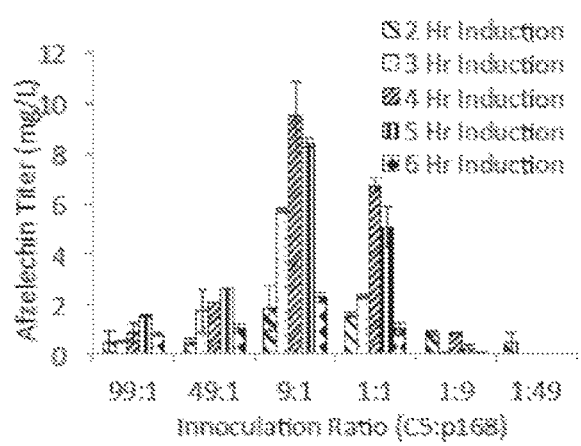
FIGS. 3A-3D show sensitivity to induction point, inoculation ratio, and induction temperature for the co-culture system. (A) Variations in induction point and inoculation ratio demonstrate orthogonal response in product titer. Data obtained in glucose only media at an induction temperature of 30° C. (B-D) Variations in the induction temperature show significant shifts to the magnitude and profile of the production landscape. Data obtained in glycerol only media. (B) 10° C. induction temperature. (C) 20° C. induction temperature. (D) 30° C. induction temperature. Data labels represent the highest titer reported in each window. Error bars represent ±1 standard deviation from duplicate or greater (n>2) experiments.

The initial inoculation ratio of upstream to downstream cells in the fermentation is another important parameter that adds to the complexity of co-culture systems. Variation of this ratio allows for changes to be made in population dynamics, accounting for differences in population growth rate and specific activity of the strains in co-culture. Interestingly, when various induction points were crossed with multiple inoculation ratios, we saw an orthogonal response in product titer from the two parameters (FIG. 3A). The system demonstrated a peak induction point of 4 hours post-inoculation regardless of inoculation ratio and a peak inoculation ratio of 9:1 regardless of induction point, resulting in the point of highest titer at a 4-hour induction and an initial inoculation ratio of 9:1 (C5:p168). This finding led to the decision to screen all future parameters across various induction points and inoculation ratios to visualize the production landscape. Furthermore, the observed trends indicate that the system is stable over a wide range of initial inoculation ratios, showing no tipping point where one strain demonstrates a propensity to dominate the population with time. Additional analysis of substrate and flavanone intermediate concentrations also vary as expected with variable inoculation ratio. In co-cultures with dominant upstream ratios, considerable initial substrate is utilized and intermediate product is accumulated, but little intermediate is converted to final product; while co-cultures with dominant downstream ratios utilized little initial substrate, limiting flux through the entire system. However, at intermediate inoculation ratios, high amounts of initial substrate are utilized while low intermediate product titers are present due to efficient conversion to the final product.

Example 11

C5 Module and p168 Module Polyculture—Effect of Carbon Source

Previous literature reports and early experimental evidence (data not shown) fueled the decision to use the Andrew's Magic Medium (AMM) with 20 g/L of glucose as the initial production media for individual strain optimization and preliminary co-culture experiments. In an attempt to reduce the production costs at the industrial scale, and because of the increased interest to utilize glycerol for industrial fermentations, we varied the proportion of glucose to glycerol in the culture media. In addition to economic incentives, the preference for glycerol over other carbon sources has been reported for different microbial strains due to strain-specific differences in gene expression and metabolite profiles upon growth on glycerol. With all media having 20 g/L total carbon source, five carbon source ratios were tested ranging from glucose only to glycerol only (FIG. 4A-E). Several trends in the production landscape were observed upon the shift from growth on glucose to glycerol. The most noticeable trend was higher optimum titers with increasing proportion of glycerol. Upon growth on increasing proportions of glycerol, a shift in the production landscape resulted in higher titers appearing at later induction points and peak inoculation ratios with higher proportion of the downstream strain. Additionally, glucose-grown cultures demonstrate a sharp peak in the production landscape, where glycerol-grown cultures show a plateau with many high-titer solutions.

Example 12

C5 Module and p168 Module Polyculture—Induction Temperature Optimization

Figure 3B:
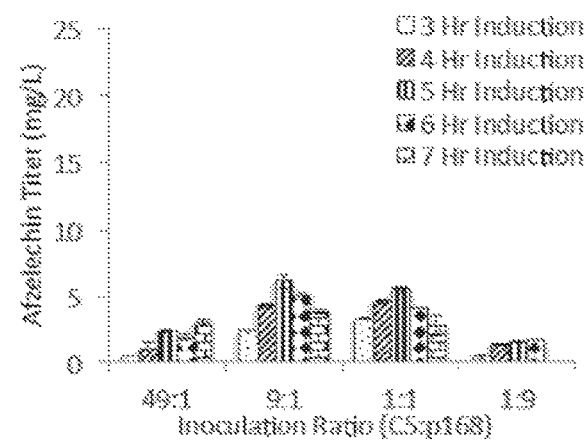
Figure 3C:
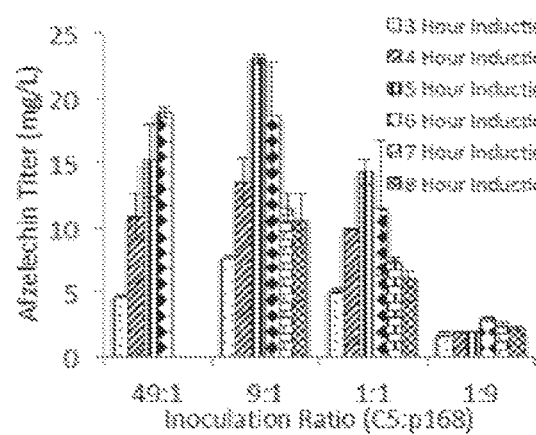
Figure 3D:
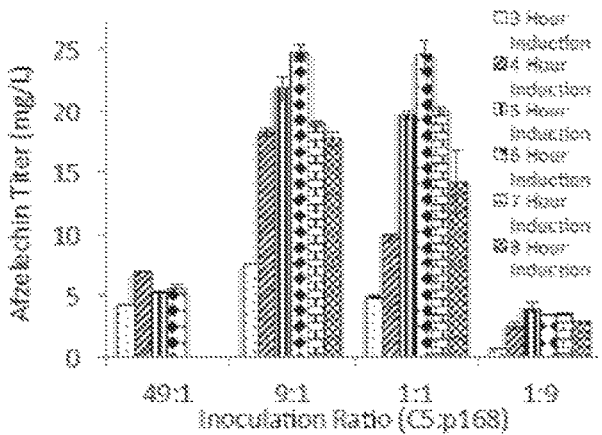
Figure 4A:
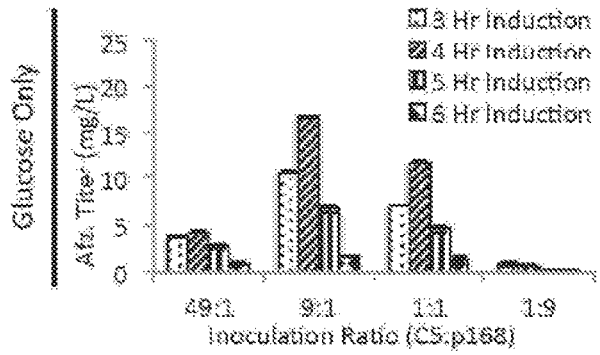
FIGS. 4A-4E show effect of carbon source composition on product titer and the shape of the production landscape. (A-E) Increasing the proportion of glycerol in the production media results in higher titers, later induction point optimums, and optimum inoculation ratios with higher proportion of the downstream strain. (A) Glucose Only. (B) 1:1 Glucose:Glycerol. (C) 1:3 Glucose:Glycerol. (D) 1:9 Glucose:Glycerol. (E) Glycerol Only. Data labels represent the highest titer reported in each window. Error bars represent ±1 standard deviation from duplicate or greater (n>2) experiments.
Figure 4B:
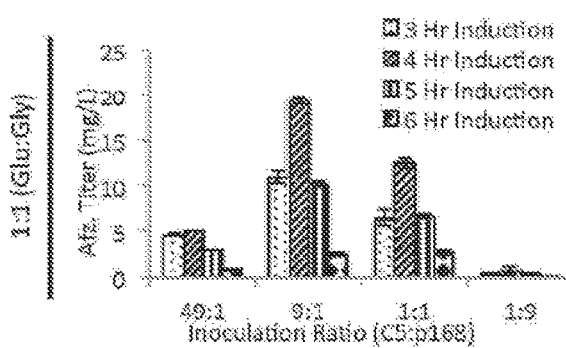
Figure 4C:
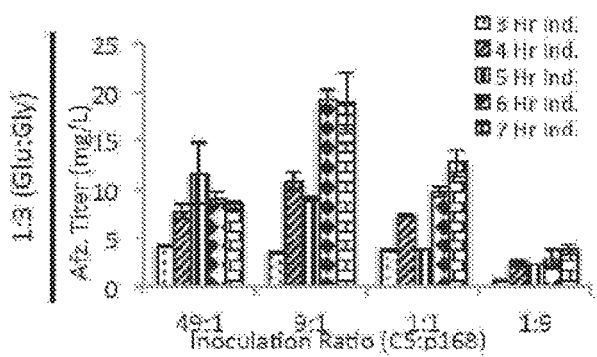
Figure 4D:
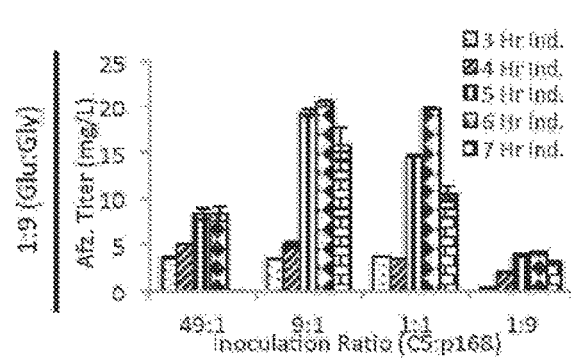
Figure 4E:
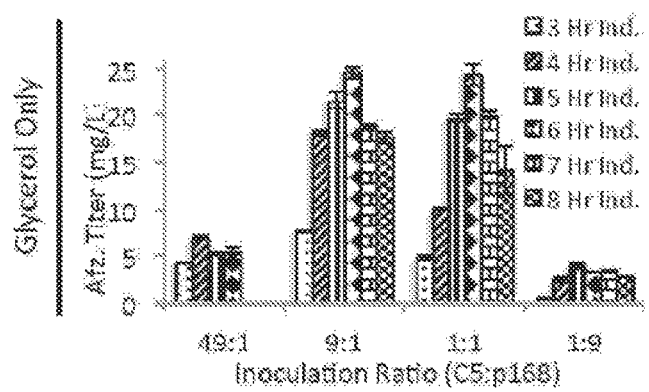

Fermentation temperature can affect cellular growth dynamics, enzyme folding, and specific enzyme activity. These effects have not been well documented on the systems level, such that optimum fermentation temperature could be predicted for any given system a priori. We therefore decided to test co-culture production at induction temperatures of 10, 20, or 30° C. The co-culture was grown at 37° C. prior to induction at which the temperature was then dropped to the specified induction temperature after induction. Previous efforts have maintained an induction temperature of 30° C. A significant decrease in optimal titer was observed in the 10° C. case with the 20 and 30° C. cases showing similar maximum achieved titers (FIG. 3B-D). Although similar in optimum titer, the 20 and 30° C. cases did show different production landscapes such that the 20° C. case had a sharp optimum while the 30° C. case demonstrated more of a plateau with many conditions resulting in moderately high titers. Additionally, similar trends were observed for increasing induction temperature as were seen for increasing proportion of glycerol in the media. Notably, increases in induction temperature resulted in a shift of the production landscape towards optimum solutions with later induction points and inoculation ratios favoring more of the downstream strain.

Example 13

C5 Module and p168 Module Polyculture—System Modeling for Prediction of Optimum Operating Conditions The aforementioned observations suggested that the titer achieved by the system could be improved by selecting optimized experimental conditions. To identify potential conditions that could result in an optimal titer, an empirical modeling approach was utilized. Due to the trends observed from preliminary data showing the dependence of titer on induction point, inoculation ratio, carbon source, and induction temperature, we constructed an empirical scaled-Gaussian model, which uses these four experimental variables as inputs and computes the titer. This model contains 21 parameters that were fitted using 72 experimental data points. In particular, titer was measured at each combination of the following: induction point—3, 4, 5, 6 hours; inoculation ratio (upstream:downstream)—49:1, 9:1, 1:1; carbon source (glucose:glycerol)—1:0, 1:1, 0:1; induction temperature—20, 30° C. The model demonstrates a close fit with the training data, and follows the general trend of additional data that were not used for model fitting. The optimal point of the model function was determined computationally, and was used to direct future experiments in search of optimal operating conditions to maximize titer. Interestingly, the optimal point of the model function was found to be at operating conditions not tested previously, and within a gap between previously tested experimental points. Specifically, the optimal conditions predicted by the model were: induction point of 5.5 hours; inoculation ratio of 7:3 (upstream: downstream); carbon source ratio of 0:1 (glucose:glycerol); and induction temperature of 25° C.

Experiments were subsequently performed at conditions in the region of the model-predicted optimum. These experiments resulted in a maximum titer of 40.7±0.1 mg/L, a 65% increase over the highest titer measured prior to computational optimization. This maximal titer was achieved experimentally at an induction point of 6 hours; inoculation ratio of 8:2 (upstream:downstream); carbon source ratio of 0:1 (glucose:glycerol); and induction temperature of 30° C. This point was within the set of experimental points we tested based on proximity with the model-predicted optimum, but the point differs slightly from the model-predicted optimum. This is not surprising, as a scaled-Gaussian model was used for fitting the data and computing the optimum, whereas the behavior of the true system is likely more complex than can be fully captured by such an empirical model. That being said, using a scaled-Gaussian model represented a good trade-off between model complexity and quality of fit for the available data, and the model was ultimately successful in guiding experiments to achieve substantially higher titers. This suggests that relatively simple empirical models can be effective tools for informing titer optimization efforts.

Example 14

C5 Module and p168 Module Polyculture—Bioreactor Scale-Up: Proof of Principle

To demonstrate the stability and scalability of our co-culture system, we showed scale-up of the fermentation from a 2 mL culture in a 48-well plate directly to a bioreactor with a 500 mL working volume. Utilizing near optimum conditions from previous small-scale optimization experiments, the bioreactor demonstrated slightly lower (34 vs. 41 mg/L) product titers than that of the optimized small-scale system. We predict this is due to a shift in the production landscape as a result of scale-up but believe that global trends due to induction point, inoculation ratio, media composition, and induction temperature will remain constant for the system. The additional control gained through the use of bioreactors also results in additional complexity from a pathway optimization standpoint. To that end, the complete fermentation optimization of our co-culture system is beyond the scope of this work but represents a promising direction for future optimization studies.

The ability to harness the power of multiple strains in co-culture allows for a division of metabolic burden across the population, as well as the ability to genetically optimize each module individually for specific co-factor and precursor requirements. Through exploitation of these advantages and empirical modeling techniques, we were able to improve production of flavonoids to 40.7±0.1 mg/L, a 970-fold improvement over previous monoculture efforts.

Example 15

TAL Module, C5 Module, p168 Module, and Antho Module Polyculture—Bacterial Strains, Vectors, and Media E. coli DH5α was used to propagate all plasmids, while BL21star™(DE3), BL21star™(DE3)ΔsucCΔfumC, rpoA14 (DE3), or QH4 was used as the hosts for flavonoid production. The expression vectors, pETM6 or pXPA, were the basis for all plasmid construction and pathway expression. Luria Broth (LB) Lennox modification (Sigma) and Andrew's Magic Media (AMM) were used where noted. Sequences of all plasmid constructs are available through addgene.org and are incorporated by reference herein.

Example 16

TAL Module, C5 Module, p168 Module, and Antho Module Polyculture—Plasmid Construction Many preexisting flavonoid modules were used directly or slightly modified for this work. All plasmids used are summarized in Table 3 and all plasmid modifications are described below. Site directed mutagenesis was performed to silently remove an internal NdeI restriction site from the open reading from of *Rhodotorula glutinis* Tyrosine Ammonia Lyase (RgTAL$^{syn}$) on pTrc-RgTAL$^{syn}$ using standard methods and primers 13-14, Table 4. The mutagenized RgTAL$^{syn}$ was PCR amplified from pTrc-RgTAL$^{syn}$ using primers 11-12, Table 4. The resulting PCR product was digested (FastDigest, Thermo Scientific) with NdeI and SpeI, gel purified (E.Z.N.A MicroElute Gel Extraction Kit, Omega Bio-tek), and ligated with pETM6 backbone also digested with NdeI and SpeI and gel extracted corresponding to standard methods to create pETM6-RgTAL$^{syn}$, (#10, Table 3). The corresponding plasmid was sequence verified (GENEWIZ, Inc.) and used together with pETM6-HpaBC (#12, Table 3) to create pETM6-RgTALsyn-HpaB-HpaC via standard ePathBrick cloning protocols.

To create the constitutive expression plasmid, pXy1A, we replaced the T7-lac feature on pETM6 with the $P_{xylA}$ promoter from *Bacillus megaterium* found on the commercial vector, pMM1522 (Mobitec). To this end, a gBlock (Integrated DNA Technologies, sequence provided in Table 5) was synthesized containing the MCS of pETM6 under the control of the $P_{xylA}$ promoter sequence, flanked by AvrII and SpeI restriction sites on the 5' and 3' ends, respectively. The $P_{xylA}$ fragment was then cloned into pETM6 and sequence verified. Two constitutive TAL expression plasmids were obtained by sub-cloning RgTAL$^{syn}$ from pETM6-RgTAL$^{syn}$ into pXy1A and pXPA-eGFP ($P_{GAP}$ promoter) at restriction sites NdeI and SpeI using standard methods.

TABLE 3

Strains and plasmids used in this study. Cited reference numbers correspond to the numbered references provided in the Bibliography.

| Number | Strain or vector | Relevant properties | Reference |
|---|---|---|---|
| S1 | Escherichia coli DH5α | F−, φ80d lacZΔM15, Δ(lacZYA-argF)U169, recA1, endA1, hsdR17(rk−, mk+), phoA, supE44λ−, thi−1, gyrA96, relA1 | Novagen |
| S2 | E. coli BL21 Star™ (DE3) | F−ompT gal dcm rne131 lon hsdS$_B$ (r$_B^-$m$_B^-$) λ(DE3) | Invitrogen |
| S3 | BLΔpgiΔppc | BL21Star™ (DE3)Δpgi::FRTΔppc::FRT-KanR-FRT | 30 |
| S4 | BLΔsumCΔfumC | BL21Star™ (DE3)ΔfumC::FRTΔsucC::FRT | 31 |
| S5 | rpoA14(DE3) | E. coli K12 ΔpheA ΔtyrR lacZ::P$_{LtetO-1}$-tyrA$^{fbr}$aroG$^{fbr}$tyrR::P$_{LtetO-1}$-tyrA$^{fbr}$aroG$^{fbr}$ hisH(L82R) pHACM-rpoA14, λ(DE3) | 16 |
| S6 | QH4 | E. coli ATCC 31884/ΔpheLA-tyrA | 21 |
| 1 | pETM6 | ePathBrick expression vector, ColE1 ori, AmpR | 18 |
| 2 | p168 | #1 with CsF3H$^{syn}$-FaDFR$^{syn}$-DuLAR$^{syn}$, monocistronic form | 32 |
| 3 | pETM6-mCherry | #1 with mCherry fluorescent reporter | 18 |
| 4 | pFlavo$^{opt}$ or C5 mutant | #17 with C4 mutant T7 promoter controlling CmCHI | 9 |
| 5 | pTrc-RgTAL$^{syn}$ | pTrcHis2B carrying codon-optimized R. glutinis TAL | 16 |
| 6 | pCS-TPTA | From pCS27, P$_L$lacO1; tyrA$^{fbr}$-ppsA-tktA-aroG$^{fbr}$ | 22 |
| 7 | pZE-TH2 | From pZE12, dual operons, P$_L$lacO1; RgTAL and EcHpaBC | 21 |
| 8 | pCA1 | pTrcHis2B carrying codon-optimized R. glutinis TAL | 23 |
| 9 | pCA3 | pCDFDuet-1 carrying codon-optimized R. glutinis TAL with a trc promoter | 23 |
| 10 | pETM6-RgTAL$^{syn}$ | #1 with RgTALsyn | This Study |
| 11 | pETM6-RgTALsyn-HpaBC | #1 with RgTALsyn, HpaB, and HpaC in monocistronic form | This Study |
| 12 | pETM6-HpaBC | #1 with HpaB and HpaC in monocistronic form | 17 |
| 13 | pXylA | #1 with constitutive PxylA promoter | This Study |
| 14 | pXPA-fapO-eGFP | pGAP promoter, rrnB terminator and ePathBrick feature carrying one copy of fapO and eGFP | 33 |
| 15 | pXylA-RgTAL$^{syn}$ | #13 carrying RgTAL$^{syn}$ | This Study |
| 16 | pXPA-fapO-RgTAL$^{syn}$ | #14 carrying RgTAL$^{syn}$ | This Study |
| 17 | pMM1522 | Amp$^R$ (E. coli), Tet$^R$ (B. meg), pBR322 ori, P$_{xylA}$ | Mobitec |
| 18 | pETM6-At3GT | #1 with 3GT from A. thaliana | This Study |
| 19 | pETM6-PhANS | #1 with ANS from P. hybrida | This Study |
| 20 | pETM6-At3GT-PhANS | #1 with At3GT and PhANS, monocistronic | This Study |

TABLE 4

Primers used in this study.

| Primer ID | Primer Name | Sequence (5'→3') |
|---|---|---|
| 1 (SEQ ID NO: 7) | ANS_XbaI_F | CCCTCTAGAAATAATTTTGTTT AACTTTAAGAAGGAGATATAC ATATGGTGAATGCAGTAGTTA C |
| 2 (SBQ ID NO: 8) | ANS_XhoI_R | CGATCTCGAGCTATTTAGATTC TTCAGCAGCAAC |
| 3 (SEQ ID NO: 9) | 3GT_NdeI_F | GCATCATATGACCAAACCCTC CGACC |
| 4 (SEQ ID NO: 10) | 3GT_XhoI_R | CGATCTCGAGTCAAATAATGT TTACAACTGCATCC |
| 5 | pETM6_ALL_inserts_flank_F | CCATCGGTGATGTCGGCGATA |

TABLE 4-continued

Primers used in this study.

| Primer ID | Primer Name | Sequence (5'→3') |
|---|---|---|
| (SEQ ID NO: 11) | | TAGG |
| 6 (SEQ ID NO: 12) | pETM6_ALL_inserts_flank_R | GTCGAGGTGCCGTAAAGCACT AAATCG |
| 7 (SEQ ID NO: 13) | ANS_mid_seq_F | CCATCTGGCCTAAAAATCCTA CTGACTACAC |
| 8 (SEQ ID NO: 14) | ANS_mid_seq_R | CCTCTTTGAAGACTTTGTGTTC AACAGCG |
| 9 (SEQ ID NO: 15) | 3GT_mid_seq_F | GCTTCATCAAATGGGTCTTGCT TTGC |
| 10 (SEQ ID NO: 16) | 3GT_mid_seq_R | GGTGTCATGACCGTACCAAAG CTAATG |
| 11 (SEQ ID NO: 17) | RgTALsyn_FWD w/NdeI | GCGGCGCATATGGCGCCTCGC CCGACTTC |
| 12 (SEQ ID NO: 18) | RgTALsyn_REV w/SpeI | GCGGCGACTAGTTTATGCCAG CATCTTCAGCAGAACATTG |
| 13 (SEQ ID NO: 19) | SDM_RgTALsyn_FWD | GCACTGCACGACGCGCACATG TTGAGCCTGTTGAGC |
| 14 (SEQ ID NO: 20) | SDM_RgTALsyn_REV | GCTCAACAGGCTCAACATGTG CGCGTCGTGCAGTGC |
| 15 (SEQ ID NO: 21) | pXylA_FOR | GCAAGCATGCGAAATGCA |
| 16 (SEQ ID NO: 22) | pXylA_REV | GAGTTTCGTTCGAGATCGC |

TABLE 5 gBlock Sequence for cloning pXylA (SEQ ID NO: 23)

GCAAGCATGCGAAATGCACCTAGGAAAAAAAACATTGAAATAAACATTTA
TTTTGTATATGATGAGATAAAGTTAGTTTATTGGATAAACAAACTAACTC
AATTAAGATAGTTGATGGATAAACTTGTTCACTTAAATCAAAGGGGGAAA
TGTACACATATGGCAGATCTCAATTGGATATCGGCCGGCCACGCGATCGC
TGACGTCGGTACCCTCGAGTCTGGTAAAGAAACCGCTGCTGCGAAATTTG
AACGCCAGCACATGGACTCGTCTACTAGTCGCAGCTTAATTAAGCGATCT
CGAACGAAACTC

*Petunia*.times.*hybrida* anthocyanidin synthase (PhANS) was amplified with primers 1 and 2 using plasmid pMAL-PhANS (unpublished) as a template, and *Arabidopsis thaliana* anthocyanidin 3-O-glucosyltransferase (At3GT) was amplified with primers 3 and 4 using plasmid pMAL-At3GT (unpublished) as a template. Following restriction digestion of PCR amplicon PhANS (XbaI/XhoI), PCR amplicon At3GT (NdeI/XhoI), and vector pETM6 (XbaI/XhoI for PhANS and NdeI/XhoI for At3GT), digested products were gel purified and ligated (Rapid DNA Ligation Kit, Thermo Scientific) to construct plasmids pETM6-PhANS and pETM6-At3GT. Constructs were transformed into DH5α and confirmed by Sanger sequencing with primers 5-10. Using the ePathBrick sub-cloning procedure, At3GT and PhANS were then assembled into monocistronic configuration by ligation of restriction digestion fragments from plasmid pETM6-At3GT (NheI/SalI) and pETM6-PhANS (AvrII/SalI), yielding plasmid pETM6-At3 GT-m-PhANS.

Example 17

TAL Module, C5 Module, p168 Module, and Antho Module Polyculture—Fermentation Protocol The small scale cultivation protocol was adapted from with only minor modification. Except where noted, the cultures were grown in AMM with 20 g/L glucose as the primary carbon source. The cultures were first grown at 37° C. and transitioned to 30° C. upon induction with 1 mM IPTG. In the case of the phenylpropanoic acid production strains, 125 mL non-baffled shake flasks containing 25 mL of media were used to confirm small scale screening studies, allow for more frequent sampling, and limit evaporation effects on final titer.

Example 18

TAL Module, C5 Module, p168 Module, and Antho Module Polyculture—Metabolite Analysis A 25 μL injection was used for all polyculture fermentations. Analysis of phenylpropanoic acid titers in monoculture required a 10-fold dilution of culture broth and a 5 μL injection volume to reach the linear region for UV detection. Absorbance at 280 nm was monitored in all cases except for anthocyanidin-3-glucosides where 518 nm was used. Product titers were determined using authentic standards, while (+)-afzelechin was quantified using the (+)-catechin standard curve in accordance with previous literature, because (+)-afzelechin is not commercially available. All experiments were performed in at least biological duplicate, with key high-titer conditions reproduced in biological and experimental triplicate. Error bars represent ±1 standard deviation from the mean. Significance of data was determined using a two-tailed unpaired t-test with a 95 percent confidence interval.

Example 19

TAL Module, C5 Module, p168 Module, and Antho Module Polyculture—Results

Expanding upon previous co-culture efforts, the development of two additional bioconversion modules has been accomplished to realize the de novo production of both flavan-3-ols and anthocyanidin-3-glucosides for the first time outside of plants. FIG. 5 shows polyculture schematic representing the realized 4-strain polyculture. Inclusion of fifth strain shows potential for extension through addition of sequential modules.

Example 20

TAL Module, C5 Module, p168 Module, and Antho Module Polyculture—Development of TAL Module Significant efforts have been focused on improving the de novo production of phenylpropanoic acids in *E. coli*. Efforts from both the Stephanopoulos and Yan labs have enabled the near gram-scale production of both p-coumaric and caffeic acid. The development of the tyrosine overproducing *E. coli* strain rpoA14(DE3) represents a major milestone for the de novo production of phenylpropanoic acids, while the discovery and optimization of the native *E. coli* non-P450 hydroxylase enabled, for the first time, efficient production of caffeic acid through the ortho-hydroxylation of p-coumaric acid. Building off of these efforts, we set out to develop a phenylpropanoic acid production module that was compatible with our previously described 'C5' and 'p168' modules to enable the de novo production of flavan-3-ols in vivo.

TABLE 6

Twenty-eight potential phenylpropanoic acid production modules. 'Q' in the strain name indicates strain QH4, while 'R' in strain name indicates strain rpoA14(DE3)

| Name | Plasmids |
| --- | --- |
| Q1 | pZE-TH2, pCS-TPTA |
| Q2 | pZE-TH2 |
| Q3 | pETM6-RgTAL$^{syn}$, pCS-TPTA |
| Q4 | pETM6-RgTAL$^{syn}$ |
| Q5 | pCA1, pCS-TPTA |
| Q6 | pCA1 |
| Q7 | pCA3, pCS-TPTA |
| Q8 | pCA3 |
| Q9 | pETM6-RgTAL$^{syn}$-HpaBC, pCS-TPTA |
| Q10 | pETM6-RgTAL$^{syn}$-HpaBC |
| Q11 | pXPA-RgTAL$^{syn}$ |
| Q12 | pXPA-RgTAL$^{syn}$, pCS-TPTA |
| Q13 | pXylA-RgTAL$^{syn}$ |
| Q14 | pXylA-RgTAL$^{syn}$, pCS-TPTA |
| R1 | pZE-TH2, pCS-TPTA |
| R2 | pZE-TH2 |
| R3 | pETM6-RgTAL$^{syn}$, pCS-TPTA |
| R4 | pETM6-RgTAL$^{syn}$ |
| R5 | pCA1, pCS-TPTA |
| R6 | pCA1 |
| R7 | pCA3, pCS-TPTA |
| R8 | pCA3 |
| R9 | pETM6-RgTAL$^{syn}$-HpaBC, pCS-TPTA |
| R10 | pETM6-RgTAL$^{syn}$-HpaBC |

TABLE 6-continued

Twenty-eight potential phenylpropanoic acid production modules. 'Q' in the strain name indicates strain QH4, while 'R' in strain name indicates strain rpoA14(DE3)

| Name | Plasmids |
| --- | --- |
| R11 | pXPA-RgTAL$^{syn}$ |
| R12 | pXPA-RgTAL$^{syn}$, pCS-TPTA |
| R13 | pXylA-RgTAL$^{syn}$ |
| R14 | pXylA-RgTAL$^{syn}$, pCS-TPTA |

Figure 6:
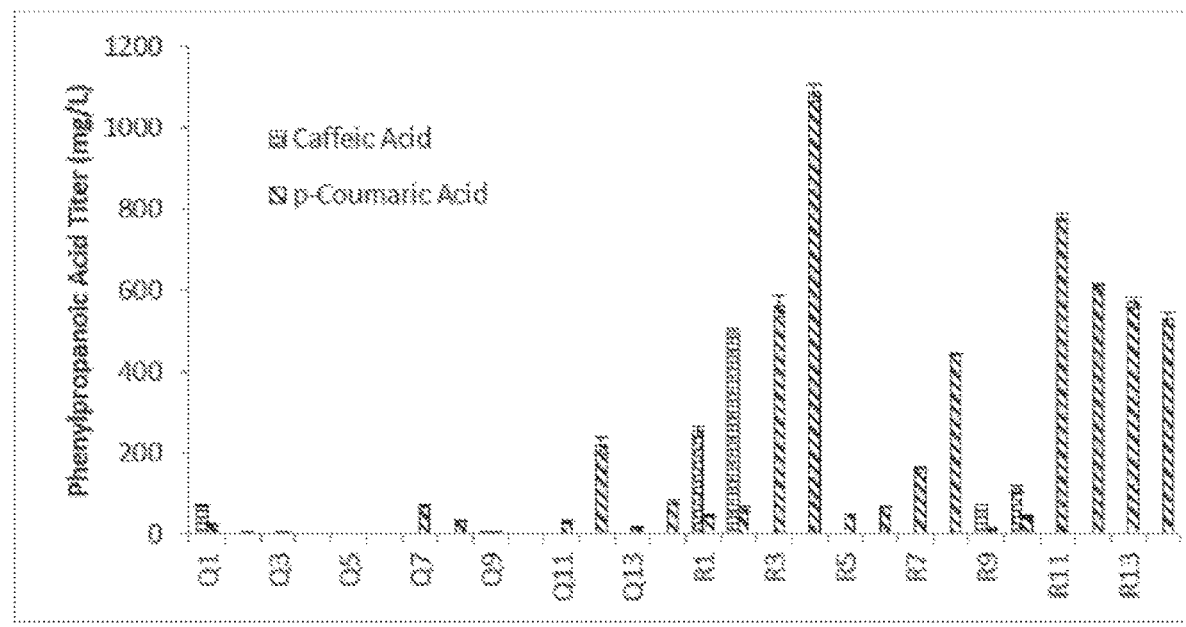
FIG. 6 shows screening of potential phenylpropanoic acid production modules. Initial screening was completed under optimal conditions for C5 and p168 co-culture (AMM-2% glycerol, 5-hour induction point, 30° C. fermentation temperature post induction with 1 mM IPTG). Constitutive expression modules (Q/R 11-14) were not induced with IPTG. Titers reported are after 2 days of cultivation in 48-well plates.

To accomplish this task, we collected the most efficient plasmids and strains from the recent literature and along with several plasmids constructed in the Koffas' lab, built 28 strain-plasmid combinations for screening of phenylpropanoic acid production, Table 6. Twenty of the 28 strains were designed for p-coumaric acid production (TAL overexpression), while the remaining 8 were targeted for caffeic acid production (TAL and HpaBC overexpression). The effect of the endogenous gene supplementation plasmid, pCS-TPTA, was also tested but did not show significant titer improvements for any of the tested combinations, FIG. 6. From the strain combinations, strain R4 represented the best p-coumaric acid production, while strain R2 was selected as the best caffeic acid producer. It is interesting to note that neither R2 nor R4 represent a strain configuration that had been previously published indicating that significant improvements can be realized through basic literature review and combinatorial screening of available modules.

Example 21

Figure 7A:
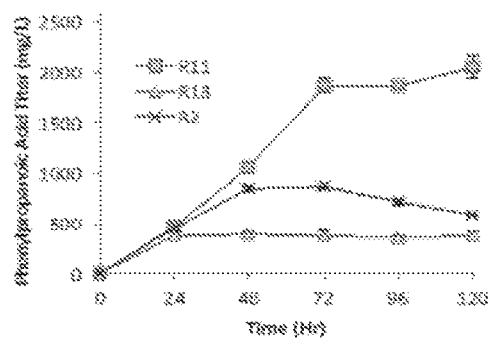
FIGS. 7A-7B show analysis of top phenylpropanoic acid production modules. (A) Glucose carbon source, 37° C., Induction 3 hr (R2 and R4 only) (B) Glycerol carbon source, 37° C., Induction 8 hr (R2 and R4 only).
Figure 7B:
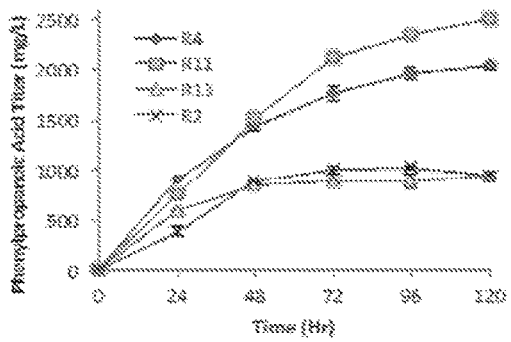

TAL Module, C5 Module, p168 Module, and Antho Module Polyculture—Optimization of Phenylpropanoic Acid Production Three p-coumaric acid (R4, R11, R13) and one caffeic acid (R2) production strains from the initial screen were subjected to further optimization to determine the full potential of these modules in monoculture. Through course optimization of induction point, inducer concentration, production temperature, and carbon source, the highest titer production to date was realized for both p-coumaric and caffeic acid at 2.51±0.03 and 1.03±0.02 g/L, respectively (FIG. 7). The production of p-coumaric acid was found to be highly sensitive to nearly all optimization parameters with highest titer production occurring in glycerol-based media (FIG. 7). Interestingly, caffeic acid production with strain R2 was found to be relatively insensitive to all factors. The titers presented here represent a 258% and 134% improvement for p-coumaric and caffeic acid, respectively, over the highest titers reported in the literature to date. Future efforts to scale-up to fed batch fermentation are underway to further improve phenylpropanoic acid titers, yields, and productivity.

Example 22

Figure 8:
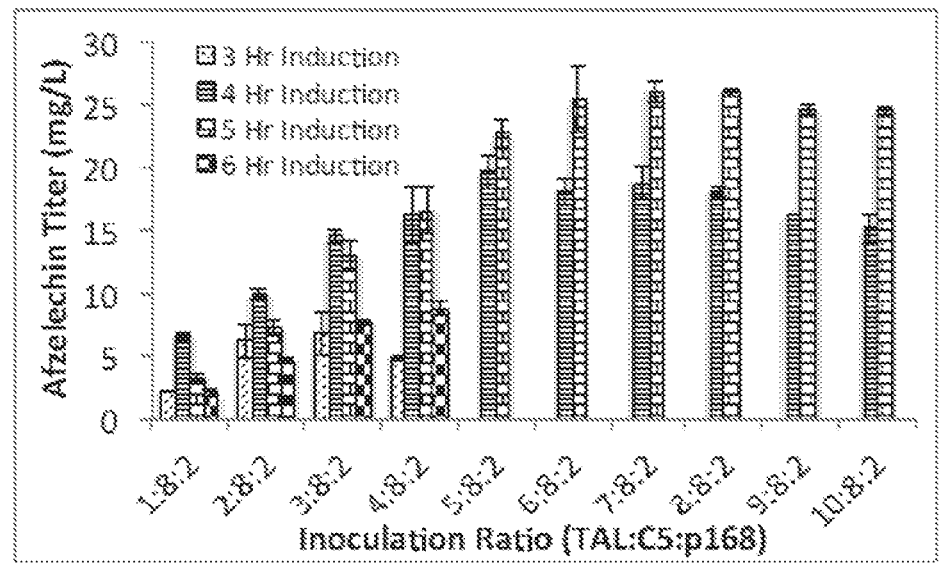
FIG. 8 shows production landscape of three-strain polyculture for the de novo production of (+)-Afzelechin. All data obtained in AMM-Glucose media at a production temperature of 30° C. Error bars represent one standard deviation of at least biological duplicate.

TAL Module, C5 Module, p168 Module, and Antho Module Polyculture—Production of Flavan-3-Ols De Novo Combining the previously published co-culture system for the efficient production of flavan-3-ols from phenylpropanoic acids with the recently developed phenylpropanoic acid production module enables the production of flavan-3-ols from glucose. Highlighting the drop-in modularity of polyculture systems we conserved the previously optimized ratio of C5:p168 of 8:2 and varied only the proportion of the TAL module over several induction points in the range of the predicted optimum from previous work. Using this simple optimization strategy, we were able to demonstrate the de novo production of afzelechin for the first time in a microbial host (FIG. 8). Furthermore, we were also to demonstrate production titers of 26.1±0.8 mg/L without extensive optimization. These successes supported the further expansion of flavonoid production using the polyculture platform.

Example 23

Figure 9:
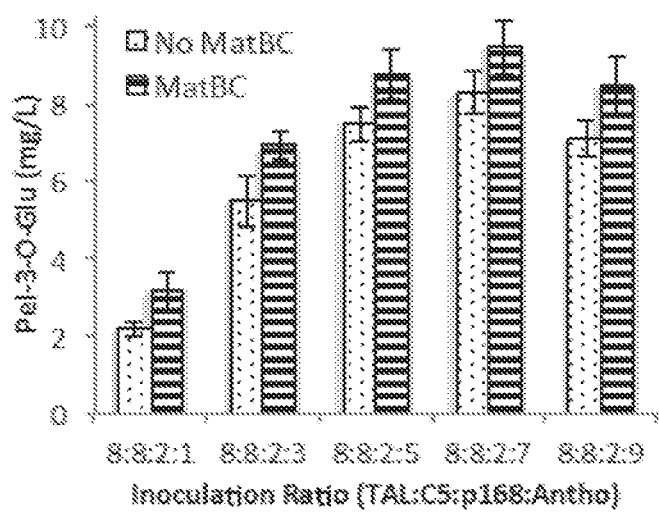
FIG. 9 shows production of anthocyanidin-3-glucosides from glucose using a four-strain polyculture. All data was obtained using a 5-hour induction point and 30° C. induction temperature. Error bars represent ±1 standard deviation from the mean of biological quadruplicates.

TAL Module, C5 Module, p168 Module, and Antho Module Polyculture—Production of Anthocyanidin-3-Glucosides De Novo Our previous successes using polycultures for the production of flavonoids has urged the further application of this technology to expand what is currently possible in vivo. Previous efforts in the Koffas' lab have developed strains capable of high titer anthocyanidin-3-glucoside production from flavan-3-ols, but efforts to further extend the pathway towards the phenylpropanoic acid precursors have not been successful. Building off of these efforts, we cloned the previously characterized ANS and 3GT enzymes into a synthetic monocistronic operon in the ePathBrick plasmid pETM6. Transforming this plasmid into our baseline host BL21star™(DE3) resulted in our 'Antho' module to be combined with the previously described TAL, C5, and p168 modules for the de novo production of anthocyanidin-3-glucosides in vivo. In a similar fashion as before, the previously determined optimum ratio 8:8:2 (TAL:C5:p168) was conserved with the fraction of the new module being varied to result in the first account of a functional synthetic four strain polyculture. This microbial consortium enabled, for the first time outside of plants, the production of the anthocyanidin-3-glucoside, callistephin, from glucose, FIG. 9).

Adding two additional enzyme overexpressions, matBC, to the previously published C5 module, further highlights the flexibility of the polyculture platform for rapid expansion and modification. These enzymes enable the uptake of externally supplemented sodium malonate and subsequent activation to malonyl-CoA, a key and limiting substrate for the chalcone synthase enzyme. Significantly (p-value<0.05) higher production of callistephin from glucose was achieved across a wide range of inoculation ratios, while conserving the optimum fermentation conditions from previous experiments.

In summary, the rapid success of these polycultures to realize the de novo production of various late-pathway flavonoid metabolites demonstrates the power of these techniques over traditional monoculture metabolic engineering efforts. Additionally, the ease at which these pathways were re-optimized through conservation of the previously optimized inoculation ratio further highlights the benefits of polyculture modularity over that of traditional monoculture techniques. In traditional monoculture techniques, extending the current heterologous overexpression pathway would require additional genes to be cloned and expressed in the previously optimized strain, consequently un-optimizing the strain from both a genetic and fermentation perspective. Genetic re-optimization is a difficult task. Oftentimes, it is impossible to regain the fluxes previously achieved, due to increased metabolic burden or natural precursor and co-factor requirements, limiting the overall titer, yield and productivity of the process. Polycultures, however, enable the genetic optimization of each module to be conserved only requiring minor fermentation optimization to adjust the inoculation ratio of the new strain. The simplicity of this optimization and the smooth trends observed in corresponding production landscapes support the hypothesis that these cultures are stable through the production phase of the fermentation.

In conclusion, we have demonstrated the development of a high-titer phenylpropanoic acid module and a plan to demonstrate its true potential through bioreactor scale-up. Utilizing this module along with the previously published modules (C5 and p168), we demonstrate the de novo production of flavan-3-ols for the first time outside of the native plant hosts. Further expanding on this polyculture theme, we incorporated a fourth module (Antho) containing the genes ANS and 3GT. Using all four modules, we were able to demonstrate the production of the anthocyindin-3-glucoside, callistephin, from glucose. This feat was possible due to the modularity of the polyculture scaffold conserving the genetic optimization of each module only requiring basic fermentation optimization to achieve peak production. Finally, we outline the path forward for expanding upon this polyculture work. These plans include potential additional modules, expansion into the terpenoid and alkaloid pathways, and methods to address the stability of the individual strain populations with time. In summary, co-culture and polyculture techniques have demonstrated their potential to rapidly expand what is deemed to be possible with metabolic engineering, but this power comes with additional complexities that must be addressed from a systematic approach to achieve the highest titer, yield, and productivities possible.

Example 24

```
Sequences RtMatB-Rhizobium trifolii
Nucleic acid sequence
                                                                    (SEQ ID NO: 24)
GTGAGCAACCATCTTTTCGACGCCATGCGGGCCGCCGCGCCCGGTAACGCACCATTC

ATCCGGATCGATAACACGCGCACATGGACCTATGACGACGCCGTCGCTCTTTCCGGC

CGCATTGCCGGCGCGATGGACACGCTCGGCATTCGCCCCGGCGACCGCGTTGCGGT

GCAGGTCGAGAAAAGTGCCGAGGCATTGATCCTCTATCTCGCCTGTCTTCGAAGCGG

CGCCGTTTACCTGCCGCTCAACACCGCCTATACGCTGGCTGAGCTCGATTATTTTATC

GGCGATGCGGAGCCGCGTTTGGTGGTTGTTGCATCGTCGGCTCGAGCGGGCGTGGA

GACAATCGCCAAGCCCCGCGGTGCGATCGTCGAAACTCTCGACGCTGATGGCAGCG

GCTCGTTGCTGGATCTCGCCCGCGATGAGCCGGCTGACTTTGTCGATGCCTCGCGCT
```

```
CCGCCGATGATCTGGCTGCGATCCTCTACACCTCGGGAACGACGGGACGCTCCAAG

GGGGCGATGCTCACGCATGGGAACCTGCTCTCGAACGCCCTGACCTTGCGAGATTTT

TGGCGCGTCACCGCCGGCGATCGACTGATCCATGCCTTGCCGATCTTCCACACGCAT

GGGCTGTTCGTCGCCACGAACGTCACTTTACTCGCCGGCGCCTCGATGTTCCTGCTG

TCGAAGTTCGACCCGGAGGAGATCCTGTCGCTGATGCCGCAGGCAACGATGCTGAT

GGGCGTGCCGACCTTCTACGTGCGCCTCCTGCAAAGCCCGCGCCTCGACAAGCAAG

CAGTCGCCAACATCCGCCTCTTCATTTCCGGTTCGGCTCCACTGCTTGCAGAAACAC

ATACCGAGTTCCAGGCACGTACCGGTCACGCCATTCTCGAGCGCTACGGCATGACG

GAAACCAATATGAACACGTCCAACCCTTATGAGGGGAAACGGATTGCCGGAACGGT

CGGCTTCCCGCTGCCTGATGTGACGGTGCGCGTCACCGATCCCGCCACCGGGCTCGC

GCTGCCGCCTGAAGAAACAGGCATGATCGAGATCAAGGGGCCGAACGTTTTCAAGG

GCTATTGGCGCATGCCCGAAAAAACCGCGGCCGAATTCACCGCCGACGGTTTCTTCA

TCAGCGGCGATCTCGGCAAGATCGACCGGGACGGTTATGTCCACATCGTCGGCCGT

GGCAAGGATCTGGTGATTTCCGGTGGATACAACATCTATCCGAAAGAGGTGGAGGG

CGAGATCGACCAGATCGAGGGTGTGGTTGAGAGCGCTGTGATCGGCGTGCCGCATC

CCGATTTCGGAGAAGGCGTGACCGCCGTCGTCGTGCGCAAACCCGGCGCTGTCCTCG

ATGAAAAGGCCATCGTCAGCGCCCTCCAGGACCGGCTCGCGCGCTACAAACAACCC

AAGCGCATCATCTTTGCCGAAGACTTGCCGCGCAACACGATGGGCAAGGTTCAGAA

AAACATCCTGCGGCAGCAATACGCCGATCTTTACACCAGGACGTAA
```

RtMatB-*Rhizobium trifolii*
Amino acid sequence
(SEQ ID NO: 25)

```
MSNHLFDAMRAAAPGNAPFIRIDNTRTWTYDDAVALSGRIAGAMDTLGIRPGDRVAVQ

VEKSAEALILYLACLRSGAVYLPLNTAYTLAELDYFIGDAEPRLVVVASSARAGVETIAK

PRGAIVETLDADGSGSLLDLARDEPADFVDASRSADDLAAILYTSGTTGRSKGAMLTHG

NLLSNALTLRDFWRVTAGDRLIHALPIFHTHGLFVATNVTLLAGASMFLLSKFDPEEILS

LMPQATMLMGVPTFYVRLLQSPRLDKQAVANIRLFISGSAPLLAETHTEFQARTGHAILE

RYGMTETNMNTSNPYEGKRIAGTVGFPLPDVTVRVTDPATGLALPPEETGMIEIKGPNV

FKGYWRMPEKTAAEFTADGFFISGDLGKIDRDGYVHIVGRGKDLVISGGYNIYPKEVEG

EIDQIEGVVESAVIGVPHPDFGEGVTAVVVRKPGAVLDEKAIVSALQDRLARYKQPKRII

FAEDLPRNTMGKVQKNILRQQYADLYTRT
```

RtMatC-*Rhizobium trifolii*
Nucleic acid sequence
(SEQ ID NO: 26)

```
ATGGGCATCGAACTGCTGAGTATTGGTCTGCTGATTGCTATGTTTATTATTGCTACGA

TTCAACCGATTAACATGGGTGCTCTGGCATTCGCAGGCGCTTTTGTGCTGGGTAGCA

TGATTATCGGCATGAAAACCAACGAAATTTTCGCAGGCTTTCCGTCTGACCTGTTTCT

GACCCTGGTGGCGGTTACGTACCTGTTTGCGATTGCCCAGATCAATGGCACCATCGA

CTGGCTGGTTGAATGCGCGGTGCGTCTGGTTCGTGGCCGCATTGGTCTGATCCCGTG

GGTGATGTTCCTGGTTGCGGCCATTATCACCGGTTTTGGTGCACTGGGTCCGGCAGC

TGTTGCAATTCTGGCACCGGTCGCACTGAGCTTCGCAGTGCAATATCGCATTCATCC

GGTTATGATGGGTCTGATGGTCATCCACGGCGCACAGGCTGGCGGTTTTTCACCGAT

TTCGATCTACGGCGGTATTACCAACCAAATCGTGGCAAAAGCAGGTCTGCCGTTCGC
```

-continued

```
ACCGACGAGTCTGTTTCTGAGCAGCTTTTTCTTTAATCTGGCAATTGCTGTCCTGGTG
TTCTTTGTGTTTGGCGGTGCACGTGTTATGAAACACGATCCGGCTTCTCTGGGTCCGC
TGCCGGAACTGCATCCGGAAGGCGTGAGCGCGTCTATTCGTGGTCATGGCGGCACC
CCGGCAAAACCGATCCGCGAACATGCGTATGGCACCGCAGCAGACACGGCAACCAC
GCTGCGTCTGAACAATGAACGCATTACCACGCTGATCGGTCTGACCGCACTGGGTAT
TGGTGCACTGGTTTTCAAATTTAACGTCGGTCTGGTGGCTATGACCGTGGCAGTGGT
TCTGGCACTGCTGAGCCCGAAAACGCAGAAAGCAGCTATTGATAAAGTCAGTTGGT
CCACCGTGCTGCTGATCGCGGGTATTATCACGTATGTTGGCGTCATGGAAAAAGCGG
GCACCGTTGACTACGTCGCCAATGGTATTAGTTCCCTGGGTATGCCGCTGCTGGTCG
CGCTGCTGCTGTGTTTCACCGGCGCCATCGTGTCCGCGTTTGCCTCATCGACGGCACT
GCTGGGTGCTATTATCCCGCTGGCCGTTCCGTTCCTGCTGCAGGGCCATATTAGTGC
AATCGGTGTCGTGGCGGCCATTGCTATCTCCACCACGATTGTGGATACCAGCCCGTT
TTCTACGAACGGCGCGCTGGTTGTCGCAAATGCTCCGGATGACTCACGTGAACAGGT
TCTGCGCCAACTGCTGATCTATTCGGCCCTGATTGCTATTATTGGTCCGATTGTCGCC
TGGCTGGTTTTCGTTGTGCCGGGTCTGGTCTAA
```

RtMatC-*Rhizobium trifolii*
Amino acid sequence
(SEQ ID NO: 27)

```
MGIELLSIGLLIAMFIIATIQPINMGALAFAGAFVLGSMIIGMKTNEIFAGFPSDLFLTLVA
VTYLFAIAQINGTIDWLVECAVRLVRGRIGLIPWVMFLVAAIITGFGALGPAAVAILAPV
ALSFAVQYRIHPVMMGLMVIHGAQAGGFSPISIYGGITNQIVAKAGLPFAPTSLFLSSFFF
NLAIAVLVFFVFGGARVMKHDPASLGPLPELHPEGVSASIRGHGGTPAKPIREHAYGTA
ADTATTLRLNNERITTLIGLTALGIGALVFKFNVGLVAMTVAVVLALLSPKTQKAAIDK
VSWSTVLLIAGIITYVGVMEKAGTVDYVANGISSLGMPLLVALLLCFTGAIVSAFASSTA
LLGAIIPLAVPFLLQGHISAIGVVAAIAISTTIVDTSPFSTNGALVVANAPDDSREQVLRQL
LIYSALIAIIGPIVAWLVFVVPGLV
```

RgTALsyn-*Rhodotorula glutinis*
Nucleic acid sequence
(SEQ ID NO: 28)

```
atggcgcctcgcccgacttcgcaaagccaggcccgcacttgcccgacgacgcaggttacccaagttgatatcgttgag
aaaatgttggcggctcctactgatagcacgctggagctggacggttatagcctgaatctgggtgatgtcgtgagcgct
gcgcgtaagggtcgtcctgtccgtgtcaaagatagcgatgaaatccgcagcaaaatcgacaagagcgttgaattcctg
cgcagccaactgagcatgtcggtttacggtgtgacgaccggattggcggctccgcggacacgcgcacggaggacgcaa
ttagcctgcaaaaggcgttgctggaacaccagctgtgtggtgtgttgccgagcagatcgacagattcgcttgggtcgt
ggtctggagaatagcctgccgttggaagtcgttcgcggtgcaatgaccattcgtgtgaattcgctgacccgtggccat
agcgctgttcgtctggttgttctggaagcactgacgaactttctgaaccacggtattaccccgattgttccgctgcgc
ggtacgatctccgcgagcggcgatctgtctccactgtcgtacattgcagcggcgattagcggtcacccgatagcaaa
gttcacgtggtccatgaaggcaaagagaagatcctgtacgcgcgcgaagcgatggcgctgtttaacctggagccggtg
gttttgggtccgaaggagggcctgggtctggtgaatggtacggcagtctccgcgagcatggcaacgctggcactgcac
gacgcgcatatgttgagcctgttgagccaatcgctgaccgcgatgaccgtggaggcgatggtcggtcacgcgggcaga
tccatccattcctgcacgatgttacgcgtccgcacccgacgcaaatcgaggtcgcgggtaacattcgcaaactgctgg
agggctcgcgcttcgcggtccaccacgaggaagaggttaaggtcaaggatgatgaaggcattttgcgtcaggatcgtt
atccgttgcgcacgagcccgcaatggttgggtccgctggtgtccgacctgattcacgctcatgccgtcttgacgatcg
aagcgggtcaaagcaccaccgataacccactgatcgatgttgagaataagaccagccatcacggtggcaactttcaag
```

-continued cggcagcggttgccaacacgatggaaaagacccgtctgggcttggcccaaatcggtaaactgaatttcacccagctga cggagatgctgaacgcgggcatgaatcgtggcttgccgagctgcctggcggctgaagacccatccctgagctatcatt gcaaaggtctggacattgcggcggctgcatatacgagcgaactgggccacctggctaacccggtcaccacccacgtcc aaccggctgaaatggcaaaccaggcggtgaatagcttggcgttgattagcgcacgtcgtaccacggaatctaacgacg ttctgtccctgctgctggcaacgcacctgtactgcgtgctgcaggcgatcgacctgcgtgcgattgagttcgagttca agaaacagtttggtcctgccattgttagcctgatcgaccaacactttggtagcgcgatgacgggtagcaatctgcgtg atgagctggttgaaaaggtcaataagactctggccaagcgtttggagcaaaccaatagctacgatctggttccgcgct ggcacgacgcttttagcttcgctgcaggcactgttgtcgaggttctgtccagcacgagcctgagcttggcggccgtga acgcatggaaggttgcggcagccgagagcgcgatctccttgacgcgccaggtccgtgaaacgttttggtccgctgcaa gcacctccagcccggcgttgtcttacttgagcccgcgcacgcagatcctgtacgcatttgtgcgtgaggaactgggtg tcaaagcccgccgtggtgacgtcttcttgggtaaacaagaagttaccatcggcagcaacgttagcaagatttacgaag ccatcaagagcggccgtatcaacaatgttctgctgaagatgctggcataa RgTALsyn-Rhodotorula glutinis
Amino acid sequence
(SEQ ID NO: 29)

MAPRPTSQSQARTCPTTQVTQVDIVEKMLAAPTDSTLELDGYSLNLGDVVSAARKGRP

VRVKDSDEIRSKIDKSVEFLRSQLSMSVYGVTTGFGGSADTRTEDAISLQKALLEHQLCG

VLPSSFDSFRLGRGLENSLPLEVVRGAMTIRVNSLTRGHSAVRLVVLEALTNFLNHGITPI

VPLRGTISASGDLSPLSYIAAAISGHPDSKVHVVHEGKEKILYAREAMALFNLEPVVLGP

KEGLGLVNGTAVSASMATLALHDAHMLSLLSQSLTAMTVEAMVGHAGSFHPFLHDVT

RPHPTQIEVAGNIRKLLEGSRFAVHHEEEVKVKDDEGILRQDRYPLRTSPQWLGPLVSDL

IHAHAVLTIEAGQSTTDNPLIDVENKTSHEIGGNFQAAAVANTMEKTRLGLAQIGKLNFT

QLTEMLNAGMNRGLPSCLAAEDPSLSYHCKGLDIAAAAYTSELGHLANPVTTHVQPAE

MANQAVNSLALISARRTTESNDVLSLLLATHLYCVLQAIDLRAIEFEFKKQFGPAIVSLID

QHFGSAMTGSNLRDELVEKVNKTLAKRLEQTNSYDLVPRWHDAFSFAAGTVVEVLSST

SLSLAAVNAWKVAAAESAISLTRQVRETFWSAASTSSPALSYLSPRTQILYAFVREELGV

KARRGDVFLGKQEVTIGSNVSKIYEAIKSGRINNVLLKMLA

At4CL-Arabidopsis thaliana
Nucleic acid sequence
(SEQ ID NO: 30)
atggcgccacaagaacaagcagtttctcaggtgatggagaaacagagcaacaacaacaacagtgacgtcattttccgatcaaagttaccgg atatttacatcccgaaccacctatctctccacgactacatcttccaaaacatctccgaattcgccactaagccttgcctaatcaacggaccaacc ggccacgtgtacacttactccgacgtccacgtcatctcccgccaaatcgccgccaattttcacaaactcggcgttaaccaaaacgacgtcgt catgctcctcctcccaaactgtcccgaattcgtcctctcttttcctcgccgcctccttccgcggcgcaaccgccaccgccgcaaaccctttcttc actccggcggagatagctaaacaagccaaagcctccaacaccaaactcataatcaccgaagctcgttacgtcgacaaaatcaaaccacttc aaaacgacgacggagtagtcatcgtctgcatcgacgacaacgaatccgtgccaatccctgaaggctgcctccgcttcaccgagttgactca gtcgacaaccgaggcatcagaagtcatcgactcggtggagatttcaccggacgacgtggtggcactaccttactcctctggcacgacggg attaccaaaaggagtgatgctgactcacaagggactagtcacgagcgttgctcagcaagtcgacggcgagaacccgaatctttatttccaca gcgatgacgtcatactctgtgttttgcccatgtttcatatctacgctttgaactcgatcatgttgtgtggtcttagagttggtgcggcgattctgata atgccgaagtttgagatcaatctgctattggagctgatccagaggtgtaaagtgacggtggctccgatggttccgccgattgtgttggccattg cgaagtatcggagacggagaagtatgatttgagctcgataagagtggtgaaatctggtgctgctcctcttggtaaagaacttgaagatgccg ttaatgccaagtttcctaatgccaaactcggtcagggatacggaatgacggaagcaggtccagtgctcgcaatgtcgttaggttttgcaaagg aaccttttccggttaagtcaggagcttgtggtactgttgtaagaaatgctgagatgaaaatagttgatccagacaccggagattctctttcgagg -continued aatcaacccggtgagatttgtattcgtggtcaccagatcatgaaaggttacctcaacaatccggcagctacagcagagaccattgataaaga cggttggcttcatactggagatattggattgatcgatgacgatgacgagcttttcatcgttgatcgattgaaagaacttatcaagtataaaggtttt caggtagctccggctgagctagaggctttgctcatcggtcatcctgacattactgatgttgctgttgtcgcaatgaaagaagaagcagctggt gaagttcctgttgcatttgtggtgaaatcgaaggattcggagttatcagaagatgatgtgaagcaattcgtgtcgaaacaggttgtgttttacaa gagaatcaacaaagtgttcttcactgaatccattcctaaagctccatcagggaagatattgaggaaagatctgagggcaaaactagcaaatg gattgtga At4CL-Arabidopsis thaliana
Amino acid sequence
(SEQ ID NO: 31)

MAPQEQAVSQVMEKQSNNNNSDVIFRSKLPDIYIPNHLSLHDYIFQNISEFATKPCLINGP

TGHVYTYSDVHVISRQIAANFHKLGVNQNDVVMLLLPNCPEFVLSFLAASFRGATATAA

NPFFTPAEIAKQAKASNTKLIITEARYVDKIKPLQNDDGVVIVCIDDNESVPIPEGCLRFTE

LTQSTTEASEVIDSVEISPDDVVALPYSSGTTGLPKGVMLTHKGLVTSVAQQVDGENPNL

YFHSDDVILCVLPMFHIYALNSIMLCGLRVGAAILIMPKFEINLLLELIQRCKVTVAPMVP

PIVLAIAKSSETEKYDLSSIRVVKSGAAPLGKELEDAVNAKFPNAKLGQGYGMTEAGPV

LAMSLGFAKEPFPVKSGACGTVVRNAEMKIVDPDTGDSLSRNQPGEICIRGHQIMKGYL

NNPAATAETIDKDGWLHTGDIGLIDDDDELFIVDRLKELIKYKGFQVAPAELEALLIGHP

DITDVAVVAMKEEAAGEVPVAFVVKSKDSELSEDDVKQFVSKQVVFYKRINKVFFTESI

PKAPSGKILRKDLRAKLANGL

Pc4CL-Petroselinum crispum
Nucleic acid sequence
(SEQ ID NO: 32)

atgggagactgtgtagcacccaaagaagaccttattttccgatcgaaactccctgatatttacatcccgaaacaccttccgttacatacttattgt ttcgaaaacatctcgaaagttggcgacaagtcctgtttaataaatggcgctacaggcgaaacgttcacttattcccaagttgagctcctttccag gaaagttgcatcagggttaaacaaactcggcattcaacagggcgataccatcatgcttttgctccctaactcccctgagtattttttcgctttctta ggcgcatcgtatcgtggtgcaatttctactatggccaatccgttttttcacttctgctgaggtgatcaaacagctcaaagcatcccaagctaagct cataattacgcaagcttgttacgtagacaaagtgaaagactacgcagcagagaaaaatatacagatcatttgcatcgatgatgctcctcagga ttgtttacatttctccaaacttatggaagctgatgaatcagaaatgcctgaggttgtgatcaattcagacgatgtcgtcgcgttaccttactcatcg ggtactacaggactaccgaaaggtgttatgttgacacacaaaggacttgttactagcgtggcacaacaagttgatggagacaatccgaattta tatatgcatagcgaggatgtgatgatctgcatattgcctttgtttcatatttattcgcttaacgcggtgttgtgctgtggactcagagcaggggtga cgatcttgattatgcagaaatttgatattgtgccattttttggaactgatacagaaatataaagttacaattggaccgtttgtgccaccaattgtgttg gcaattgcgaaaagtccagtggtggataaatatgacttgtcgtcggtgaggacggttatgtctggagctgctccgttagggaaggagcttga agatgctgttagagctaagtttcctaatgccaaacttggtcagggatatggaatgacagaggcagggccagttttagcaatgtgcctggcgttt gcaaaggaaccatacgagatcaaatcgggtgcctgtggaactgttgtgaggaatgctgaaatgaaaattgtggatcctgagaccaacgcct ctcttccacgaaaccaacgcggagagatttgcattcgaggtgaccaaattgaaaggctacctcaatgatcctgaatcaacaaggacaaca atagacgaagaaggctggttgcacacaggagatataggcttcattgacgacgatgatgagctatttattgttgatagacttaaggaaataatca aatacaaaggatccaggttgcccctgctgaacttgaagctctgctacttactcatcctaccatttccgatgctgcagttgttcccatgatagatg agaaagcaggagaggtgcctgtggatttgttgtgagaacaaacggificaccaccactgaggaagaaatcaagcaattcgtctcgaaaca ggtggtgttctacaagagaatatttcgtgtatttttttgttgatgcaattccgaaatcaccatctggaaagattcttcgaaaggacttgagagcaaa aatagcatccggtgatcttcccaaataa Pc4CL-Petroselinum crispum
Amino acid sequence
(SEQ ID NO: 33)

MGDCVAPKEDLIFRSKLPDIYIPKHLPLHTYCFENISKVGDKSCLINGATGETFTYSQVEL

LSRKVASGLNKLGIQQGDTIMLLLPNSPEYFFAFLGASYRGAISTMANPFFTSAEVIKQLK

```
ASQAKLIITQACYVDKVKDYAAEKNIQIICIDDAPQDCLHFSKLMEADESEMPEVVINSD

DVVALPYSSGTTGLPKGVMLTHKGLVTSVAQQVDGDNPNLYMHSEDVMICILPLFHIYS

LNAVLCCGLRAGVTILIMQKFDIVPFLELIQKYKVTIGPFVPPIVLAIAKSPVVDKYDLSS

VRTVMSGAAPLGKELEDAVRAKFPNAKLGQGYGMTEAGPVLAMCLAFAKEPYEIKSG

ACGTVVRNAEMKIVDPETNASLPRNQRGEICIRGDQIMKGYLNDPESTRTTIDEEGWLH

TGDIGFIDDDDELFIVDRLKEIIKYKGFQVAPAELEALLLTHPTISDAAVVPMIDEKAGEV

PVAFVVRTNGFTTTEEEIKQFVSKQVVFYKRIFRVFFVDAIPKSPSGKILRKDLRARIASG

DLPK
```

Vv4CL-Vitis vinifera
Nucleic acid sequence (SEQ ID NO: 34)

```
atgattagtattgaaacgcaaaacccggatgttagcaacctggacacctcgcactctattccgaaaatggcaaaccgtattgatgaccatgtgt
ttcgttctaaactgccggaaattccgatcagtaaccatctgccgctgcacacgtattgcttcgaaaattactcgcagtttgcagaccgtccgtgt
ctgattgttggctcgacgaacaaaacctatagatcgctgaaaccatctgatctctcgcaaagtgggcgcaggttttgctcacctgggtctga
acagggcgatgtggttatgattctgctgcaaaattgcgcggaatttgccttcagctttctgggtgcgtctatggttggcgccgtcaccacgac
cgcaaacccgttctacacgtccgcggaaatcttcaaacagctgaacgcatcaaaagctaaaatcgtcgtgacccaggcgcaatatgtggat
aaactgcgcgactacccggatggtcaagttgccaaaattggcgaaggtttcacggtcattaccatcgatgacccgccggaaaactgtatgca
ttttagtgttgtctccgaagcgaacgaaagcgaactgccggaagtctcaattaattggatgacccggtggccctgccgtttagctctggtac
gaccggcctgccgaaaggcgtggttctgacgcacaaatcactgatcacctcggtcgcccagcaagtggatggtgaaaacccgaatctgca
tctgaccccggatgacgtcgtgctgtgcgtgctgccgctgttccacatttatagcctgaactctgttctgctgtgtagtctgcgtgcaggtgcag
cagtgctgctgatgcagaaatttgaaattggtaccctgctggaactgatccaacgttaccgcgtgagcgttgcagctgttgtcccgccgctgg
ttctggcactggctaaaaatccgatggtggaatcgtttgatctgagttccatccgtgtggttctgagcggtgcagcaccgctgggcaaagaac
tggaagcagctctgcgttcccgcgttccgcaggcagtcctgggccaaggttatggcatgacggaagcaggcccggtgctgtcaatgtgcct
gggttttcgctaaacagccgtttccgacgaaatcaggttcgtgtggcaccgtcgtgcgtaacgcggaactgaaagttgtggatccggaaacc
ggttgctccctgggccgtaatcagccgggtgaaatttgtatccgcggccagcaaattatgaaaggttatctgaatgatccggaagcgacggc
ctctaccattgacgttgatggctggctgcataccggtgacatcggctacgtggatgacgatgaagaagtgttcattgttgatcgcgtcaaaga
actgatcaaattcaaaggtMcaggttccgccggcagaactggaagctctgctggtgtctcacccgtccattgccgatgcggccgtggttcc
gcaaaaagacgatgttgctggcgaagtcccggtggcgttcgtcgtgcgttctaacggttttgaactgaccgaagaagcagtgaaagaattca
tcagtaaacaggttgtcttttataaacgcctgcataaagtgtactttgttcacgcgattccgaaaagcccgtctggcaaaatcctgcgtaaagat
ctgcgcgcgaaactggccgaaaaaaccccggaaccgaac
```

Vv4CL-Vitis vinifera
Amino acid sequence (SEQ ID NO: 35)

```
MISIETQNPDVSNLDTSHSIPKMANRIDDHVFRSKLPEIPISNHLPLHTYCFENYSQFADRP

CLIVGSTNKTYSFAETHLISRKVGAGFAHLGLKQGDVVMILLQNCAEFAFSFLGASMVG

AVTTTANPFYTSAEIFKQLNASKAKIVVTQAQYVDKLRDYPDGQVAKIGEGFTVITIDDP

PENCMHFSVVSEANESELPEVSINSDDPVALPFSSGTTGLPKGVVLTHKSLITSVAQQVD

GENPNLHLTPDDVVLCVLPLFHIYSLNSVLLCSLRAGAAVLLMQKFEIGTLLELIQRYRV

SVAAVVPPLVLALAKNPMVESFDLSSIRVVLSGAAPLGKELEAALRSRVPQAVLGQGYG

MTEAGPVLSMCLGFAKQPFPTKSGSCGTVVRNAELKVVDPETGCSLGRNQPGEICIRGQ

QIMKGYLNDPEATASTIDVDGWLHTGDIGYVDDDEEVFIVDRVKELIKFKGFQVPPAEL

EALLVSHPSIADAAVVPQKDDVAGEVPVAFVVRSNGFELTEEAVKEFISKQVVFYKRLH

KVYFVHAIPKSPSGKILRKDLRAKLAEKTPEPN
```

PhCHS-Petunia X hybrida

Nucleic acid sequence (SEQ ID NO: 36)

atggtgacagtcgaggagtatcgtaaggcacaacgtgctgaaggtccagccactgtcatggccattggaacagccacaccttcaaactgtg ttgatcaaagcacttaccctgattttttattttcgtatcactaacagtgagcacaagactgatcttaaggagaaatttaagcgcatgtgtgaaaaat caatgattaagaaaaggtacatgcacttaacagaggaaatcttgaaagagaatcctagtatgtgtgaatacatggcaccttctcttgatgctag gcaagacatagtggtggttgaagtgcccaaacttggcaaagaggcagctcaaaaggccatcaaggaatggggccagcccaagtccaaaa ttacccatttggtcttttgcacaaccagtggtgtggacatgcctgggtgtgactatcaactcactaagctacttgggcttcgtccatcggtcaag aggcttatgatgtaccaacaaggttgctttgctggtggcacggttcttcggttagccaaggacttggctgaaaacaacaagggcgctcgagt cctgttgtttgttcagaaatcaccgcggtcactttccgtgggccaaatgatactcatttggatagtttagttggccaagcacttttttggtgatggg gcaggcgcgatcattataggttctgatccaattccaggggtcgaaaggcctttgttcgagctcgtttcagcagcccaaactcttctcccagata gccatggtgctattgatggccatctccgtgaagttgggcttacattccacttactcaaagatgttcctgggctgatctcaaaaaatattgagaag agccttgaggaagcattcaaacctttgggcatttctgattggaactctctattctggattgctcatccaggtgggcctgcaattttggaccaagtt gaaataaagttgggcctaaagcccgagaaacttaaggctacaaggaatgtgttaagtaactatggtaacatgtcaagtgcttgtgtactgtttat tttggatgaaatgagaaaggcctcagccaaagaaggtttaggaactactggtgaagggcttgagtggggtgttctttttggatttgggcctgg gctaacagttgagactgttgtcctccacagtgttgctacttaa PhCHS-Petunia X hybrida
Amino acid sequence (SEQ ID NO: 37)

MVTVEEYRKAQRAEGPATVMAIGTATPSNCVDQSTYPDFYFRITNSEHKTDLKEKFKR

MCEKSMIKKRYMHLTEEILKENPSMCEYMAPSLDARQDIVVVEVPKLGKEAAQKAIKE

WGQPKSKITHLVFCTTSGVDMPGCDYQLTKLLGLRPSVKRLMMYQQGCFAGGTVLRL

AKDLAENNKGARVLVVCSEITAVTFRGPNDTHLDSLVGQALFGDGAGAIIIGSDPIPGVE

RPLFELVSAAQTLLPDSHGAIDGHLREVGLTFHLLKDVPGLISKNIEKSLEEAFKPLGISD

WNSLFWIAHPGGPAILDQVEIKLGLKPEKLKATRNVLSNYGNMSSACVLFILDEMRKAS

AKEGLGTTGEGLEWGVLFGFGPGLTVETVVLHSVAT

CmCHS-Citrus maxima
Nucleic acid sequence (SEQ ID NO: 38)

atggctacggtccaagaaatccgcaacgctcaacgcgcagatggtccggcgacggtcctggcaatcggcacggcaaccccggctcatag cgtgaaccaggcagattatccggactattactttcgtattaccaaatctgaacacatgacggaactgaaagaaaaattcaaacgtatgtgcgat aaaagtatgattaaaaaacgctacatgtacctgaccgaagaaatcctgaaagaaaacccgaatatgtgtgcctacatggcaccgagcctgg atgcgcgccaggacattgtggttgtcgaagttccgaaactgggtaaagaagcggccaccaaagccatcaaagaatggggccaaccgaaa tcaaaaattacgcacctgatcttttgcaccacgtcgggtgtggatatgccgggtgcagactatcagctgaccaaactgctgggtctgcgtccg agcgttaaacgctttatgatgtaccagcaaggctgcttcgcaggcggtacggtcctgcgtctggctaaagatctggcggaaaacaataaag gtgctcgcgttctggtggtttgtagtgaaattaccgctgtcacgtttcgtggtccggcggatacccatctggactccctggttggccaggccct gttcggcgatggtgcagctgcggttatcgtcggcgcagatccggacacgagtgtggaacgtccgctgtatcagctggtttcaacctcgcaa acgattctgccggattccgacggtgcgatcgatggccatctgcgcgaagtgggtctgacctttcacctgctgaaagacgttccgggcctgat ttcaaaaaacatcgaaaaagcctgtctgaagcctttgcaccggttggtatttcggattggagctctattttctggatcgcacatccgggcggtc cggcaatcctggaccaggtggaaagcaaactgggtctgaaagaagaaaaactgaaagctacccgtcaagtcctgtctgaatacggcaata tgagttccgcgtgtgtgctgttcattctggatgaaatgcgcaaaaaatctgccgaagaagctaaagcgaccacgggcgaaggtctggattgg ggcgtgctgtttggtttcggtccgggtctgaccgtcgaaacggtcgtgctgcacagtgtgccgatcaaagcgggcggtggcggttccggcg gtggtggtagtggtggtggtggctctccgccgccggccctgccgccgaaacgtcgtcgctaa CmCHS-Citrus maxima
Amino acid sequence (SEQ ID NO: 39)

MATVQEIRNAQRADGPATVLAIGTATPAHSVNQADYPDYYFRITKSEHMTELKEKFKR

-continued

```
MCDKSMIKKRYMYLTEEILKENPNMCAYMAPSLDARQDIVVVEVPKLGKEAATKAIKE

WGQPKSKITHLIFCTTSGVDMPGADYQLTKLLGLRPSVKRFMMYQQGCFAGGTVLRLA

KDLAENNKGARVLVVCSEITAVTFRGPADTHLDSLVGQALFGDGAAAVIVGADPDTSV

ERPLYQLVSTSQTILPDSDGAIDGHLREVGLTFHLLKDVPGLISKNIEKSLSEAFAPVGISD

WSSIFWIAHPGGPAILDQVESKLGLKEEKLKATRQVLSEYGNMSSACVLFILDEMRKKS

AEEAKATTGEGLDWGVLFGFGPGLTVETVVLHSVPIKAGGGGSGGGGSGGGGSPPPAL

PPKRRR
```

CmCHI-Citrus maxima
Nucleic acid sequence
(SEQ ID NO: 40)

```
atgaatccgtcgccgtctgttaccgaactgcaagtggaaaatgtcacctttacgccgagtctgcaaccgccgggctctaccaaatcgcatttt ctgggcggtgcaggtgaacgtggcctggaaatcgaaggcaaatttgttaaattcaccgctattggtgtctatctggaagaaaacgccgtgcc gctgctggcaggcaaatggaaaggcaaaaccgccggtgaactgacggaatctgtcgaattttttccgcgatgtggttaccggcccgtttgaa aaattcatgaaagtgaccatgatcctgccgctgacgggtgcgcagtattcagaaaaagttgctgaaaattgcatggcgatttggaaattttttcg gcatctacaccgatgcagaagctaaagcgattgaaaaatttacggaagtgttcaaagacgaaatttttccgccgggcagctctatcctgttca cccaaagttccggttcgctgacgatttcattttttcgaaagatggcagcatcccgaaagacggtgtcgcggtgattgaaaacaatctgctgagc gaagccgttctggaatctatgatcggtaaaaacggcgtcagtccggcggccaaaaaatcccctggccgaacgtctgtcagcactgctgaatg ttgatccgacaaaatgaaaggcggtggcggctcaggtggcggtggctctggtggcggtggttcaggcgtcaaagaaagtctggtgtga
```

CmCHI-Citrus maxima
Amino acid sequence
(SEQ ID NO: 41)

```
MNPSPSVTELQVENVTFTPSLQPPGSTKSHFLGGAGERGLEIEGKFVKFTAIGVYLEENA

VPLLAGKWKGKTAGELTESVEFFRDVVTGPFEKFMKVTMILPLTGAQYSEKVAENCMA

IWKFFGIYTDAEAKAIEKFTEVFKDEIFPPGSSILFTQSSGSLTISFSKDGSIPKDGVAVIE

NNLLSEAVLESMIGKNGVSPAAKKSLAERLSALLNVASDKMKGGGGSGGGGSGGGGS

GVKESLV
```

MsCHI-Medicago sativa
Nucleic acid sequence
(SEQ ID NO: 42)

```
atggctgcatcaatcaccgcaatcactgtggagaaccttgaatacccagcggtggttacctctccggtcaccggcaaatcatatttcctcggt ggcgctggggagagaggattgaccattgaaggaaacttcatcaagttcactgccataggtgtttatttggaagatatagcagtggcttcacta gctgccaaatggaagggtaaatcatctgaagagttacttgagacccttgacttttacagagacatcatctcaggtccctttgaaaagttaattag agggtcaaagattagggaattgagtggtcctgagtactcaaggaaggttatggagaactgtgtggcacacttgaaatcagttggaacttatgg agatgcagaagctgaagctatgcaaaaatttgctgaagctttcaagcctgttaattttccacctggtgcctctgttttctacaggcaatcacctaa tggaatattagggcttagtttctctccggatacaagtataccagaaaaggaggctgcactcatagagaacaaggcagtttcatcagcagtgtt ggagactatgatcggcgagcacgctgtttcccctgatcttaagcgctgtttagctgcaagattacctgcgttgttgaacgagggtgctttcaag attggaaactga
```

MsCHI-Medicago sativa
Amino acid sequence
(SEQ ID NO: 43)

```
MAASITAITVENLEYPAVVTSPVTGKSYFLGGAGERGLTIEGNFIKFTAIGVYLEDIAVA

SLAAKWKGKSSEELLETLDFYRDIISGPFEKLIRGSKIRELSGPEYSRKVMENCVAHLKS

VGTYGDAEAEAMQKFAEAFKPVNFPPGASVFYRQSPNGILGLSFSPDTSIPEKEAALIEN

KAVSSAVLETMIGEHAVSPDLKRCLAARLPALLNEGAFKIGN
```

CsF3H-Camellia sinensis
Nucleic acid sequence
(SEQ ID NO: 44)

```
atggcaccgaccaccaccctgaccgcactggcagaagaaaaaagcctgcagcagaaatttgttcgtgatgaagatgaacgtccgaaagtt
```

-continued

```
gcctataatgtgtttagcaatgaaatcccggttattagcctggcaggtattgatgaaattgaaggtcgtcgtagcgaaatttgccgtaaaattgtt gaagcatgtgaaggttggggtgttttcaggttgttgatcatggtgttgatgcaaatctgattgcagaaatgacccgtctggcacgtgaattttt gcactgcctccggaagaaaaactgcgttttgatatgagcggtggtaaaaaaggtggttttattgttagcagccatctgcagggtgaagcagtt caggattggcgtgaaattgttacctatttcagctatccgattcgtgcacgtgattatagccgttggcctgataaaccggaaggttggcgtgcag ttaccgaaacctatagcgaaaaactgatggatctggcatgtaaactgctggaagttctgagcgaagcaatgggtctggaaaaagaggcact gaccaaagcatgtgttgatatggatcagaaagtggtgatcaacttctatccgaaatgtccgcagccggatctgaccctgggtctgaaacgtca taccgatccgggtacaattaccctgctgctgcaagatcaggtgggtggtctgcaggcaacccgtgatggtggcaaaacctggattaccgttc agccggttgaaggtgcatttgttgttaatctgggtgatcatggccattatctgagcaatggtcgctttaaaaacgcagatcatcaggcagttgtt aatagcaattgtagccgtctgagcattgcaacctttcagaatccggcaccggaagcaaccgtttatccgctgaaaattcgtgaaggtgaaaaa ccgattctggaagaaccgattacctttgccgatatgtataaacgcaaaatgagcaaagatatcgagctggccaaactgaaaaaactggcgaa agaaaaaaaactgctgcaagaccagcaggatatcgaaaaagcaaaactggaaatcaaaagcaccgatgaaatcttcgccctggttggtgc actgatgcatgttatgcagaaaacgtagccgtgcaattcatagcagtgatgaaggtgaagatcaagccggtgatgaagatgaggat
```

CsF3H-Camellia sinensis
Amino acid sequence
(SEQ ID NO: 45)

MAPTTTLTALAEEKSLQQKFVRDEDERPKVAYNVFSNEIPVISLAGIDEIEGRRSEICRKIV

EACEGWGVFQVVDHGVDANLIAEMTRLAREFFALPPEEKLRFDMSGGKKGGFIVSSHL

QGEAVQDWREIVTYFSYPIRARDYSRWPDKPEGWRAVTETYSEKLMDLACKLLEVLSE

AMGLEKEALTKACVDMDQKVVINFYPKCPQPDLTLGLKRHTDPGTITLLLQDQVGGLQ

ATRDGGKTWITVQPVEGAFVVNLGDHGHYLSNGRFKNADHQAVVNSNCSRLSIATFQN

PAPEATVYPLKIREGEKPILEEPITFADMYKRKMSKDIELAKLKKLAKEKKLLQDQQDIE

KAKLEIKSTDEIFALVGALMHVMQKRSRAIHSSDEGEDQAGDEDED

MdF3H-Malus domestica
Nucleic acid sequence
(SEQ ID NO: 46)

```
atggcaccgcctgcaaccaccctgaccagcattgcacatgaaaaacccctgcagcagaaatttgttcgtgatgaagatgaacgtccgaaag tggcctataatgaatttagcaacgaaatcccgattattagcctggcaggtattgatgaagttgaaggtcgtcgtgccgaaatctgcaaaaaat cgttgaagcatgtgaagattggggcattttttcagattgttgatcatggtgttgatgccgaactgattagcgaaatgaccggtctggcaaaagaa ttttttgatctgccgagcgaagaaaaactgcgttttgatatgagcggtggtaaaaaaggtggttttattgttagcagccatctgcagggtgaagc agttcaggattggcgtgaaattgttacctatttcctgtatccgattcgccaccgtgattatagccgttggcctgataaaccggaagcatggcgtg aagttaccaaaaaatacagtgatgaactgatgggtctggcatgtaaactgctgggtgttctgagcgaagcaatgggcctggataccgaagc actgaccaaagcatgtgttgatatggatcagaaagtggtggttaacttctatccgaaatgtccgcagccggatctgaccctgggtctgaaacg tcataccgatccgggtacaattaccctgctgctgcaagatcaggttggcggtctgcaggcaacccgtgatgatggtaaaacctggattaccg ttcagccggttgaaggtgcatttgttgttaatctgggtgatcatggccatttctgagcaatggtcgctttaaaaacgcagatcatcaggcagttg ttaatagcaatagcagccgtctgagcattgcaacctttcagaatccggcacaggatgcaattgtttatccgctgagcgttcgtgaaggtgaaa aaccgattctggaagcaccgattacctataccgagatgtataaaaaaaaaatgagcaaagatctggaactggcacgcctgaaaaaactggc caaagaacagcagctgcaggatctggaaaaagcaaaagttgaaaccaaaccggcagatgatatctttgccctggttggtgcactgatgcat gttatgcagaaaacgtagccgtgcaattcatagcagtgatgaaggtgaagatcaagccggtgatgaagatgaggat
```

MdF3H-Malus domestica
Amino acid sequence
(SEQ ID NO: 47)

MAPPATTLTSIAHEKTLQQKFVRDEDERPKVAYNEFSNEIPIISLAGIDEVEGRRAEICKKI

VEACEDWGIFQIVDHGVDAELISEMTGLAKEFFDLPSEEKLRFDMSGGKKGGFIVSSHLQ

GEAVQDWREIVTYFLYPIRHRDYSRWPDKPEAWREVTKKYSDELMGLACKLLGVLSEA

MGLDTEALTKACVDMDQKVVVNFYPKCPQPDLTLGLKRHTDPGTITLLLQDQVGGLQ

ATRDDGKTWITVQPVEGAFVVNLGDHGHFLSNGRFKNADHQAVVNSNSSRLSIATFQN

PAQDAIVYPLSVREGEKPILEAPITYTEMYKKKMSKDLELARLKKLAKEQQLQDLEKAK

VETKPADDIFALVGALMHVMQKRSRAIHSSDEGEDQAGDEDED

PcF3H-Petroselinum crispum
Nucleic acid sequence (SEQ ID NO: 48)

atggcaccgagcaccctgaccgcactggcacaagaaaaaaccctgaatagcaaatttgtgcgcgacgaagatgaacgtccgaaaattgca tataacaaattcagcgacgaaatcccggttattagcctggcaggtattgatgatgatagcgttgataaacgtagccagatttgccgtaaaattgt tgaagcatgtgaagattggggcatttttcaggttgttgatcatggcattgatatcgatctgattagcgaaatgacccgtctggcacgtcagttttttt gcactgcctgcagaagaaaaactgcgttttgatatgaccggtggtaaaaaaggtggttttattgttagcagccatctgcagggtgaagcagtt caggattggcgtgaaattgttacctatttcagctatccgattcaggcacgtgattatagccgttggcctgataaaccggaaggttggcgtagca ttaccgaaatgtatagtgatgaactgatggcactggcatgtaaactgctggaagttctgagcgaagcaatgggtctggaaaaagagggtctg accaaagcatgtgttgatatggatcagaaagtgatcgtgaactactatccgaaatgtccgcagccgaatctgaccctgggtctgaaacgtcat accgatccgggtacaattaccctgctgctgcaggatcaggttggtggtctgcaggcgacccgtgatggtggcaaaacctggattaccgttca gccggttgaaggtgcatttgttgttaatctgggtgatcatggtcactatctgagcaatggtcgctttaaaaacgcagatcatcaggcagttgtta atagcaatagcagccgtatgagcattgcaaccttccagaatccggcaccgaatgcaaccgtttatccgctgaaaattcgtgaaggtgaaaaa gccgttatggaagaaccgattacctttgccgagatgtataaacgtaaaatgagccgtgatattgaaatggccaccctgaaaaaactggccaa agaaaaagttctgcaggaccaagaagtggaaaaagcaaaactgcagatgaccccgaaaagcgcagatgaaatttttgccctggttggtgc actgatgcatgttatgcagaaacgtagccgtgcaattcatagcagtgatgaaggtgaagatcaagccggtgatgaagatgaggat PcF3H-Petroselinum crispum
Amino acid sequence (SEQ ID NO: 49)

MAPSTLTALAQEKTLNSKFVRDEDERPKIAYNKFSDEIPVISLAGIDDDSVDKRSQICRK

IVEACEDWGIFQVVDHGIDIDLISEMTRLARQFFALPAEEKLRFDMTGGKKGGFIVSSHL

QGEAVQDWREIVTYFSYPIQARDYSRWPDKPEGWRSITEMYSDELMALACKLLEVLSE

AMGLEKEGLTKACVDMDQKVIVNYYPKCPQPNLTLGLKRHTDPGTITLLLQDQVGGLQ

ATRDGGKTWITVQPVEGAFVVNLGDHGHYLSNGRFKNADHQAVVNSNSSRMSIATFQ

NPAPNATVYPLKIREGEKAVMEEPITFAEMYKRKMSRDIEMATLKKLAKEKVLQDQEV

EKAKLQMTPKSADEIFALVGALMHVMQKRSRAIHSSDEGEDQAGDEDED

AaDFR-Anthurium andraeanum
Nucleic acid sequence (SEQ ID NO: 50)

atgatgcataaaggcaccgtttgtgttaccggtgcagcaggttttgttggtagctggctgattatgcgtctgctggaacagggttatagcgttaa agcaaccgttcgtgatccgagcaatatgaaaaaagttaaacatctgctggatctgcctggtgcagcaaatcgtctgaccctgtgaaagcag atctggttgatgaaggtagattgatgaaccgattcagggttgtaccggtgttttcatgttgcaaccccgatggattttgaaagcaaagatccg gaaagcgaaatgattaaaccgaccattgaaggtatgctgaatgttctgcgtagctgtgcccgtgcaagcagcaccgttcgtcgtgttgttttta ccagcagcgcaggtacagttagcattcatgaaggtcgtcgtcatctgtatgatgaaaccagttggagtgatgttgatttttgccgtgccaaaaa aatgaccggctggatgtattttgttagcaaaaccctggcagaaaaagcagcatgggattttgcagagaaaaataacatcgacttcatcagcat tattccgaccctggttaatggtccgtttgttatgccgaccatgcctccgagcatgctgagcgcactggcactgattacccgtaatgaaccgcat tatagcattctgaatccggtgcagtttgttcatctggatgatctgtgtaacgccacattttctgtttgaatgtccggatgcaaaaggtcgttatat ttgtagcagccatgatgttaccattgcaggtctggcacagattctgcgtcagcgttatccggaatttgatgttccgaccgaatttggtgaaatgg aagtgtttgatatcatcagctatagcagcaaaaaactgacggatctgggtttcgaattcaaatatagcctggaagatatgttcgatggtgcaatt cagagctgtcgtgaaaaaggtctgctgcctccggcaaccaaagaaccgagctatgcaacggaacagcgattgcaaccggtcaggataat ggtcatcctcctcctgcactgcctccgaaacgtcgtcgt AaDFR-Anthurium andraeanum
Amino acid sequence -continued

MMHKGTVCVTGAAGFVGSWLIMIRLLEQGYSVKATVRDPSNMKKVKHLLDLPGAANR (SEQ ID NO: 51)

LTLWKADLVDEGSFDEPIQGCTGVEHVATPMDFESKDPESEMIKPTIEGMLNVLRSCAR

ASSTVRRVVFTSSAGTVSIHEGRRHLYDETSWSDVDFCRAKKMTGWMYFVSKTLAEKA

AWDFAEKNNIDFISIIPTLVNGPFVMPTMPPSMLSALALITRNEPHYSILNPVQFVHLDDL

CNAHIFLFECPDAKGRYICSSHDVTIAGLAQILRQRYPEEDVPTEFGEMEVEDIISYSSKK

LTDLGFEFKYSLEDMFDGAIQSCREKGLLPPATKEPSYATEQLIATGQDNGHPPPALPPK

RRR

CsDFR-Camellia sinensis
Nucleic acid sequence
(SEQ ID NO: 52)

atgaaagatagcgttgcaagcgcaaccgcaagcgcaccgggtacagtttgtgttaccggtgcagcaggttttattggtagctggctggttatg cgtctgctggaacgtggttatattgttcgtgcaaccgttcgtgatccggcaaatctgaaaaaagttaaacatctgctggatctgccgaaagcag ataccaatctgaccctgtggaaagccgatctgaatgaagagggtagctttgatgaagcaattgaaggttgtagcggtgttttcatgttgcaac cccgatggattttgaaagcaaagatccggaaaacgaagtgattaaaccgaccattaacggtgtgctgagcattattcgtagctgtaccaaag caaaaaccgttaaacgtctggttttaccagcagcgcaggtacagttaatgttcaagaacatcagcagccggtgtttgatgaaaacaattgga gcgatctgcacttcatcaacaaaaaaaaatgaccggctggatgtattttgtgagcaaaaccctggcagaaaaagcagcatgggaagcagc aaaagaaaacaacattgatttcatcagcattatcccgaccctggttggtggtccgtttattatgccgaccttccgcctagcctgattaccgcact gagcccgattacccgtaatgaaggtcattattccattatcaaacagggccagtttgtgcatctggatgatctgtgtgaaagccacattttctgta tgaacgtccgcaggcagaaggtcgttatatttgtagcagccatgatgcaaccattcatgatctggccaaactgatgcgtgaaaaatggcctga atataatgttccgaccgaattcaaaggcatcgataaagatctgccggttgttagcttttccagcaaaaaactgattggcatgggcttcgagttca aatatagcctggaagatatgtttcgtggtgccattgatacctgtcgtgaaaaaggtctgctgccgcatagctttgcagaaatccggttaatgg caacaaagtgcctcctcctgcactgcctccgaaacgtcgtcgt CsDFR-Camellia sinensis
Amino acid sequence
(SEQ ID NO: 53)

MKDSVASATASAPGTVCVTGAAGFIGSWLVMRLLERGYIVRATVRDPANLKKVKHLL

DLPKADTNLTLWKADLNEEGSFDEAIEGCSGVFHVATPMDFESKDPENEVIKPTINGVLS

IIRSCTKAKTVKRLVFTSSAGTVNVQEHQQPVFDENNWSDLHFINKKKMTGWMYFVSK

TLAEKAAWEAAKENNIDFISIIPTLVGGPFIMPTFPPSLITALSPITRNEGHYSIIKQGQFVH

LDDLCESHIFLYERPQAEGRYICSSHDATIHDLAKLMREKWPEYNVPTEFKGIDKDLPVV

SFSSKKLIGMGFEEKYSLEDMERGAIDTCREKGLLPHSFAENPVNGNKVPPPALPPKRRR

FaDFR-Fragaria x ananassa N
ucleic acid sequence
(SEQ ID NO: 54)

atgggtctgggtgcagaaagcggtagcgtttgtgttaccggtgcaagcggttttgttggtagctggctggttatgcgtctgctggaacatggtt ataccgttcgtgcaaccgtgcgtgatccggcaaatctgaaaaaagttcgtcatctgctggaactgccgcaggcagcaaccgtctgaccctg tggaaagcagatctggatgttgaaggtagattgatgaagccattaaaggttgtaccggtgttttcatgttgcaaccccgatggattttgaaag cgaagatccggaaaacgaagttattaaaccgaccattaacggcatgctggatattatgaaagcatgcctgaaagcaaaaaccgttcgtcgtc tggttttaccagcagtgccggtgcagttgcaattgaagaacatccgaaagaagtgtacagcgaaataactggtcagatgttgtgttttgccg caaagttaaaatgaccggctggatgtattttgtgagcaaaaccctggcagaacaggcagcatggaaatttgcaaaagaaaacaacatcgac ttcatcaccattattccgaccctggttattggtccgtttctggcaccgagcatgcctccgagcctgattagcggtctgagtccgctgaccggtaa tgaagcacattatggtattatcaaacagtgccagtatgtgcatctggatgatctgtgtcagagccatattttctgtatgaacatgcaaaagccga gggtcgttatatttgtagcagccatgatgcaaccattcacgatattgcaaaactgctgaacgagaaatacccgaaatacaacgttccgaaaaa attcaaaggcatcgaagaaaacctgaccaacattcactttagcagcaaaaaactgaaagagatgggcttcgaatttaaacacagcctggaa gatatgtttacaggtgccgttgatgcatgtcgtgaaaaaggtctgctgccgctgccgcaagaagaagaaaccgaaaaacgtcgtgcaggtc -continued ctcctcctgcactgcctccgaaacgtcgtcgt FaDFR-Fragaria x ananassa
Amino acid sequence (SEQ ID NO: 55)

MGLGAESGSVCVTGASGFVGSWLVMRLLEHGYTVRATVRDPANLKKVRHLLELPQAA

TRLTLWKADLDVEGSFDEAIKGCTGVFHVATPMDFESEDPENEVIKPTINGMLDIMKAC

LKAKTVRRLVFTSSAGAVAIEEHPKEVYSENNWSDVVFCRKVKMTGWMYFVSKTLAE

QAAWKFAKENNIDFITIIPTLVIGPFLAPSMPPSLISGLSPLIGNEAHYGIIKQCQYVHLDD

LCQSHIFLYEHAKAEGRYICSSHDATIHDIAKLLNEKYPKYNVPKKFKGIEEENLTNIHFSS

KKLKEMGFEEKHSLEDMFTGAVDACREKGLLPLPQEEETEKRRAGPPPALPPKRRR

CsLAR-Camellia sinensis
Nucleic acid sequence (SEQ ID NO: 56)

atggcaatggccatggcaaccaccaccacaaccaccaaaccgatgattggtgcaaaagcagcatgtgttgttggtggcaccggttttgttgc agcaacccctggttaaaatgctgctggaacgtggttatagcgttaataccaccgttcgtgatccggacaacaaaaaaaacattagccatctggt tgcactggaaggtatgggtaatctgaaaatctttcgtgcagatctgaccgatgaacagagctttgatgcaccgattgcaggttgtgatctggttt ttgatgttgccacaccggttaattttgcaagcgaagatccgaaaacgacatgattaaactggcaattcagggtgttctgaatgtgctgaaagc atgtgccaaagcaggcaccgttaaacgtgttattctgaccagcagcgcagcaagcgttaccattaatcagctggatggtacaggtctggttat ggatgaaagccattggagtgatgttgaatttctgacctcagttaaaccgcctacctgggtcatccggttagcaaaaccctggcagaaaaag cagcctggaaatttgcagaagaaaataacctgaatctgattaccgttgttccgaccctgaccgcaggtccgagcctgaccagcgaagttccg aatagcattgaactggccatgagcctgattacgggtaatgaattcctgattgatggtctgaaaggtatgcgtattctgtcaggtagcattagcat tacccatgttgaagatgtttgtggtgcccatatttttgtggccgaaaaagaaagcgcaagcggtcgttatatttgttgtggtgttaatagcagcgt gccggaactggcacgttttctgaataaacgttatccgcagtataatgtgccgaccgattttggtgatctgccgagcaaagcaaaactgattatt agcagcgagaaactgatcaaagaaggatcagatcaaatatggcatcgaagaaatttttgcacacagcgttgcatatctgaaaaccaaagg tctgctgcagaacggtgttaaagaaagcctggtt CsLAR-Camellia sinensis
Amino acid sequence (SEQ ID NO: 57)

MAMAMATTTTTTKPMIGAKAACVVGGTGEVAATLVKMLLERGYSVNTTVRDPDNKK

NISHLVALEGMGNLKIFRADLTDEQSFDAPIAGCDLVEDVATPVNEASEDPENDMIKLAI

QGVLNVLKACAKAGTVKRVILTSSAASVTINQLDGTGLVMDESHWSDVEFLTSVKPPT

WGHPVSKTLAEKAAWKFAEENNLNLITVVPTLTAGPSLTSEVPNSIELAMSLITGNEFLI

DGLKGMRILSGSISITHVEDVCGAHIEVAEKESASGRYICCGVNSSVPELARFLNKRYPQ

YNVPTDFGDLPSKAKLIISSEKLIKEGFSFKYGIEEIFAHSVAYLKTKGLLQNGVKESLV

DuLAR-Desmodium uncinatum
ucleic acid sequence (SEQ ID NO: 58)

atgaccgttagcggtgcaattccgagcatgaccaaaaatcgtaccctggttgttggtggcaccggttttattggtcagtttattaccaaagcaa gcctgggttttggttatccgacctttctgctggttcgtccgggtccggttagcccgagcaaagcagttattatcaaaaacctttcaggataaaggt gccaaagtgatttatggcgtgatcaacgataaagaatgcatggaaaaaattctgaaagagtacgagatcgacgttgttattagcctggtgggt ggtgcacgtctgctggatcagctgaccctgctggaagcaattaaaagcgttaaaaccatcaaacgttttctgccgagcgaatttggccatgat gttgatcgtaccgatccggttgaaccgggtctgaccatgtataaagaaaaacgtctggtgcgtcgtgccgttgaagaatatggtattccgttta ccaatatctgctgcaatagcattgcaagctggccgtattatgataattgtcatccgagccaggttccgcctccgatggatcagtttcagatttatg gtgatggtaacaccaaagcctatttcattgatggcaacgatatcggcaaatttaccatgaaaaccatcgatgatattcgcaccctgaacaaaaa tgttcattttcgtccgagcagcaactgctacagcattaatgaactggcaagcctgtgggagaaaaaatcggtcgtacactgctcgttttacc gttaccgcagataaactgctggcacatgcagcagaaaacattattccggaaagcattgttagcagctttacccacgatatctttattaacggttg -continued ccaggtgaactttagcatcgatgaacatagtgatgtggaaatcgatacactgtatccggatgaaaaatttcgtagcctggatgattgctatgaa gattttgttccgatggtgcacgataaaattcatgcaggtaaaagcggtgaaatcaaaatcaaagatggtaaaccgctggttcagaccggcac cattgaagaaattaacaaagacattaaaaccctggtggaaacccagccgaatgaagagatcaaaaaagatatgaaagcactggttgaagcc gttccgattagcgcaatgggtggtgttaaagaaagcctggtt DuLAR-Desmodium uncinatum
Amino acid sequence
(SEQ ID NO: 59)

MTVSGAIPSMTKNRTLVVGGTGFIGQFITKASLGFGYPTFLLVRPGPVSPSKAVIIKTFQ

DKGAKVIYGVINDKECMEKILKEYEIDVVISLVGGARLLDQLTLLEAIKSVKTIKRFLPS

EFGHDVDRTDPVEPGLTMYKEKRLVRRAVEEYGIPFTNICCNSIASWPYYDNCHPSQVP

PPMDQFQIYGDGNTKAYFIDGNDIGKFTMKTIDDIRTLNKNVHFRPSSNCYSINELASLW

EKKIGRTLPRFTVTADKLLAHAAENIIPESIVSSFTHDIFINGCQVNFSIDEHSDVEIDTL

YPDEKFRSLDDCYEDFVPMVHDKIHAGKSGEIKIKDGKPLVQTGTIEEINKDIKTLVETQ

PNEEIKKDMKALVEAVPISAMGGVKESLV

PhANS-Petunia X hybrida
Nucleic acid sequence
(SEQ ID NO: 60)

atggtgaatgcagtagttacaactccttcaagagttgaaagcttggctaaaagtggaatccaggccatccctaaggagtatgtgaggccaca agaagagttgaatggaatcggaaacatcttcgaggaagagaagaaagatgaagggcctcaagtaccaacaattgatttgaaagaaattgac tccgaggacaaggagattcgcgagaaatgccaccaggagttgaagaaagcagccatggaatgggtgtcatgcaccttgtgaatcatggc atatccgatgagctaatcaatcgtgtcaaggttgctggagagaccttctttgatcaacctgttgaagaaaaggagaagtatgctaatgaccaa gccaatggcaatgtccaaggctacggcagcaagctagcaaatagtgcttgtggtcagcttgagtggaggattattttcttccattgtgctttcc ctgaagacaagcgcgacttgtccatctggcctaaaaatcctactgactacactccagcaacaagtgaatatgccaagcagatcagggccct agcaacaaagattttgacagtgctttctatgggctggggctggaagaaggaagactagagaaggaagttggaggcatggaggatctgctg cttcaaatgaagattaactactatcccaagtgcccccaaccagaactagcacttggcgtcgaagctcatacagatgtcagcgcactgactttc atcctccacaatatggtgcccggcttgcaactcttctatgaaggccagtgggtaactgctaagtgtgtgcctaattctatcatcatgcatagg ggacaccattgaaatcctaagcaatggaaagtacaagagcatccttcatagaggggttgtgaataaagagaaagtaaggatctcatgggcc attttctgcgagccacctaaggagaagatcatccttaagcccctacctgagactgtcactgaggctgagccacctcgattcccacctgcacc tttgcacagcatatggcacacaagctcttcaggaaggatgacaaggatgccgctgttgaacacaaagtcttcaaagaggatgaactggatac tgctgctgaacataaggtcctcaagaaggataatcaggatgctgttgctgagaataaagacatcaaggaggatgaacagtgtggccctgct gagcacaaagatatcaaggaggatggacagggtgccgctgctgagaacaaagtcttcaaggagaataatcaggatgttgctgctgaagaa tctaaatag PhANS-Petunia X hybrida
Amino acid sequence
(SEQ ID NO: 61)

MVNAVVTTPSRVESLAKSGIQAIPKEYVRPQEELNGIGNIFEEEKKDEGPQVPTIDLKEI

DSEDKEIREKCHQELKKAAMEWGVMHLVNHGISDELINRVKVAGETFFDQPVEEKEKY

ANDQANGNVQGYGSKLANSACGQLEWEDYFFHCAFPEDKRDLSIWPKNPTDYTPATSE

YAKQIRALATKILTVLSIGLGLEEGRLEKEVGGMEDLLLQMKINYYPKCPQPELALGVE

AHTDVSALTFILHNMVPGLQLFYEGQWVTAKCVPNSIIMHIGDTIEILSNGKYKSILHRG

VVNKEKVRISWAIFCEPPKEKIILKPLPETVTEAEPPRFPPRTFAQHMAHKLFRKDDKDA

AVEHKVFKEDELDTAAEHKVLKKDNQDAVAENKDIKEDEQCGPAEHKDIKEDGQGAA

AENKVFKENNQDVAAEESK

At3GT-Arabidopsis thaliana
Nucleic acid sequence
(SEQ ID NO: 62)

atgaccaaaccctccgacccaaccagagactcccacgtggcagttctcgcttttcctttcggcactcatgcagctcctctcctcaccgtcacg -continued

```
cgccgcctcgcctccgcctctccttccaccgtcttctctttcttcaacaccgcacaatccaactcttcgttattttcctccggtgacgaagcagat
cgtccggcgaacatcagagtatacgatattgccgacggtgttccggagggatacgtgtttagcgggagaccacaggaggcgatcgagctg
tttcttcaagctgcgccggagaatttccggagagaaatcgcgaaggcggagacggaggttggtacggaagtgaaatgtttgatgactgatg
cgttatctggttcgcggctgatatggcgacggagataaatgcgtcgtggattgcgttttggaccgccggagcaaactcactctctgctcatct
ctacacagatctcatcagagaaaccatcggtgtcaaagaagtaggtgagcgtatggaggagacaataggggttatctcaggaatggagaa
gatcagagtcaaagatacaccagaaggagttgtgtttggaaatttagactctgttttctcaaagatgcttcatcaaatgggtatgctttgcctcg
tgccactgctgttttcatcaattcttttgaagatttggatcctacattgacgaataacctcagatcgagatttaaacgatatctgaacatcggtcctc
tcgggttattatcttctacattgcaacaactagtgcaagatcctcacggttgtttggcttggatggagaagatcttctggttctgtggcgtacat
tagattggtacggtcatgacaccgcctcctggagagatgcggcgatagcagaagggttggaatcgagtaaagtgccgtttgtttggtcgct
taaggagaagagcttggttcagttaccaaaagggttttggataggacaagagagcaagggatagtggttccatgggcaccgcaagtggaa
ctgctgaaacacgaagcaacgggtgtgtttgtgacgcattgtggatggaactcggtgttggagagtgtatcgggtggtgtaccgatgatttgc
aggccatttttggggatcagagattgaacggaagagcggtggaggttgtgtgggagattggaatgacgattatcaatggagtatcacgaa
agatgggtttgagaagtgtttggataaagttttagttcaagatgatggtaagaagatgaaatgtaatgctaagaaacttaaagaactagcttacg
aagctgtctcttctaaaggaaggtcctctgagaatttcagaggattgttggatgcagttgtaaacattatttga
```

At3GT-Arabidopsis thaliana
Amino acid sequence (SEQ ID NO: 63)

MTKPSDPTRDSHVAVLAFPFGTHAAPLLTVTRRLASASPSTVFSFFNTAQSNSSLFSSGD

EADRPANIRVYDIADGVPEGYVFSGRPQEAIELFLQAAPENFRREIAKAETEVGTEVKCL

MTDAFFWFAADMATEINASWIAFWTAGANSLSAHLYTDLIRETIGVKEVGERMEETIGV

ISGMEKIRVKDTPEGVVFGNLDSVFSKMLHQMGLALPRATAVFINSFEDLDPTLTNNLRS

RFKRYLNIGPLGLLSSTLQQLVQDPHGCLAWMEKRSSGSVAYISFGTVMTPPPGELAAIA

EGLESSKVPFVWSLKEKSLVQLPKGFLDRTREQGIVVPWAPQVELLKHEATGVFVTHCG

WNSVLESVSGGVPMICRPFFGDQRLNGRAVEVVWEIGMTIINGVFTKDGFEKCLDKVLV

QDDGKKMKCNAKKLKELAYEAVSSKGRSSENFRGLLDAVVNII

Fragaria x ananassa 3GT
Amino acid sequence (SEQ ID NO: 64)

MGSAVAVELVFIPAPGVGHIMSTMEMAKLLINRHQSIATTVLLIHPPYSSSVLTNYIQSLL

TNPIQRIRFIQLPQDQETASKLDLKAPFTSFYEFINSHRNYVRNVVSDMLSRPGSVRITGL

VVDILCTGMIDVANEFSIPSYAFFTSNAAFLGFKLYMDTLCRNQKQEGIIALSKSDGELRI

PSFVKPVPMTVYPAVYQTRDGLDFLTVSIQKFREAKAIMVNTFLELETHAIESFSSYTNFP

SVYAVGPVLNLNGVAGKDEDKDVIRWLDGQPPSSVVFLCFGSMGSFEEVQLKEIAYAL

ERSGHRFVWSVRRPPSPEQSFKVLPDDYDDPRSILPDGFLERTNGFGKVIGWAPQVSILA

HEAVGGFVSHCGWNSVLESICCKVPILAWPMMAEQHLNARMVVEEIKIGLRVETCDGS

VRGFVQADGLKKMVKELMEGENGEIVRKRVEGIGEGAKKAMAEGGSSWRTLNELIDE

LQCVRNSNGGRFPSSEGDSDKSKGESYVPMDNLSLVSI

Vitis vinifera 3GT
Amino acid sequence (SEQ ID NO: 65)

MSQTTTNPHVAVLAFPFSTHAAPLLAVVRRLAAAAPHAVFSFFSTSQSNASVFHDSMHT

MQCNIKSYDVSDGVPEGYVFAGRPQEDIELFMRAAPEGFRQGMVMAVAETGRPVSCLV

ADAFIWFAADMAAEMGVAWLPFWTAGPNSLSTHVYTDEIREKIGVSGIQGREDELLNFI

PGMYEVRFRDLQEGIVFGNLNSLFSRMLHRMGQVLPKATAVFINSFEELDDSLTNDLKS

KLKTYLNIGPFNLITPPPVVPNTTGCLQWLKERKPTSVVYISFGTVTTPPPAELVALAEAL

-continued

EASRVPFIWSLRDKARVHLPEGFLEKTRGYGMVVPWAPQAEVLAHEAVGAFVTHCGW

NSLWESVAGGVPLICRPFFGDQRLNGRMVEDVLEIGVRIEGGVFTKSGLMSCFDQILSQE

KGKKLRENLRALRETADRAVGPKGSSTENFKTLVDLVSKPKDV

Forsynthia 3GT
Amino acid sequence
(SEQ ID NO: 66)

MAIHSHIGVLAFPFGTHAAPLLTLVRRLVLDSSSQGITFSFFNTAKSNCAIFSGQEFDNIKA

YDVWDGTHEGEAFTGSNILEAMQLFLAATPGNFEKVMKEAEVKNGMKISCLLSDAFLW

FTCDLAEERGIPWVSFWTAASCSLSAHMYTDQIWSLMRSTGTAKTEEKTLSFVPGMTSV

RFSDLPEEILSDNLESPLTLMIYKMVQKLSKSTAIVVNSFEEIDPVITNDLKSKFQNFLNIG

PSILSSPTLSNGDSGQECLLWLEKQRHASVIYISFGTVITPQPREMAGLAEALETGEFPFL

WSLRDNAMKLLPDGFLDRTSKFGMIVSWAPQLKVLENPSVGAFITHCGWNSILESISFG

VPMICRPFFGDQNLNSKMVEDVWKIGVRLEGGVFTKNGTIEALHSVMLNETGKAIRENI

NKLKRKAQNAVKFDGTSTKNFRALLELIKSPRGI

Eggplant 3GT
Amino acid sequence
(SEQ ID NO: 67)

MTTSQLHIAFLAFPFGTHATPLLTLVQKISPFLPSSTIFSFFNTSSSNSSIFSKVPNQENIKIY

NVWDGVKEGNDTPFGLEAIKLFIQSTLLISKITEEAEEETGVKFSCIFSDAFLWCFLVKLP

KKMNAPGVAYWTGGSCSLAVHLYTDLIRSNKETSLKIPGFSSTLSINDIPPEVTAEDLEGP

MSSMLYNMALNLHKADAVVLNSFQELDRDPLINKDLQKNLQKVFNIGPLVLQSSRKLD

ESGCIQWLDKQKEKSVVYLSFGTVTTLPPNEIGSIAEALETKKTPFIWSLRNNGVKNLPK

GFLERTKEFGKIVSWAPQLEIAHKSVGVFVTHCGWNSILEGISFGVPMICRPFFGDQKL

NSRMVESVWEIGLQIEGGIFTKSGIISALDTFFNEEKGKILRENVEGLKEKALEAVNQMM

EVQQKISRF

Gentian 3 GT
Amino acid sequence
(SEQ ID NO: 68)

MDQLHVFFFPFLANGHILPTIDMAKLFSSRGVKATLITTHNNSAIFLKAINRSKILGFDISV

LTIKFPSAEFGLPEGYETADQARSIDMMDEFFRACILLQEPLEELLKEHRPQALVADLFFY

WANDAAAKFGIPRLLFHGSSSFAMIAAESVRRNKPYKNLSSDSDPFVVPDIPDKIILTKSQ

VPTPDETEENNTHITEMWKNISESENDCYGVIVNSFYELEPDYVDYCKNVLGRRAWHIG

PLSLCNNEGEDVAERGKKSDIDAHECLNWLDSKNPDSVVYVCFGSMANFNAAQLHELA

MGLEESGQEFIWVVRTCVDEEDESKWFPDGFEKRVQENNKGLIIKGWAPQVLILEHEAV

GAFVSHCGWNSTLEGICGGVAMVTWPLFAEQFYNEKLMTDILRTGVSVGSLQWSRVTT

SAVVVKRESISKAVRRLMAEEEGVDIRNRAKALKEKAKKAVEGGGSSYSDLSALLVELS

SYPHN

Petunia x hybrida 3GT
Amino acid sequence
(SEQ ID NO: 69)

MTTSQLHIALLAFPFGSHAAPLLTLVQKLSPFLPSDTIFSFFNTSQSNTSIFSEGSKPDNIKV

YNVWDGVTETNGNKPVGLEAIKLFIQATPTNFEKVMKEAEEETGVKFSCIFSDAFLWFS

YKLAEKINVPWIAFWTAASGSLSVHLYTDFIRSNDETSLNIPGFSSTLKISDMPPEVMAEN

LDLPMPSMLYNMALNLHKAAAVVLNSFEELDPTINKDLKVKLQKVLNIGPLVLQPTSPK

KVLDACDERGCIIWLEKQKEESVVYLSFGTVTTLPPNEIVAVAEALEAKKFPFIWSLKDN

GIKNLPTGFLERTGQFGKIVSWAPQLEILNHSAVGVFVTHCGWNSILEGISCGVPMICRPF

-continued

FGDQKLNSRMVESVWQIGLQIEGGSFTKIGTISALDTFFSEEKGKVLRENVKGLKERALE

AVKPDGSSSKNFKDLVELVKCHKLT

Malus domestica ANS
Amino acid sequence
(SEQ ID NO: 70)

MVSSDSVNSRVETLAGSGISTIPKEYIRPKDELVNIGDIFEQEKNNEGPQVPTIDLKEIESD

NEKVRAKCREKLKKATVDWGVMHLVNHGISDELMDKVRKAGKAFFDLPIEQKEKYAN

DQASGKIQGYGSKLANNASGQLEWEDYFFHCVYPEDKRDLSIWPQTPADYIEATAEYA

KQLRELATKVLKVLSLGLGLDEGRLEKEVGGLEELLLQMKINYYPKCPQPELALGVEAH

TDVSALTFILHNMVPGLQLFYEGKWVTAKCVPNSIVMHIGDTLEILSNGKYKSILHRGM

VNKEKVRISWAVFCEPPKEKIILKPLPETVSEDEPAMFPPRTFAEHIQHKLFRKSQEALLP

K

Pyrus communis ANS
Amino acid sequence
(SEQ ID NO: 71)

MVSSDSVNSRVETLAGSGISTIPKEYIRPKDELVNIGDIFEQEKNNEGPQVPTIDLKEIESD

NEKVRAKCREELKKAAVDWGVMHLVNHGISDELMDKVRKAGKAFFDLPIEQKEKYAN

DQASGKIQGYGSKLANNASGQLEWEDYFFHCVYPEDKRDLSIWPQTPADYIEATAEYA

KQLRELATKVLKVLSLGLGLDEGRLEKEVGGLEELLLQMKINYYPKCPQPELALGVEAH

TDVSALTFILHNMVPGLQLFYEGKWVTAKCVPNSIVMHIGDTLEILSNGKYKSILHRGM

VNKEKVRISWAVFCEPPKEKIILKPLPETVSEDEPAMFPPRTFAEHIQHKLFRKSQEALLP

K

Prunus avium ANS
Amino acid sequence
(SEQ ID NO: 72)

MVSSDSVNSRVETLASSGIATIPKEYIRPKEELINIGDIFEQEKSTDGPQVPTIDLKEIDSEN

EKVRERCREELNKAAVDWGVMHLVNHGISDELMDRVRKAGKAFFDLPIEQKEKYAND

QASGKIQGYGSKLANNASGQLEWEDYFFHLIFPEDKRDLSIWPQTPADYIEATAEYAKE

LRALATKVLRVLSLGLGLEEGRLEKEVGGLEELLLQMKINYYPVCPQPELALGVEAHTD

VSALTFILHNMVPGLQLFYEGKWVTAKCVPNSIVMHIGDTIEILSNGKYKSILHRGMVN

KEKVRISWAVFCEPPKEKIILKPLPETVSETEPPIFPPRTFAEHIQHKLFRKSQEALLNK

Fragaria x ananassa ANS
Amino acid sequence
(SEQ ID NO: 73)

MVTAASIGSRVESLASSGISTIPKEYVRPEEELVNIGDIFEDEKSTEGPQVPTIDLKEIDSED

IKVREKCREELKKAAIDWGVMHLVNHGISDELMERVKKAGKAFFDLPVEQKEKYAND

QASGKIQGYGSKLANNASGQLEWEDYFFHCVYPEDKRDLSIWPQTPSDYIVATSEYAKE

LRGLTTKILSILSLGLGLEEGRLEKEVGGLEELLLQMKINYYPKCPQPELALGVEAHTDIS

ALTFILHNMVPGLQLFYGGKWVTAKCVPNSVVMHIGDTLEILSNGKYKSILHRGLVNKE

KVRISWAVFCEPPKEKIILKPLPETVSEEEPAIFPPRTFFEHIQHKLFRQSQEALVSTKESAA

LKSTKESALKSTKEAALISTN

Vitis vinifera ANS
Amino acid sequence
(SEQ ID NO: 74)

MVTSVAPRVESLSSSGIQSIPKEYIRPQEELTSIGNVFEEEKKDEGPQVPTIDLKDIESEDE

VVRERCREELKKAAMEWGVMHLVNHGISDDLINRVKVAGETFFNLPMEEKEKYANDQ

ASGKIAGYGSKLANNASGQLEWEDYFFHLIFPEDKRDMTIWPKTPSDYVPATCEYSVKL

RSLATKILSVLSLGLGLEEGRLEKEVGGMEELLLQKKINYYPKCPQPELALGVEAHTDVS

-continued

ALTFILHNMVPGLQLFYEGKWVTAKCVPNSIIMHIGDTIEILSNGKYKSILHRGLVNKEK

VRISWAVFCEPPKEKIILKPLPETVSETEPPLFPPRTFSQHIQHKLFRKTQEALLSK

Ipomoea purpurea anthocyanidin synthase (ANS)
Amino acid sequence (SEQ ID NO: 75)

MLSTITATVPSRVERLAGSGIERIPKEYIRPEEERRSIGDIFEEEKIAGGPQVPTVDLKGINS

EDLEVREKCREELRKAAVDWGVMHLVNHGIPEELTGRVKAAGEGFFGQPIEEKEKYAN

DQAAGNVQGYGSKLANNASGQLEWEDYFFHCIFPEDKTDLSIWPKTPSDYIDATREYAK

QLRALATKVLAVLSLGLGLEEGRLEKEVGGMEELLLQMKINYYPKCPQPELALGVEAH

TDVSALTFILHNMVPGLQLFYGGKWVTAKCVPNSIIMHVGDTVEILSNGKYKSILHRGV

VNREKVRVSWAVFCEPPKDKILLQPLPETVSEAEPPRFPPRTFAQHIKHKLFRQSDQEAA

HTPKPDNDDDHQSN

Camellia sinensis ANS
Amino acid sequence (SEQ ID NO: 76)

MTTVAAPRVQSLATSGIESIPKEYVRPKEELTGIGNIFEEEKNEEGPQVPTIDLKDIDSEVE

EVRERCREALKKAAVDWGVMHLVNHGIADDVRERVKVAGEGFFEQPVEEKEKYANDP

DNGNLQGYGSKLANNACGQFEWEDYFFHLAYPEDKCDMSIWPKTPTDYIPATVEYAKQ

LRALATKTLSILSLGLGLEENKLEKEVGGKEELLLQMKINYYPKCPQPELALGVEAHTDL

SAVSFILPSMVPGLQLFYEGKWITAKCVPNSIIMLIGDTVEILSNGKYKSILHRGLVNKEK

VRISWAVFCEPPKEKIILKPLPETVSEAEPPLEPPRTFAQHIQHKLFRKSQELGSK

Citrus sinensis anthocyanidin synthase (ANS)
Amino acid sequence (SEQ ID NO: 77)

MVTPTARRVESLARSGIQAIPKEYVRPKEELMGIGNIFEEEEKDEGPQVPTIDLKEIDSED

RVEREKCREELKKAAMDWGVMHLVNHGISDDLTERVKRAGQAFFDQPVEEKEKYANE

QASGKIQGYGSKLANNASGQLEWEDYFFHLIYPEDKRDMSIWPKTPSDYTEATSEYARQ

LRSLATKILAVLSLGLGLEEGRLEKEVGGLEELLLQMKINYYPKCPQPELALGVEAHTD

VSALTFILHNMVPGLQLFYKDKWVTAKCVPNSIILHIGDTIEILSNGEYKSILHRGLVNKE

KVRISWAVFCEPPKDKIILKPLPETVSEQKPAMFPPRTFQQHIEHKLFRRTQDALLSDEE

Vaccinium ashei ANS
Amino acid sequence (SEQ ID NO: 78)

MVSTMVAAPSR VESLASSGIQSIPKEYVRPKEELTSIGNIFEEEKKHEGPQVPTIDLEDLVS

EDKEARERCHEALKKAATEWGVMHLVNHGVPEELMDRVRVAGEGFENQPVEEKEKY

ANDHDTGNSGKIQGYGSKLANNASGQLEWEDYFFHTVYPEDKRDMKIWPKNPSDYIPA

TSEYANHLRALTTKVLSALSVCLGLEEDRLEKEVGGKDELVIQMKINYYPKCPQPELAL

GVEAHTDVSALTFILHNMVPGLQLFYEGKWITAKCVPNSIIMHIGDTVEILSNGKYKSIL

HRGLVNKEKVRISWAAFCEPPKEKIILKPLPETVSETEPARYPPRTFSQHIEHKLFRKTQA

LNGA

Populus trichocarpa ANS
Amino acid sequence (SEQ ID NO: 79)

MMVTSSFVVPRVESLASSGIQSIPKEYIRPQEELSSIRDVFEEEKKVEGPQVPTIDLKEMES

EDKVVREKCREELVKAATEWGVMHLVNHGIPDDLIDRVKKAGQAFFDLPIEEKEKHAN

DQASGNVQGYGSKLANNASGQLEWEDYFFHLIFPEDKRDFSIWPKTPSDYTEVTSEYAR

QLRSLATKILSVLSLGLGLEEGRLEKEVGGLEELLLQMKINYYPKCPQPDLALGVEAHSD

VSALTFILHNMVPGLQLLYEGKWITAKCVPNSIIMHIGDTVEILSNGKYKSIIHRGLVNKE

```
KVRISWAVFCEPPKAKIILKPLAEIVTEAEPPLFPPRTFSQHIEHKLFRKTQDSLLPRKAN
```

Rhodobacter capsulatus TAL
Amino acid sequence
(SEQ ID NO: 80)

```
MLDATIGRKRMTLQSQTAKDCLALDGALTLVQCEAIATHRSRISVTPALRERCARAHAR

LEHAIAEQRHIYGITTGEGPLANRLIGADQGAELQQNLIYHLATGVGPKLSWAEARALM

LARLNSILQGASGASPETIDRIVAVLNAGFAPEVPAQGTVGASGDLTPLAHMVLALQGR

GRMIDPSGRVQEAGAVMDRLCGGPLTLAARDGLALVNGTSAMTAIAALTGVEAARAID

AALRHSAVLMEVLSGHAEAWHPAFAELRPHPGQLRATERLAQALDGAGRVCRTLTAA

RRLTAADLRPEDHPAQDAYSLRVVPQLVGAVWDTLDWHDRVVTCELNSVTDNPIFPEG

CAVPALHGGNFMGVHVALASDALNAALVTLAGLVERQIARLTDEKLNKGLPAFLHGG

QAGLQSGFMGAQVTATALLAEMRANATPVSVQSLSTNGANQDVVSMGTIAARRARAQ

LLPLSQIQAILALALAQAMDLLDDPEGQAGWSLTARDLRDRIRAVSPGLRADRPLAGHIE

AVAQGLRHPSAAADPPA
```

Rice TAL
Amino acid sequence
(SEQ ID NO: 81)

```
MAGNGPINKEDPLNWGAAAAEMAGSHLDEVKRMVAQFREPLVKIQGATLRVGQVAA

VAQAKDAARVAVELDEEARPRVKASSEWILTCIAHGGDIYGVTTGFGGTSHRRTKDGP

ALQVELLRYLNAGIFGTGSDGHTLPSETVRAAMLVRINTLLQGYSGIRFEILEAITKLLNT

GVTPCLPLRGTITASGDLVPLSYIAGLITGRPNAQAISPDGRKVDAAEAFKLAGIEGGFFT

LNPKEGLAIVNGTSVGSALAATVMFDANILAVLSEVLSAVFCEVMNGKPEYTDHLTHKL

KHHPGSIDAAAIMEHILAGSSFMSHAKKVNEMDPLLKPKQDRYALRTSPQWLGPQIQVI

RAATKSIEREVNSVNDNPVIDVHRGKALHGGNFQGTPIGVSMDNARLAIANIGKLMFAQ

FSELVNEFYNNGLTSNLAGSRNPSLDYGFKGTEIAMASYSSELQYLANPITNHVQSAEQH

NQDVNSLGLVSARKTLEAVDILKLMTSTYIVALCQAVDLRHLEENIKSSVKNCVTQVAK

KVLTMNPTGDLSSARFSEKNLLTAIDREAVFSYADDPCSANYPLMQKLRAVLVEHALTS

GDRRARGLRVLQDHQVRGGAPLCAAPGDRGRPRRRRQRTAPVANRIVESRSFPLYRFV

REELGCVFLTGEKLKSPGEECNKVFLGISQGKLIDPMLDCLKEWNGEPLPIN
```

Parsley TAL
Amino acid sequence
(SEQ ID NO: 82)

```
FLNAGIFGNGSDNTLPHSATRAAMLVRINTLLQGYSGIRFEILEAITKFLNQNITPCLPLRG

TITASGDLVPLSYIAGLLTGRPNSKAVGPTGVILSPEEAFKLAGVEGGFFELQPKEGLALV

NGTAVGSGMASMVLFEANILAVLAEVMSAIFAEVMQGKPEFTDHLTHKLKHHPGQIEA

AAIMEHILDGSAYVKAAQKLHEMDPLQKPKQDRYALRTSPQWLGPQIEVIRSSTKMIER

EINSVNDNPLIDVSRNKAIHGGNFQGTPIGVSMDNTRLAIAAIGKLMFAQFSELVNDFYN

NGLPSNLSGGRNPSLDYGFKGAEIAMASYCSELQFLANPVTNHVQSAEQHNQDVNSLG

LISSRKTSEAVEILKLMSTTFLVGLCQAIDLRHLEENLKSTVKNTVSSVAKRVLTMGVNG

ELHPSRFCEKDLLRVVDREYIFAYIDDPCSATYPLMQKLRQTLVEHALKNGDNERNLST

SIFQKIATFEDELKALLPKEVESARAALESGNPAIPNRIEECRSYPLYKFVRKELGTEYLT

GEKVTSPGEEFEKVFIAMSKGEIIDPLLECLESWNGAPLPIC
```

Tomato TAL
Amino acid sequence
(SEQ ID NO: 83)

```
MDLCKKSINDPLNWEMAADSLRGSHLDEVKKMVDEFRKPIVKLGGETLSVAQVASIAN

VDDKSNGVKVELSESARAGVKASSDWVMDSMSKGTDSYGVTAGFGATSHRRTKNGG
```

ALQKELIRFLNAGVFGNGIESFHTLPHSATRAAMLVRINTLLQGYSGIRFEILEAITKLINS

NITPCLPLRGTITASGDLVPLSYIAGLLTGRPNSKAVGPNGEKLNAEEAFCVAGISGGFFE

LQPKEGLALVNGTAVGSAMASIVLFESNIFAVMSEVLSAIFTEVMNGKPEFTDYLTHKL

KHHPGQIEAAAIMEHILDGSSYVKVAQKLHEMDPLQKPKQDRYALRTSPQWLGPQIEVI

RAATKMIEREINSVNDNPLIDVSRNKALHGGNFQGTPIGVSMDNTRLALASIGKLMFAQ

FSELVNDYYNNGLPSNLTAGRNPSLDYGFKGAEIAMASYCSELQFLANPVTNHVQSAEQ

HNQDVNSLGLISARKTAKAVDILKIMSSTYLVALCQAIDLRHLEENLKSVVKNTVSQVA

KRTLTMGANGELHPARFSEKELLRVVDREYLFAYADDPCSSNYPLMQKLRQVLVDQA

MKNGESEKNVNSSIFQKIGAFEDELIAVLPKEVESVRAVFESGNPLIRNRITECRSYPLYR

LVREELGTELLTGEKVRSPGEEIDKVFTAICNGQIIDPLLECLKSWNGAPLPIC

Arabidopsis TAL
Amino acid sequence (SEQ ID NO: 84)

MEINGAHKSNGGGVDAMLCGGDIKTKNMVINAEDPLNWGAAAEQMKGSHLDEVKRM

VAEFRKPVVNLGGETLTIGQVAAISTIGNSVKVELSETARAGVNASSDWVMESMNKGT

DSYGVTTGFGATSHRRTKNGVALQKELIRFLNAGIFGSTKETSHTLPHSATRAAMLVRIN

TLLQGFSGIRFEILEAITSFLNNNITPSLPLRGTITASGDLVPLSYIAGLLTGRPNSKATGPN

GEALTAEEAFKLAGISSGFFDLQPKEGLALVNGTAVGSGMASMVLFETNVLSVLAEILS

AVFAEVMSGKPEFTDHLTHRLKHHPGQIEAAAVMEHILDGSSYMKLAQKLHEMDPLQK

PKQDRYALRTSPQWLGPQIEVIRYATKSIEREINSVNDNPLIDVSRNKAIHGGNFQGTPIG

VSMDNTRLAIRAIGKLMFAQFSELVNDFYNNGLPSNLTASRNPSLDYGFKGAEIAMASY

CSELQYLANPVTSHVQSAEQHNQDVNSLGLISSRKTSEAVDILKLMSTTFLVAICQAVDL

RHLEENLRQTVKNTVSQVAKKVLTTGVNGELHPSRFCEKDLLKVVDREQVYTYADDPC

SATYPLIQKLRQVIVDHALVNGESEKNAVTSIFHKIGAFEEELKAVLPKEVEAARAAYDN

GTSAIPNRIKECRSYPLYRFVREELGTELLTGEKVTSPGEEFDKVFTAICEGKIIDPMMEC

LNEWNGAPIPIC

While only certain features of the invention have been illustrated and described herein, many modifications and changes will occur to those skilled in the art. It is, therefore, to be understood that the appended claims are intended to cover all such modifications and changes as falling within the true spirit of the invention.

Throughout this application, various references are referred to. The disclosures of these publications in their entireties are hereby incorporated by reference as if written herein.

What is claimed is:

1. A microbial polyculture comprising a first module cell and at least a second module cell, the first and the at least a second module cell including:
   a TAL module cell comprising an exogenous gene encoding for a tyrosine ammonia lyase (TAL);
   a C5 module cell comprising an exogenous gene encoding for a 4-coumaroyl-CoA ligase (4CL), an exogenous gene encoding for a chalcone synthase (CHS), an exogenous gene encoding for a chalcone isomerase (CHI), or, the C5 module cell comprises an exogenous gene encoding for a 4-coumaroyl-CoA ligase (4CL), an exogenous gene encoding for a chalcone synthase (CHS), an exogenous gene encoding for a chalcone isomerase (CHI) and further comprises an exogenous gene encoding for malonyl-CoA synthetase (MatB) and an exogenous gene encoding for putative dicarboxylate carrier protein (MatC);
   a p168 module cell comprising an exogenous gene encoding for a flavanone 3(3-hydroxylase (F3H), an exogenous gene encoding for a dihydroflavonol 4-reductase (DFR), and an exogenous gene encoding for a leucoanthocyanidin reductase (LAR); and
   an Antho module cell comprising an exogenous gene encoding for an anthocyanidin synthase (ANS) and an exogenous gene encoding for a 3-glucosyl transferase (3GT);
   wherein the exogenous gene encoding for TAL encodes a polypeptide having at least 85% amino acid identity with the amino acid sequence of *Rhodotorula glutinis* tyrosine ammonia lyase (RgTAL) of SEQ ID NO: 29, *Rhodobacter capsulatus* TAL of SEQ ID NO: 80, Rice TAL of SEQ ID NO: 81, Parsley TAL of SEQ ID NO: 82, Tomato TAL of SEQ ID NO: 83, *Arabidopsis* TAL of SEQ ID NO: 84, or a combination thereof, having TAL activity,
   the exogenous gene encoding for 4CL encodes a polypeptide having at least 85% amino acid identity with the amino acid sequence of *Arabidopsis thaliana* 4-coumaroyl-CoA ligase (At4CL) of SEQ ID NO: 31, *Petroselinum crispum* 4-coumaroyl-CoA ligase (Pc4CL) of SEQ ID NO: 33, *Vitis vinifera* 4-coumaroyl-CoA ligase (Vv4CL) of SEQ ID NO: 35, or a combination thereof, having 4CL activity,
   the exogenous gene encoding for CHS encodes a polypeptide having at least 85% amino acid identity with the amino acid sequence of *Petunia X hybrida* chalcone synthase (PhCHS) of SEQ ID NO: 37, *Citrus maxima* chalcone synthase (CmCHS) of SEQ ID NO: 39, or a combination thereof, having CHS activity,
   the exogenous gene encoding for CHI encodes a polypeptide having at least 85% amino acid identity with the amino acid sequence of *Medicago sativa* chalcone isomerase (MsCHI) of SEQ ID NO: 43, *Citrus maxima* chalcone isomerase (CmCRE) of SEQ ID NO: 41, or a combination thereof, having CHI activity,
   the exogenous gene encoding for MatB encodes a polypeptide having at least 85% amino acid identity with the amino acid sequence of *Rhizobium trifolii* malonyl-CoA synthetase (RtMatB) of SEQ ID NO: 25 having MatB activity,
   the exogenous gene encoding for MatC encodes a polypeptide having at least 85% amino acid identity with the amino acid sequence of *Rhizobium trifolii* putative dicarboxylate carrier protein (RtMatC) of SEQ ID NO: 26 having MatC activity,
   the exogenous gene encoding for F3H encodes a polypeptide having at least 85% amino acid identity with the amino acid sequence of *Camellia sinensis* flavanone 3(3-hydroxylase (CsF3H) of SEQ ID NO: 45, *Malus domestica* flavanone 33-hydroxylase (MdF3H) of SEQ ID NO: 47, *Petroselinum crispum* flavanone 33-hydroxylase (PcF3H) of SEQ ID NO: 49, or a combination thereof, having F3H activity,
   the exogenous gene encoding for DFR encodes a polypeptide having at least 85% amino acid identity with the amino acid sequence of *Anthrium andraeanum* dihydroflavonol 4-reductase (AaDFR) of SEQ ID NO: 51, *Camellia sinensis* dihydroflavonol 4-reductase (CsDFR) of SEQ ID NO: 53, *Fragaria* x *ananassa* dihydroflavonol 4-reductase (FaDFR) of SEQ ID NO: 55, or a combination thereof, having DFR activity, the exogenous gene encoding for LAR encodes a polypeptide having at least 85% amino acid identity with the amino acid sequence of *Camellia sinensis* leucoanthocyanidin reductase (CsLAR) of SEQ ID NO: 57, *Desmodium uncinatum* leucoanthocyanidin reductase (DuLAR) of SEQ ID NO: 59, or a combination thereof, having LAR activity, the exogenous gene encoding for ANS encodes a polypeptide having at least 85% amino acid identity with the amino acid sequence of *Petunia X hybrida* anthocyanidin synthase (PhANS) of SEQ ID NO: 61, *Malus domestica* ANS of SEQ ID NO: 70, *Pyrus communis* ANS of SEQ ID NO: 71, *Prunus avium* ANS of SEQ ID NO: 72, *Fragaria* x *ananassa* ANS of SEQ ID NO: 73, *Vitis vinifera* ANS of SEQ ID NO: 74, *Ipomoea purpurea* anthocyanidin synthase of SEQ ID NO: 75, *Camellia sinensis* ANS of SEQ ID NO: 76, *Citrus sinensis* anthocyanidin synthase (ANS) of SEQ ID NO: 77, *Vaccinium ashei* ANS of SEQ ID NO: 78, *Populus trichocarpa* ANS of SEQ ID NO: 79, or combinations thereof, having ANS activity, and the exogenous gene encoding for 3GT encodes a polypeptide having at least 85% amino acid identity with the amino acid sequence of *Arabidopsis thaliana* 3-glucosyl transferase (At3GT) of SEQ ID NO: 63, *Fragaria* x *ananassa* 3GT of SEQ ID NO: 64, *Vitis vinifera* 3GT of SEQ ID NO: 65, Forsythia 3GT of SEQ ID NO: 66, Eggplant 3GT of SEQ ID NO: 67, Gentian 3GT of SEQ ID NO: 68, *Petunia* x *hybrida* 3GT of SEQ ID NO: 69, or a combination thereof, having 3GT activity;

with a proviso that:
the first module cell in the microbial polyculture comprises the TAL module cell and the second module cell is the C5 module cell; or
the microbial polyculture comprises the C5 module cell and the p168 module cell; or
the microbial polyculture comprises the p168 module cell and the Antho module cell; or
the microbial polyculture comprises the TAL module cell, the C5 module cell, and the p168 module cell; or
the microbial polyculture comprises the C5 module cell, the p168 module cell, and the Antho module cell; or
the microbial polyculture comprises the TAL module cell, the C5 module cell, the p168 module cell, and the Antho module cell.

2. The microbial polyculture of claim 1, wherein the exogenous gene encoding for the tyrosine ammonia lyase (TAL) is a gene encoding for *Rhodotorula glutinis* tyrosine ammonia lyase (RgTAL).

3. The microbial polyculture of claim 1, wherein:
the exogenous gene encoding for the 4-coumaroyl-CoA ligase (4CL) is a gene encoding for *Arabidopsis thaliana* 4-coumaroyl-CoA ligase (At4CL);
the exogenous gene encoding for the chalcone synthase (CHS) is a gene encoding for *Petunia X hybrida* chalcone synthase (PhCHS);

the exogenous gene encoding for the chalcone isomerase (CHI) is a gene encoding for *Citrus maxima* chalcone isomerase (CmCHI);
the exogenous gene encoding for the malonyl-CoA synthetase (MatB) is a gene encoding for *Rhizobium trifolii* malonyl-CoA synthetase (RtMatB); and
the exogenous gene encoding for the dicarboxylate carrier protein (MatC) is a gene encoding for *Rhizobium trifolii* putative dicarboxylate carrier protein (RtMatC).

4. The microbial polyculture of claim 1, wherein:
the exogenous gene encoding for the flavanone 3β-hydroxylase (F3H) is a gene encoding for *Camellia sinensis* flavanone 3β-hydroxylase (CsF3H);
the exogenous gene encoding for the dihydroflavonol 4-reductase (DFR) is a gene encoding for *Fragaria* x *ananassa* dihydroflavonol 4-reductase (FaDFR); and
the exogenous gene encoding for the leucoanthocyanidin reductase (LAR) is a gene encoding for *Desmodium uncinatum* leucoanthocyanidin reductase (DuLAR).

5. The microbial polyculture of claim 1, wherein the exogenous gene encoding for the anthocyanidin synthase (ANS) is a gene encoding for *Petunia X hybrida* anthocyanidin synthase (PhANS).

6. The microbial polyculture of claim 1, wherein the exogenous gene encoding for the 3-glucosyl transferase (3GT) is a gene encoding for *Arabidopsis thaliana* 3-glucosyl transferase (At3GT).

7. The microbial polyculture of claim 1, wherein:
a host cell for the TAL module cell is *E. coli* rpoA14 (DE3);
a host cell for the C5 module cell is *E. coli* BL21star™ (DE3)ΔsucCΔfumC;
a host cell for the p168 module cell is *E. coli* BL21star™ (DE3); and
a host cell for the Antho module cell is *E. coli* BL21star™ (DE3).

8. A method of producing a phenylpropanoic acid in a TAL module cell, wherein the TAL module cell is a microbial cell comprising an exogenous gene encoding for a tyrosine ammonia lyase (TAL);
the method comprising:
providing a substrate to the TAL module cell, wherein the substrate comprises glucose, glycerol, or a combination thereof;
culturing the TAL module cell under conditions permitting synthesis of the phenylpropanoic acid by the TAL module cell; and
isolating the phenylpropanoic acid synthesized by the TAL module cell;
wherein the exogenous gene encoding for TAL encodes a polypeptide having at least 85% amino acid identity with the amino acid sequence of *Rhodotorula glutinis* tyrosine ammonia lyase (RgTAL) of SEQ ID NO: 29, *Rhodobacter capsulatus* TAL of SEQ ID NO: 80, Rice TAL of SEQ ID NO: 81, Parsley TAL of SEQ ID NO: 82, Tomato TAL of SEQ ID NO: 83, *Arabidopsis* TAL of SEQ ID NO: 84, or a combination thereof, having TAL activity.

9. The method of claim 8, wherein the phenylpropanoic acid is p-coumaric acid, caffeic acid, cinnamic acid, ferulic acid or a combination thereof.

10. The method of claim 9, wherein the host cell for the TAL module cell is *E. coli* rpoA14(DE3).

* * * * *